US010188772B2

(12) United States Patent
McClain et al.

(10) Patent No.: US 10,188,772 B2
(45) Date of Patent: Jan. 29, 2019

(54) DRUG DELIVERY MEDICAL DEVICE

(71) Applicant: Micell Technologies, Inc., Durham, NC (US)

(72) Inventors: James B. McClain, Ocracoke, NC (US); Charles Douglas Taylor, Franklinton, NC (US); Meagan M. Fagan, Raleigh, NC (US)

(73) Assignee: Micell Technologies, Inc., Durham, NC (US)

( * ) Notice: Subject to any disclaimer, the term of this patent is extended or adjusted under 35 U.S.C. 154(b) by 0 days.

(21) Appl. No.: 14/437,097

(22) PCT Filed: Oct. 18, 2013

(86) PCT No.: PCT/US2013/065777
§ 371 (c)(1),
(2) Date: Apr. 20, 2015

(87) PCT Pub. No.: WO2014/063111
PCT Pub. Date: Apr. 24, 2014

(65) Prior Publication Data
US 2015/0250926 A1     Sep. 10, 2015

Related U.S. Application Data

(60) Provisional application No. 61/715,768, filed on Oct. 18, 2012.

(51) Int. Cl.
*A61M 25/00* (2006.01)
*A61L 29/08* (2006.01)
*A61L 29/16* (2006.01)
*A61L 29/14* (2006.01)
*A61M 25/10* (2013.01)

(52) U.S. Cl.
CPC .......... *A61L 29/085* (2013.01); *A61L 29/148* (2013.01); *A61L 29/16* (2013.01); *A61L 2300/416* (2013.01); *A61L 2300/622* (2013.01); *A61L 2300/624* (2013.01); *A61L 2300/63* (2013.01); *A61M 2025/105* (2013.01)

(58) Field of Classification Search
CPC ................. A61M 2025/105; A61M 25/00
See application file for complete search history.

(56) References Cited

U.S. PATENT DOCUMENTS

| 3,087,860 | A | 4/1963 | Endicott et al. |
|---|---|---|---|
| 3,123,077 | A | 3/1964 | Alcamo |
| 3,457,280 | A | 7/1969 | Schmitt et al. |
| 3,597,449 | A | 8/1971 | Deprospero et al. |
| 3,737,337 | A | 6/1973 | Schnoring et al. |
| 3,773,919 | A | 11/1973 | Boswell et al. |
| 3,929,992 | A | 12/1975 | Sehgal et al. |
| 4,000,137 | A | 12/1976 | Dvonch et al. |
| 4,188,373 | A | 2/1980 | Krezanoski |
| 4,285,987 | A | 8/1981 | Ayer et al. |
| 4,326,532 | A | 4/1982 | Hammar |
| 4,336,381 | A | 6/1982 | Nagata et al. |
| 4,389,330 | A | 6/1983 | Tice et al. |
| 4,474,572 | A | 10/1984 | McNaughton et al. |
| 4,474,751 | A | 10/1984 | Haslam et al. |
| 4,478,822 | A | 10/1984 | Haslam et al. |
| 4,530,840 | A | 7/1985 | Tice et al. |
| 4,582,731 | A | 4/1986 | Smith |
| 4,606,347 | A | 8/1986 | Fogarty et al. |
| 4,617,751 | A | 10/1986 | Johansson |
| 4,655,771 | A | 4/1987 | Wallsten |
| 4,675,189 | A | 6/1987 | Kent et al. |
| 4,733,665 | A | 3/1988 | Palmaz |
| 4,734,227 | A | 3/1988 | Smith |
| 4,734,451 | A | 3/1988 | Smith |
| 4,758,435 | A | 7/1988 | Schaaf |
| 4,762,593 | A | 8/1988 | Youngner |
| 4,931,037 | A | 6/1990 | Wetterman |

(Continued)

FOREIGN PATENT DOCUMENTS

| CA | 2237466 A1 | 11/1998 |
|---|---|---|
| CA | 2589761 A1 | 6/2006 |

(Continued)

OTHER PUBLICATIONS

Abreu Filho et al., "Influence of metal alloy and the profile of coronary stents in patients with multivessel coronary lisease," Clinics 2011 ;66(6):985-989.
Akoh et al., "One-Stage Synthesis of Raffinose Fatty Acid Polyesters. "Journal Food Science (1987) 52:1570.
Albert et al., "Antibiotics tor preventing recurrent urinary tract infection in nonpregnant women,"Cochrane Database System Rev. 3, CD001209 (2004).
Analytical Ultracentrifugation of Polymers and Nanoparticles, W. Machtle and L. Borger, (Springer) 2006, p. 41.
Au et al., "Methods to improve efficacy of intravesical mitomycin C: Results of a randomized phase III trial," Journal of the National Cancer Institute, 93 (8 ), 597-604 (2001).

(Continued)

*Primary Examiner* — Audrea B Coniglio
(74) *Attorney, Agent, or Firm* — Lerner, David, Littenberg, Krumholz & Mentlik, LLP

(57) ABSTRACT

A medical device that releases a pharmaceutical agent to a target site is disclosed. The medical device includes a balloon, and a coating on at least a portion of the balloon. The coating includes particles of a pharmaceutical agent. Each particle of the particles of the pharmaceutical agent is at least partially encapsulated in a polymer material. A method of releasing a pharmaceutical agent at a target site is also disclosed. The method includes the steps of providing a device including a balloon, and a coating on at least a portion of the balloon, the coating including particles of a pharmaceutical agent, and each particle of the pharmaceutical agent is at least partially encapsulated in a polymer material; positioning the device to allow the balloon to reach the target site; and inflating the balloon of the device.

39 Claims, 6 Drawing Sheets

(56) References Cited

U.S. PATENT DOCUMENTS

| | | |
|---|---|---|
| 4,950,239 A | 8/1990 | Gahara et al. |
| 4,985,625 A | 1/1991 | Hurst |
| 5,000,519 A | 3/1991 | Moore |
| 5,090,419 A | 2/1992 | Palestrant |
| 5,096,848 A | 3/1992 | Kawamura |
| 5,102,417 A | 4/1992 | Palmaz |
| 5,104,404 A | 4/1992 | Wolff |
| 5,106,650 A | 4/1992 | Hoy et al. |
| 5,125,570 A | 6/1992 | Jones |
| 5,158,986 A | 10/1992 | Cha et al. |
| 5,185,776 A | 2/1993 | Townsend |
| 5,195,969 A | 3/1993 | Wang et al. |
| 5,243,023 A | 9/1993 | Dezem |
| 5,270,086 A | 12/1993 | Hamlin |
| 5,288,711 A | 2/1994 | Mitchell et al. |
| 5,320,634 A | 6/1994 | Vigil et al. |
| 5,324,049 A | 6/1994 | Mistrater et al. |
| 5,340,614 A | 8/1994 | Perman et al. |
| 5,342,621 A | 8/1994 | Eury |
| 5,350,361 A | 9/1994 | Tsukashima et al. |
| 5,350,627 A | 9/1994 | Nemphos et al. |
| 5,356,433 A | 10/1994 | Rowland et al. |
| 5,360,403 A | 11/1994 | Mische |
| 5,362,718 A | 11/1994 | Skotnicki et al. |
| 5,366,504 A | 11/1994 | Andersen et al. |
| 5,368,045 A | 11/1994 | Clement et al. |
| 5,372,676 A | 12/1994 | Lowe |
| 5,385,776 A | 1/1995 | Maxfield et al. |
| 5,387,313 A | 2/1995 | Thorns |
| 5,403,347 A | 4/1995 | Roby et al. |
| 5,470,603 A | 11/1995 | Staniforth et al. |
| 5,494,620 A | 2/1996 | Liu et al. |
| 5,500,180 A | 3/1996 | Anderson et al. |
| 5,514,379 A | 5/1996 | Weissleder et al. |
| 5,545,208 A | 8/1996 | Wolff et al. |
| 5,556,383 A | 9/1996 | Wang et al. |
| 5,562,922 A | 10/1996 | Lambert |
| 5,569,463 A | 10/1996 | Helmus et al. |
| 5,570,537 A | 11/1996 | Black et al. |
| 5,578,709 A | 11/1996 | Woiszwillo |
| 5,599,576 A | 2/1997 | Opolski |
| 5,605,696 A | 2/1997 | Eury et al. |
| 5,607,442 A | 3/1997 | Fischell et al. |
| 5,609,629 A | 3/1997 | Fearnot et al. |
| 5,626,611 A | 5/1997 | Liu et al. |
| 5,626,862 A | 5/1997 | Brem et al. |
| 5,632,772 A | 5/1997 | Alcime et al. |
| 5,669,932 A | 9/1997 | Fischell et al. |
| 5,674,192 A | 10/1997 | Sahatjian et al. |
| 5,674,242 A | 10/1997 | Phan et al. |
| 5,725,570 A | 3/1998 | Heath |
| 5,733,303 A | 3/1998 | Israel et al. |
| 5,766,158 A | 6/1998 | Opolski |
| 5,800,511 A | 9/1998 | Mayer |
| 5,807,404 A | 9/1998 | Richter |
| 5,811,032 A | 9/1998 | Kawai et al. |
| 5,824,049 A | 10/1998 | Ragheb et al. |
| 5,837,313 A | 11/1998 | Ding et al. |
| 5,843,120 A | 12/1998 | Israel et al. |
| 5,871,436 A | 2/1999 | Eury |
| 5,873,904 A | 2/1999 | Ragheb et al. |
| 5,876,426 A | 3/1999 | Kume et al. |
| 5,876,452 A | 3/1999 | Athanasiou et al. |
| 5,913,895 A | 6/1999 | Burpee et al. |
| 5,924,631 A | 7/1999 | Rodrigues et al. |
| 5,948,020 A | 9/1999 | Yoon et al. |
| 5,957,975 A | 9/1999 | Lafont et al. |
| 5,981,568 A | 11/1999 | Kunz et al. |
| 5,981,719 A | 11/1999 | Woiszwillo et al. |
| 6,013,855 A | 1/2000 | McPherson et al. |
| 6,036,978 A | 3/2000 | Gombotz et al. |
| 6,039,721 A | 3/2000 | Johnson et al. |
| 6,068,656 A | 5/2000 | Von Oepen |
| 6,071,308 A | 6/2000 | Ballou et al. |
| 6,077,880 A | 6/2000 | Castillo et al. |
| 6,090,925 A | 7/2000 | Woiszwillo et al. |
| 6,129,755 A | 10/2000 | Mathis et al. |
| 6,143,037 A | 11/2000 | Goldstein et al. |
| 6,143,314 A | 11/2000 | Chandrashekar et al. |
| 6,146,356 A | 11/2000 | Wang et al. |
| 6,146,404 A | 11/2000 | Kim et al. |
| 6,153,252 A | 11/2000 | Hossainy et al. |
| 6,171,327 B1 | 1/2001 | Daniel et al. |
| 6,190,699 B1 | 2/2001 | Luzzi et al. |
| 6,193,744 B1 | 2/2001 | Ehr et al. |
| 6,206,914 B1 | 3/2001 | Soykan et al. |
| 6,217,608 B1 | 4/2001 | Penn et al. |
| 6,231,599 B1 | 5/2001 | Ley |
| 6,231,600 B1 | 5/2001 | Zhong |
| 6,245,104 B1 | 6/2001 | Alt |
| 6,248,127 B1 | 6/2001 | Shah et al. |
| 6,248,129 B1 | 6/2001 | Froix |
| 6,251,980 B1 | 6/2001 | Lan et al. |
| 6,268,053 B1 | 7/2001 | Woiszwillo et al. |
| 6,273,913 B1 | 8/2001 | Wright et al. |
| 6,284,758 B1 | 9/2001 | Egi et al. |
| 6,299,635 B1 | 10/2001 | Frantzen |
| 6,309,669 B1 | 10/2001 | Setterstrom et al. |
| 6,319,541 B1 | 11/2001 | Pletcher et al. |
| 6,325,821 B1 | 12/2001 | Gaschino et al. |
| 6,336,934 B1 | 1/2002 | Gilson et al. |
| 6,342,062 B1 | 1/2002 | Suon et al. |
| 6,344,055 B1 | 2/2002 | Shukov |
| 6,355,691 B1 | 3/2002 | Goodman |
| 6,358,556 B1 | 3/2002 | Ding et al. |
| 6,361,819 B1 | 3/2002 | Tedeschi et al. |
| 6,362,718 B1 | 3/2002 | Patrick et al. |
| 6,364,903 B2 | 4/2002 | Tseng et al. |
| 6,368,658 B1 | 4/2002 | Schwarz et al. |
| 6,372,246 B1 | 4/2002 | Wei et al. |
| 6,387,121 B1 | 5/2002 | Alt |
| 6,409,716 B1 | 6/2002 | Sahatjian et al. |
| 6,414,050 B1 | 7/2002 | Howdle et al. |
| 6,416,779 B1 | 7/2002 | D'Augustine et al. |
| 6,448,315 B1 | 9/2002 | Lidgren et al. |
| 6,458,387 B1 | 10/2002 | Scott et al. |
| 6,461,380 B1 | 10/2002 | Cox |
| 6,461,644 B1 | 10/2002 | Jackson et al. |
| 6,488,703 B1 | 12/2002 | Kveen et al. |
| 6,495,163 B1 | 12/2002 | Jordan |
| 6,497,729 B1 | 12/2002 | Moussy et al. |
| 6,506,213 B1 | 1/2003 | Mandel et al. |
| 6,517,860 B1 | 2/2003 | Roser et al. |
| 6,521,258 B1 | 2/2003 | Mandel et al. |
| 6,524,698 B1 | 2/2003 | Schmoock |
| 6,530,951 B1 | 3/2003 | Bates et al. |
| 6,537,310 B1 | 3/2003 | Palmaz et al. |
| 6,541,033 B1 | 4/2003 | Shah |
| 6,572,813 B1 | 6/2003 | Zhang et al. |
| 6,602,281 B1 | 8/2003 | Klein |
| 6,610,013 B1 | 8/2003 | Fenster et al. |
| 6,627,246 B2 | 9/2003 | Mehta et al. |
| 6,649,627 B1 | 11/2003 | Cecchi et al. |
| 6,660,176 B2 | 12/2003 | Tepper et al. |
| 6,669,785 B2 | 12/2003 | DeYoung et al. |
| 6,669,980 B2 | 12/2003 | Hansen |
| 6,670,407 B2 | 12/2003 | Howdle et al. |
| 6,682,757 B1 | 1/2004 | Wright |
| 6,706,283 B1 | 3/2004 | Appel et al. |
| 6,710,059 B1 | 3/2004 | Labrie et al. |
| 6,720,003 B2 | 4/2004 | Chen et al. |
| 6,723,913 B1 | 4/2004 | Barbetta |
| 6,726,712 B1 | 4/2004 | Raeder-Devens et al. |
| 6,736,996 B1 | 5/2004 | Carbonell et al. |
| 6,743,505 B2 | 6/2004 | Antal et al. |
| 6,749,902 B2 | 6/2004 | Yonker et al. |
| 6,755,871 B2 | 6/2004 | Damaso et al. |
| 6,756,084 B2 | 6/2004 | Fulton et al. |
| 6,767,558 B2 | 7/2004 | Wang |
| 6,780,475 B2 | 8/2004 | Fulton et al. |
| 6,794,902 B2 | 9/2004 | Becker et al. |
| 6,800,663 B2 | 10/2004 | Asgarzadeh et al. |

(56) References Cited

U.S. PATENT DOCUMENTS

| | | |
|---|---|---|
| 6,815,218 B1 | 11/2004 | Jacobson et al. |
| 6,821,549 B2 | 11/2004 | Jayaraman |
| 6,837,611 B2 | 1/2005 | Kuo |
| 6,838,089 B1 | 1/2005 | Carlsson et al. |
| 6,838,528 B2 | 1/2005 | Zhao |
| 6,858,598 B1 | 2/2005 | McKearn et al. |
| 6,860,123 B1 | 3/2005 | Uhlin |
| 6,868,123 B2 | 3/2005 | Bellas et al. |
| 6,884,377 B1 | 4/2005 | Burnham et al. |
| 6,884,823 B1 | 4/2005 | Pierick et al. |
| 6,897,205 B2 | 5/2005 | Beckert et al. |
| 6,905,555 B2 | 6/2005 | DeYoung et al. |
| 6,908,624 B2 | 6/2005 | Hossainy et al. |
| 6,916,800 B2 | 7/2005 | McKearn et al. |
| 6,923,979 B2 | 8/2005 | Fotland et al. |
| 6,936,270 B2 | 8/2005 | Watson et al. |
| 6,939,569 B1 | 9/2005 | Green et al. |
| 6,973,718 B2 | 12/2005 | Sheppard, Jr. et al. |
| 7,056,591 B1 | 6/2006 | Pacetti et al. |
| 7,094,256 B1 | 8/2006 | Shah et al. |
| 7,148,201 B2 | 12/2006 | Stern et al. |
| 7,152,452 B2 | 12/2006 | Kokish |
| 7,160,592 B2 | 1/2007 | Rypacek et al. |
| 7,163,715 B1 | 1/2007 | Kramer |
| 7,169,404 B2 | 1/2007 | Hossainy et al. |
| 7,171,255 B2 | 1/2007 | Holupka et al. |
| 7,201,750 B1 | 4/2007 | Eggers et al. |
| 7,201,940 B1 | 4/2007 | Kramer |
| 7,229,837 B2 | 6/2007 | Chen |
| 7,278,174 B2 | 10/2007 | Villalobos |
| 7,279,174 B2 | 10/2007 | Pacetti et al. |
| 7,282,020 B2 | 10/2007 | Kaplan |
| 7,308,748 B2 | 12/2007 | Kokish |
| 7,323,454 B2 | 1/2008 | De Nijs et al. |
| 7,326,734 B2 | 2/2008 | Zi et al. |
| 7,329,383 B2 | 2/2008 | Stinson |
| 7,378,105 B2 | 5/2008 | Burke et al. |
| 7,419,696 B2 | 9/2008 | Berg et al. |
| 7,429,378 B2 | 9/2008 | Serhan et al. |
| 7,444,162 B2 | 10/2008 | Hassan |
| 7,455,658 B2 | 11/2008 | Wang |
| 7,455,688 B2 | 11/2008 | Furst et al. |
| 7,456,151 B2 | 11/2008 | Li et al. |
| 7,462,593 B2 | 12/2008 | Cuttitta et al. |
| 7,485,113 B2 | 2/2009 | Varner et al. |
| 7,498,042 B2 | 3/2009 | Igaki et al. |
| 7,524,865 B2 | 4/2009 | D'Amato et al. |
| 7,537,610 B2 | 5/2009 | Reiss |
| 7,537,785 B2 | 5/2009 | Loscalzo et al. |
| 7,553,827 B2 | 6/2009 | Attawia et al. |
| 7,713,538 B2 | 5/2010 | Lewis et al. |
| 7,727,275 B2 | 6/2010 | Betts et al. |
| 7,745,566 B2 | 6/2010 | Chattopadhyay et al. |
| 7,763,277 B1 | 7/2010 | Canham et al. |
| 7,771,468 B2 | 8/2010 | Whitbourne et al. |
| 7,837,726 B2 | 11/2010 | Von Oepen et al. |
| 7,842,312 B2 | 11/2010 | Burgermeister et al. |
| 7,919,108 B2 | 4/2011 | Reyes et al. |
| 7,955,383 B2 | 6/2011 | Krivoruchko et al. |
| 7,967,855 B2 | 6/2011 | Furst et al. |
| 7,972,661 B2 | 7/2011 | Pui et al. |
| 8,070,796 B2 | 12/2011 | Furst et al. |
| 8,109,904 B1 | 2/2012 | Papp |
| 8,295,565 B2 | 10/2012 | Gu et al. |
| 8,298,565 B2 | 10/2012 | Taylor et al. |
| 8,377,356 B2 | 2/2013 | Huang et al. |
| 8,535,372 B1 | 9/2013 | Fox et al. |
| 8,709,071 B1 | 4/2014 | Huang et al. |
| 8,753,659 B2 | 6/2014 | Lewis et al. |
| 8,753,709 B2 | 6/2014 | Hossainy et al. |
| 8,758,429 B2 | 6/2014 | Taylor et al. |
| 8,795,762 B2 | 8/2014 | Fulton et al. |
| 8,834,913 B2 | 9/2014 | Shaw et al. |
| 8,852,625 B2 | 10/2014 | DeYoung et al. |
| 8,900,651 B2 | 12/2014 | McClain et al. |
| 9,433,516 B2 | 9/2016 | McClain et al. |
| 9,486,431 B2 | 11/2016 | McClain et al. |
| 2001/0026804 A1 | 10/2001 | Boutignon |
| 2001/0034336 A1 | 10/2001 | Shah et al. |
| 2001/0037143 A1 | 11/2001 | Oepen |
| 2001/0044629 A1 | 11/2001 | Stinson |
| 2001/0049551 A1 | 12/2001 | Tseng et al. |
| 2002/0007209 A1 | 1/2002 | Scheerder et al. |
| 2002/0051485 A1 | 5/2002 | Bottomley |
| 2002/0051845 A1 | 5/2002 | Mehta et al. |
| 2002/0082680 A1 | 6/2002 | Shanley et al. |
| 2002/0091433 A1 | 7/2002 | Ding et al. |
| 2002/0099332 A1 | 7/2002 | Slepian et al. |
| 2002/0125860 A1 | 9/2002 | Schworm et al. |
| 2002/0133072 A1 | 9/2002 | Wang et al. |
| 2002/0144757 A1 | 10/2002 | Craig et al. |
| 2002/0151959 A1 | 10/2002 | Von Oepen |
| 2003/0001830 A1 | 1/2003 | Wampler et al. |
| 2003/0004563 A1 | 1/2003 | Jackson et al. |
| 2003/0028244 A1 | 2/2003 | Bates et al. |
| 2003/0031699 A1 | 2/2003 | Van Antwerp |
| 2003/0077200 A1 | 4/2003 | Craig et al. |
| 2003/0088307 A1 | 5/2003 | Shulze et al. |
| 2003/0125800 A1 | 7/2003 | Shulze et al. |
| 2003/0143315 A1 | 7/2003 | Pui et al. |
| 2003/0170305 A1 | 9/2003 | O'Neil et al. |
| 2003/0180376 A1 | 9/2003 | Dalal et al. |
| 2003/0185964 A1 | 10/2003 | Weber et al. |
| 2003/0204238 A1 | 10/2003 | Tedeschi |
| 2003/0209835 A1 | 11/2003 | Chun et al. |
| 2003/0222017 A1 | 12/2003 | Fulton et al. |
| 2003/0222018 A1 | 12/2003 | Yonker et al. |
| 2003/0232014 A1 | 12/2003 | Burke et al. |
| 2004/0013792 A1 | 1/2004 | Epstein et al. |
| 2004/0018228 A1 | 1/2004 | Fischell et al. |
| 2004/0022400 A1 | 2/2004 | Magrath |
| 2004/0022853 A1 | 2/2004 | Ashton et al. |
| 2004/0044397 A1 | 3/2004 | Stinson |
| 2004/0059290 A1 | 3/2004 | Palasis |
| 2004/0096477 A1 | 5/2004 | Chauhan et al. |
| 2004/0102758 A1 | 5/2004 | Davila et al. |
| 2004/0106982 A1 | 6/2004 | Jalisi |
| 2004/0122205 A1 | 6/2004 | Nathan |
| 2004/0126542 A1 | 7/2004 | Fujiwara et al. |
| 2004/0143317 A1 | 7/2004 | Stinson et al. |
| 2004/0144317 A1 | 7/2004 | Chuman et al. |
| 2004/0147904 A1 | 7/2004 | Hung et al. |
| 2004/0157789 A1 | 8/2004 | Geall |
| 2004/0170685 A1 | 9/2004 | Carpenter et al. |
| 2004/0193177 A1 | 9/2004 | Houghton et al. |
| 2004/0193262 A1 | 9/2004 | Shadduck |
| 2004/0220660 A1 | 11/2004 | Shanley et al. |
| 2004/0224001 A1 | 11/2004 | Pacetti et al. |
| 2004/0236416 A1 | 11/2004 | Falotico |
| 2004/0260000 A1 | 12/2004 | Chaiko |
| 2005/0003074 A1 | 1/2005 | Brown et al. |
| 2005/0004661 A1 | 1/2005 | Lewis et al. |
| 2005/0010275 A1 | 1/2005 | Sahatjian et al. |
| 2005/0015046 A1 | 1/2005 | Weber et al. |
| 2005/0019747 A1 | 1/2005 | Anderson et al. |
| 2005/0033414 A1 | 2/2005 | Zhang et al. |
| 2005/0038498 A1 | 2/2005 | Dubrow et al. |
| 2005/0048121 A1 | 3/2005 | East et al. |
| 2005/0049694 A1 | 3/2005 | Neary |
| 2005/0060028 A1 | 3/2005 | Horres et al. |
| 2005/0069630 A1 | 3/2005 | Fox et al. |
| 2005/0070989 A1 | 3/2005 | Lye et al. |
| 2005/0070990 A1 | 3/2005 | Stinson |
| 2005/0070997 A1 | 3/2005 | Thornton et al. |
| 2005/0074479 A1 | 4/2005 | Weber et al. |
| 2005/0075714 A1 | 4/2005 | Cheng et al. |
| 2005/0079199 A1 | 4/2005 | Heruth et al. |
| 2005/0079274 A1 | 4/2005 | Palasis et al. |
| 2005/0084533 A1 | 4/2005 | Howdle et al. |
| 2005/0131008 A1 | 6/2005 | Betts et al. |
| 2005/0131513 A1 | 6/2005 | Myers |
| 2005/0147734 A1 | 7/2005 | Seppala et al. |
| 2005/0159704 A1 | 7/2005 | Scott et al. |
| 2005/0166841 A1 | 8/2005 | Robida |

(56) References Cited

U.S. PATENT DOCUMENTS

| | | |
|---|---|---|
| 2005/0175772 A1 | 8/2005 | Worsham et al. |
| 2005/0177223 A1 | 8/2005 | Palmaz |
| 2005/0191491 A1 | 9/2005 | Wang et al. |
| 2005/0196424 A1 | 9/2005 | Chappa |
| 2005/0208102 A1 | 9/2005 | Schultz |
| 2005/0209244 A1 | 9/2005 | Prescott et al. |
| 2005/0209680 A1 | 9/2005 | Gale et al. |
| 2005/0216075 A1 | 9/2005 | Wang et al. |
| 2005/0220839 A1 | 10/2005 | DeWitt et al. |
| 2005/0222676 A1 | 10/2005 | Shanley et al. |
| 2005/0238829 A1 | 10/2005 | Motherwell et al. |
| 2005/0245637 A1 | 11/2005 | Hossainy et al. |
| 2005/0255327 A1 | 11/2005 | Chaney et al. |
| 2005/0260186 A1 | 11/2005 | Bookbinder et al. |
| 2005/0268573 A1 | 12/2005 | Yan |
| 2005/0288481 A1 | 12/2005 | DesNoyer et al. |
| 2005/0288629 A1 | 12/2005 | Kunis |
| 2006/0001011 A1 | 1/2006 | Wilson et al. |
| 2006/0002974 A1 | 1/2006 | Pacetti et al. |
| 2006/0020325 A1 | 1/2006 | Burgermeister et al. |
| 2006/0030652 A1 | 2/2006 | Adams et al. |
| 2006/0045901 A1 | 3/2006 | Weber |
| 2006/0067974 A1 | 3/2006 | Labrecque et al. |
| 2006/0073329 A1 | 4/2006 | Boyce et al. |
| 2006/0089705 A1 | 4/2006 | Ding et al. |
| 2006/0093771 A1 | 5/2006 | Rypacek et al. |
| 2006/0094744 A1 | 5/2006 | Maryanoff et al. |
| 2006/0104969 A1 | 5/2006 | Oray et al. |
| 2006/0106455 A1 | 5/2006 | Furst et al. |
| 2006/0116755 A1 | 6/2006 | Stinson |
| 2006/0121080 A1 | 6/2006 | Lye et al. |
| 2006/0121089 A1 | 6/2006 | Michal et al. |
| 2006/0134168 A1 | 6/2006 | Chappa et al. |
| 2006/0134211 A1 | 6/2006 | Lien et al. |
| 2006/0136041 A1 | 6/2006 | Schmid et al. |
| 2006/0147698 A1 | 7/2006 | Carroll et al. |
| 2006/0153729 A1 | 7/2006 | Stinson et al. |
| 2006/0160455 A1 | 7/2006 | Sugyo et al. |
| 2006/0188547 A1 | 8/2006 | Bezwada |
| 2006/0193886 A1 | 8/2006 | Owens et al. |
| 2006/0193890 A1 | 8/2006 | Owens et al. |
| 2006/0198868 A1 | 9/2006 | DeWitt et al. |
| 2006/0210638 A1 | 9/2006 | Liversidge et al. |
| 2006/0216324 A1 | 9/2006 | Stucke et al. |
| 2006/0222756 A1 | 10/2006 | Davila et al. |
| 2006/0228415 A1 | 10/2006 | Oberegger et al. |
| 2006/0228453 A1 | 10/2006 | Cromack et al. |
| 2006/0235506 A1 | 10/2006 | Ta et al. |
| 2006/0276877 A1 | 12/2006 | Owens et al. |
| 2006/0287611 A1 | 12/2006 | Fleming |
| 2007/0009564 A1 | 1/2007 | McClain et al. |
| 2007/0009664 A1 | 1/2007 | Fallais et al. |
| 2007/0026041 A1 | 2/2007 | DesNoyer et al. |
| 2007/0026042 A1 | 2/2007 | Narayanan |
| 2007/0032864 A1 | 2/2007 | Furst et al. |
| 2007/0038227 A1 | 2/2007 | Massicotte et al. |
| 2007/0038289 A1 | 2/2007 | Nishide et al. |
| 2007/0043434 A1 | 2/2007 | Meerkin et al. |
| 2007/0059350 A1 | 3/2007 | Kennedy et al. |
| 2007/0065478 A1 | 3/2007 | Hossainy |
| 2007/0110888 A1 | 5/2007 | Radhakrishnan et al. |
| 2007/0123973 A1 | 5/2007 | Roth et al. |
| 2007/0123977 A1 | 5/2007 | Cottone et al. |
| 2007/0128274 A1 | 6/2007 | Zhu et al. |
| 2007/0148251 A1 | 6/2007 | Hossainy et al. |
| 2007/0154513 A1 | 7/2007 | Atanasoska et al. |
| 2007/0154554 A1 | 7/2007 | Burgermeister et al. |
| 2007/0196242 A1 | 8/2007 | Boozer et al. |
| 2007/0196423 A1 | 8/2007 | Ruane et al. |
| 2007/0198081 A1 | 8/2007 | Castro et al. |
| 2007/0200268 A1 | 8/2007 | Dave |
| 2007/0203569 A1 | 8/2007 | Burgermeister et al. |
| 2007/0219579 A1 | 9/2007 | Paul |
| 2007/0225795 A1 | 9/2007 | Granada et al. |
| 2007/0250157 A1 | 10/2007 | Nishide et al. |
| 2007/0259017 A1 | 11/2007 | Francis |
| 2007/0280992 A1 | 12/2007 | Margaron et al. |
| 2008/0030066 A1 | 2/2008 | Mercier et al. |
| 2008/0051866 A1 | 2/2008 | Chen et al. |
| 2008/0065192 A1 | 3/2008 | Berglund |
| 2008/0071347 A1 | 3/2008 | Cambronne |
| 2008/0071358 A1 | 3/2008 | Weber et al. |
| 2008/0071359 A1 | 3/2008 | Thornton et al. |
| 2008/0075753 A1 | 3/2008 | Chappa |
| 2008/0077232 A1 | 3/2008 | Nishide |
| 2008/0085880 A1 | 4/2008 | Viswanath et al. |
| 2008/0091008 A1 | 4/2008 | Viswanath et al. |
| 2008/0095919 A1 | 4/2008 | McClain et al. |
| 2008/0097575 A1 | 4/2008 | Cottone |
| 2008/0097591 A1 | 4/2008 | Savage et al. |
| 2008/0098178 A1 | 4/2008 | Veazey et al. |
| 2008/0107702 A1 | 5/2008 | Jennissen |
| 2008/0118543 A1 | 5/2008 | Pacetti et al. |
| 2008/0124372 A1 | 5/2008 | Hossainy et al. |
| 2008/0138375 A1 | 6/2008 | Yan et al. |
| 2008/0206304 A1 | 8/2008 | Lindquist et al. |
| 2008/0213464 A1 | 9/2008 | O'Connor |
| 2008/0233267 A1 | 9/2008 | Berglund |
| 2008/0255510 A1 | 10/2008 | Wang |
| 2008/0269449 A1 | 10/2008 | Chattopadhyay et al. |
| 2008/0286325 A1 | 11/2008 | Reyes et al. |
| 2008/0292776 A1 | 11/2008 | Dias et al. |
| 2008/0300669 A1 | 12/2008 | Hossainy |
| 2008/0300689 A1 | 12/2008 | McKinnon et al. |
| 2009/0043379 A1 | 2/2009 | Prescott |
| 2009/0062909 A1 | 3/2009 | Taylor et al. |
| 2009/0068266 A1 | 3/2009 | Raheja et al. |
| 2009/0076446 A1 | 3/2009 | Dubuclet, IV et al. |
| 2009/0082855 A1 | 3/2009 | Borges et al. |
| 2009/0098178 A1 | 4/2009 | Hofmann et al. |
| 2009/0105687 A1 | 4/2009 | Deckman et al. |
| 2009/0105809 A1 | 4/2009 | Lee et al. |
| 2009/0110711 A1 | 4/2009 | Trollsas et al. |
| 2009/0111787 A1 | 4/2009 | Lim et al. |
| 2009/0123515 A1 | 5/2009 | Taylor et al. |
| 2009/0123521 A1 | 5/2009 | Weber et al. |
| 2009/0186069 A1 | 7/2009 | DeYoung et al. |
| 2009/0202609 A1 | 8/2009 | Keough et al. |
| 2009/0216317 A1 | 8/2009 | Cromack et al. |
| 2009/0227949 A1 | 9/2009 | Knapp et al. |
| 2009/0231578 A1 | 9/2009 | Ling et al. |
| 2009/0263460 A1 | 10/2009 | McDonald |
| 2009/0285974 A1 | 11/2009 | Kerrigan et al. |
| 2009/0292351 A1 | 11/2009 | McClain et al. |
| 2009/0292776 A1 | 11/2009 | Nesbitt et al. |
| 2009/0297578 A1 | 12/2009 | Trollsas et al. |
| 2009/0300689 A1 | 12/2009 | Conte et al. |
| 2010/0000328 A1 | 1/2010 | Mahmoud |
| 2010/0006358 A1 | 1/2010 | Ishikawa |
| 2010/0015200 A1 | 1/2010 | McClain et al. |
| 2010/0030261 A1 | 2/2010 | McClain |
| 2010/0042206 A1 | 2/2010 | Yadav et al. |
| 2010/0055145 A1 | 3/2010 | Betts et al. |
| 2010/0055294 A1 | 3/2010 | Wang et al. |
| 2010/0063570 A1 | 3/2010 | Pacetti et al. |
| 2010/0063580 A1 | 3/2010 | McClain et al. |
| 2010/0074934 A1 | 3/2010 | Hunter |
| 2010/0131044 A1 | 5/2010 | Patel |
| 2010/0155496 A1 | 6/2010 | Stark et al. |
| 2010/0166869 A1 | 7/2010 | Desai et al. |
| 2010/0196482 A1 | 8/2010 | Radovic-Moreno et al. |
| 2010/0198330 A1 | 8/2010 | Hossainy et al. |
| 2010/0198331 A1 | 8/2010 | Rapoza et al. |
| 2010/0211164 A1 | 8/2010 | McClain et al. |
| 2010/0228348 A1 | 9/2010 | McClain et al. |
| 2010/0233332 A1 | 9/2010 | Xing et al. |
| 2010/0239635 A1 | 9/2010 | McClain et al. |
| 2010/0241220 A1 | 9/2010 | McClain et al. |
| 2010/0256746 A1 | 10/2010 | Taylor et al. |
| 2010/0256748 A1 | 10/2010 | Taylor et al. |
| 2010/0262224 A1 | 10/2010 | Kleiner |
| 2010/0272775 A1 | 10/2010 | Cleek et al. |
| 2010/0272778 A1 | 10/2010 | McClain et al. |
| 2010/0285085 A1 | 11/2010 | Stankus et al. |

(56) References Cited

U.S. PATENT DOCUMENTS

| | | |
|---|---|---|
| 2010/0298928 A1 | 11/2010 | McClain et al. |
| 2010/0305689 A1 | 12/2010 | Venkatraman et al. |
| 2011/0009953 A1 | 1/2011 | Luk et al. |
| 2011/0034422 A1 | 2/2011 | Kannan et al. |
| 2011/0060073 A1 | 3/2011 | Huang et al. |
| 2011/0159069 A1 | 6/2011 | Shaw et al. |
| 2011/0160751 A1 | 6/2011 | Granja Filho |
| 2011/0172763 A1 | 7/2011 | Ndondo-Lay |
| 2011/0189299 A1 | 8/2011 | Okubo et al. |
| 2011/0190864 A1 | 8/2011 | McClain et al. |
| 2011/0223212 A1* | 9/2011 | Taton .............. A61L 27/34 424/400 |
| 2011/0238161 A1 | 9/2011 | Fulton et al. |
| 2011/0243884 A1 | 10/2011 | O'Shea et al. |
| 2011/0257732 A1 | 10/2011 | McClain et al. |
| 2011/0264190 A1 | 10/2011 | McClain et al. |
| 2011/0301697 A1 | 12/2011 | Hoffmann et al. |
| 2012/0064124 A1 | 3/2012 | McClain et al. |
| 2012/0064143 A1 | 3/2012 | Sharp et al. |
| 2012/0065723 A1 | 3/2012 | Drasler et al. |
| 2012/0101566 A1 | 4/2012 | Mews et al. |
| 2012/0150275 A1 | 6/2012 | Shaw-Klein |
| 2012/0160408 A1 | 6/2012 | Clerc et al. |
| 2012/0172787 A1 | 7/2012 | McClain et al. |
| 2012/0177742 A1 | 7/2012 | McClain et al. |
| 2012/0231037 A1 | 9/2012 | Levi et al. |
| 2012/0271396 A1 | 10/2012 | Zheng et al. |
| 2012/0280432 A1 | 11/2012 | Chen et al. |
| 2012/0290075 A1 | 11/2012 | Mortisen et al. |
| 2012/0323311 A1 | 12/2012 | McClain et al. |
| 2013/0006351 A1 | 1/2013 | Taylor et al. |
| 2013/0035754 A1 | 2/2013 | Shulze et al. |
| 2013/0087270 A1 | 4/2013 | Hossainy et al. |
| 2013/0172853 A1 | 7/2013 | McClain et al. |
| 2014/0343667 A1 | 11/2014 | McClain |
| 2014/0350522 A1 | 11/2014 | McClain et al. |
| 2014/0371717 A1 | 12/2014 | McClain et al. |
| 2015/0024116 A1 | 1/2015 | Matson et al. |
| 2015/0025620 A1 | 1/2015 | Taylor et al. |
| 2015/0250926 A1 | 9/2015 | McClain et al. |
| 2016/0095726 A1 | 4/2016 | McClain et al. |

FOREIGN PATENT DOCUMENTS

| | | |
|---|---|---|
| CA | 2615452 A1 | 1/2007 |
| CA | 2650590 A1 | 11/2007 |
| CA | 2679712 A1 | 7/2008 |
| CA | 2684482 A1 | 10/2008 |
| CA | 2721832 A1 | 12/2009 |
| CN | 2423899 Y | 3/2001 |
| CN | 1465410 A | 1/2004 |
| CN | 1575860 A | 2/2005 |
| CN | 1649551 A | 8/2005 |
| CN | 1684641 A | 10/2005 |
| CN | 101161300 A | 4/2008 |
| CN | 102481195 A | 5/2012 |
| DE | 4336209 A1 | 3/1995 |
| DE | 29702671 U1 | 4/1997 |
| DE | 29716476 U1 | 12/1997 |
| DE | 19633901 A1 | 2/1998 |
| DE | 29716467 U1 | 2/1998 |
| DE | 19740506 A1 | 3/1998 |
| DE | 19754870 A1 | 8/1998 |
| DE | 19822157 A1 | 11/1999 |
| DE | 69611186 T2 | 5/2001 |
| EP | 0335341 | 10/1989 |
| EP | 0604022 A1 | 6/1994 |
| EP | 800801 A1 | 10/1997 |
| EP | 0876806 A1 | 11/1998 |
| EP | 0982041 A1 | 3/2000 |
| EP | 1195822 A2 | 4/2002 |
| EP | 1325758 A2 | 7/2003 |
| EP | 1327422 A1 | 7/2003 |
| EP | 1454677 A2 | 9/2004 |
| EP | 1502655 A2 | 2/2005 |
| EP | 1909973 A2 | 4/2008 |
| EP | 2197070 A1 | 6/2010 |
| EP | 2293357 A1 | 3/2011 |
| EP | 2293366 A1 | 3/2011 |
| FR | 2758253 A1 | 7/1998 |
| JP | 698902 | 4/1994 |
| JP | H06218063 A | 8/1994 |
| JP | H08206223 A | 8/1996 |
| JP | H0956807 A | 3/1997 |
| JP | H1029524 A | 2/1998 |
| JP | H10151207 A | 6/1998 |
| JP | H10314313 A | 12/1998 |
| JP | H1157018 A | 3/1999 |
| JP | 2000316981 A | 11/2000 |
| JP | 2001521503 A | 11/2001 |
| JP | 2002239013 A | 8/2002 |
| JP | 2003205037 A | 7/2003 |
| JP | 2003533286 A | 11/2003 |
| JP | 2003533492 A | 11/2003 |
| JP | 2003533493 A | 11/2003 |
| JP | 2004512059 A | 4/2004 |
| JP | 2004173770 A | 6/2004 |
| JP | 2004518458 A | 6/2004 |
| JP | 2004528060 A | 9/2004 |
| JP | 2004529674 A | 9/2004 |
| JP | 2005505318 | 2/2005 |
| JP | 2005168646 A | 6/2005 |
| JP | 2005519080 A | 6/2005 |
| JP | 2005523119 A | 8/2005 |
| JP | 2005523332 A | 8/2005 |
| JP | 2005296690 A | 10/2005 |
| JP | 2006506191 A | 2/2006 |
| JP | 2006512175 A | 4/2006 |
| JP | 2007502281 A | 2/2007 |
| JP | 2007215620 A | 8/2007 |
| JP | 2009501566 A | 1/2009 |
| JP | 2010052503 A | 3/2010 |
| JP | 2010515539 A | 5/2010 |
| JP | 2010516307 A | 5/2010 |
| JP | 2011517589 A | 6/2011 |
| JP | 2013153822 A | 8/2013 |
| KR | 1020040034064 | 4/2004 |
| KR | 10-1231197 B1 | 2/2013 |
| WO | 9409010 A1 | 4/1994 |
| WO | 9506487 A2 | 3/1995 |
| WO | 9616691 A1 | 6/1996 |
| WO | 9620698 A2 | 7/1996 |
| WO | 9632907 A1 | 10/1996 |
| WO | 9641807 A1 | 12/1996 |
| WO | 9745502 A1 | 12/1997 |
| WO | 9802441 A2 | 1/1998 |
| WO | 9908729 A1 | 2/1999 |
| WO | 9915530 A1 | 4/1999 |
| WO | 9917680 A1 | 4/1999 |
| WO | 99016388 A1 | 4/1999 |
| WO | 0006051 A1 | 2/2000 |
| WO | 0025702 A1 | 5/2000 |
| WO | 000322238 A1 | 6/2000 |
| WO | 0114387 A1 | 3/2001 |
| WO | 2001054662 | 8/2001 |
| WO | 0187345 A1 | 11/2001 |
| WO | 0187368 A1 | 11/2001 |
| WO | 0187372 A1 | 11/2001 |
| WO | 01087371 A2 | 11/2001 |
| WO | 0226281 A1 | 4/2002 |
| WO | 0240702 | 5/2002 |
| WO | 0243799 | 6/2002 |
| WO | 02055122 A1 | 7/2002 |
| WO | 02074194 A2 | 9/2002 |
| WO | 02090085 A1 | 11/2002 |
| WO | 02100456 A1 | 12/2002 |
| WO | 03039553 A1 | 5/2003 |
| WO | 03082368 A1 | 10/2003 |
| WO | 03090684 A2 | 11/2003 |
| WO | 03101624 A1 | 12/2003 |
| WO | 2004009145 A1 | 1/2004 |
| WO | 2004028406 A1 | 4/2004 |
| WO | 2004028589 A2 | 4/2004 |

(56) References Cited

FOREIGN PATENT DOCUMENTS

| | | |
|---|---|---|
| WO | 2004043506 A1 | 5/2004 |
| WO | 2004045450 A2 | 6/2004 |
| WO | 04098574 A1 | 11/2004 |
| WO | 2005018696 A1 | 3/2005 |
| WO | 05042623 A1 | 5/2005 |
| WO | 2005063319 A1 | 7/2005 |
| WO | 05069889 A2 | 8/2005 |
| WO | 2005117942 A2 | 12/2005 |
| WO | 2006014534 A2 | 2/2006 |
| WO | 2006052575 A2 | 5/2006 |
| WO | 2006063430 A1 | 6/2006 |
| WO | 2006065685 A2 | 6/2006 |
| WO | 06083796 A2 | 8/2006 |
| WO | 2006099276 A2 | 9/2006 |
| WO | 07002238 A2 | 1/2007 |
| WO | 2007011707 A2 | 1/2007 |
| WO | 2007011708 A2 | 1/2007 |
| WO | 2007017707 A2 | 1/2007 |
| WO | 2007017708 A3 | 1/2007 |
| WO | 07092179 A2 | 8/2007 |
| WO | 2007127363 A2 | 11/2007 |
| WO | 07143609 A2 | 12/2007 |
| WO | 2008024626 A2 | 2/2008 |
| WO | 08046641 A2 | 4/2008 |
| WO | 08046642 A2 | 4/2008 |
| WO | 2008042909 A2 | 4/2008 |
| WO | 08052000 A2 | 5/2008 |
| WO | 2008070996 A1 | 6/2008 |
| WO | 2008086369 A1 | 7/2008 |
| WO | 2008131131 A1 | 10/2008 |
| WO | 2008148013 A1 | 12/2008 |
| WO | 09039553 A1 | 4/2009 |
| WO | 09051614 A1 | 4/2009 |
| WO | 2009051614 A1 | 4/2009 |
| WO | 2009051780 A1 | 4/2009 |
| WO | 2009096822 A1 | 8/2009 |
| WO | 2009113605 A1 | 9/2009 |
| WO | 2009120361 A2 | 10/2009 |
| WO | 2009146209 A1 | 12/2009 |
| WO | 2010001932 A1 | 1/2010 |
| WO | 2010009335 A1 | 1/2010 |
| WO | 10075590 A2 | 7/2010 |
| WO | 2010111196 A2 | 9/2010 |
| WO | 2010111232 A2 | 9/2010 |
| WO | 2010111238 A2 | 9/2010 |
| WO | 2010120552 A2 | 10/2010 |
| WO | 2010121187 A2 | 10/2010 |
| WO | 10136604 A1 | 12/2010 |
| WO | 2010136604 A1 | 12/2010 |
| WO | 2011009096 A1 | 1/2011 |
| WO | 2011097103 A1 | 8/2011 |
| WO | 11119762 A1 | 9/2011 |
| WO | 2011119159 A1 | 9/2011 |
| WO | 11130448 A1 | 10/2011 |
| WO | 11133655 A1 | 10/2011 |
| WO | 2011140519 A2 | 11/2011 |
| WO | 12009684 A2 | 1/2012 |
| WO | 2012009684 A2 | 1/2012 |
| WO | WO2012/009684 A2 * | 1/2012 ............... A61K 9/70 |
| WO | 12034079 A2 | 3/2012 |
| WO | 2012082502 A1 | 6/2012 |
| WO | 12092504 A2 | 7/2012 |
| WO | 12142319 A1 | 10/2012 |
| WO | 12166819 A1 | 12/2012 |
| WO | 2013003644 A1 | 1/2013 |
| WO | 2013012689 A1 | 1/2013 |
| WO | 2013025535 A1 | 2/2013 |
| WO | 13059509 A1 | 4/2013 |
| WO | 13177211 A1 | 11/2013 |
| WO | 2013173657 A1 | 11/2013 |
| WO | 2014063111 A1 | 4/2014 |
| WO | 2014165264 A1 | 10/2014 |
| WO | 2014186532 A1 | 11/2014 |

OTHER PUBLICATIONS

Balss et al., "Quantitative spatial distribution of sirolumus and polymers in drugeluting stents using confocal Raman microscopy," J. of Biomedical Materials Research Part A, 258-270 (2007).
Belu el al., "Three-Dimensional Compositional Analysis of Drug Eluting Stent Coatings Using Cluster Secondary Ioan Mass Spectrometry," Anal. Chem. 80:624-632 (2008).
Belu, et al., "Chemical imaging of drug eluting coatings: Combining surface analysis and confocal Rama microscopy" J. Controlled Release 126: 111-121 (2008).
Boneff, "Topical Treatment of Chronic Prostatitis and Premature Ejaculation," International Urology and Nephrology 4(2):183-186 (1971).
Bookbinder et al., "A recombinant human enzyme for enhanced interstitial transport of therapeutics," Journal of Controlled Release 114:230-241 (2006).
Borchert et al., "Prevention and treatment of urinary tract infection with probiotics: Review and research perspective," Indian Journal Urol. 24(2): 139-144 (2008).
Brunstein et al., "Histamine, a vasoactive agent with vascular disrupting potential, improves tumour response by enhancing local drug delivery," British Journal of Cancer 95:1663-1669 (2006).
Bugay et al., "Raman Analysis of Pharmaceuticals," in "Applications of Vibrational Spectroscopy in Pharmaceutical Research and Development," Edited by Pivonka, D.E., Chalmers, J.M., Griffiths, P.R. (2007) Wiley and Sons.
Cadieux et al., Use of triclosan-eluting ureteral stents in patients with long-term stents, J. Endourol (Epub) (Jun. 19, 2009).
Chalmers, et al. (2007) Wiley and Sons.
Channon et al., "Nitric Oxide Synthase in Atherosclerosis and Vascular Injury: Insights from Experimental Gene Therapy," Arteriosclerosis, Thrombosis and Vascular Biology, 20(8):1873-1881 (2000).
Chen et al. Immobilization of heparin on a silicone surface through a heterobifunctional PEG spacer. Biomaterials. Dec. 2005;26(35):7418-24.
Chlopek et al., "The influence of carbon fibres on the resorption time and mechanical properties of the lactide-glycolide copolymer", J. Biomater. Sci. Polymer Edn. vol. 18, No. 11, pp. 1355-1368 (2007).
Clair and Burks, "Thermoplastic/Melt-Processable Polyimides," NASA Conf. Pub. #2334 (1984), pp. 337-355.
Cohen et al., "Sintering Technique for the Preparation of Polymer Matrices for the Controlled Release of Macromolecules", Journal of Pharmaceutical Sciences, vol. 73, No. 8, 1984, p. 1034-1037.
Colombo et al. "Selection of Coronary Stents," Journal of the American College of Cardiology, vol. 40, No. 6, 2002, p. 1021-1033.
CRC Handbook of chemistry and physics. 71st ed. David R. Lide, Editor-in-Chief. Boca Raton, FL, CRC Press; 1990; 6-140.
Cyrus et al., "Intramural delivery of rapamycin with alphavbeta3-targeted paramagnetic nanoparticles inhibits stenosis after balloon injury," Arterioscler Thromb Vasc Biol 2008; 28:820-826.
Derwent-ACC-No. 2004-108578 Abstracting 2004003077; Jan. 8, 2004; 3 pages.
Di Mario, C. et al., "Drug-Eluting Bioabsorbable Magnesium Stent," J. Interventional Cardiology 16(6):391-395 (2004).
Di Stasi et al., "Percutaneous sequential bacillus Calmette-Guerin and mitomycin C for panurothelial carcinomatosis," Can. J. Urol. 12(6):2895-2898 (2005).
Domb and Langer, "Polyanhydrides. I. Preparation of High Molecular Weight Polyanhydrides."J. Polym Sci. 25:3373-3386 (1987).
Domingo, C., et al., "Precipication of ultrafine organic crystals from the rapid expansion of supercritical solutions ove a capillary and a frit nozzle", J. Supercritical Fluids 10:39-55 (1997).
Dzik-Jurasz, "Molecular imaging in vivo: an introduction," The British Journal of Radiology, 76:S98-S109 (2003).
Electrostatic Process, Wiley Encyclopedia of Electrical and Electronics Engineering, John Wiley & Sons, Inc. 1999; 1:15-39.
Eltze et al., "Imidazoquinolinon, imidazopyridine, and isoquinolindione derivatives as novel and potent inhibitors of the poly (ADP-ribose)

(56) References Cited

OTHER PUBLICATIONS polymerase (PARP): a comparison with standard PARP inhibitors," Mol. Pharmacal 74(6)1587-1598(2008).

Ettmayer et al. Lessons learned from marketed and investigational prodrugs. J Med Chem. 2004 May 6;47(10):2393-404.

European International Search Report of PCT/EP01/05736 dated Oct. 24, 2001.

Fibbi et al., "Chronic inflammation in the pathogenesis of benign prostatic hyperplasia," Int J Androl. Jun. 1, 2010;33(3)475-88.

Finn et al. Differential Response of Delayed Healing . . . Circulation vol. 112 (2005) 270-8.

Fleischmann et al., "High Expression of Gastrin-Releasing Peptide Receptors in the Vascular bed of Urinary Tract Cancers: Promising Candidates for Vascular Targeting Applications." Jun. 2009, Endocr. Relat. Cancer 16(2):623-33.

Froehlich et al., "Conscious sedation for gastroscopy: patient tolerance and cardiorespiratory parameters," Gastroenterology 108(3):697-704 (1995).

Fujiwara et al., "Insulin-like growth factor 1 treatment via hydrogels rescues cochlear hair cells from ischemic injury," Oct. 29, 2008, NeuroReport 19(16):1585-1588.

Fulton et al. Thin Fluoropolymer films and nanoparticle coatings from the rapid expansion of supercritical carbon dioxide solutions with electrostatic collection, Polymer Communication. 2003; 2627-3632.

Greco et al. (Journal of Thermal Analysis and Calorimetry, vol. 72 (2003) 1167-1174.).

Green et al., "Simple conjugated polymer nanoparticles as biological labels," Proc Roy Soc A. published online Jun. 24, 2009 doi:10.1098/rspa.2009.0181.

Griebenow et al., "On Protein Denaturation in Aqueous-Organic Mixtures but not in Pure Organic Solvents," J. Am Chem Soc., vol. 118. No. 47, 11695-11700 (1996).

Hamilos et al., "Ditlerential etlects ofDmg-Eluting Stents on Local Endothelium-Dependent Coronary Vasomotion." JACC vol. 51, No. 22,2008, Endothelium and DES Jun. 3, 2008:2123-9.

Han, et al., "Studies of a Novel Human Thrombomodulin Immobilized Substrate: Surface Characterization and Anticoagulation Activity Evaluation." J. Biomater. Sci. Polymer Edn, 2001, 12 (10), 1075-1089.

Hartmann et al., "Tubo-ovarian abscess in virginal adolescents: exposure or the underlying etiology," J. Pediatr Adolesc Gynecol, 22(3):313-16 (2009).

Hasegawa et al., "Nylong 6/Na-montmorillonite nanocomposites prepared by compounding Nylon 6 with Na-montmorillonite slurry," Polymer 44 (2003) 2933-2937.

Higuchi, Rate of Release of Medicaments from Ointment Bases Containing Drugs in Suspension, Journal of Pharmaceutical Sciences, vol. 50, No. 10, p. 874, Oct. 1961.

Hinds, WC. Aerosol Technology, Properties, Behavior and Measurement of Airborne Particles, Department of Environmental Health Sciences, Harvard University School of Public Health, Boston, Massachusetts. 1982; 283-314.

Hladik et al., "Can a topical microbicide prevent rectal HIV transmission?" PLoS Med. 5(8):e167 (2008).

Iconomidou et al., "Secondary Structure of Chorion Proteins of the Teleosatan Fish Dentex dentex by ATR FR-IR and FT-Raman Spectroscopy," J. of Structural Biology, 132, 112-122(2000).

Jackson et al., "Characterization of perivascular poly(lactic-co-glycolic acid) films containing paclitaxel" Int. J. ofPhannaceutics, 283:97-109 (2004), incorporated in its entirety herein by reference.

Jensen et al., Neointimal hyperplasia after sirollmus-eluting and paclitaxel-eluting stend implantation in diabetic patients: the randomized diabetes and dmg eluting stent (DiabeDES) intravascular ultrasound trial. European heartjoumal (29), pp. 2733-2741 Oct. 2, 2008. Retrieved from the Internet. Retrieved on [ Jul. 17, 2012]. URL: <http :/ /eurheartj .oxfordjournals.org/ content/2 9/22/2 73 3. full. pdf> entire document.

Jewell, et al., "Release ofPlasmid DNA from Intravascular Stents Coated with Ultrathin Multilayered Polyelectrolyte Films" Biomacromolecules. 7: 2483-2491 (2006).

Ji, et al., "96-Wellliquid-liquid extraction liquid chromatographytandem mass spectrometry method for the quantitative determination of ABT-578 in human blood samples" Journal of Chromatography B. 805:67-75 (2004).

Johns, H.E., J.R.Cunningham, Thomas, Charles C., Publisher, "The Physics of Radiology,"1983, Springfield, IL, pp. 133-143.

Joner et al. "Site-specific targeting of nanoparticle prednisolone reduces in-stent restenosis in a rabbit model of established atheroma," Arterioscler Thromb Vase Biol.2008 ;28: 1960-1966.

Jovanovic et al. "Stabilization of Proteins in Dry Powder Formulations Using Supercritical Fluid Technology," Pharm. Res. 2004; 21(11).

Kazemi et al., "The effect ofbetamethasone gel in reducing sore throat, cough, and hoarseness after laryngo-tracheal intubation," Middle East J. Anesthesiol. 19(1):197-204 (2007).

Kehinde et al., "Bacteriology of urinary tract infection associated with indwelling J ureteral stents," J. Endourol. 18(9):891-896 (2004).

Kelly et al., "Double-balloon trapping technique for embolization of a large widenecked superior cerebellar artery aneurysm: case report," Neurosurgery 63(4 Suppl 2):291-292 (2008).

Khan et al., "Chemistry and the new uses or Sucrose: How Important?" Pur and Appl. Chem (1984) 56:833-844.

Khan et al., "Enzymic Regioselective Hydrolysis of Peracctylated Reducing Disaccharides, Specifically at the Anomeric Centre: Intermediates for the Synthesis of Oligosaccharides." Tetrahedron Letters (1933) 34:7767.

Khan et al., Cyclic Acetals of 4,1',6'-Trichloro-4,1,6',-Trideoxy-Trideoxy-galacto-Sucrose and their Conversion into Methyl Ether Derivatives. Carb. ResCarb. Res. (1990) 198:275-283.

Khayankarn et al., "Adhesion and Permeability of Polyimide-Clay Nanocomposite Films for Protective Coatings," Journal of Applied Polymer Science, vol. 89,2875-2881 (2003).

Koh et al., "A novel nanostructured poly(lactic-co-glycolic-acid) multi-walled carbon nanotube composite for blood-contacting application. Thrombogenicity studies", Acta Biomaterials 5 (2009): 3411-3422.

Kurt et al., "Tandem oral, rectal and nasal administrations of Ankaferd Blood Stopper to control profuse bleeding leading to hemodynamic instability," Am J. Emerg. Med. 27(5):631, e1-2 (2009).

Labhasetwar et al., "Arterial uptake of biodegradable nanoparticles: effect of surface modifications," Journal of Pharmaceutical Sciences, vol. 87, No. 10, Oct. 1998; 1229-1234.

Lamm et al., "Bladder Cancer: Current Optimal Intravesical Treatment: Pharmacologic Treatment," Urologic Nursing 25 (5):323-6, 331-2 (Oct. 26, 2005).

Latella et al., "Nanoindentation hardness. Young's modulus, and creep behavior of organic-inorganic silica-based sol-gel thin films on copper," J Mater Res 23(9): 2357-2365 (2008).

Lawrance et al., "Rectal tacrolimus in the treatment of resistant ulcerative proctitis,"Aliment. Pharmacol Ther. 28(10):1214-20 (2008).

Lee et al., "Novel therapy for hearing loss: delivery of insulin-like growth factor 1 to the cochlea using gelatin hydrogel,"Otol. Neurotol. 28(7):976-81 (2007).

Lehmann et al, "Drug treatment of nonviral sexually transmitted diseases: specific issues in adolescents," Paediatr Drugs 3(7):481-494 (2001).

Levit, et al., "Supercritical C02 Assisted Electrospinning" J. of Supercritical Fluids, 329-333, vol. 31, Issue 3, (Nov. 2004).

Lewis, D. H., "Controlled Release of Bioactive Agents from Lactides/ Glycolide Polymers" in Biodegradable Polymers as Drug Delivery Systems, Chasin, M. and Langer, R., eds., Marcel Decker (1990).

Luzzi, L.A., J. Phann. Psy. 59:1367 (1970).

Mahoney et al., "Three-Dimensional Compositional Analysis ofDmg Eluting Stent Coatings Using Cluster Secondary Ion mass Spectrometry," Anal. Chem. , 80, 624-632 (2008).

Matsumoto, D, et al. Neointimal Coverage of Sirolimus-Eluting Stents at 6-month Follow-up: Evaluated by Optical Coherence Tomography, European Heart Journal, Nov. 29, 2006; 28:961-967.

(56) References Cited

OTHER PUBLICATIONS

McAlpine, J.B. et al., "Revised NMR Assignments for Rapamycine," J. Antibiotics 44:688-690 (1991).
Mehik et al., "Alfuzosin treatment for chronic prostatitis/chronic pelvic pain syndrome: a prospecitve, randomized, double-blind, placebo-controlled, pilot study," Urology 62(3):425-429 (2003).
Mei et al., "Local Delivery of Modified Paclitaxel-Loaded Poly(£-caprolactone)/Pluronic F68 Nanoparticles for Long-Term Inhibition of Hyperplasia," Journal of Pharmaceutical Sciences, Vol. 98, No. 6, Jun. 2009.
Melonakos et al., Treatment of low-grade bulbar transitional cell carcinoma with urethral instillation ormitmnycin C, Oct. 28, 2008, Adv. Urol., 173694 Epub.
Merrett et al., "Interaction of corneal cells with transforming growth factor beta2-modified poly dimethyl siloxane surfaces," Journal of Biomedical Materials Research, Part A, vol. 67A, No. 3, pp. 981-993 (2003).
Merriam-Webster Online Dictionary, obtained online at: <http://www.merriamwebster.com/dictionay/derivative>, downloaded Jan. 23, 2013.
Middleton and Tipton, Synthetic biodegradable polymers as orthopedic devises. Biomaterials 2000; 21:2335-46.
Minchin, "Nanomedicine: sizing up targets with nanoparticles," Nature Nanotechnology, vol. 33, Jan. 12-13, 2008.
Minoque et al., "Laryngotracheal topicalization with lidocaine before intubation decreases the incidence of coughing on emergence from general anesthesia," Anesth. Analg. 99(4):1253-1257 (2004).
Mishima et al. "Microencapsulation of Proteins by Rapid Expansion orSupercritical Solution with a Nonsolvent," AIChE J. 2000;46(4):857-65.
Mocco et al., "Pharos neurovascular intracranail stent: Elective use for a symptomatic stenosis refractory to medical herapy," Catheter Cardiovasc. Interv. (epub) (Mar. 2009).
Mollen et al., "Prevalence oftubo-ovarian abcess in adolescents diagnosed with pelvice inflammatory disease in a pediatric emergency department," Pediatr. Emerg. Care, 22(9): 621-625 (2006).
Moroni et al., "Post-ischemic brain damage:targeting PARP-1 within the ischemic neurovaschular units as a realistic avenue to stroke treatment," FEBS J. 276(1 ):36-45 (2009).
Muhlen et al., "Magnetic Resonance Imaging Contrast Agent Targeted Toward Activated Platelets Allows in Vivo Detection of Thrombosis and Monitoring of Thrombolysis Circulation," 118:258-267 (2008).
Murphy et al., "Chronic prostatitis: management strategies," Drugs 69(1): 71-84 (2009).
O'Donnell et al., "Salvage intravesical therapy with interferon-alpha 2b plus low dose bacillus Calmette-Guerin is effective in patients with superficial bladder cancer in whom bacillus calmette-guerin alone previously failed," Journ. Urology, 166(4): 1300-1304 (2001).
O'Neil et al., "Extracellular matrix binding mixed micelles for drug delivery applications," Journal of Controlled Release 137 (2009) 146-151.
Olbert et al., "In vitro and in vivo effects of CpG-Oligodeoxynucleotides (CpG-ODN) on murine transitional cell carcinoma and on the native murine urinary bladder wall," Anticancer Res. 29(6):2067-2076 (2009).
Ong and Serruys, "Technology Insight: an overview of research in drug-eluting stents," Nat. Clin. Parct. Cardiovas. Med. 2(12):647 (2005).
Park et al., Pharm. Res. (1987) 4(6):457-464.
PCT/EP01/05736 International Preliminary Examination Report dated Jan. 14, 2002.
Wang et al., "Treatment with melagatran alone or in combination with thrombolytic therapy reduced ischemic brain injury," Exp. Neuro. 213(1):171-175 (2008).
Wang, X.; Venkatraman, S.S.; Boey, F.Y.C.; Loo, J.S.C.; Tan, L.P. "Controlled release of sirolimus from a multilayered PLGA stent matrix" Biomaterials 2006, 27, 5588-5595.

Warner et al., "Mitomycin C and airway surgery: how well does it work?" Ontolaryngol Head Neck Surg. 138(6):700-709 (2008).
Wermuth, CG, "Similarity in drugs: reflections on analogue design", Drug Discov Today. Apr. 2006.11(7-8):348-54.
Wu et al., "Study on the preparation and characterization of biodegradable polylactide/multi-walled carbon nanotubes nanocomposites", Polymer 48 (2007) 4449-4458.
Xu et al., "Biodegradation of poly(L-lactide-co-glycolide) tube stents in bile", Polymer Degradation and Stability. 93:811-817 (2008).
Xue et al., "Spray-as-you-go airway topical anesthesia in patients with a difficult airway: a randomized, double-blind comparison of2% and 4% lidocaine," Anesth. blind comparison of 2% and 4% lidocaine, Anesth. Analg. 108(2): 536-543 (2009).
Yepes et al., "Tissue-type plasminogen activator in the ischemic brain: more than a thrombolytic," Trends Neurosci. 32(1):48-55 (2009).
Yousuf et al., "Resveratrol exerts its neuroprotective effect by modulating mitochondrial dysfunction and associated cell death during cerebral ischemia", Brain Res. 1250:242-253 (2009).
Zhou, S ; Deng, X.; Li, X ; Jia, W ; Liu, L. "Synthesis and Characterization of Biodegradable Low Molecular Weight Aliphatic Polyesters and Their Use in Protein-Delivery Systems" J. Appl. Polym. Sci. 2004, 91, 1848-1856.
Zilberman et al., Drug-Eluting bioresorbable steuts for various applications, Annu Rev Biomed Eng,., 2006;8:158-180.
PCT/EP2000/004658 International Search Report from dated Sep. 15, 2000.
PCT/US06/24221 International Preliminary Report on Patentability dated Dec. 24, 2007.
PCT/US06/24221 International Search Report dated Jan. 29, 2007.
PCT/US06/27321 International Preliminary Report on Patentability dated Jan. 16, 2008.
PCT/US06/27321 International Search Report dated Oct. 16, 2007.
PCT/US06/27321 Written Opinion dated Oct. 16, 2007.
PCT/US06/27322 International Preliminary Report on Patentability dated Jan. 16, 2008.
PCT/US06/27322 International Search Report dated Apr. 25, 2007.
PCT/US07/10227 International Preliminary Report on Patentability dated Oct. 28, 2008.
PCT/US07/10227 International Search Report dated Aug. 8, 2008.
PCT/US07/80213 International Preliminary Report on Patentability dated Apr. 7, 2009.
PCT/US07/80213 International Search Report dated Apr. 16, 2008.
PCT/US07/82275 International Search Report dated Apr. 18, 2008.
PCT/US07/82775 International Preliminary Report on Patentablity dated May 5, 2009.
PCT/US08/11852 International Preliminary Report on Patentability dated Apr. 20, 2010.
PCT/US08/11852 International Search Report dated Dec. 19, 2008.
PCT/US08/50536 International Preliminary Report on Patentability dated Jul. 14, 2009.
PCT/US08/50536 International Search Report dated Jun. 2, 2008.
PCT/US08/60671 International Preliminary Report on Patentability dated Oct. 20, 2009.
PCT/US08/60671 International Search Report dated Sep. 5, 2008.
PCT/US08/64732 International Preliminary Report on Patentability dated Dec. 1, 2009.
PCT/US08/64732 International Search Report dated Sep. 4, 2008.
PCT/US09/41045 International Preliminary Report on Patentability dated Oct. 19, 2010.
PCT/US09/41045 International Search Report dated Aug. 11, 2009.
PCT/US09/50883 International Preliminary Report on Patentability dated Jan. 18, 2011.
PCT/US09/50883 International Search Report dated Nov. 17, 2009.
PCT/US09/69603 International Preliminary Report on Patentability dated Jun. 29, 2011.
PCT/US09/69603 International Search Report dated Nov. 5, 2010.
PCT/US10/28195 International Preliminary Report on Patentability dated Sep. 27, 2011.
PCT/US10/28195 Search Report and Written Opinion dated Jan. 21, 2011.

(56) References Cited

OTHER PUBLICATIONS

PCT/US10/28253 International Preliminary Report on Patentability dated Sep. 27, 2011.
PCT/US10/28253 Search Report and Written Opinion dated Dec. 6, 2010.
PCT/US10/28265 International Report on Patentability dated Sep. 27, 2011.
PCT/US10/28265 Search Report and Written Opinion dated Dec. 13, 2010.
PCT/US10/29494 International Preliminary Report on Patentability dated Oct. 4, 2011.
PCT/US10/29494 Search Report and Written Opinion dated Feb. 7, 2011.
PCT/US10/31470 International Preliminary Report on Patentability dated Oct. 18, 2011.
PCT/US10/31470 Search Report and Written Opinion dated Jan. 28, 2011.
PCT/US10/42355 International Preliminary Report on Patentability dated Jan. 17, 2012.
PCT/US10/42355 Search Report dated Sep. 2, 2010.
PCT/US11/22623 International Preliminary Report on Patentability dated Aug. 7, 2012.
PCT/US11/22623 Search Report and Written Opinion dated Mar. 28, 2011.
PCT/US11/29667 International Search Report and Written Opinion dated Jun. 1, 2011.
PCT/US11/32371 International Report on Patentability dated Oct. 16, 2012.
PCT/US11/32371 International Search Report dated Jul. 7, 2011.
PCT/US11/33225 International Search Report and Written Opinion dated Jul. 7, 2011.
PCT/US11/44263 International Preliminary Report on Patentability dated Jan. 22, 2013.
PCT/US11/44263 International Search Report and Written Opinion dated Feb. 9, 2012.
PCT/US11/51092 International Preliminary Report on Patentability dated Mar. 12, 2013.
PCT/US11/51092 International Search Report dated Mar. 27, 2012.
PCT/US11/51092 Written Opinion dated Mar. 27, 2012.
PCT/US11/67921 International Preliminary Report on Patentability dated Jul. 2, 2013.
PCT/US11/67921 Search Report and Written Opinion dated Jun. 22, 2012.
PCT/US12/33367 International Preliminary Report on Patentability dated Oct. 15, 2013.
PCT/US12/33367 International Search Report dated Aug. 1, 2012.
PCT/US12/40040 International Search Report dated Sep. 7, 2012.
PCT/US12/46545 International Search Report dated Nov. 20, 2012.
PCT/US12/50408 International Search Report dated Oct. 16, 2012.
PCT/US12/60896 International Search Report and Written Opinion dated Dec. 28, 2012.
PCT/US13/41466 International Preliminary Report on Patentability dated Nov. 18, 2014.
PCT/US13/41466 International Search Report and Written Opinion dated Oct. 17, 2013.
PCT/US13/42093 International Preliminary Report on Patentability dated Nov. 25, 2014.
PCT/US13/42093 International Search Report and Written Opinion dated Oct. 24, 2013.
PCT/US13/65777 International Search Report and Written Opinion dated Jan. 29, 2014.
PCT/US14/25017 International Search Report and Written Opinion dated Jul. 7, 2014.
PCT/US14/38117 International Search Report and Written Opinion dated Oct. 7, 2014.
Perry et al., Chemical Engineer's Handbook, 5th Edition, McGraw-Hill, New York, 1973; 20-106.
Plas et al., "Tubers and tumors: rapamycin therapy for benign and malignant tumors", Curr Opin Cell Bio 21:230-236, (2009).
Poling et al., The Properties of Gases and Liquids. McGraw-Hill. 2001; 9:1-9.97.
Pontari, "Chronic prostatitislchronic pelvic pain syndrome in elderly men: toward better understanding and treatment," Drugs Aging 20(15): 1111-1115 (2003).
Pontari, "Inflammation and anti-inflammatory therapy in chronic prostatits," Urology 60(6Suppl):29-33 (2002).
Putkisto, K et al. "Polymer Coating of Paper Using Dry Surface Treatment-Coating Structure and Performance", ePlace newsletter, Apr. 12, 2004, vol. 1, No. 8, pp. 1-20.
Ranade et al., "Physical characterization of controlled release of paclitaxel from the TAXUS Express2 drug-eluting stent," J. Biomed Mater. Res. 71 (4):625 -634 (2004).
Ranganath et al., "Hydrogel matrix entrapping PLGA-paclitaxel microspheres: drug delivery with near zero-order release and implantability advantages for malignant brain tumour chemotherapy," Pharm Res (Epub) Jun. 20, 2009).
Reddy et al., "Inhibition of apoptosis through localized delivery of rapamycin-loaded nanoparticles prevented heointimal hyperplasia and reendothelialized injured artery," Circ Cardiovasc Intery 2008;1 ;209-216.
Ristikankare et al., "Sedation, topical phamygeal anesthesia and cardiorespiratory safety during gastroscopy," J. Clin Gastorenterol. 40(1 ):899-905 (2006).
Sahajanand Medical Technologies (Supralimus Core; Jul. 6, 2008).
Salo et al., "Biofilm formation by *Escherichia coli* isolated from patients with urinary tract infections," Clin Nephrol. 71(5):501-507 (2009).
Saxena et al., "Haemodialysis catheter-related bloodstream infections: current treatment options and strategies for prevention," Swiss Med Wkly 135:127-138 (2005).
Schetsky, L McDonald, "Shape Memory Alloys", Encyclopedia of Chemical Technology (3d Ed), John Wiley & Sons 1982, vol. 20 pp. 726-736.
Scheufler et al., "Crystal Structure of Human Bone Morphogenetic Protein-2 at 2.7 Angstrom resolution," Journal of Molecular Biology, vol. 287, Issue 1, Mar. 1999, pp. 103-115, [retrieved online] at http://www.sciencedirect.comIscience/article/pii/S002283 699925901.
Schmidt et al., "A Comparison of the Mechanical Performance Characteristics of Seven Drug-Eluting Stent Systems," Catheterization and Cardiovascular Interventions 73:350-360 (2009).
Schmidt et al., "In vitro measurement of quality parameters of stent-catheter systems," Biomed Techn 50(SI):1505-1506 (2005).
Schmidt et al., "New aspects of in vitro testing of arterial stents based on the new European standard," EN 14299, [online] (2009), [retrieved on Mar. 10, 2001] <http://www.libOev .de/pl/pdf/EN14 299. pdf> (2009).
Schmidt et al., "Trackability, Crossability, and Pushability of Coronary Stent Systems—An Experimental Approach," Biomed Techn 47 (2002), Erg. 1, S. 124-126.
Schreiber, S.L. et al., "Atomic Structure of the Rapamycin Human Immunophilin FKBP-12 Complex," J. Am. Chem. Soc. 113:7433-7435 (1991).
Sen et al., "Topical heparin: A promising agent for the prevention of tracheal stenosis in airway surgery," J. Surg. Res (Epub ahead of print) Feb. 21, 2009.
Serruys, Patrick et al., Comparison of Coronary-Artery Bypass Surgery and Stenting for the Treatment of Multivessel Disease, N. Engl. J. Med., 2001, vol. 344, No. 15, pp. 1117-1124.
Shekunov et al., "Crystallization Processes in Pharmaceutical Technology and Drup Delivery Design", Journal of Crystal Growth 211 (2000), pp. 122-136.
Smith et al., "Mitomycin C and the endoscopic treatment of laryngotracheal stenosis: Are two applications better than one?" Laryngoscope 119(2):272-283 (2009).
Sumathi et al., "Controlled comparison between betamethasone gel and lidocaine jelly applied over tracheal tube to reduce postoperative sore throat, cough, and hoarseness of voice," Br. J. Anaesth. 100(2):215-218 (2008).
Szabadits et al., "Flexibility and trackability of laser cut coronary stent systems," Acta of Bioengineering and Biomechanics 11 (3 ): 11-18 (2009).

(56) References Cited

OTHER PUBLICATIONS

Testa, B., "Prodrug research: futile or fertile?", Biochem. Pharmacal. Dec. 1, 2004;68(11):2097-2106.

Thalmann et al., "Long-term experience with bacillus Calmette-Guerin therapy of upper urinary tract transitional cell carcinoma in patients not eligible for surgery," J Urol. 168(4 Pt 1):1381-1385 (2002).

Torchlin, "Micellar Nanocarriers: Pharmaecutial Perspectives," Pharmaceutical Research, vol. 24, No. 1, Jan. 2007.

Unger et al., "Poly(ethylene carbonate): A thermoelastic and biodegradable biomaterial for drug eluting stent coatings?" Journal to Controlled Release, vol. 117, Issue 3, 312-321 (2007).

Verma et al., "Effect of surface properties on nanoparticle-cell interactions," Small 2010,6,No. 1, 12-21.

Wagenlehner et al., "A pollen extract (Cemilton) in patients with inflammatory chronic prostatitis/chronic pelvic pain syndrome: a multicentre, randomized, prospective, double-blind, placebo-controlled phase 3 study," Eur Urol 9 (Epub) (Jun. 3, 2009).

Wang et al. "Synthesis, characterization, biodegradation, and drug delivery application of biodegradable lactic/glycolic acid polymers: I. Synthesis and characterization" J. Biomater. Sci. Polymer Edn. 11(3):301-318 (2000).

David Grant, Crystallization Impact on the Nature and Properties of the Crystalline Product, 2003, SSCI, http://www.ssci-inc.com/Information/RecentPublications/ApplicationNotes/CrystallizationImpact/tabid/138/Default.aspx.

Extended European Search Report for Application No. 14797966.0 dated Dec. 19, 2016.

Search Report from Singapore Application No. 2013054127 dated Jul. 26, 2017, 5 pages.

Third Party Submission for Application No. JP2015-538086 dated Jun. 4, 2018.

\* cited by examiner

DRUG DELIVERY MEDICAL DEVICE

CROSS-REFERENCE OF RELATED APPLICATION

The present application is a national phase entry 35 U.S.C. § 371 of International Application No. PCT/US2013/065777 filed Oct. 18, 2013, and claims benefit of U.S. Provisional Application No. 61/715,768, filed Oct. 18, 2012; and relates to PCT Application No. PCT/US2012/060896 filed Oct. 18, 2012, U.S. Provisional Application No. 61/548,650 filed Oct. 18, 2011, U.S. Provisional Application No. 61/581,544 filed Dec. 29, 2011, and PCT Application No. PCT/US2012/046545 filed on Jul. 12, 2012 the contents of each of which are incorporated herein in their entirety.

BACKGROUND OF THE INVENTION

There is a need for medical device technology that can rapidly, efficiently, reproducibly and safely transfer a Drug Delivery Formulation from the surface of a percutaneous medical device (a coating) onto/into a specific site in the body.

SUMMARY OF THE INVENTION

Provided herein is a medical device comprising a balloon, and a coating on at least a portion of the balloon, wherein the coating comprises particles of a pharmaceutical agent, and wherein each particle of the pharmaceutical agent are at least partially encapsulated in a polymer material.

In one embodiment, at least 50% of the surface area of the pharmaceutical agent is encapsulated in the polymer material. In another embodiment, at least 75% of the surface area of the pharmaceutical agent is encapsulated in the polymer material. In another embodiment, at least 90% of the surface area of the pharmaceutical agent is encapsulated in the polymer material. In another embodiment, at least 95% of the surface area of the pharmaceutical agent is encapsulated in the polymer material.

In one embodiment, the polymer layer has an average thickness of from 2 microns to 20 microns. In another embodiment, the polymer layer has an average thickness of from 5 microns to 15 microns. In another embodiment, the polymer layer has an average thickness of about 10 microns.

In one embodiment, the pharmaceutical agent has a crystallinity of at least 5%. In another embodiment, the pharmaceutical agent has a crystallinity of at least 20%. In another embodiment, the pharmaceutical agent has a crystallinity of from 25% to 95%.

In one embodiment, an average particle size of the encapsulated pharmaceutical agent is from 5 nm to 150 nm. In a further refinement, an average particle size of the pharmaceutical agent is from 10 nm to 100 nm. In another embodiment, an average particle size of the encapsulated pharmaceutical agent is from 1 micron to 50 micron. In another embodiment, an average particle size of the encapsulated pharmaceutical agent is from 1 micron to 20 micron. In another embodiment, an average particle size of the encapsulated pharmaceutical agent is from 1 micron to 10 micron. In a refinement, an average particle size of the encapsulated pharmaceutical agent is from 1 micron to 5 micron.

In one embodiment, a weight ratio between the pharmaceutical agent and the polymer material is from 1:99 to 70:30. In another embodiment, a weight ratio between the pharmaceutical agent and the polymer material is from 25:75 to 40:60. In another embodiment, a weight ratio of the pharmaceutical agent and the polymer material is from 40:60 to 60:40.

In one embodiment, the pharmaceutical agent is at least partially encapsulated in the polymer layer by spray-drying a mixture of the pharmaceutical agent, the polymer, and a solvent. In a refinement, the mixture is a solution and the solvent is a polar aprotic solvent. In a further refinement, the polar aprotic solvent is selected from tetrahydrofuran, acetonitrile, and mixtures thereof. In another refinement, the mixture is a slurry and the solvent is water.

In one embodiment, the pharmaceutical agent is at least partially encapsulated in the polymer material by spraying and drying a solution of the bioabsorbable polymer on the particles of the pharmaceutical agent. In a refinement, the solution comprises the polymer and a polar aprotic solvent. In a further refinement, the polar aprotic solvent is selected from tetrahydrofuran, acetonitrile, and mixtures thereof.

In one embodiment, the pharmaceutical agent is at least partially encapsulated in the polymer material by adding particles of the polymer to the pharmaceutical agent in a tumbling vessel. In a refinement, the particles of the polymer have an average particle size of from 10 microns to 100 microns. In another refinement, the particles of the polymer are added at a rate of from 100 µg to 1000 µg per minute. In another refinement, the particles of the polymer are added at a rate of from 300 µg to 500 µg per minute.

In one embodiment, the pharmaceutical agent is at least partially encapsulated in the polymer layer by forming an emulsion-based mixture comprising the pharmaceutical agent and the polymer material, and separating the polymer-encapsulated pharmaceutical agent from the emulsion-based mixture. In a refinement, the polymer material is a mixture of PVA or PLGA. In further refinement, the PLGA has a weight ratio from about 40:60 to about 60:40 lactic acid: glycolic acid. In another refinement, the pharmaceutical agent is amorphous.

In a further refinement the pharmaceutical agent is at least partially encapsulated in the polymer material by forming an emulsion-based mixture comprising the pharmaceutical agent and the polymer material, evaporating a portion of the emulsion, and filtering the remaining emulsion. In a further refinement, the encapsulated pharmaceutical agent is resuspended and lyophilized. In another refinement, the emulsion-based mixture is formed by combining a first polymer solution, a second polymer solution, a third polymer solution, and a pharmaceutical agent solution. In a further refinement, the first and third polymer solutions comprise a first polymer and water. In a further refinement, the first polymer is PVA. In a further refinement, the first polymer solution has a polymer concentration of from about 1% to about 5%. In another refinement, the third polymer solution has a polymer concentration of from about 0.5% to about 2%. In another refinement the second polymer solution is comprised of a second polymer and an organic solvent. In a further refinement the second polymer is PLGA. In another refinement the organic solvent is dochloromethane. In another refinement the pharmaceutical agent solution comprises the pharmaceutical agent and a polar aprotic solvent. In a further refinement the aprotic solvent is dimethylsulfoxide. In another refinement, the emulsion is formed by mixing the pharmaceutical agent solution and the second polymer solution, adding the first polymer solution to that mixture, homogenizing the mixture, and adding the third polymer solution.

In another refinement the pharmaceutical agent is crystalline. In a further embodiment the pharmaceutical agent is at least partially encapsulated in the polymer material by forming an emulsion-based mixture comprising the pharmaceutical agent and at least one polymer and filtering the emulsion. In a further refinement the encapsulated pharmaceutical agent is resuspended and lyophilized. In another refinement the emulsion-based mixture is formed by combining a first polymer solution, a second polymer solution, a third polymer solution, and the crystalline pharmaceutical agent. In a further refinement the first polymer solution comprises a first polymer and an organic solvent. In a further refinement the first polymer solution is combined with the second polymer solution and the organic solvent is allowed to evaporate. In a further refinement, the first polymer is PLGA. In another refinement the organic solvent is dichloromethane. In another refinement, the second and third polymer solutions comprise a second polymer and water. In a further refinement the second polymer is PVA. In a further refinement the second polymer solution has a polymer concentration of from about 0.5% to about 2%. In another refinement, the third polymer solution has a polymer concentration of from about 1% to about 5%. In another refinement the emulsion is formed by mixing the first polymer solution and the secdon polymer solution to form an emulsion, mixing the pharmaceutical agent and the third polymer solution to form a suspension, and combining the emulsion and suspension.

In one embodiment, the pharmaceutical agent is a macrolide immunosuppressant. In a refinement, the macrolide immunosuppressant is rapamycin or a derivative, a prodrug, a hydrate, an ester, a salt, a polymorph, a derivative or an analog thereof. In another refinement, the macrolide immunosuppressant is selected from the group consisting of rapamycin, 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxyl)propyl-rapamycin 40-O-(6-Hydroxyl)hexyl-rapamycin 40-O-[2-(2-Hydroxyl)ethoxy]ethyl-rapamycin 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin 40-O-(2-Nicotinoyloxy)ethyl-rapamycin, 40-O-[2-(N-Morpholino)acetoxy]ethyl-rapamycin 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxyl)ethyl-rapamycin, 28-O-Methyl-rapamycin, 40-O-(2-Aminoethyl)-rapamycin, 40-O-(2-Acetaminoethyl)-rapamycin 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin. In another refinement, the pharmaceutical agent is rapamycin.

In one embodiment, the polymer material comprises a bioabsorbable polymer. In a refinement, the bioabsorbable polymer is selected from the group consisting of polylactides (PLA); poly(lactide-co-glycolide) (PLGA); polyanhydrides; polyorthoesters; poly(N-(2-hydroxypropyl) methacrylamide); poly(dl-lactide) (DLPLA); poly(l-lactide) (LPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); poly(glycolide-co-trimethylene carbonate-co-dioxanone) (PDO-PGA-TMC), polyarginine, polyvinyl alcohol (PVA), and mixtures or co-polymers thereof. In another refinement, the bioabsorbable polymer is PLGA, PVA, polyarginine, or mixtures thereof. In a further refinement, the bioabsorbable polymer is a mixture of PLGA and PVA.

In one embodiment, the polymer layer comprises PLGA. In a refinement, the polymer layer is made of PLGA. In another embodiment, the polymer layer comprises polyarginine. In a refinement, the polymer layer is made of polyarginine. In a refinement, the PLGA comprises about 50:50 lactic acid:glycolic acid. In another embodiment, the polymer layer comprises a durable polymer.

In one embodiment, the medical device further comprises a binding agent deposited on an exterior surface of the encapsulated particles of the pharmaceutical agent. In a refinement, a weight ratio between the binding agent and the polymer is from 1:99 to 25:75. In another refinement, a weight ratio between the binding agent and the polymer is from 1:99 to 10:90.

In one embodiment, the binding agent is deposited by spraying and drying a solution of the binging agent on the encapsulated particles of the pharmaceutical agent. In a refinement, the solution comprises the binding agent and water.

In one embodiment, the binding agent comprises at least one of: Polyarginine, Polyarginine 9-L-pArg, DEAE-Dextran (Diethylaminoethyl cellulose-Dextran), DMAB (Didodecyldimethylammonium bromide), PEI (Polyethyleneimine), TAB (Tetradodecylammonium bromide), and DMTAB (Dimethylditetradecylammonium bromide). In a refinement, the binding agent is Polyarginine. In a further refinement, the Polyarginine has an average molecular weight of about 70 kDa. In another refinement, the Polyarginine has an average molecular weight of 5-15 kDa.

In one embodiment, the encapsulated particles of the pharmaceutical agent are deposited on the balloon using an eSTAT coating process.

In one embodiment, the medical device releases at least 3% of the pharmaceutical agent upon inflation of the balloon. In another embodiment, the medical device releases at least 5% or at least 10% of the pharmaceutical agent upon inflation of the balloon. In another embodiment, the medical device releases at least about 2 ng/mg, at least about 3 ng/mg, at least about 5 ng/mg, at least about 10 ng/mg, at least about 20 ng/mg, at least about 30 ng/mg, or at least about 40 ng/mg of the pharmaceutical agent 72 hours after inflation of the balloon.

In one embodiment, the balloon is an invertable balloon having an abluminal side; wherein the coating is provided on the abluminal side of the invertable balloon. In a refinement, the balloon is inverted within a catheter. In a further refinement, the balloon is capable of being pushed out of the catheter using balloon inflation pressure or by moving the distal end of the balloon distally through the balloon, or a combination thereof. In another refinement, the invertible balloon is inverted on an outside of a catheter. In a further refinement, a treatment length of the invertible balloon is controlled by partially un-inverting the invertible balloon on the outside of the catheter. In another further refinement, the medical device further comprises a sheath provided over the invertible balloon. In another further refinement, the sheath is retractable once the coated balloon reaches the treatment site, is positioned near the treatment site, is positioned at the treatment site, is proximal to the treatment site, is distal to the treatment site, or is within the treatment site.

In one embodiment, the medical device further comprises an occluder configured to block the flow of bodily fluids toward the balloon before the balloon is inflated. In a refinement, the occluder comprises a second balloon. In another refinement, the balloon comprises first and second sections, the first section comprising the occluder and the second section comprising the coating. In another refinement, the balloon comprises a distal node and a proximal node wherein the distal node comprises the coating and wherein the proximal node comprises the occluder, or wherein the proximal node comprises the coating and wherein the distal node comprises the occluder. In still another refinement, a distal portion of the balloon is coated and wherein a proximal portion of the balloon is not coated, and wherein the proximal portion of the balloon is the occlude, or wherein a proximal portion of the balloon is coated and wherein a distal portion of the balloon is not coated, and wherein the distal portion of the balloon is the occluder.

Also provided herein is a method of releasing a pharmaceutical agent at a target site, comprising providing a device comprising a balloon, and a coating on at least a portion of the balloon, wherein the coating comprises particles of a pharmaceutical agent, and wherein each particle of the pharmaceutical agent is at least partially encapsulated in a polymer material; positioning the device to allow the balloon to reach the target site; and inflating the balloon of the device, wherein at least some of the pharmaceutical agent is released to the target site upon inflating the balloon.

In one embodiment, the target site is a blood vessel, such as an artery.

INCORPORATION BY REFERENCE

All publications and patent applications mentioned in this specification are herein incorporated by reference to the same extent as if each individual publication or patent application was specifically and individually indicated to be incorporated by reference. This application relates to U.S. Provisional Application No. 61/081,691, filed Jul. 17, 2008, U.S. Provisional Application No. 61/226,239 filed Jul. 16, 2009, U.S. Provisional Application No. 61/212,964, filed Apr. 17, 2009, U.S. application Ser. No. 12/504,597, filed Jul. 16, 2009, U.S. application Ser. No. 12/729,580, filed Mar. 23, 2010, PCT Application No. PCT/US2009/050883, filed Jul. 16, 2009, PCT Application No. PCT/US2010/028253, filed Mar. 23, 2010, and PCT Application No. PCT/US2010/042355, filed Jul. 16, 2010. The contents of these applications are incorporated herein by reference in their entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
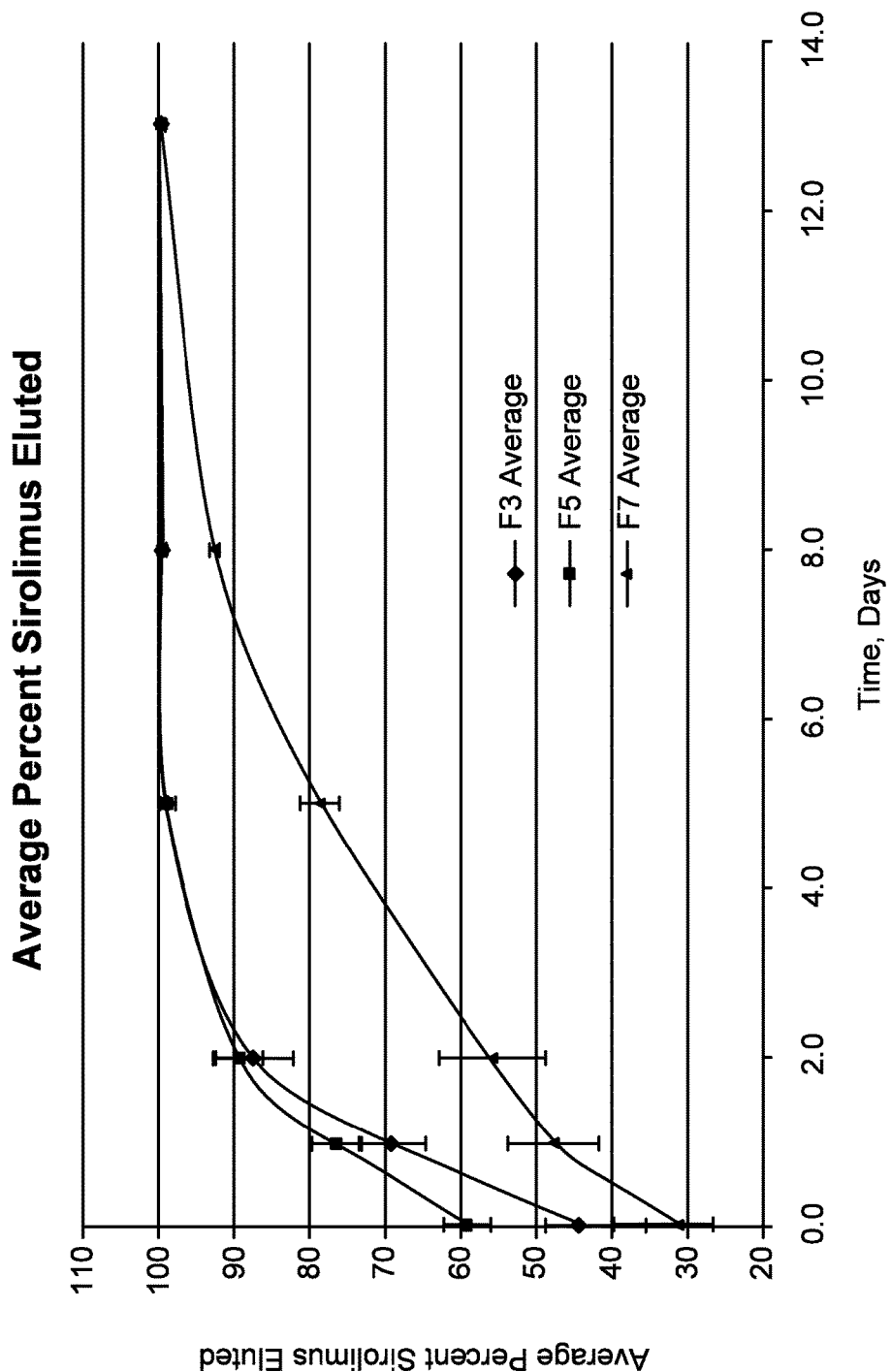
FIG. 1 indicates the Average percent Sirolimus Eluted from the balloons at various time points for Formulations F3, F5, and F7.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Definitions

As used in the present specification, the following words and phrases are generally intended to have the meanings as set forth below, except to the extent that the context in which they are used indicates otherwise.

"Substrate" as used herein, refers to any surface upon which it is desirable to deposit a coating. Biomedical implants are of particular interest for the present invention; however the present invention is not intended to be restricted to this class of substrates. Those of skill in the art will appreciate alternate substrates that could benefit from the coating process described herein, such as pharmaceutical tablet cores, as part of an assay apparatus or as components in a diagnostic kit (e.g. a test strip). Examples of substrates that can be coated using the methods of the invention include surgery devices or medical devices, e.g., a catheter, a balloon, a cutting balloon, a wire guide, a cannula, tooling, an orthopedic device, a structural implant, stent, stent-graft, graft, vena cava filter, a heart valve, cerebrospinal fluid shunts, pacemaker electrodes, axius coronary shunts, endocardial leads, an artificial heart, and the like.

"Biomedical implant" as used herein refers to any implant for insertion into the body of a human or animal subject, including but not limited to stents (e.g., coronary stents, vascular stents including peripheral stents and graft stents, urinary tract stents, urethral/prostatic stents, rectal stent, oesophageal stent, biliary stent, pancreatic stent), electrodes, catheters, leads, implantable pacemaker, cardioverter or defibrillator housings, joints, screws, rods, ophthalmic implants, femoral pins, bone plates, grafts, anastomotic devices, perivascular wraps, sutures, staples, shunts for hydrocephalus, dialysis grafts, colostomy bag attachment devices, ear drainage tubes, leads for pace makers and implantable cardioverters and defibrillators, vertebral disks, bone pins, suture anchors, hemostatic barriers, clamps, screws, plates, clips, vascular implants, tissue adhesives and sealants, tissue scaffolds, various types of dressings (e.g., wound dressings), bone substitutes, intraluminal devices, vascular supports, etc.

The implants may be formed from any suitable material, including but not limited to polymers (including stable or inert polymers, organic polymers, organic-inorganic copolymers, inorganic polymers, and biodegradable polymers), metals, metal alloys, inorganic materials such as silicon, and composites thereof, including layered structures with a core of one material and one or more coatings of a different material. Substrates made of a conducting material facilitate electrostatic capture. However, the invention contemplates the use of electrostatic capture, as described herein, in conjunction with substrate having low conductivity or which are non-conductive. To enhance electrostatic capture when a non-conductive substrate is employed, the substrate is processed for example while maintaining a strong electrical field in the vicinity of the substrate. In some embodiments, however, no electrostatic capture is employed in applying a coating to the substrate. In some embodiments of the methods and/or devices provided herein, the substrate is not charged in the coating process. In some embodiments of the methods and/or devices provided herein, an electrical potential is not created between the substrate and the coating apparatus.

Subjects into which biomedical implants of the invention may be applied or inserted include both human subjects (including male and female subjects and infant, juvenile, adolescent, adult and geriatric subjects) as well as animal subjects (including but not limited to pig, rabbit, mouse, dog, cat, horse, monkey, etc.) for veterinary purposes and/or medical research.

As used herein, a biological implant may include a medical device that is not permanently implanted. A biological implant in some embodiments may comprise a device which is used in a subject on a transient basis. For non-limiting example, the biomedical implant may be a balloon, which is used transiently to dilate a lumen and thereafter may be deflated and/or removed from the subject during the medical procedure or thereafter. In some embodiments, the biological implant may be temporarily implanted for a limited time, such as during a portion of a medical procedure, or for only a limited time (some time less than permanently implanted), or may be transiently implanted and/or momentarily placed in the subject. In some embodiments, the biological implant is not implanted at all, rather it is merely inserted into a subject during a medical procedure, and subsequently removed from the subject prior to or at the time the medical procedure is completed. In some embodiments, the biological implant is not permanently implanted since it completely resorbs into the subject (i.e. is completely resorbed by the subject). In a preferred embodiment the biomedical implant is an expandable balloon that can be expanded within a lumen (naturally occurring or non-naturally occurring) having a coating thereon that is freed (at least in part) from the balloon and left behind in the lumen when the balloon is removed from the lumen.

Examples of pharmaceutical agents employed in conjunction with the invention include, rapamycin, 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxyl)propyl-rapamycin 40-O-(6-Hydroxyl)hexyl-rapamycin 40-O-[2-(2-Hydroxyl)ethoxy]ethyl-rapamycin 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin 40-O-(2-Nicotinoyloxy)ethyl-rapamycin, 40-O-[2-(N-Morpholino)acetoxy]ethyl-rapamycin 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxyl)ethyl-rapamycin, 28-O-Methyl-rapamycin, 40-O-(2-Aminoethyl)-rapamycin, 40-O-(2-Acetaminoethyl)-rapamycin 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin (temsirolimus). The active agent in some embodiments of the devices, coatings and/or methods provided herein comprises a macrolide immunosuppressive drug. In some embodiments the macrolide immunosuppressive drug comprises one or more of rapamycin, 40-O-(2-Hydroxyethyl) rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin 40-O-(2-Hydroxy)ethoxycar-bonylmethyl-rapamycin, 40-O-(3-Hydroxyl)propyl-rapamycin 40-O-(6-Hydroxyl)hexyl-rapamycin 40-O-[2-(2-Hydroxyl)ethoxy]ethyl-rapamycin 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin 40-O-(2-Nicotinoyloxy)ethyl-rapamycin, 40-O-[2-(N-Morpholino)acetoxy]ethyl-rapamycin 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxyl)ethyl-rapamycin, 28-O-Methyl-rapamycin, 40-O-(2-Aminoethyl)-rapamycin, 40-O-(2-Acetaminoethyl)-rapamycin 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin (temsirolimus). The active agent may be selected from a macrolide immunosuppressive drug, a prodrug, a hydrate, an ester, a salt, a polymorph, a derivative, and an analog thereof. The active agent may be selected from sirolimus, a prodrug, a hydrate, an ester, a salt, a polymorph, a derivative, and an analog thereof.

The pharmaceutical agents may, if desired, also be used in the form of their pharmaceutically acceptable salts or derivatives (meaning salts which retain the biological effectiveness and properties of the compounds of this invention and which are not biologically or otherwise undesirable), and in the case of chiral active ingredients it is possible to employ both optically active isomers and racemates or mixtures of diastereoisomers. As well, the pharmaceutical agent may include at least one of: a prodrug, a hydrate, an ester, a salt, a polymorph, a derivative, and an analog thereof.

The pharmaceutical agent may be an antibiotic agent, as described herein.

In some embodiments of the methods, coatings, and/or devices provided herein, the size of the active agent in the coating is controlled. In some embodiments, the active agent is sirolimus and wherein the sirolimus has an average size (mean diameter) of at least one of: 1.5 µm, 2.5 µm, 645 nm, 100-200 nm, another controlled size, or a combination thereof. In some embodiments, the active agent is sirolimus and wherein the sirolimus has a median size of at least one of: 1.5 µm, 2.5 µm, 645 nm, 100-200 nm, another controlled size, or a combination thereof. In some embodiments, the active agent is sirolimus and wherein the sirolimus has an average size (mean diameter) of at least one of: about 1.5 µm, about 2.5 µm, about 645 nm, about 100-200 nm, another controlled size, or a combination thereof. In some embodiments, the active agent is sirolimus and wherein the sirolimus has a median size of at least one of: about 1.5 µm, about 2.5 µm, about 645 nm, about 100-200 nm, another controlled size, or a combination thereof. In some embodiments, the active agent is sirolimus and wherein sirolimus at least 75% of the sirolimus as is 1.5 µm, 2.5 µm, 645 nm, 100-200 nm, or another controlled size. In some embodiments, the active agent is sirolimus and wherein sirolimus at least 50% of the sirolimus as is 1.5 µm, 2.5 µm, 645 nm, 100-200 nm, or another controlled size. In some embodiments, the active agent is sirolimus and wherein sirolimus at least 90% of the sirolimus as is 1.5 µm, 2.5 µm, 645 nm, 100-200 nm, or another controlled size.

In some embodiments of the methods and/or devices provided herein, the macrolide immunosuppressive drug is at least 50% crystalline. In some embodiments, the macrolide immunosuppressive drug is at least 75% crystalline. In some embodiments, the macrolide immunosuppressive drug is at least 90% crystalline. In some embodiments of the methods and/or devices provided herein the macrolide immunosuppressive drug is at least 95% crystalline. In some embodiments of the methods and/or devices provided herein the macrolide immunosuppressive drug is at least 97% crystalline. In some embodiments of the methods and/or devices provided herein macrolide immunosuppressive drug is at least 98% crystalline. In some embodiments of the methods and/or devices provided herein the macrolide immunosuppressive drug is at least 99% crystalline.

In some embodiments of the methods and/or devices provided herein the pharmaceutical agent is at least 50% crystalline. In some embodiments of the methods and/or devices provided herein the pharmaceutical agent is at least 75% crystalline. In some embodiments of the methods and/or devices provided herein the pharmaceutical agent is at least 90% crystalline. In some embodiments of the methods and/or devices provided herein the pharmaceutical agent is at least 95% crystalline. In some embodiments of the methods and/or devices provided herein the pharmaceutical agent is at least 97% crystalline. In some embodiments of the methods and/or devices provided herein pharmaceutical agent is at least 98% crystalline. In some embodiments of the methods and/or devices provided herein the pharmaceutical agent is at least 99% crystalline.

"Prodrugs" are derivative compounds derivatized by the addition of a group that endows greater solubility to the compound desired to be delivered. Once in the body, the prodrug is typically acted upon by an enzyme, e.g., an esterase, amidase, or phosphatase, to generate the active compound.

An "anti-cancer agent", "anti-tumor agent" or "chemotherapeutic agent" refers to any agent useful in the treatment of a neoplastic condition. There are many chemotherapeutic agents available in commercial use, in clinical evaluation and in pre-clinical development that are useful in the devices and methods of the present invention for treatment of cancers.

"Stability" as used herein in refers to the stability of the drug in a coating deposited on a substrate in its final product form (e.g., stability of the drug in a coated stent). The term "stability" and/or "stable" in some embodiments is defined by 5% or less degradation of the drug in the final product form. The term stability in some embodiments is defined by 3% or less degradation of the drug in the final product form. The term stability in some embodiments is defined by 2% or less degradation of the drug in the final product form. The term stability in some embodiments is defined by 1% or less degradation of the drug in the final product form.

In some embodiments, the pharmaceutical agent is at least one of: 50% crystalline, 75% crystalline, 80% crystalline, 90% crystalline, 95% crystalline, 97% crystalline, and 99% crystalline following sterilization of the device. In some embodiments, the pharmaceutical agent crystallinity is stable wherein the crystallinity of the pharmaceutical agent following sterilization is compared to the crystallinity of the pharmaceutical agent at least one of: 1 week after sterilization, 2 weeks after sterilization, 4 weeks after sterilization, 1 month after sterilization, 2 months after sterilization, 45 days after sterilization, 60 days after sterilization, 90 days after sterilization, 3 months after sterilization, 4 months after sterilization, 6 months after sterilization, 9 months after sterilization, 12 months after sterilization, 18 months after sterilization, and 2 years after sterilization. In some embodiments, the pharmaceutical agent crystallinity is stable wherein the crystallinity of the pharmaceutical agent prior to sterilization is compared to the crystallinity of the pharmaceutical agent at least one of: 1 week after sterilization, 2 weeks after sterilization, 4 weeks after sterilization, 1 month after sterilization, 2 months after sterilization, 45 days after sterilization, 60 days after sterilization, 90 days after sterilization, 3 months after sterilization, 4 months after sterilization, 6 months after sterilization, 9 months after sterilization, 12 months after sterilization, 18 months after sterilization, and 2 years after sterilization. In such embodiments, different devices may be tested from the same manufacturing lot to determine stability of the pharmaceutical agent at the desired time points.

In some embodiments, the pharmaceutical agent crystallinity is stable at least one of: 1 week after sterilization, 2 weeks after sterilization, 4 weeks after sterilization, 1 month after sterilization, 2 months after sterilization, 45 days after sterilization, 60 days after sterilization, 90 days after sterilization, 3 months after sterilization, 4 months after sterilization, 6 months after sterilization, 9 months after sterilization, 12 months after sterilization, 18 months after sterilization, and 2 years after sterilization.

In some embodiments, the pharmaceutical agent crystallinity on the device tested at a time point after sterilization does not differ more than 1%, 2%, 3%, 4%, and/or 5% from the crystallinity tested on a second device manufactured from the same lot of devices and the same lot of pharmaceutical agent at testing time point before sterilization (i.e. the crystallinity drops no more than from 99 to 94% crystalline, for example, which is a 5% difference in crystallinity; the crystallinity drops no more than from 99 to 95% crystalline, which is a 4% difference in crystallinity; the crystallinity drops no more than from 99 to 96% crystalline, for example, which is a 3% difference in crystallinity; the crystallinity drops no more than from 99 to 97% crystalline, for example, which is a 2% difference in crystallinity; the crystallinity drops no more than from 99 to 98% crystalline, for example, which is a 1% difference in crystallinity; in other examples, the starting crystallinity percentage is one of 100%, 98%, 96%, 97%, 96%, 95%, 90%, 85%, 80%, 75%, 70%, 60%, 50%, 30%, 25%, and/or anything in between).

In some embodiments, crystallinity of the pharmaceutical agent on the device tested at a time point after sterilization does not differ more than 1%, 2%, 3%, 4%, and/or 5% from the crystallinity of pharmaceutical from the same lot of pharmaceutical agent tested at testing time point before sterilization of the pharmaceutical agent.

In some embodiments, crystallinity of the pharmaceutical agent does not drop more than 1%, 2%, 3%, 4%, and/or 5% between two testing time points after sterilization neither of which time point being greater than 2 years after sterilization. In some embodiments, crystallinity of the pharmaceutical agent does not drop more than 1%, 2%, 3%, 4%, and/or 5% between two testing time points after sterilization neither of which time point being greater than 5 years after sterilization. In some embodiments, two time points comprise two of: 1 week after sterilization, 2 weeks after sterilization, 4 weeks after sterilization, 1 month after sterilization, 2 months after sterilization, 45 days after sterilization, 60 days after sterilization, 90 days after sterilization, 3 months after sterilization, 4 months after sterilization, 6 months after sterilization, 9 months after sterilization, 12 months after sterilization, 18 months after sterilization, 2 years after sterilization, 3 years after sterilization, 4 years after sterilization, and 5 years after sterilization.

"Polymer" as used herein, refers to a series of repeating monomeric units that have been cross-linked or polymerized. Any suitable polymer can be used to carry out the present invention. It is possible that the polymers of the invention may also comprise two, three, four or more different polymers. In some embodiments of the invention only one polymer is used. In certain embodiments a combination of two polymers is used. Combinations of polymers can be in varying ratios, to provide coatings with differing properties. Polymers useful in the devices and methods of the present invention include, for example, stable or inert polymers, organic polymers, organic-inorganic copolymers, inorganic polymers, bioabsorbable, bioresorbable, resorbable, degradable, and biodegradable polymers. Those of skill in the art of polymer chemistry will be familiar with the different properties of polymeric compounds.

In some embodiments, the coating further comprises a polymer. In some embodiments, the active agent comprises a polymer. In some embodiments, the polymer comprises at least one of polyalkyl methacrylates, polyalkylene-co-vinyl acetates, polyalkylenes, polyurethanes, polyanhydrides, aliphatic polycarbonates, polyhydroxyalkanoates, silicone containing polymers, polyalkyl siloxanes, aliphatic polyesters, polyglycolides, polylactides, polylactide-co-glycolides, poly(e-caprolactone)s, polytetrahalooalkylenes, polystyrenes, poly(phosphasones), copolymers thereof, and combinations thereof.

In embodiments, the polymer is capable of becoming soft after implantation, for example, due to hydration, degradation or by a combination of hydration and degradation. In embodiments, the polymer is adapted to transfer, free, and/or dissociate from the substrate when at the intervention site due to hydrolysis of the polymer. In various embodiments, the device is coated with a bioabsorbable polymer that is capable of resorbtion in at least one of: about 1 day, about 3 days, about 5 days, about 7 days, about 14 days, about 3 weeks, about 4 weeks, about 45 days, about 60 days, about 90 days, about 180 days, about 6 months, about 9 months, about 1 year, about 1 to about 2 days, about 1 to about 5 days, about 1 to about 2 weeks, about 2 to about 4 weeks, about 45 to about 60 days, about 45 to about 90 days, about 30 to about 90 days, about 60 to about 90 days, about 90 to about 180 days, about 60 to about 180 days, about 180 to about 365 days, about 6 months to about 9 months, about 9 months to about 12 months, about 9 months to about 15 months, and about 1 year to about 2 years.

Examples of polymers that may be used in the present invention include, but are not limited to polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, aliphatic polyesters, polyurethanes, polystyrenes, copolymers, silicones, silicone containing polymers, polyalkyl siloxanes, polyorthoesters, polyanhydrides, copolymers of vinyl monomers, polycarbonates, polyethylenes, polypropytenes, polylactic acids, polylactides, polyglycolic acids, polyglycolides, polylactide-co-glycolides, polycaprolactones, poly(e-caprolactone)s, polyhydroxybutyrate valerates, polyacrylamides, polyethers, polyurethane dispersions, polyacrylates, acrylic latex dispersions, polyacrylic acid, polyalkyl methacrylates, polyalkylene-co-vinyl acetates, polyalkylenes, aliphatic polycarbonates polyhydroxyalkanoates, polytetrahalooalkylenes, poly(phosphasones), polytetrahalooalkylenes, poly(phosphasones), and mixtures, combinations, and copolymers thereof.

The polymers of the present invention may be natural or synthetic in origin, including gelatin, chitosan, dextrin, cyclodextrin, Poly(urethanes), Poly(siloxanes) or silicones, Poly(acrylates) such as [rho]oly(methyl methacrylate), poly(butyl methacrylate), and Poly(2-hydroxy ethyl methacrylate), Poly(vinyl alcohol)Poly(olefins) such as poly(ethylene), [rho]oly(isoprene), halogenated polymers such as Poly(tetrafluoroethylene)- and derivatives and copolymers such as those commonly sold as Teflon® products, Poly(vinylidine fluoride), Poly(vinyl acetate), Poly(vinyl pyrrolidone), Poly(acrylic acid), Polyacrylamide, Poly(ethylene-co-vinyl acetate), Poly(ethylene glycol), Poly(propylene glycol), Poly(methacrylic acid); etc.

Suitable polymers also include absorbable and/or resorbable polymers including the following, combinations, copolymers and derivatives of the following: Polylactides (PLA), Polyglycolides (PGA), PolyLactide-co-glycolides (PLGA), Polyanhydrides, Polyorthoesters, Poly(N-(2-hydroxypropyl) methacrylamide), Poly(l-aspartamide), including the derivatives DLPLA—poly(dl-lactide); LPLA—poly(l-lactide); PDO—poly(dioxanone); PGA-TMC—poly(glycolide-co-trimethylene carbonate); PGA-LPLA—poly(l-lactide-co-glycolide); PGA-DLPLA—poly(dl-lactide-co-glycolide); LPLA-DLPLA—poly(l-lactide-co-dl-lactide); and PDO-PGA-TMC—poly(glycolide-co-trimethylene carbonate-co-dioxanone), and combinations thereof.

In some embodiments of the devices, coatings and/or methods provided herein the polymer comprises PLGA. In some embodiments of the methods, coatings, or devices provided herein, the PLGA comprises about 50:50 Lactic acid:Glycolic acid. The PLGA may have at least one of: a MW of about 30 KDa and a Mn of about 15 KDa, a Mn of about 10 KDa to about 25 KDa, and a MW of about 15 KDa to about 40 KDa. In some embodiments of the methods, coatings, or devices provided herein, the PLGA comprises 50:50 Lactic acid:Glycolic acid. In some embodiments of the methods, coatings, or devices provided herein, the PLGA comprises from 40:60 to 60:40 Lactic acid:Glycolic acid. In some embodiments of the methods, coatings, or devices provided herein, the PLGA comprises from 45:55 to 55:45 Lactic acid:Glycolic acid. In some embodiments of the methods, coatings, or devices provided herein, the PLGA comprises from 48:52 to 52:48 Lactic acid:Glycolic acid. In some embodiments of the methods, coatings, or devices provided herein, the PLGA comprises from 49:51 to 51:49 Lactic acid:Glycolic acid. The use of the term "about" with regard to the ratio of Lactic acid to Glycolic acid in the PLGA, as used herein, refers to ranges of ratios from 40:60 to 60:40, or from 45:55 to 55:45, or from 48:52 to 52:48 or from 49:51 to 51:49, depending on the embodiment.

"Copolymer" as used herein refers to a polymer being composed of two or more different monomers. A copolymer may also and/or alternatively refer to random, block, graft, copolymers known to those of skill in the art.

"Biocompatible" as used herein, refers to any material that does not cause injury or death to the animal or induce an adverse reaction in an animal when placed in intimate contact with the animal's tissues. Adverse reactions include for example inflammation, infection, fibrotic tissue formation, cell death, or thrombosis. The terms "biocompatible" and "biocompatibility" when used herein are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, causes inflammation or irritation, or induces an immune reaction in the host. It is not necessary that any subject composition have a purity of 100% to be deemed biocompatible. Hence, a subject composition may comprise 99%, 98%, 97%, 96%, 95%, 90% 85%, 80%, 75% or even less of biocompatible agents, e.g., including polymers and other materials and excipients described herein, and still be biocompatible. "Non-biocompatible" as used herein, refers to any material that may cause injury or death to the animal or induce an adverse reaction in the animal when placed in intimate contact with the animal's tissues. Such adverse reactions are as noted above, for example.

The terms "bioabsorbable," "biodegradable," "bioerodible," "bioresorbable," and "resorbable" are art-recognized synonyms. These terms are used herein interchangeably. Bioabsorbable polymers typically differ from non-bioabsorbable polymers in that the former may be absorbed (e.g.; degraded) during use. In certain embodiments, such use involves in vivo use, such as in vivo therapy, and in other certain embodiments, such use involves in vitro use. In general, degradation attributable to biodegradability involves the degradation of a bioabsorbable polymer into its component subunits, or digestion, e.g., by a biochemical process, of the polymer into smaller, non-polymeric subunits. In certain embodiments, biodegradation may occur by enzymatic mediation, degradation in the presence of water (hydrolysis) and/or other chemical species in the body, or both. The bioabsorbability of a polymer may be indicated in-vitro as described herein or by methods known to one of skill in the art. An in-vitro test for bioabsorbability of a polymer does not require living cells or other biologic materials to indicate bioabsorption properties (e.g. degradation, digestion). Thus, resorbtion, resorption, absorption, absorbtion, erosion may also be used synonymously with the terms "bioabsorbable," "biodegradable," "bioerodible," and "bioresorbable." Mechanisms of degradation of a bioabsorbable polymer may include, but are not limited to, bulk degradation, surface erosion, and combinations thereof.

As used herein, the term "biodegradation" encompasses both general types of biodegradation. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of the implant, and the mode and location of administration. For example, the greater the molecular weight, the higher the degree of crystallinity, and/or the greater the biostability, the biodegradation of any bioabsorbable polymer is usually slower.

"Degradation" as used herein refers to the conversion or reduction of a chemical compound to one less complex, e.g., by splitting off one or more groups of atoms. Degradation of the coating may reduce the coating's cohesive and adhesive binding to the device, thereby facilitating transfer of the coating to the intervention site As used herein, the term "durable polymer" refers to a polymer that is not bioabsorbable (and/or is not bioerodable, and/or is not biodegradable, and/or is not bioresorbable) and is, thus biostable. In some embodiments, the device comprises a durable polymer. The polymer may include a cross-linked durable polymer. Example biocompatible durable polymers include, but are not limited to: polyester, aliphatic polyester, polyanhydride, polyethylene, polyorthoester, polyphosphazene, polyurethane, polycarbonate urethane, aliphatic polycarbonate, silicone, a silicone containing polymer, polyolefin, polyamide, polycaprolactam, polyamide, polyvinyl alcohol, acrylic polymer, acrylate, polystyrene, epoxy, polyethers, celluiosics, expanded polytetrafluoroethylene, phosphorylcholine, polyethyleneyerphthalate, polymethylmethavrylate, poly(ethylmethacrylate/n-butylmethacrylate), parylene C, polyethylene-co-vinyl acetate, polyalkyl methacrylates, polyalkylene-co-vinyl acetate, polyalkylene, polyalkyl siloxanes, polyhydroxyalkanoate, polyfluoroalkoxyphasphazine, poly(styrene-b-isobutylene-b-styrene), poly-butyl methacrylate, poly-bytadiene, and blends, combinations, homopolymers, condensation polymers, alternating, block, dendritic, cross-linked, and copolymers thereof. The polymer may include a thermoset material. The polymer may provide strength for the coated implanable medical device. The polymer may provide durability for the coated implanable medical device. The coatings and coating methods provided herein provide substantial protection from these by establishing a multi-layer coating which can be bioabsorbable or durable or a combination thereof, and which can both deliver active agents and provide elasticity and radial strength for the vessel in which it is delivered.

"Therapeutically desirable morphology" as used herein refers to the gross form and structure of the pharmaceutical agent, once deposited on the substrate, so as to provide for optimal conditions of ex vivo storage, in vivo preservation and/or in vivo release. Such optimal conditions may include, but are not limited to increased shelf life (i.e., shelf stability), increased in vivo stability, good biocompatibility, good bioavailability or modified release rates. Typically, for the present invention, the desired morphology of a pharmaceutical agent would be crystalline or semi-crystalline or amorphous, although this may vary widely depending on many factors including, but not limited to, the nature of the pharmaceutical agent, the disease to be treated/prevented, the intended storage conditions for the substrate prior to use or the location within the body of any biomedical implant. Preferably at least 10%, 20%, 30%, 40%, 50%, 60%, 70%, 80%, 90%, 95%, 97%, 98%, 99%, 99.5%, and/or 100% of the pharmaceutical agent is in crystalline or semi-crystalline form.

In some embodiments of the methods and/or devices provided herein, the macrolide immunosuppressive drug is at least 50% crystalline. In some embodiments, the macrolide immunosuppressive drug is at least 75% crystalline. In some embodiments, the macrolide immunosuppressive drug is at least 90% crystalline. In some embodiments of the methods and/or devices provided herein the macrolide immunosuppressive drug is at least 95% crystalline. In some embodiments of the methods and/or devices provided herein the macrolide immunosuppressive drug is at least 97% crystalline. In some embodiments of the methods and/or devices provided herein macrolide immunosuppressive drug is at least 98% crystalline. In some embodiments of the methods and/or devices provided herein the macrolide immunosuppressive drug is at least 99% crystalline.

In some embodiments of the methods and/or devices provided herein wherein the pharmaceutical agent is at least 50% crystalline. In some embodiments of the methods and/or devices provided herein the pharmaceutical agent is at least 75% crystalline. In some embodiments of the methods and/or devices provided herein the pharmaceutical agent is at least 90% crystalline. In some embodiments of the methods and/or devices provided herein the pharmaceutical agent is at least 95% crystalline. In some embodiments of the methods and/or devices provided herein the pharmaceutical agent is at least 97% crystalline. In some embodiments of the methods and/or devices provided herein pharmaceutical agent is at least 98% crystalline. In some embodiments of the methods and/or devices provided herein the pharmaceutical agent is at least 99% crystalline.

"Stabilizing agent" as used herein refers to any substance that maintains or enhances the stability of the biological agent. Ideally these stabilizing agents are classified as Generally Regarded As Safe (GRAS) materials by the US Food and Drug Administration (FDA). Examples of stabilizing agents include, but are not limited to carrier proteins, such as albumin, gelatin, metals or inorganic salts. Pharmaceutically acceptable excipient that may be present can further be found in the relevant literature, for example in the Handbook of Pharmaceutical Additives: An International Guide to More Than 6000 Products by Trade Name, Chemical, Function, and Manufacturer; Michael and Irene Ash (Eds.); Gower Publishing Ltd.; Aldershot, Hampshire, England, 1995.

"Intervention site" as used herein refers to the location in the body where the coating is intended to be delivered (by transfer from, freeing from, and/or dissociating from the substrate). The intervention site can be any substance in the medium surrounding the device, e.g., tissue, cartilage, a body fluid, etc. The intervention site can be the same as the treatment site, i.e., the substance to which the coating is delivered is the same tissue that requires treatment. Alternatively, the intervention site can be separate from the treatment site, requiring subsequent diffusion or transport of the pharmaceutical or other agent away from the intervention site.

"Compressed fluid" as used herein refers to a fluid of appreciable density (e.g., >0.2 g/cc) that is a gas at standard temperature and pressure. "Supercritical fluid," "near-critical fluid," "near-supercritical fluid," "critical fluid," "densified fluid," or "densified gas," as used herein refers to a compressed fluid under conditions wherein the temperature is at least 80% of the critical temperature of the fluid and the pressure is at least 50% of the critical pressure of the fluid, and/or a density of +50% of the critical density of the fluid.

Examples of substances that demonstrate supercritical or near critical behavior suitable for the present invention include, but are not limited to carbon dioxide, isobutylene, ammonia, water, methanol, ethanol, ethane, propane, butane, pentane, dimethyl ether, xenon, sulfur hexafluoride, halogenated and partially halogenated materials such as chlorofluorocarbons, hydrochlorofluorocarbons, hydrofluorocarbons, perfluorocarbons (such as perfluoromethane and perfluoropropane, chloroform, trichloro-fluoromethane, dichloro-difluoromethane, dichloro-tetrafluoroethane) and mixtures thereof. Preferably, the supercritical fluid is hexafluoropropane (FC-236EA), or 1,1,1,2,3,3-hexafluoropropane. Preferably, the supercritical fluid is hexafluoropropane (FC-236EA), or 1,1,1,2,3,3-hexafluoropropane for use in PLGA polymer coatings.

"Sintering" as used herein refers to the process by which parts of the polymer or the entire polymer becomes continuous (e.g., formation of a continuous polymer film). As discussed herein, the sintering process is controlled to produce a fully conformal continuous polymer (complete sintering) or to produce regions or domains of continuous coating while producing voids (discontinuities) in the polymer. As well, the sintering process is controlled such that some phase separation is obtained or maintained between polymer different polymers (e.g., polymers A and B) and/or to produce phase separation between discrete polymer particles. Through the sintering process, the adhesions properties of the coating are improved to reduce flaking of detachment of the coating from the substrate during manipulation in use. As described herein, in some embodiments, the sintering process is controlled to provide incomplete sintering of the polymer. In embodiments involving incomplete sintering, a polymer is formed with continuous domains, and voids, gaps, cavities, pores, channels or, interstices that provide space for sequestering a therapeutic agent which is released under controlled conditions. Depending on the nature of the polymer, the size of polymer particles and/or other polymer properties, a compressed gas, a densified gas, a near critical fluid or a super-critical fluid may be employed. In one example, carbon dioxide is used to treat a substrate that has been coated with a polymer and a drug, using dry powder and RESS electrostatic coating processes. In another example, isobutylene is employed in the sintering process. In other examples a mixture of carbon dioxide and isobutylene is employed. In another example, 1,1,2,3,3-hexafluoropropane is employed in the sintering process.

When an amorphous material is heated to a temperature above its glass transition temperature, or when a crystalline material is heated to a temperature above a phase transition temperature, the molecules comprising the material are more mobile, which in turn means that they are more active and thus more prone to reactions such as oxidation. However, when an amorphous material is maintained at a temperature below its glass transition temperature, its molecules are substantially immobilized and thus less prone to reactions. Likewise, when a crystalline material is maintained at a temperature below its phase transition temperature, its molecules are substantially immobilized and thus less prone to reactions. Accordingly, processing drug components at mild conditions, such as the deposition and sintering conditions described herein, minimizes cross-reactions and degradation of the drug component. One type of reaction that is minimized by the processes of the invention relates to the ability to avoid conventional solvents which in turn minimizes -oxidation of drug, whether in amorphous, semi-crystalline, or crystalline form, by reducing exposure thereof to free radicals, residual solvents, protic materials, polar-protic materials, oxidation initiators, and autoxidation initiators.

"Rapid Expansion of Supercritical Solutions" or "RESS" as used herein involves the dissolution of a polymer into a compressed fluid, typically a supercritical fluid, followed by rapid expansion into a chamber at lower pressure, typically near atmospheric conditions. The rapid expansion of the supercritical fluid solution through a small opening, with its accompanying decrease in density, reduces the dissolution capacity of the fluid and results in the nucleation and growth of polymer particles. The atmosphere of the chamber is maintained in an electrically neutral state by maintaining an isolating "cloud" of gas in the chamber. Carbon dioxide, nitrogen, argon, helium, or other appropriate gas is employed to prevent electrical charge is transferred from the substrate to the surrounding environment.

"Electrostatic Rapid Expansion of Supercritical Solutions" or "e-RESS" or "eRESS" as used herein refers to Electrostatic Capture as described herein combined with Rapid Expansion of Supercritical Solutions as described herein. In some embodiments, Electrostatic Rapid Expansion of Supercritical Solutions refers to Electrostatic capture as described in the art, e.g., in U.S. Pat. No. 6,756,084, "Electrostatic deposition of particles generated from rapid expansion of supercritical fluid solutions," incorporated herein by reference in its entirety.

Electrostatic Capture may be used for depositing a coating on a device (e.g. a balloon), and may be referred to as "eSTAT" herein. Coating is applied to the balloons via eSTAT attraction, where the positively charged coating coat a negatively charged device. For example, in some embodiments, sirolimus in crystalline form is applied to the balloons via eSTAT attraction where the positively charged drug particles coat the negatively charged balloons. The sirolimus coated on the balloon, in some embodiments, has an inherently positive charge.

Figure 2:
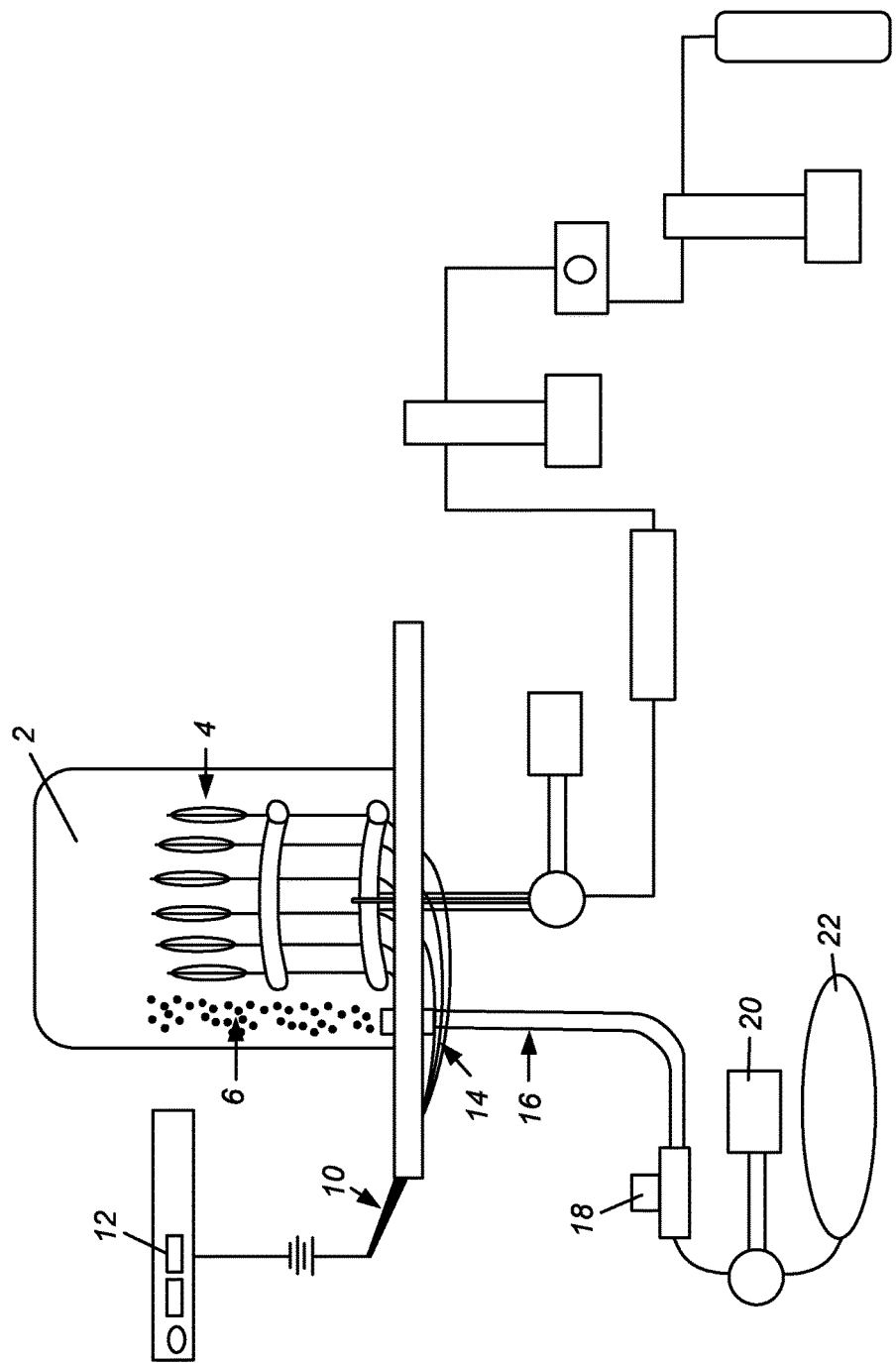
FIG. 2 depicts an example eSTAT process for coating 12 angioplasty balloons with sirolimus.

FIG. 2 depicts an example eSTAT process for coating 12 angioplasty balloons with sirolimus. In this example process, an eight liter aluminum foil coated bell jar 2 is kept in place, but is not electrically grounded. Milled sirolimus (15.5 mg) is placed in a Swagelok ½" tee filter 18 (Swagelok, Inc., Supplemental Figure S15) connected to a pulsed pneumatic valve 20 (Swagelok, Inc., Supplemental Figure S16) attached to a cylinder of compressed nitrogen 22. The tee filter is connected on the other end to the eSTAT nozzle 14, a ½"×⅜" Swagelok reducing union fitted to a modified ⅜" Swagelok bulkhead union (Swagelok, Inc., Supplemental Figure S17) via ½" (outer diameter) polypropylene tubing 16. Balloon(s) 4 are mounted in place under the bell jar 2. In this example, twelve 3.0 mm width balloons at a time are coated with the positively charged milled sirolimus 6. The balloons 4 may be of various lengths, such as lengths ranging from 17 mm to 23 mm, however, in other embodiments, other sizes may be used. In some embodiments, fewer or more balloons may be coated at a time. The balloons 4 used during the coating process are typically mounted on catheters having wires 10 disposed therein 8 which are coupled to a high voltage power supply 12 (such as a Spellman SL30 high voltage power supply), which may be set at −15 kV, for example.

In some embodiments, the lengths of the balloons may be any length from 5 mm to 35 mm, or any of the following lengths, for example: about 5 mm, about 7 mm, about 8 mm, about 10 mm, about 12 mm, about 13 mm, about 15 mm, about 18 mm, about 20 mm, about 21 mm, about 23 mm, about 25 mm, about 28 mm, about 30 mm, about 32 mm, about 33 mm, and about 35 mm. The term "about" when used in the context of balloon length, can mean variations of for example, 10%, 25%, 50%, 0.1 mm, 0.25 mm, 0.5 mm, 1 mm, 2 mm, and 5 mm, depending on the embodiment.

In some embodiments, the diameters (ie. widths) of the balloons may be any diameter from 1.5 mm to 6.0 mm, or any of the following diameters, for example: about 1.5 mm, about 1.8 mm, about 2.0 mm, about 2.25 mm, about 2.5 mm, about 2.75 mm, about 3.0 mm, about 3.25 mm, about 3.5 mm, about 3.75 mm, about 4.0 mm, about 4.25 mm, about 4.5 mm, about 4.75 mm, about 5.0 mm, about 5.25 mm, and about 5.5 mm. The term "about" when used in the context of balloon diameter (or width), can mean variations of for example, 10%, 25%, 50%, 0.1 mm, 0.25 mm, 0.3 mm, 0.4 mm, 0.5 mm, 0.75 mm, 1 mm, and 2 mm, depending on the embodiment.

In some embodiments a minimum of one balloon is coated at a time. In some embodiments, at least one of: at least 3 balloons, at least 5 balloons, at least 6 balloons, at least 8 balloons, at least 10 balloons, at least 12 balloons, at least 15 balloons, at least 16 balloons, at least 20 balloons, at least 24 balloons, and at least 30 balloons are coated at a time.

These balloons may or may not be pre-coated with a polymer, such as PLGA. Coating of the balloons may be achieved by various means, such as dip coating, spray coating, or coating using an RESS method. For example, a polymer (e.g. PLGA) is applied to the balloons via rapid expansion of supercritical solutions (RESS), where the solute (e.g. PLGA) is dissolved in a supercritical fluid then rapidly expanded with sudden decompression by passing through a short nozzle into an area of low temperature and pressure. These conditions cause the dissolved PLGA to rapidly precipitate as a fine powder with a narrow distribution of particle size resulting in a uniform coating on angioplasty balloons.

Figure 3:
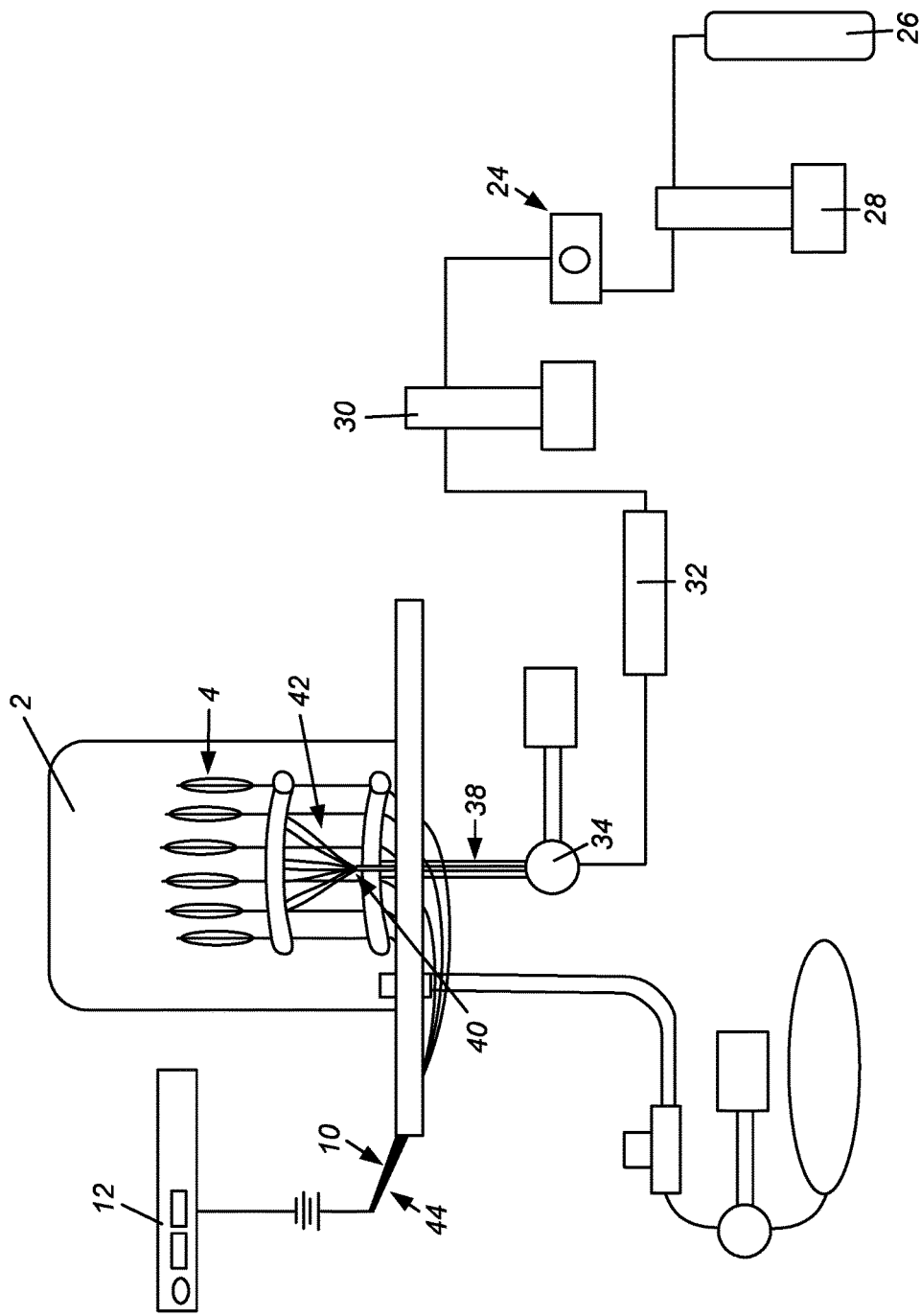
FIG. 3 depicts coating balloons according to an RESS process.

FIG. 3 depicts an example RESS process for coating balloons 4 with PLGA. The PLGA is loaded into a vessel 24 in which it is dissolved in HFC236ea from a HFC236ea cylinder 26 which is sent to the vessel 24 through a syringe pump 28 (for example, an Isco 260D syringe pump). The PLGA thus forms a supercritical solution with the HFC236 ea, which is stirred at a high pressure (5500 psi) in mixing view cells (50 cc). The PLGA solution is sent through a syringe pump 30 (for example, an Isco 260D syringe pump) which sends the solution through a heater block 32 (with temperature control feedback) and then through a timed pneumatic valve 34 which is heated at 137 C. The PLGA solution is then sent through a capillary tube 36 (e.g. PEEKsil capillary tube 1/16" outer diameter by 100 micron inner diameter by 10 cm long) which is surrounded by a stainless steel sheath (e.g. ¼ inches thick stainless steel sheath). The PLGA is then ejected through a nozzle 40 which is electrically grounded (for example, via a stainless steel sheath). When the PLGA solution exits the nozzle 40, the PLGA is ejected as dry PLGA particles 42, as the solution comprising PLGA and HFC236ea rapidly expands. The balloons 4 used during the coating process are typically mounted on catheters having wires 10 disposed therein 8 which are electrically grounded 44. The wires 10 may be coupled to a high voltage power supply 12 (such as a Spellman SL30 high voltage power supply), in order to facilitate the eSTAT coating of the balloons with the active agent, however, during the RESS process described in this embodiment, the balloons are electrically grounded and no current flows from the power supply 12.

When viewed in combination, FIGS. 2 and 3 indicate a single apparatus that can both coat according to an RESS process and an eSTAT process. Elements called out and depicted in FIG. 2 may similarly be called out in FIG. 3, and vice versa. Alternatively, separate coating apparatuses may be used to separately coat according to an RESS process and an eSTAT process.

"Solution Enhanced Dispersion of Supercritical Solutions" or "SEDS" as used herein involves a spray process for the generation of polymer particles, which are formed when a compressed fluid (e.g. supercritical fluid, preferably supercritical $CO_2$) is used as a diluent to a vehicle in which a polymer is dissolved (one that can dissolve both the polymer and the compressed fluid). The mixing of the compressed fluid diluent with the polymer-containing solution may be achieved by encounter of a first stream containing the polymer solution and a second stream containing the diluent compressed fluid, for example, within one spray nozzle or by the use of multiple spray nozzles. The solvent in the polymer solution may be one compound or a mixture of two or more ingredients and may be or comprise an alcohol (including diols, triols, etc.), ether, amine, ketone, carbonate, or alkanes, or hydrocarbon (aliphatic or aromatic) or may be a mixture of compounds, such as mixtures of alkanes, or mixtures of one or more alkanes in combination with additional compounds such as one or more alcohols, (e.g., from 0 or 0.1 to 5% of a Ci to $Ci_5$ alcohol, including diols, triols, etc.). See for example U.S. Pat. No. 6,669,785, incorporated herein by reference in its entirety. The solvent may optionally contain a surfactant, as also described in, e.g., U.S. Pat. No. 6,669,785.

In one embodiment of the SEDS process, a first stream of fluid comprising a polymer dissolved in a common solvent is co-sprayed with a second stream of compressed fluid. Polymer particles are produced as the second stream acts as a diluent that weakens the solvent in the polymer solution of the first stream. The now combined streams of fluid, along with the polymer particles, flow out of the nozzle assembly into a collection vessel. Control of particle size, particle size distribution, and morphology is achieved by tailoring the following process variables: temperature, pressure, solvent composition of the first stream, flow-rate of the first stream, flow-rate of the second stream, composition of the second stream (where soluble additives may be added to the compressed gas), and conditions of the capture vessel. Typically the capture vessel contains a fluid phase that is at least five to ten times (5-10×) atmospheric pressure.

"Electrostatic Dry Powder Coating" or "e-DPC" or "eDPC" as used herein refers to Electrostatic Capture as described herein combined with Dry Powder Coating. e-DPC deposits material (including, for example, polymer or impermeable dispersed solid) on the device or other substrate as dry powder, using electrostatic capture to attract the powder particles to the substrate. Dry powder spraying ("Dry Powder Coating" or "DPC") is well known in the art, and dry powder spraying coupled with electrostatic capture has been described, for example in U.S. Pat. Nos. 5,470,603, 6,319,541, and 6,372,246, all incorporated herein by reference in their entirety. Methods for depositing coatings are described, e.g., in WO 2008/148013, "Polymer Films for Medical Device Coating," incorporated herein by reference in its entirety.

"Dipping Process" and "Spraying Process" as used herein refer to methods of coating substrates that have been described at length in the art. These processes can be used for coating medical devices with pharmaceutical agents. Spray coating, described in, e.g., U.S. Pat. No. 7,419,696, "Medical devices for delivering a therapeutic agent and method of preparation" and elsewhere herein, can involve spraying or airbrushing a thin layer of solubilized coating or dry powder coating onto a substrate. Dip coating involves, e.g., dipping a substrate in a liquid, and then removing and drying it. Dip coating is described in, e.g., U.S. Pat. No. 5,837,313 "Drug release stent coating process," incorporated herein by reference in its entirety.

"Bulk properties" properties of a coating including a pharmaceutical or a biological agent that can be enhanced through the methods of the invention include for example: adhesion, smoothness, conformality, thickness, and compositional mixing.

"Electrostatically charged" or "electrical potential" or "electrostatic capture" as used herein refers to the collection of the spray-produced particles upon a substrate that has a different electrostatic potential than the sprayed particles. Thus, the substrate is at an attractive electronic potential with respect to the particles exiting, which results in the capture of the particles upon the substrate. i.e. the substrate and particles are oppositely charged, and the particles transport through the gaseous medium of the capture vessel onto the surface of the substrate is enhanced via electrostatic attraction. This may be achieved by charging the particles and grounding the substrate or conversely charging the substrate and grounding the particles, by charging the particles at one potential (e.g. negative charge) and charging the substrate at an opposite potential (e.g. positive charge), or by some other process, which would be easily envisaged by one of skill in the art of electrostatic capture.

"Depositing the active agent by an e-RESS, an e-SEDS, or an e-DPC process without electrically charging the substrate" as used herein refers to any of these processes as performed without intentionally electrically charging the substrate. It is understood that the substrate might become electrically charged unintentionally during any of these processes.

"Depositing the active agent by an e-RESS, an e-SEDS, or an e-DPC process without creating an electrical potential between the substrate and a coating apparatus" as used herein refers to any of these processes as performed without intentionally generating an electrical potential between the substrate and the coating apparatus. It is understood that electrical potential between the substrate and the coating apparatus might be generated unintentionally during any of these processes.

"Intimate mixture" as used herein, refers to two or more materials, compounds, or substances that are uniformly distributed or dispersed together.

"Layer" as used herein refers to a material covering a surface or forming an overlying part or segment. Two different layers may have overlapping portions whereby material from one layer may be in contact with material from another layer. Contact between materials of different layers can be measured by determining a distance between the materials. For example, Raman spectroscopy may be employed in identifying materials from two layers present in close proximity to each other.

While layers defined by uniform thickness and/or regular shape are contemplated herein, several embodiments described herein relate to layers having varying thickness and/or irregular shape. Material of one layer may extend into the space largely occupied by material of another layer. For example, in a coating having three layers formed in sequence as a first polymer layer, a pharmaceutical agent layer and a second polymer layer, material from the second polymer layer which is deposited last in this sequence may extend into the space largely occupied by material of the pharmaceutical agent layer whereby material from the second polymer layer may have contact with material from the pharmaceutical layer. It is also contemplated that material from the second polymer layer may extend through the entire layer largely occupied by pharmaceutical agent and contact material from the first polymer layer.

It should be noted however that contact between material from the second polymer layer (or the first polymer layer) and material from the pharmaceutical agent layer (e.g.; a pharmaceutical agent crystal particle or a portion thereof) does not necessarily imply formation of a mixture between the material from the first or second polymer layers and material from the pharmaceutical agent layer. In some embodiments, a layer may be defined by the physical three-dimensional space occupied by crystalline particles of a pharmaceutical agent (and/or biological agent). It is contemplated that such layer may or may not be continuous as physical space occupied by the crystal particles of pharmaceutical agents may be interrupted, for example, by polymer material from an adjacent polymer layer. An adjacent polymer layer may be a layer that is in physical proximity to be pharmaceutical agent particles in the pharmaceutical agent layer. Similarly, an adjacent layer may be the layer formed in a process step right before or right after the process step in which pharmaceutical agent particles are deposited to form the pharmaceutical agent layer.

As described herein, material deposition and layer formation provided herein are advantageous in that the pharmaceutical agent remains largely in crystalline form during the entire process. While the polymer particles and the pharmaceutical agent particles may be in contact, the layer formation process is controlled to avoid formation of a mixture between the pharmaceutical agent particles the polymer particles during formation of a coated device.

In some embodiments, the coating comprises a plurality of layers deposited on the substrate, wherein at least one of the layers comprises the active agent. In some embodiments, at least one of the layers comprises a polymer. In some embodiments, the polymer is bioabsorbable. In some embodiments, the active agent and the polymer are in the same layer, in separate layers, or form overlapping layers. In some embodiments, the plurality of layers comprise five layers deposited as follows: a first polymer layer, a first active agent layer, a second polymer layer, a second active agent layer and a third polymer layer.

In some embodiments of the methods and/or devices provided herein, the coating comprises a plurality of layers deposited on the substrate, wherein at least one of the layers comprises the active agent. In some embodiments, at least one of the layers comprises a polymer. In some embodiments, the polymer is bioabsorbable. In some embodiments, the active agent and the polymer are in the same layer, in separate layers, or form overlapping layers. In some embodiments, the coating comprises a plurality of layers deposited on the substrate, wherein at least one of the layers comprises the pharmaceutical agent. In some embodiments, the pharmaceutical agent and the polymer are in the same layer, in separate layers, or form overlapping layers. In some embodiments, the plurality of layers comprise five layers deposited as follows: a first polymer layer, a first active agent layer, a second polymer layer, a second active agent layer and a third polymer layer. In some embodiments, the plurality of layers comprise five layers deposited as follows: a first polymer layer, a first pharmaceutical agent layer, a second polymer layer, a second pharmaceutical agent layer and a third polymer layer. In some embodiments, the plurality of layers comprise five layers deposited as follows: a first polymer layer, a first active biological agent layer, a second polymer layer, a second active biological agent layer and a third polymer layer.

In some embodiments, the device provides the coating to the intervention site over an area of delivery greater than the outer surface contact area of the substrate. In some embodiments, the area of delivery is at least 110% greater than the outer surface contact area of the substrate. In some embodiments, the area of delivery is at least 110% to 200% greater than the outer surface contact area of the substrate. In some embodiments, the area of delivery is at least 200% greater than the outer surface contact area of the substrate.

"Laminate coating" as used herein refers to a coating made up of two or more layers of material. Means for creating a laminate coating as described herein (e.g.; a laminate coating comprising bioabsorbable polymer(s) and pharmaceutical agent) may include coating the stent with drug and polymer as described herein (e-RESS, e-DPC, compressed-gas sintering). The process comprises performing multiple and sequential coating steps (with sintering steps for polymer materials) wherein different materials may be deposited in each step, thus creating a laminated structure with a multitude of layers (at least 2 layers) including polymer layers and pharmaceutical agent layers to build the final device (e.g.; laminate coated stent).

"Portion of the coating" and "portion of the active agent" as used herein refer to an amount or percentage of the coating or active agent that is freed, dissociated, and/or transferred from the substrate to the intervention site, either at a designated point in delivery, during a certain period of delivery, or in total throughout the entire delivery process. In embodiments, the device and methods of the invention are adapted to free, dissociate, and/or transfer a certain amount of the coating and/or active agent.

For example, in embodiments, at least about 10%, at least about 20%, at least about 30%, at least about 50%, at least about 75%, at least about 85%, at least about 90%, at least about 95%, and/or at least about 99% of the coating is adapted to be freed, dissociated, and/or to be transferred from the substrate to the intervention site. In embodiments, at least about 10%, at least about 20%, at least about 30%, at least about 50%, at least about 75%, at least about 85%, at least about 90%, at least about 95%, and/or at least about 99% of the active agent is adapted to be freed, dissociated, and/or to be transferred from the substrate to the intervention site.

The portion of the coating and/or that is freed, dissociated, or transferred from the device substrate is influenced by any or a combination of, e.g., the size, shape, and flexibility of the device substrate, the size, shape, surface qualities of and conditions (e.g., blood or lymph circulation, temperature, etc.) at the intervention site, the composition of the coating, including the particular active agent(s) and specific polymer component(s) used in the coating, the relative proportions of these components, the use of any release agent(s), and substrate characteristics. Any one or more of these and other aspects of the device and methods of the invention can be adapted to influence the portion of the coating and/or active agent freed, dissociated, and/or transferred, as desired to produce the desired clinical outcome.

"Substantially all of the coating" as used herein refers to at least about 50%, at least about 75%, at least about 85%, at least about 90%, at least about 95%, at least about 97%, and/or at least about 99% percent of the coating that was present on the device prior to use.

"At least a portion of the substrate" as used herein refers to an amount and/or percentage of the substrate. In embodiments of the device and methods of the invention wherein a coating is on "at least a portion of the substrate," at least about 10%, at least about 20%, at least about 30%, at least about 50%, at least about 75%, at least about 85%, at least about 90%, at least about 95%, and/or at least about 99% of the substrate is coated. In embodiments wherein "at least a portion of the substrate" is bioabsorbable, at least about 10%, at least about 20%, at least about 30%, at least about 50%, at least about 75%, at least about 85%, at least about 90%, at least about 95%, and/or at least about 99% of the substrate is bioabsorbable.

"Transferring at least a portion" as used herein in the context of transferring a coating or active agent from the substrate to an intervention site refers to an amount and/or percentage of the coating or active agent that is transferred from the substrate to an intervention site. In embodiments of the device and methods of the invention wherein at least a portion of a coating or active agent is transferred from the substrate to an intervention site, at least about 10%, at least about 20%, at least about 30%, at least about 50%, at least about 75%, at least about 85%, at least about 90%, at least about 95%, and/or at least about 99% of the coating or active agent is transferred from the substrate to the intervention site. In some embodiments, at least about 10%, at least about 20%, at least about 30%, at least about 50%, at least about 75%, at least about 85%, at least about 90%, at least about 95%, and/or at least about 99% of the coating is adapted to transfer from the substrate to the intervention site. In some embodiments, at least about 10% of the coating is adapted to transfer from the substrate to the intervention site. In some embodiments, at least about 20% of the coating is adapted to transfer from the substrate to the intervention site. In some embodiments, at least about 30% of the coating is adapted to transfer from the substrate to the intervention site. In some embodiments, at least about 50% of the coating is adapted to transfer from the substrate to the intervention site. In some embodiments, at least about 75% of the coating is adapted to transfer from the substrate to the intervention site. In some embodiments, at least about 85% of the coating is adapted to transfer from the substrate to the intervention site. In some embodiments, at least about 90% of the coating is adapted to transfer from the substrate to the intervention site. In some embodiments, at least about 95% of the coating is adapted to transfer from the substrate to the intervention site. In some embodiments, at least about 99% of the coating is adapted to transfer from the substrate to the intervention site. As used herein, "about" when used in reference to a percentage of the coating can mean ranges of 1%-5%, of 5%-10%, of 10%-20%, and/or of 10%-50% (as a percent of the percentage of the coating transferred, or as a variation of the percentage of the coating transferred).

In some embodiments, the coating portion that is adapted to transfer upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, device is adapted to transfer less than about 1%, less than about 5%, less than about 10%. less than about 15%, less than about 25%, less than about 50%, less than about 70%, less than about 80%, and/or less than about 90% of the coating absent stimulation of the coating.

In some embodiments, at least about 10%, at least about 20%, at least about 30%, at least about 50%, at least about 75%, at least about 85%, at least about 90%, at least about 95%, and/or at least about 99% of the active agent is adapted to transfer from the substrate to the intervention site. In some embodiments, at least about 10% of the active agent is adapted to transfer from the substrate to the intervention site. In some embodiments, at least about 20% of the active agent is adapted to transfer from the substrate to the intervention site. In some embodiments, at least about 30% of the active agent is adapted to transfer from the substrate to the intervention site. In some embodiments, at least about 50% of the active agent is adapted to transfer from the substrate to the intervention site. In some embodiments, at least about 75% of the active agent is adapted to transfer from the substrate to the intervention site. In some embodiments, at least about 85% of the active agent is adapted to transfer from the substrate to the intervention site. In some embodiments, at least about 90% of the active agent is adapted to transfer from the substrate to the intervention site. In some embodiments, at least about 95% of the active agent is adapted to transfer from the substrate to the intervention site. In some embodiments, at least about 99% of the active agent is adapted to transfer from the substrate to the intervention site. As used herein, "about" when used in reference to a percentage of the active agent can mean ranges of 1%-5%, of 5%-10%, of 10%-20%, and/or of 10%-50% (as a percent of the percentage of the active agent transferred, or as a variation of the percentage of the active agent transferred).

In some embodiments, the active agent portion that is adapted to transfer upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, the device is adapted to transfer less than about 1%, less than about 5%, less than about 10%. less than about 15%, less than about 25%, less than about 50%, less than about 70%, less than about 80%, and/or less than about 90% of the active agent absent stimulation of the coating.

In some embodiments, the device is adapted to transfer at least about 10%, at least about 20%, at least about 30%, at least about 50%, at least about 75%, at least about 85%, at least about 90%, at least about 95%, and/or at least about 99% of the coating from the substrate to the intervention site. In some embodiments, the device is adapted to transfer at least about 10% of the coating from the substrate to the intervention site. In some embodiments, the device is adapted to transfer at least about 20% of the coating from the substrate to the intervention site. In some embodiments, the device is adapted to transfer at least about 30% of the coating from the substrate to the intervention site. In some embodiments, the device is adapted to transfer at least about 50% of the coating from the substrate to the intervention site. In some embodiments, the device is adapted to transfer at least about 75% of the coating from the substrate to the intervention site. In some embodiments, the device is adapted to transfer at least about 85% of the coating from the substrate to the intervention site. In some embodiments, the device is adapted to transfer at least about 90% of the coating from the substrate to the intervention site. In some embodiments, the device is adapted to transfer at least about 95% of the coating from the substrate to the intervention site. In some embodiments, the device is adapted to transfer at least about 99% of the coating from the substrate to the intervention site. As used herein, "about" when used in reference to a percentage of the coating can mean ranges of 1%-5%, of 5%-10%, of 10%-20%, and/or of 10%-50% (as a percent of the percentage of the coating transferred, or as a variation of the percentage of the coating transferred).

In some embodiments, the coating portion that transfers upon stimulation is on at least one of a distal surface of the substrate, a middle surface of the substrate, a proximal surface of the substrate, and an abluminal surface of the substrate. In some embodiments, stimulation decreases the contact between the coating and the substrate. In some embodiments, the device is adapted to transfer less than about 1%, less than about 5%, less than about 10%. less than about 15%, less than about 25%, less than about 50%, less than about 70%, less than about 80%, and/or less than about 90% of the coating absent stimulation of the coating.

In some embodiments, the device is adapted to transfer at least about 10%, at least about 20%, at least about 30%, at least about 50%, at least about 75%, at least about 85%, at least about 90%, at least about 95%, and/or at least about 99% of the active agent from the substrate to the intervention site. In some embodiments, the device is adapted to transfer at least about 10% of the active agent from the substrate to the intervention site. In some embodiments, the device is adapted to transfer at least about 20% of the active agent from the substrate to the intervention site. In some embodiments, the device is adapted to transfer at least about 30% of the active agent from the substrate to the intervention site. In some embodiments, the device is adapted to transfer at least about 50% of the active agent from the substrate to the intervention site. In some embodiments, the device is adapted to transfer at least about 75% of the active agent from the substrate to the intervention site. In some embodiments, the device is adapted to transfer at least about 85% of the active agent from the substrate to the intervention site. In some embodiments, the device is adapted to transfer at least about 90% of the active agent from the substrate to the intervention site. In some embodiments, the device is adapted to transfer at least about 95% of the active agent from the substrate to the intervention site. In some embodiments, the device is adapted to transfer at least about 99% of the active agent from the substrate to the intervention site. As used herein, "about" when used in reference to a percentage of the active agent can mean ranges of 1%-5%, of 5%-10%, of 10%-20%, and/or of 10%-50% (as a percent of the percentage of the active agent transferred, or as a variation of the percentage of the active agent transferred).

In some embodiments, the coating portion that transfers upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, the device is adapted to transfer less than about 1%, less than about 5%, less than about 10%. less than about 15%, less than about 25%, less than about 50%, less than about 70%, less than about 80%, less than about 90% of the active agent absent stimulation of the coating.

"Freeing at least a portion" as used herein in the context of freeing a coating and/or active agent from the substrate at an intervention site refers to an amount and/or percentage of a coating or active agent that is freed from the substrate at an intervention site. In embodiments of the device and methods of the invention wherein at least a portion of a coating or active agent is freed from the substrate at an intervention site, at least about 10%, at least about 20%, at least about 30%, at least about 50%, at least about 75%, at least about 85%, at least about 90%, at least about 95%, and/or at least about 99% of the coating or active agent is freed from the substrate at the intervention site. In some embodiments, the device is adapted to free at least about 10%, at least about 20%, at least about 30%, at least about 50%, at least about 75%, at least about 85%, at least about 90%, at least about 95%, and/or at least about 99% of the coating from the substrate. In some embodiments, the device is adapted to free at least about 10% of the coating from the substrate to the intervention site. In some embodiments, the device is adapted to free at least about 20% of the coating from the substrate to the intervention site. In some embodiments, the device is adapted to free at least about 30% of the coating from the substrate to the intervention site. In some embodiments, the device is adapted to free at least about 50% of the coating from the substrate to the intervention site. In some embodiments, the device is adapted to free at least about 75% of the coating from the substrate to the intervention site. In some embodiments, the device is adapted to free at least about 85% of the coating from the substrate to the intervention site. In some embodiments, the device is adapted to free at least about 90% of the coating from the substrate to the intervention site. In some embodiments, the device is adapted to free at least about 95% of the coating from the substrate to the intervention site. In some embodiments, the device is adapted to free at least about 99% of the coating from the substrate to the intervention site. As used herein, "about" when used in reference to a percentage of the coating can mean ranges of 1%-5%, of 5%-10%, of 10%-20%, and/or of 10%-50% (as a percent of the percentage of the coating freed, or as a variation of the percentage of the coating freed).

In some embodiments, the coating portion that frees upon stimulation is on at least one of a distal surface of the substrate, a middle surface of the substrate, a proximal surface of the substrate, and an abluminal surface of the substrate.

In some embodiments, the stimulation decreases the contact between the coating and the substrate. In some embodiments, the device is adapted to free less than about 1%, less than about 5%, less than about 10%. less than about 15%, less than about 25%, less than about 50%, less than about 70%, less than about 80%, less than about 90% of the coating absent stimulation of the coating.

"Dissociating at least a portion" as used herein in the context of dissociating a coating and/or active agent from the substrate at an intervention site refers to an amount and/or percentage of a coating and/or active agent that is dissociated from the substrate at an intervention site. In embodiments of the device and methods of the invention wherein at least a portion of a coating and/or active agent is dissociated from the substrate at an intervention site, at least about 10%, at least about 20%, at least about 30%, at least about 50%, at least about 75%, at least about 85%, at least about 90%, at least about 95%, and/or at least about 99% of the coating and/or active agent is dissociated from the substrate at the intervention site.

In some embodiments, the device is adapted to dissociate at least about 10%, at least about 20%, at least about 30%, at least about 50%, at least about 75%, at least about 85%, at least about 90%, at least about 95%, and/or at least about 99% of the coating from the substrate. In some embodiments, the device is adapted to dissociate at least about 10% of the coating from the substrate to the intervention site. In some embodiments, the device is adapted to dissociate at least about 20% of the coating from the substrate to the intervention site. In some embodiments, the device is adapted to dissociate at least about 30% of the coating from the substrate to the intervention site. In some embodiments, the device is adapted to dissociate at least about 50% of the coating from the substrate to the intervention site. In some embodiments, the device is adapted to dissociate at least about 75% of the coating from the substrate to the intervention site. In some embodiments, the device is adapted to dissociate at least about 85% of the coating from the substrate to the intervention site. In some embodiments, the device is adapted to dissociate at least about 90% of the coating from the substrate to the intervention site. In some embodiments, the device is adapted to dissociate at least about 95% of the coating from the substrate to the intervention site. In some embodiments, the device is adapted to dissociate at least about 99% of the coating from the substrate to the intervention site. As used herein, "about" when used in reference to a percentage of the coating can mean ranges of 1%-5%, of 5%-10%, of 10%-20%, and/or of 10%-50% (as a percent of the percentage of the coating dissociated, or as a variation of the percentage of the coating dissociated).

In some embodiments, the coating portion that dissociates upon stimulation is on at least one of a distal surface of the substrate, a middle surface of the substrate, a proximal surface of the substrate, and an abluminal surface of the substrate. In some embodiments, stimulation decreases the contact between the coating and the substrate. In some embodiments, the device is adapted to dissociate less than about 1%, less than about 5%, less than about 10%. less than about 15%, less than about 25%, less than about 50%, less than about 70%, less than about 80%, less than about 90% of the coating absent stimulation of the coating.

"Depositing at least a portion" as used herein in the context of a coating and/or active agent at an intervention site refers to an amount and/or percentage of a coating and/or active agent that is deposited at an intervention site. In embodiments of the device and methods of the invention wherein at least a portion of a coating and/or active agent is deposited at an intervention site, at least about 10%, at least about 20%, at least about 30%, at least about 50%, at least about 75%, at least about 85%, at least about 90%, at least about 95%, and/or at least about 99% of the coating and/or active agent is deposited at the intervention site. In some embodiments, stimulating decreases the contact between the coating and the substrate. In some embodiments, depositing deposits less than about 1%, less than about 5%, less than about 10%. less than about 15%, less than about 25%, less than about 50%, less than about 70%, less than about 80%, and/or less than about 90% of the coating absent stimulating at least one of the coating and the substrate.

"Delivering at least a portion" as used herein in the context of a coating and/or active agent at an intervention site refers to an amount and/or percentage of a coating and/or active agent that is delivered to an intervention site. In embodiments of the device and methods of the invention wherein at least a portion of a coating and/or active agent is delivered to an intervention site, at least about 10%, at least about 20%, at least about 30%, at least about 50%, at least about 75%, at least about 85%, at least about 90%, at least about 95%, and/or at least about 99% of the coating and/or active agent is delivered to the intervention site.

In some embodiments, the device is adapted to deliver at least about 10%, at least about 20%, at least about 30%, at least about 50%, at least about 75%, at least about 85%, at least about 90%, at least about 95%, and/or at least about 99% of the coating to the intervention site. In some embodiments, the device is adapted to deliver at least about 10% of the coating to the intervention site. In some embodiments, the device is adapted to deliver at least about 20% of the coating to the intervention site. In some embodiments, the device is adapted to deliver at least about 30% of the coating to the intervention site. In some embodiments, the device is adapted to deliver at least about 50% of the coating to the intervention site. In some embodiments, the device is adapted to deliver at least about 75% of the coating to the intervention site. In some embodiments, the device is adapted to deliver at least about 85% of the coating to the intervention site. In some embodiments, the device is adapted to deliver at least about 90% of the coating to the intervention site. In some embodiments, the device is adapted to deliver at least about 95% of the coating to the intervention site. In some embodiments, the device is adapted to deliver at least about 99% of the coating to the intervention site. As used herein, "about" when used in reference to a percentage of the coating can mean ranges of 1%-5%, of 5%-10%, of 10%-20%, and/or of 10%-50% (as a percent of the percentage of the coating delivered, or as a variation of the percentage of the coating delivered).

In some embodiments, the coating portion that is delivered upon stimulation is on at least one of a distal surface of the substrate, a middle surface of the substrate, a proximal surface of the substrate, and an abluminal surface of the substrate. In some embodiments, the stimulation decreases the contact between the coating and the substrate. In some embodiments, the device is adapted to deliver less than about 1%, less than about 5%, less than about 10%. less than about 15%, less than about 25%, less than about 50%, less than about 70%, less than about 80%, less than about 90% of the coating absent stimulation of the coating.

In some embodiments, depositing at least a portion of the coating comprises depositing at least about 10%, at least about 20%, at least about 30%, at least about 50%, at least about 75%, at least about 85%, at least about 90%, at least about 95%, and/or at least about 99% of the coating at the intervention site. In some embodiments, stimulating decreases the contact between the coating and the substrate. In some embodiments, depositing deposits less than about 1%, less than about 5%, less than about 10%. less than about 15%, less than about 25%, less than about 50%, less than about 70%, less than about 80%, and/or less than about 90% of the coating absent stimulating at least one of the coating and the substrate.

"Tacking at least a portion" as used herein in the context of tacking at least a portion of the coating to an intervention site refers to an amount and/or percentage of a coating and/or active agent that is tacked at an intervention site. In embodiments of the device and methods of the invention wherein at least a portion of a coating and/or active agent is tacked at an intervention site, at least about 10%, at least about 20%, at least about 30%, at least about 50%, at least about 75%, at least about 85%, at least about 90%, at least about 95%, and/or at least about 99% of the coating and/or active agent is tacked at the intervention site. In some embodiments, stimulating decreases the contact between the coating and the substrate. In some embodiments, tacking tacks less than about 1%, less than about 5%, less than about 10%. less than about 15%, less than about 25%, less than about 50%, less than about 70%, less than about 80%, and/or less than about 90% of the coating absent stimulating at least one of the coating and the substrate. In some embodiments, the device comprises a tacking element that cooperates with the stimulation to tack the coating to the intervention site. In some embodiments, the device comprises a tacking element that tacks the coating to the substrate until stimulating with a stimulation.

"Adhere," "adherence," "adhered," "cohere," "coherence," "cohered," and related terms, as used herein in the context of adherence or coherence of the substrate to the coating refer to an interaction between the substrate and the coating that is sufficiently strong to maintain the association of the coating with the substrate for an amount of time prior to the stimulation, e.g., mechanical, chemical, thermal, electromagnetic, or sonic stimulation, that is intended to cause the coating to be freed, dissociated, and/or transferred. These same terms, as used in the context of an interaction between the coating and the target tissue area and/or intervention site refer to an interaction between the coating and the target tissue area and/or intervention site that is sufficient to keep the coating associated with the target tissue area and/or intervention site for an amount of time as desired for treatment, e.g., at least about 12 hours, about 1 day, about 3 days, about 5 days, about 7 days, about 14 days, about 3 weeks, about 4 weeks, about 45 days, about 60 days, about 90 days, about 180 days, about 6 months, about 9 months, about 1 year, about 1 to about 2 days, about 1 to about 5 days, about 1 to about 2 weeks, about 2 to about 4 weeks, about 45 to about 60 days, about 45 to about 90 days, about 30 to about 90 days, about 60 to about 90 days, about 90 to about 180 days, about 60 to about 180 days, about 180 to about 365 days, about 6 months to about 9 months, about 9 months to about 12 months, about 9 months to about 15 months, and about 1 year to about 2 years.

"Balloon" as used herein refers to a flexible sac that can be inflated within a natural or non-natural body lumen or cavity, or used to create a cavity, or used to enlarge an existing cavity. The balloon can be used transiently to dilate a lumen or cavity and thereafter may be deflated and/or removed from the subject during the medical procedure or thereafter. In embodiments, the balloon can be expanded within the body and has a coating thereon that is freed (at least in part) from the balloon and left behind in the lumen or cavity when the balloon is removed. A coating can be applied to a balloon either after the balloon has been compacted for insertion, resulting in a coating that partially covers the surface of the balloon, or it can be applied prior to or during compaction. In embodiments, a coating is applied to the balloon both prior to and after compaction of the balloon. In embodiments, the balloon is compacted by, e.g., crimping or folding. Methods of compacting balloons have been described, e.g., in U.S. Pat. No. 7,308,748, "Method for compressing an intraluminal device," and U.S. Pat. No. 7,152,452, "Assembly for crimping an intraluminal device and method of use," relating to uniformly crimping a balloon onto a catheter or other intraluminal device, and U.S. Pat. No. 5,350,361 "Tri-fold balloon for dilatation catheter and related method," relating to balloon folding methods and devices, all incorporated herein by reference in their entirety. In some embodiments the balloon is delivered to the intervention site by a delivery device. In some embodiments, the delivery device comprises catheter. In some embodiments, the balloon is an angioplasty balloon. Balloons can be delivered, removed, and visualized during delivery and removal by methods known in the art, e.g., for inserting angioplasty balloons, stents, and other medical devices. Methods for visualizing a treatment area and planning instrument insertion are described, e.g., in U.S. Pat. No. 7,171,255, "Virtual reality 3D visualization for surgical procedures" and U.S. Pat. No. 6,610,013, "3D ultrasound-guided intraoperative prostate brachytherapy," incorporated herein by reference in their entirety.

"Compliant balloon" as used herein refers to a balloon which conforms to the intervention site relatively more than a semi-compliant balloon and still more so than a non-compliant balloon. Compliant balloons expand and stretch with increasing pressure within the balloon, and are made from such materials as polyethylene or polyolefin copolymers. There is in the art a general classification of balloons based on their expandability or "compliance" relative to each other, as described e.g., in U.S. Pat. No. 5,556,383, "Block copolymer elastomer catheter balloons." Generally, "non-compliant" balloons are the least elastic, increasing in diameter about 2-7%, typically about 5%, as the balloon is pressurized from an inflation pressure of about 6 atm to a pressure of about 12 atm, that is, they have a "distension" over that pressure range of about 5%. "Semi-compliant" balloons have somewhat greater distensions, generally 7-16% and typically 10-12% over the same pressurization range. "Compliant" balloons are still more distensible, having distensions generally in the range of 16-40% and typically about 21% over the same pressure range. Maximum distensions, i.e. distension from nominal diameter to burst, of various balloon materials may be significantly higher than the distension percentages discussed above because wall strengths, and thus burst pressures, vary widely between balloon materials. These distension ranges are intended to provide general guidance, as one of skill in the art will be aware that the compliance of a balloon is dependent on the dimensions and/or characteristics of the cavity and/or lumen walls, not only the expandability of the balloon.

A compliant balloon may be used in the vasculature of a subject. A compliant balloon might also be used in any tube or hole outside the vasculature (whether naturally occurring or man-made, or created during an injury). For a non-limiting example, a compliant balloon might be used in a lumpectomy to put a coating at the site where a tumor was removed, to: treat an abscess, treat an infection, prevent an infection, aid healing, promote healing, or for a combination of any of these purposes. The coating in this embodiment may comprise a growth factor.

"Non-Compliant balloon" as used herein refers to a balloon that does not conform to the intervention site, but rather, tends to cause the intervention site to conform to the balloon shape. Non-compliant balloons, commonly made from such materials as polyethylene terephthalate (PET) or polyamides, remain at a preselected diameter as the internal balloon pressure increases beyond that required to fully inflate the balloon. Non-compliant balloons are often used to dilate spaces, e.g., vascular lumens. As noted with respect to a compliant balloon, one of skill in the art will be aware that the compliance of a balloon is dependent on the dimensions and/or characteristics of the cavity and/or lumen walls, not only the expandability of the balloon.

"Cutting balloon" as used herein refers to a balloon commonly used in angioplasty having a special balloon tip with cutting elements, e.g., small blades, wires, etc. The cutting elements can be activated when the balloon is inflated. In angioplasty procedures, small blades can be used score the plaque and the balloon used to compress the fatty matter against the vessel wall. A cutting balloon might have tacks or other wire elements which in some embodiments aid in freeing the coating from the balloon, and in some embodiments, may promote adherence or partial adherence of the coating to the target tissue area, or some combination thereof. In some embodiments, the cutting balloon cutting elements also score the target tissue to promote the coating's introduction into the target tissue. In some embodiments, the cutting elements do not cut tissue at the intervention site. In some embodiments, the cutting balloon comprises tacking elements as the cutting elements.

"Inflation pressure" as used herein refers to the pressure at which a balloon is inflated. As used herein the nominal inflation pressure refers to the pressure at which a balloon is inflated in order to achieve a particular balloon dimension, usually a diameter of the balloon as designed. The "rated burst pressure" or "RBP" as used herein refers to the maximum statistically guaranteed pressure to which a balloon can be inflated without failing. For PTCA and PTA catheters, the rated burst pressure is based on the results of in vitro testing to the PTCA and/or PTA catheters, and normally means that at least 99.9% of the balloons tested (with 95% confidence) will not burst at or below this pressure.

"Tacking element" as used herein refers to an element on the substrate surface that is used to influence transfer of the coating to the intervention site. For example, the tacking element can comprise a projection, e.g., a bump or a spike, on the surface of the substrate. In embodiments, the tacking element is adapted to secure the coating to the cutting balloon until inflation of the cutting balloon. In some embodiments, tacking element can comprise a wire, and the wire can be shaped in the form of an outward pointing wedge. In certain embodiments, the tacking element does not cut tissue at the intervention site.

As used herein, a "surgical tool" refers to any tool used in a surgical procedure. Examples of surgical tools include, but are not limited to: As used herein, a "surgical tool" refers to any tool used in a surgical procedure. Examples of surgical tools include, but are not limited to: a knife, a scalpel, a guidewire, a guiding catheter, a introduction catheter, a distracter, a needle, a syringe, a biopsy device, an articulator, a Galotti articulator, a bone chisel, a bone crusher, a cottle cartilage crusher, a bone cutter, a bone distractor, an Ilizarov apparatus, an intramedullary kinetic bone distractor, a bone drill, a bone extender, a bone file, a bone lever, a bone mallet, a bone rasp, a bone saw, a bone skid, a bone splint, a bone button, a caliper, a cannula, a catheter, a cautery, a clamp, a coagulator, a curette, a depressor, a dilator, a dissecting knife, a distractor, a dermatome, forceps, dissecting forceps, tissue forceps, sponge forceps, bone forceps, Carmalt forceps, Cushing forceps, Dandy forceps, DeBakey forceps, Doyen intestinal forceps, epilation forceps, Halstead forceps, Kelly forceps, Kocher forceps, mosquito forceps, a hemostat, a hook, a nerve hook, an obstetrical hook, a skin hook, a hypodermic needle, a lancet, a luxator, a lythotome, a lythotript, a mallet, a partsch mallet, a mouth prop, a mouth gag, a mammotome, a needle holder, an occluder, an osteotome, an Epker osteotome, a periosteal elevator, a Joseph elevator, a Molt periosteal elevator, an Obweg periosteal elevator, a septum elevator, a Tessier periosteal elevator, a probe, a retractor, a Senn retractor, a Gelpi retractor, a Weitlaner retractor, a USA-Army/Navy retractor, an O'Connor-O'Sullivan retractor, a Deaver retractor, a Bookwalter retractor, a Sweetheart retractor, a Joseph skin hook, a Lahey retractor, a Blair (Rollet) retractor, a rigid rake retractor, a flexible rake retractor, a Ragnell retractor, a Linde-Ragnell retractor, a Davis retractor, a Volkman retractor, a Mathieu retractor, a Jackson tracheal hook, a Crile retractor, a Meyerding finger retractor, a Little retractor, a Love Nerve retractor, a Green retractor, a Goelet retractor, a Cushing vein retractor, a Langenbeck retractor, a Richardson retractor, a Richardson-Eastmann retractor, a Kelly retractor, a Parker retractor, a Parker-Mott retractor, a Roux retractor, a Mayo-Collins retractor, a Ribbon retractor, an Alm retractor, a self retaining retractor, a Weitlaner retractor, a Beckman-Weitlaner retractor, a Beckman-Eaton retractor, a Beckman retractor, an Adson retractor, a rib spreader, a rongeur, a scalpel, an ultrasonic scalpel, a laser scalpel, scissors, iris scissors, Kiene scissors, Metzenbaum scissors, Mayo scissors, Tenotomy scissors, a spatula, a speculum, a mouth speculum, a rectal speculum, Sim's vaginal speculum, Cusco's vaginal speculum, a sternal saw, a suction tube, a surgical elevator, a surgical hook, a surgical knife, surgical mesh, a surgical needle, a surgical snare, a surgical sponge, a surgical spoon, a surgical stapler, a suture, a syringe, a tongue depressor, a tonsillotome, a tooth extractor, a towel clamp, towel forceps, Backhaus towel forceps, Lorna towel forceps, a tracheotome, a tissue expander, a subcutaneous inflatable balloon expander, a trephine, a trocar, tweezers, and a venous clipping. In some embodiments, a surgical tool may also and/or alternatively be referred to as a tool for performing a medical procedure. In some embodiments, a surgical tool may also and/or alternatively be a tool for delivering to the intervention site a biomedical implant.

"Stimulation" as used herein refers to any mechanical stimulation, chemical stimulation, thermal stimulation, electromagnetic stimulation, and/or sonic stimulation that influences, causes, initiates, and/or results in the freeing, dissociation, and/or the transfer of the coating and/or active agent from the substrate.

"Mechanical Stimulation" as used herein refers to use of a mechanical force that influences the freeing, dissociation, and/or transfer of the coating and/or the active agent from the substrate. For example, mechanical stimulation can comprise a shearing force, a compressive force, a force exerted on the coating from a substrate side of the coating, a force exerted on the coating by the substrate, a force exerted on the coating by an external element, a translation, a rotation, a vibration, or a combination thereof. In embodiments, the mechanical stimulation comprises balloon expansion, stent expansion, etc. In embodiments, the mechanical stimulation is adapted to augment the freeing, dissociation and/or transfer of the coating from the substrate. In embodiments, the mechanical stimulation is adapted to initiate the freeing, dissociation and/or transfer of the coating from the substrate. In embodiments, the mechanical stimulation can be adapted to cause the freeing, dissociation and/or transference of the coating from the substrate. In embodiments, an external element is a part of the subject. In embodiments, the external element is not part of the device. In embodiments the external element comprises a liquid, e.g., saline or water. In certain embodiments the liquid is forced between the coating and the substrate. In embodiments, the mechanical stimulation comprises a geometric configuration of the substrate that maximizes a shear force on the coating.

"Chemical Stimulation" as used herein refers to use of a chemical force to influence the freeing, dissociation, and/or transfer of the coating from the substrate. For example, chemical stimulation can comprise bulk degradation, interaction with a bodily fluid, interaction with a bodily tissue, a chemical interaction with a non-bodily fluid, a chemical interaction with a chemical, an acid-base reaction, an enzymatic reaction, hydrolysis, or a combination thereof. In embodiments, the chemical stimulation is adapted to augment the freeing, dissociation and/or transfer of the coating from the substrate. In embodiments, the chemical stimulation is adapted to initiate the freeing, dissociation and/or transfer of the coating from the substrate. In embodiments, the chemical stimulation is adapted to cause the freeing, dissociation and/or transfer of the coating from the substrate. In embodiments, the chemical stimulation is achieved through the use of a coating that comprises a material that is adapted to transfer, free, and/or dissociate from the substrate when at the intervention site in response to an in-situ enzymatic reaction resulting in a weak bond between the coating and the substrate.

"Thermal Stimulation" as used herein refers to use of a thermal stimulus to influence the freeing, dissociation, and/or transfer of the coating from the substrate. For example, thermal stimulation can comprise at least one of a hot stimulus and a cold stimulus. In embodiments, thermal stimulation comprises at least one of a hot stimulus and a cold stimulus adapted to augment the freeing, dissociation and/or transference of the coating from the substrate. In embodiments, thermal stimulation comprises at least one of a hot stimulus and a cold stimulus adapted to initiate the freeing, dissociation and/or transference of the coating from the substrate. In embodiments, thermal stimulation comprises at least one of a hot stimulus and a cold stimulus adapted to cause the freeing, dissociation and/or transference of the coating from the substrate.

"Electromagnetic Stimulation" as used herein refers to use of an electromagnetic stimulus to influence the freeing, dissociation, and/or transfer of the coating from the substrate. For example, the electromagnetic stimulation is an electromagnetic wave comprising at least one of, e.g., a radio wave, a micro wave, a infrared wave, near infrared wave, a visible light wave, an ultraviolet wave, a X-ray wave, and a gamma wave. In embodiments, the electromagnetic stimulation is adapted to augment the freeing, dissociation and/or transference of the coating from the substrate. In embodiments, the electromagnetic stimulation is adapted to initiate the freeing, dissociation and/or transference of the coating from the substrate. In embodiments, the electromagnetic stimulation is adapted to cause the freeing, dissociation and/or transference of the coating from the substrate.

"Sonic Stimulation" as used herein refers to use of a sonic stimulus to influence the freeing, dissociation, and/or transfer of the coating from the substrate. For example, sonic stimulation can comprise a sound wave, wherein the sound wave is at least one of an ultrasound wave, an acoustic sound wave, and an infrasound wave. In embodiments, the sonic stimulation is adapted to augment the freeing, dissociation and/or transfer of the coating from the substrate. In embodiments, the sonic stimulation is adapted to initiate the freeing, dissociation and/or transfer of the coating from the substrate. In embodiments, the sonic stimulation is adapted to cause the freeing, dissociation and/or transfer of the coating from the substrate.

"Release Agent" as used herein refers to a substance or substrate structure that influences the ease, rate, or extent, of release of the coating from the substrate. In certain embodiments wherein the device is adapted to transfer a portion of the coating and/or active agent from the substrate to the intervention site, the device can be so adapted by, e.g., substrate attributes and/or surface modification of the substrate (for non-limiting example: substrate composition, substrate materials, substrate shape, substrate deployment attributes, substrate delivery attributes, substrate pattern, and/or substrate texture), the delivery system of the substrate and coating (for non-limiting example: control over the substrate, control over the coating using the delivery system, the type of delivery system provided, the materials of the delivery system, and/or combinations thereof), coating attributes and/or physical characteristics of the coating (for non-limiting example: selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute), release agent attributes (for non-limiting example: through the selection a particular release agent and/or the manner in which the release agent is employed to transfer the coating and/or the active agent, and/or the amount of the release agent used), and/or a combination thereof. Release agents may include biocompatible release agents, non-biocompatible release agents to aggravate and/or otherwise induce a healing response or induce inflammation, powder release agents, lubricants (e.g. ePTFE, sugars, other known lubricants), micronized drugs as the release agent (to create a burst layer after the coating is freed from the substrate, physical release agents (patterning of the substrate to free the coating, others), and/or agents that change properties upon insertion (e.g. gels, lipid films, vitamin E, oil, mucosal adhesives, adherent hydrogels, etc.). Methods of patterning a substrate are described, e.g., in U.S. Pat. No. 7,537,610, "Method and system for creating a textured surface on an implantable medical device." In embodiments, more than one release agent is used, for example, the substrate can be patterned and also lubricated. In some embodiments, the release agent comprises a viscous fluid.

In some embodiments, the release agent comprises a viscous fluid. In some embodiments, the viscous fluid comprises oil. In some embodiments, the viscous fluid is a fluid that is viscous relative to water. In some embodiments, the viscous fluid is a fluid that is viscous relative to blood. In some embodiments, the viscous fluid is a fluid that is viscous relative to urine. In some embodiments, the viscous fluid is a fluid that is viscous relative to bile. In some embodiments, the viscous fluid is a fluid that is viscous relative to synovial fluid. In some embodiments, the viscous fluid is a fluid that is viscous relative to saline. In some embodiments, the viscous fluid is a fluid that is viscous relative to a bodily fluid at the intervention site.

In some embodiments, the release agent comprises a physical characteristic of the substrate. In some embodiments, the physical characteristic of the substrate comprises at least one of a patterned coating surface and a ribbed coating surface. In some embodiments, the patterned coating surface comprises a stent framework. In some embodiments, the ribbed coating surface comprises an undulating substrate surface. In some embodiments, the ribbed coating surface comprises an substrate surface having bumps thereon.

In some embodiments, the release agent comprises a physical characteristic of the coating. In some embodiments, the physical characteristic of the coating comprises a pattern. In some embodiments, the pattern is a textured surface on the substrate side of the coating, wherein the substrate side of the coating is the part of the coating on the substrate. In some embodiments, the pattern is a textured surface on the intervention site side of the coating, wherein the intervention site side of the coating is the part of the coating that is transferred to, and/or delivered to, and/or deposited at the intervention site.

"Extrusion" and/or "Extruded" and/or to "Extrude" as used herein refers to the movement of a substance away from another substance or object, especially upon stimulation, e.g., by a mechanical force. For example, in embodiments of the invention, the coating is extruded from the substrate.

Provided herein is a medical device comprising a substrate and a coating on at least a portion of the substrate, wherein the coating comprises an active agent, wherein the coating is patterned, and wherein at least a portion of the coating is adapted to free from the substrate upon stimulation of the coating.

Provided herein is a medical device comprising a substrate and a coating on at least a portion of the substrate, wherein the coating comprises an active agent, wherein the coating is patterned, and wherein at least a portion of the coating is adapted to dissociate from the substrate upon stimulation of the coating.

Provided herein is a medical device comprising a substrate and a coating on at least a portion of the substrate, wherein the coating comprises an active agent, wherein the coating is patterned, and wherein at least a portion of the coating is adapted to transfer from the substrate to an intervention site upon stimulation of the coating.

In some embodiments, the patterned coating comprises at least two different shapes.

"Patterned" as used herein in reference to the coating refers to a coating having at least two different shapes. The shapes can be formed by various methods, including for example, etching, masking, electrostatic capture, and/or by the coating methods described herein. For example the coating may have voids that are at least partially through the thickness of the coating. In some embodiments, the voids extend fully through the coating. The voids may be in a regular configuration, or irregular in shape. The voids may form a repeating configuration to form the patterned coating. The voids may have been removed from a smooth or solid coating to form a patterned coating. The coating may in some embodiments be patterned by having a surface that is ribbed, wavy or bumpy. The coating may in some embodiments be patterned by having been cut and/or etched from a coating sheath and/or sheet in a particular design. The sheath and/or sheet in such embodiments may have been formed using the coating methods for manufacture as described herein. The pattern design may be chosen to improve the freeing, transfer, and/or dissociation from the substrate. The pattern design may be chosen to improve the transfer and/or delivery to the intervention site.

Patterned coatings may be created using the methods and processes described herein, for non-limiting example, by providing a substrate having a patterned design thereon comprising, for example, a material that is chosen to selectively capture the coating particles (whether active agent, polymer, or other coating particles) to coat only a desired portion of the substrate. This portion that is coated may be the patterned design of the substrate.

The term "image enhanced polymer" or "imaging agent" as used herein refer to an agent that can be used with the devices and methods of the invention to view at least one component of the coating, either while the coating is on the substrate or after it is freed, dissociated and/or transferred. In embodiments, an image enhanced polymer serves as a tracer, allowing the movement or location of the coated device to be identified, e.g., using an imaging system. In other embodiments, an image enhanced polymer allows the practitioner to monitor the delivery and movement of a coating component. In embodiments, use of an image enhanced polymer enables the practitioner to determine the dose of a component of the coating (e.g., the active agent) that is freed, dissociated and/or transferred. Information provided by the image enhanced polymer or imaging agent about the amount of coating transferred to the intervention site can allow the practitioner to determine the rate at which the coating will be released, thereby allowing prediction of dosing over time. Imaging agents may comprise barium compounds such as, for non-limiting example, barium sulfate. Imaging agents may comprise iodine compounds. Imaging agents may comprise any compound that improves radiopacity.

In embodiments, an image enhanced polymer is used with the device and methods of the invention for a purpose including, but not limited to, one or more of the following: monitoring the location of the substrate, e.g., a balloon or other device; assessing physiological parameters, e.g., flow and perfusion; and targeting to a specific molecule. In embodiments, "smart" agents that activate only in the presence of their intended target are used with the device and methods of the invention.

Provided herein is a method comprising: providing a medical device, wherein the medical device comprises a substrate and a coating on at least a portion of the substrate, wherein the coating comprises an active agent; and tacking at least a portion of the coating to an intervention site. In some embodiments, the tacking the coating portion (i.e. the portion of the coating) to the intervention site is upon stimulating the coating with a stimulation.

In some embodiments, the substrate comprises a balloon. In some embodiments, the portion of the balloon having coating thereon comprises an outer surface of the balloon. In some embodiments, the outer surface is a surface of the balloon exposed to a coating prior to balloon folding. In some embodiments, the outer surface is a surface of the balloon exposed to a coating following balloon folding. In some embodiments, the outer surface is a surface of the balloon exposed to a coating following balloon crimping. In some embodiments, the coating comprises a material that undergoes plastic deformation at pressures provided by inflation of the balloon. In some embodiments, the coating comprises a material that undergoes plastic deformation at a pressure that is less than the rated burst pressure of the balloon.

In some embodiments, the coating comprises a material that undergoes plastic deformation at a pressure that is less than the nominal inflation pressure of the balloon. In some embodiments, the coating comprises a material that undergoes plastic deformation with at least 8 ATM of pressure. In some embodiments, the coating comprises a material that undergoes plastic deformation with at least 6 ATM of pressure. In some embodiments, the coating comprises a material that undergoes plastic deformation with at least 4 ATM of pressure. In some embodiments, the coating comprises a material that undergoes plastic deformation with at least 2 ATM of pressure.

In some embodiments, the balloon is a compliant balloon. In some embodiments, the balloon is a semi-compliant balloon. In some embodiments, the balloon is a non-compliant balloon. In some embodiments, the balloon conforms to a shape of the intervention site.

In some embodiments, the balloon comprises a cylindrical portion. In some embodiments, the balloon comprises a substantially spherical portion. In some embodiments, the balloon comprises a complex shape. In some embodiments, the complex shape comprises at least one of a double noded shape, a triple noded shape, a waisted shape, an hourglass shape, and a ribbed shape.

Some embodiments provide devices that can serve interventional purposes in addition to delivery of therapeutics, such as a cutting balloon. In some embodiments, the substrate comprises a cutting balloon. In some embodiments, the cutting balloon comprises at least one tacking element adapted to tack the coating to the intervention site. In some embodiments, the tacking element is adapted to secure the coating to the cutting balloon until inflation of the cutting balloon. In some embodiments, the tacking element comprises a wire. In some embodiments, the wire is shaped in the form of an outward pointing wedge. In some embodiments, the tacking element does not cut tissue at the intervention site.

One illustration devices provided herein include a cutting balloon for the treatment of vascular disease (e.g.; occluded lesions in the coronary or peripheral vasculature). In this embodiment, the coating may be preferentially located on the 'cutting wire' portion of the device. Upon deployment, the wire pushes into the plaque to provide the desired therapeutic 'cutting' action. During this cutting, the polymer and drug coating is plastically deformed off of the wire by the combination of compressive and shear forces acting on the wire—leaving some or all of the coating embedded in the plaque and/or artery wall. A similar approach may be applied to delivery of oncology drugs (a) directly to tumors and/or, (b) to the arteries delivering blood to the tumors for site-specific chemotherapy, and/or (c) to the voids left after the removal of a tumor (lumpectomy). These oncology (as well as other non-vascular) applications may not require the 'cutting' aspects and could be provided by coatings directly onto the balloon or onto a sheath over the balloon or according to an embodiment wherein the coating forms a sheath over the deflated (pleated) balloon.

A cutting balloon embodiment described herein provides several advantages. Such embodiment allows for concentrating the mechanical force on the coating/wire as the balloon is inflated—the wire may serve to concentrate the point-of-contact-area of the balloon expansion pressure resulting in a much higher force for plastic deformation of the drug and polymer coating vs. the non-cutting plain balloon which may distribute the pressure over a much larger area (therefore lower force proportional to the ratio of the areas). Embodiments involving a cutting balloon provide for the use of polymers that would otherwise be too rigid (higher modulus) to deform from a non-cutting balloon.

Other embodiments provided herein are based on geometric configurations of the device that optimize both the deformation and the bulk-migration of the coating from the device. In one embodiment wherein the device is a cutting balloon, the (coated) wire of the cutting balloon is shaped like a wedge, pointed outward.

Another embodiment provides catheter-based devices where the drug-delivery formulation is delivered to the therapeutic site in the vasculature via inflation of a balloon.

One embodiment provides coated percutaneous devices (e.g.; balloons, whether cutting balloons or other balloon types) that, upon deployment at a specific site in the patient, transfer some or all of the drug-delivery formulation (5-10%, 10-25%, 25-50%, 50-90%, 90-99%, 99-100%) to the site of therapeutic demand. In certain embodiments, the balloon is at least in part cylindrical as expanded or as formed. In certain embodiments, the balloon is at least in part bulbous as expanded or as formed. In certain embodiments, the balloon is at least in part spherical as expanded or as formed. In certain embodiments, the balloon has a complex shape as expanded or as formed (such as a double noded shape, a triple noded shape, has a waist, and/or has an hourglass shape, for non-limiting example).

In some embodiments, transferring at least a portion of the active agent comprises transferring at least about 3%, at least about 5%, at least about 10%, at least about 20%, at least about 30%, greater than 35%, at least about 50%, at least about 75%, at least about 85%, at least about 90%, at least about 95%, and/or at least about 99% of the active agent from the substrate. In some embodiments, stimulating decreases the contact between the coating and the substrate. In some embodiments, transferring transfers less than about 1%, less than about 5%, less than about 10%. less than about 15%, less than about 25%, at most about 35%, less than about 50%, less than about 70%, less than about 80%, and/or less than about 90% of the active agent absent stimulating at least one of the coating and the substrate.

The term "adapted to transfer at least a portion" of the coating or active agent to an intervention site refers to a device that is designed to transfer any portion of the coating or active agent to an intervention site.

The term "adapted to free" a portion of a coating and/or active agent from the substrate refers to a device, coating, and/or substrate that is designed to free a certain percentage of the coating and/or active agent from the substrate. As used herein, a device, coating, and/or substrate that is designed to free a certain percentage of the coating and/or active agent from the substrate is designed to unrestrain the coating and/or active agent from the substrate, and/or to remove any obstruction and/or connection the coating may have to the substrate (whether direct or indirect).

In some embodiments, the device is adapted to free a portion of the coating and/or active agent from the substrate. For non-limiting example, the device is so adapted by substrate attributes (for non-limiting example: substrate composition, substrate materials, shape, substrate deployment attributes, substrate delivery attributes, substrate pattern, and/or substrate texture), the delivery system of the substrate and coating (for non-limiting example: control over the substrate, control over the coating using the delivery system, the type of delivery system provided, the materials of the delivery system, and/or combinations thereof), coating attributes (for non-limiting example: selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute), release agent attributes (for non-limiting example: through the selection a particular release agent and/or how the release agent is employed to transfer the coating and/or the active agent, and/or how much of the release agent is used), and/or a combination thereof.

In some embodiments, the substrate is adapted to free a portion of the coating and/or active agent from the substrate. For non-limiting example, the substrate is so adapted by selection of the substrate composition, substrate materials, shape, substrate deployment attributes, substrate delivery attributes, substrate pattern, and/or substrate texture, and/or combinations thereof. For example, a balloon can be designed to only partially inflate within the confines of the intervention site. Partial inflation can prevent a designated portion of coating from being freed.

In some embodiments, the coating is adapted to free a portion of the coating and/or active agent from the substrate. For non-limiting example the coating may be so adapted by selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute.

In some embodiments, the substrate is adapted to free a portion of the coating and/or active agent from the substrate to the intervention site. For non-limiting example, the substrate is so adapted by selection of the substrate composition, substrate materials, shape, substrate deployment attributes, substrate delivery attributes, substrate pattern, and/or substrate texture, and/or combinations thereof. For example, a balloon can be designed to only partially inflate within the confines of the intervention site. Partial inflation can prevent a designated portion of coating from being freed.

In some embodiments, the coating is adapted to free a portion of the coating and/or active agent from the substrate to the intervention site. For non-limiting example the coating may be so adapted by selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute.

In some embodiments, freeing at least a portion of the coating comprises freeing at least about 10%, at least about 20%, at least about 30%, greater than 35%, at least about 50%, at least about 75%, at least about 85%, at least about 90%, at least about 95%, and/or at least about 99% of the coating from the substrate. In some embodiments, stimulating decreases the contact between the coating and the substrate. In some embodiments, freeing frees less than about 1%, less than about 5%, less than about 10%. less than about 15%, less than about 25%, at most about 35%, less than about 50%, less than about 70%, less than about 80%, and/or less than about 90% of the coating absent stimulating at least one of the coating and the substrate.

The term "adapted to dissociate" a portion of a coating and/or active agent from the substrate refers to a device, coating, and/or substrate that is designed to dissociate a certain percentage of the coating and/or active agent from the substrate. As used herein, a device, coating, and/or substrate that is designed to dissociate a certain percentage of the coating and/or active agent from the substrate is designed to remove from association between the coating (and/or active agent) and the substrate. Also and/or alternatively, as used herein, a device, coating, and/or substrate that is designed to dissociate a certain percentage of the coating and/or active agent from the substrate is designed to separate the coating (and/or active agent) from the substrate. This separation may be reversible in some embodiments. This separation may not be reversible in some embodiments.

In some embodiments, the device is adapted to dissociate a portion of the coating and/or active agent from the substrate. For non-limiting example, the device is so adapted by substrate attributes (for non-limiting example: substrate composition, substrate materials, shape, substrate deployment attributes, substrate delivery attributes, substrate pattern, and/or substrate texture), the delivery system of the substrate and coating (for non-limiting example: control over the substrate, control over the coating using the delivery system, the type of delivery system provided, the materials of the delivery system, and/or combinations thereof), coating attributes (for non-limiting example: selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute), release agent attributes (for non-limiting example: through the selection a particular release agent and/or how the release agent is employed to transfer the coating and/or the active agent, and/or how much of the release agent is used), and/or a combination thereof.

In some embodiments, the substrate is adapted to dissociate a portion of the coating and/or active agent from the substrate. For non-limiting example, the substrate is so adapted by selection of the substrate composition, substrate materials, shape, substrate deployment attributes, substrate delivery attributes, substrate pattern, and/or substrate texture, and/or combinations thereof. For example, a balloon can be designed to only partially inflate within the confines of the intervention site. Partial inflation can prevent a designated portion of coating from being freed.

In some embodiments, the coating is adapted to dissociate a portion of the coating and/or active agent from the substrate. For non-limiting example the coating may be so adapted by selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute.

In some embodiments, the substrate is adapted to free a portion of the coating and/or active agent from the substrate to the intervention site. For non-limiting example, the substrate is so adapted by selection of the substrate composition, substrate materials, shape, substrate deployment attributes, substrate delivery attributes, substrate pattern, and/or substrate texture, and/or combinations thereof. For example, a balloon can be designed to only partially inflate within the confines of the intervention site. Partial inflation can prevent a designated portion of coating from being freed.

In some embodiments, the coating is adapted to dissociate a portion of the coating and/or active agent from the substrate to the intervention site. For non-limiting example the coating may be so adapted by selection of the active agent and/or the polymer and/or the polymer-active agent composition, or by the coating having a particular pattern—e.g. a ribbed pattern, a textured surface, a smooth surface, and/or another pattern, coating thickness, coating layers, and/or another physical and/or compositional attribute.

In some embodiments, dissociating at least a portion of the coating comprises dissociating at least about 10%, at least about 20%, at least about 30%, greater than 35%, at least about 50%, at least about 75%, at least about 85%, at least about 90%, at least about 95%, and/or at least about 99% of the coating from the substrate. In some embodiments, stimulating decreases the contact between the coating and the substrate. In some embodiments, dissociating dissociates less than about 1%, less than about 5%, less than about 10%. less than about 15%, less than about 25%, at most about 35%, less than about 50%, less than about 70%, less than about 80%, and/or less than about 90% of the coating absent stimulating at least one of the coating and the substrate.

"Plastic deformation" as used herein is the change in the physical shape of the coating by forces induced on the device. Plastic deformation results in increasing the contact area of the coating on the tissue and decreasing the contact area of the coating on the device. This change in contact area results in some or all of the coating being preferentially exposed to the tissue instead of the device. The terms "plastic deformation" and "plastically deform," as used herein in the context of a coating, are intended to include the expansion of the coating material beyond the elastic limit of the material such that the material is permanently deformed. "Elastic deformation" as used herein refers to a reversible alteration of the form or dimensions of the object under stress or strain, e.g., inflation pressure of a balloon substrate. The terms "plastic deformation" and "plastically deform," as used herein in the context of a balloon or other substrate, are intended to include the expansion of the substrate beyond the elastic limit of the substrate material such that the substrate material is permanently deformed. Once plastically deformed, a material becomes substantially inelastic and generally will not, on its own, return to its pre-expansion size and shape. "Residual plastic deformation" refers to a deformation capable of remaining at least partially after removal of the inflation stress, e.g., when the balloon is deflated. "Elastic deformation" as used herein refers to a reversible alteration of the form or dimensions of the object (whether it is the coating or the substrate) under stress or strain, e.g., inflation pressure.

"Shear transfer" as used herein is the force (or component of forces) orthogonal to the device that would drive the coating away from the device substrate. This could be induced on the device by deployment, pressure-response from the surrounding tissue and/or in-growth of tissue around the coating.

"Bulk migration" as used herein is the incorporation of the coating onto/into the tissue provided by the removal of the device and/or provided by degradation of the coating over time and/or provided by hydration of the coating over time. Degradation and hydration of the coating may reduce the coating's cohesive and adhesive binding to the device, thereby facilitating transfer of the coating to the tissue.

One embodiment may described by analogy to contact printing whereby a biochemically active 'ink' (the polymer+ drug coating) from a 'die' (the device) to the 'stock' (the site in the body).

The devices and methods described in conjunction with some of the embodiments provided herein are advantageously based on specific properties provided for in the drug-delivery formulation. One such property, especially well-suited for non-permanent implants such as balloon catheters, cutting balloons, etc. is 'soft' coating that undergoes plastic deformation at pressures provided by the inflation of the balloon (range 2-25 ATM, typically 10-18 ATM). Another such property, especially well-suited to permanent implants such as stents is coatings where the polymer becomes 'soft' at some point after implant either by hydration or by degradation or by combinations of hydration and degradation.

Some embodiments provide devices that can advantageously be used in conjunction with methods that can aid/promote the transfer of the coating. These include introducing stimuli to the coated device once on-site in the body (where the device is delivered either transiently or permanently). Such stimuli can be provided to induce a chemical response (light, heat, radiation, etc.) in the coating or can provide mechanical forces to augment the transfer of the coating into the tissue (ultrasound, translation, rotation, vibration and combinations thereof).

In some embodiments, the coating is freed, dissociated, and/or transferred from the substrate using a mechanical stimulation. In some embodiments, the coating is freed from the substrate using a mechanical stimulation. In some embodiments, the coating is dissociated from the substrate using a mechanical stimulation. In some embodiments, the coating is transferred from the substrate using a mechanical stimulation. In some embodiments, the coating is transferred to the intervention site using a mechanical stimulation. In some embodiments, the coating is delivered to the intervention site using a mechanical stimulation. In some embodiments, the mechanical stimulation is adapted to augment the freeing, dissociation and/or transference of the coating from the substrate. In some embodiments, the mechanical stimulation is adapted to initiate the freeing, dissociation and/or transference of the coating from the substrate. In some embodiments, the mechanical stimulation is adapted to cause the freeing, dissociation and/or transference of the coating from the substrate. In some embodiments, the mechanical stimulation comprises at least one of a compressive force, a shear force, a tensile force, a force exerted on the coating from a substrate side of the coating, a force exerted on the coating by the substrate, a force exerted on the coating from an external element, a translation, a rotation, a vibration, and a combination thereof. In some embodiments, the external element is a part of the subject. In some embodiments, the external element is not part of the device.

In some embodiments, the external element comprises a liquid. In some embodiments, the liquid is forced between the coating and the substrate. In some embodiments, the liquid comprises saline. In some embodiments, the liquid comprises water. In some embodiments, the mechanical stimulation comprises a geometric configuration of the substrate that maximizes a shear force on the coating. In some embodiments, the mechanical stimulation comprises a geometric configuration of the substrate that increases a shear force on the coating. In some embodiments, the mechanical stimulation comprises a geometric configuration of the substrate that enhances a shear force on the coating.

In some embodiments, the coating is freed, dissociated, and/or transferred from the substrate using a chemical stimulation. In some embodiments, the coating is freed from the substrate using a chemical stimulation. In some embodiments, the coating is dissociated from the substrate using a chemical stimulation. In some embodiments, the coating is transferred from the substrate using a chemical stimulation. In some embodiments, the coating is transferred to the intervention site using a chemical stimulation. In some embodiments, the coating is delivered to the intervention site using a chemical stimulation. In some embodiments, the chemical stimulation comprises at least one of bulk degradation, interaction with a bodily fluid, interaction with a bodily tissue, a chemical interaction with a non-bodily fluid, a chemical interaction with a chemical, an acid-base reaction, an enzymatic reaction, hydrolysis, and combinations thereof. In some embodiments, the chemical stimulation comprises bulk degradation of the coating. In some embodiments, the chemical stimulation comprises interaction of the coating or a portion thereof with a bodily fluid. In some embodiments, the chemical stimulation comprises interaction of the coating or a portion thereof with a bodily tissue. In some embodiments, the chemical stimulation comprises a chemical interaction of the coating or a portion thereof with a non-bodily fluid. In some embodiments, the chemical stimulation comprises a chemical interaction of the coating or a portion thereof with a chemical. In some embodiments, the chemical stimulation comprises an acid-base reaction. In some embodiments, the chemical stimulation comprises an enzymatic reaction. In some embodiments, the chemical stimulation comprises hydrolysis.

In some embodiments, the chemical stimulation is adapted to augment the freeing, dissociation and/or transference of the coating from the substrate. In some embodiments, the chemical stimulation is adapted to initiate the freeing, dissociation and/or transference of the coating from the substrate. In some embodiments, the chemical stimulation is adapted to cause the freeing, dissociation and/or transference of the coating from the substrate. In some embodiments, the coating comprises a material that is adapted to transfer, free, and/or dissociate from the substrate when at the intervention site in response to an in-situ enzymatic reaction resulting in a weak bond between the coating and the substrate.

In some embodiments, the coating is freed, dissociated, and/or transferred from the substrate using a thermal stimulation. In some embodiments, the coating is freed from the substrate using a thermal stimulation. In some embodiments, the coating is dissociated from the substrate using a thermal stimulation. In some embodiments, the coating is transferred from the substrate using a thermal stimulation. In some embodiments, the coating is transferred to the intervention site using a thermal stimulation. In some embodiments, the coating is delivered to the intervention site using a thermal stimulation. In some embodiments, the thermal stimulation comprises at least one of a hot stimulus and a cold stimulus adapted to augment the freeing, dissociation and/or transference of the coating from the substrate. In some embodiments, the thermal stimulation is adapted to cause the freeing, dissociation and/or transference of the coating from the substrate. In some embodiments, the thermal stimulation comprises at least one of a hot stimulus and a cold stimulus adapted to initiate the freeing, dissociation and/or transference of the coating from the substrate. In some embodiments, the thermal stimulation comprises at least one of a hot stimulus and a cold stimulus adapted to initiate the freeing, dissociation and/or transference of the coating from the substrate.

In some embodiments, the coating is freed, dissociated, and/or transferred from the device by a electromagnetic stimulation. In some embodiments, the coating is freed from the substrate using a electromagnetic stimulation. In some embodiments, the coating is dissociated from the substrate using a electromagnetic stimulation. In some embodiments, the coating is transferred from the substrate using a electromagnetic stimulation. In some embodiments, the coating is transferred to the intervention site using a electromagnetic stimulation. In some embodiments, the coating is delivered to the intervention site using a electromagnetic stimulation. In some embodiments, the electromagnetic stimulation comprises an electromagnetic wave comprising at least one of a radio wave, a micro wave, a infrared wave, near infrared wave, a visible light wave, an ultraviolet wave, a X-ray wave, and a gamma wave. In some embodiments, the electromagnetic stimulation is adapted to augment the freeing, dissociation and/or transference of the coating from the substrate. In some embodiments, the electromagnetic stimulation is adapted to initiate the freeing, dissociation and/or transference of the coating from the substrate. In some embodiments, the electromagnetic stimulation is adapted to cause the freeing, dissociation and/or transference of the coating from the substrate.

In some embodiments, the coating is freed, dissociated, and/or transferred from the device by a sonic stimulation. In some embodiments, the coating is freed from the substrate using a sonic stimulation. In some embodiments, the coating is dissociated from the substrate using a sonic stimulation. In some embodiments, the coating is transferred from the substrate using a sonic stimulation. In some embodiments, the coating is transferred to the intervention site using a sonic stimulation. In some embodiments, the coating is delivered to the intervention site using a sonic stimulation. In some embodiments, the sonic stimulation comprises a sound wave, wherein the sound wave is at least one of an ultrasound wave, an acoustic sound wave, and an infrasound wave. In some embodiments, the sonic stimulation is adapted to augment the freeing, dissociation and/or transference of the coating from the substrate. In some embodiments, the sonic stimulation is adapted to initiate the freeing, dissociation and/or transference of the coating from the substrate. In some embodiments, the sonic stimulation is adapted to cause the freeing, dissociation and/or transference of the coating from the substrate.

In some embodiments, the coating is freed, dissociated, and/or transferred from the device by a combination of at least two of a mechanical stimulation, a chemical stimulation, an electromagnetic stimulation, and a sonic stimulation.

In some embodiments, the coating is freed, dissociated, and/or transferred from the substrate by extrusion.

Provided herein are device geometries that maximize the shear forces on the coating. Such geometric design of the device provides two advantages: (1) increases (concentrates) the force to plastically deform the drug and polymer coating (2) decreases the force of adhesion of the coating. For example, a wedge-shape aligns the forces of deformation along a shear plan as opposed to direct compression. This embodiment provides for: (1) increased efficiency in terms of % of the coating transferred (2) increased precision in amount transferred on a case-by-case basis (3) utilization of 'harder/stiffer' materials (biopolymers) that would otherwise not deform and/or not bulk-migrate under deployment conditions (4) minimize the chance of particulate shedding via purposefully designing the shape and direction of both the deformation and bulk migration. For example for a wedge, particles would be less likely because the coating would be pre-disposed as a shear from the device in a sheet form—with the use of soft materials, this may be illustrated as a coating of silicone caulk being extruded from the pressure of a rod being pushed into a mattress.

Another embodiment provide a geometric arrangement of the coating whereby layers, e.g. a laminate structure, are provided in the coating to modulate and control the plastic deformation, shearing and bulk-migration of the coating into the tissue.

One embodiment provides coated substrates that, upon deployment at a specific site in the patient, transfer some or all of the coating (5-10%, 10-25%, 25-50%, 50-90%, 90-99%, 99-100%) to the site of therapeutic demand.

In some embodiments, the device further comprises a release agent. In some embodiments, the release agent is biocompatible. In some embodiments, the release agent is non-biocompatible. In some embodiments, the release agent comprises a powder. In some embodiments, the release agent comprises a lubricant. In some embodiments, the release agent comprises a surface modification of the substrate.

In some embodiments, the release agent comprises a physical characteristic of the coating. In some embodiments, the physical characteristic of the coating comprises a pattern. In some embodiments, the pattern is a textured surface on the substrate side of the coating, wherein the substrate side of the coating is the part of the coating on the substrate. In some embodiments, the pattern is a textured surface on the intervention site side of the coating, wherein the intervention site side of the coating is the part of the coating that is transferred to, and/or delivered to, and/or deposited at the intervention site.

In some embodiments, the release agent comprises a viscous fluid. In some embodiments, the viscous fluid comprises oil. In some embodiments, the viscous fluid is a fluid that is viscous relative to water. In some embodiments, the viscous fluid is a fluid that is viscous relative to blood. In some embodiments, the viscous fluid is a fluid that is viscous relative to urine. In some embodiments, the viscous fluid is a fluid that is viscous relative to bile. In some embodiments, the viscous fluid is a fluid that is viscous relative to synovial fluid. In some embodiments, the viscous fluid is a fluid that is viscous relative to saline. In some embodiments, the viscous fluid is a fluid that is viscous relative to a bodily fluid at the intervention site.

In some embodiments, the release agent comprises a gel.

In some embodiments, the release agent comprises at least one of the active agent and another active agent. The active agent may be placed on the substrate prior to the coating in order to act as the release agent. The active agent may be a different active agent than the active agent in the coating. The active agent that is the release agent may provide for a second source of drug to be delivered to the intervention site or another location once the coating is released from (or transferred from, or freed from, or dissociated from) the substrate.

In some embodiments, the release agent comprises a physical characteristic of the substrate. In some embodiments, the physical characteristic of the substrate comprises at least one of a patterned coating surface and a ribbed coating surface. In some embodiments, the patterned coating surface comprises a stent framework. In some embodiments, the ribbed coating surface comprises an undulating substrate surface. In some embodiments, the ribbed coating surface comprises an substrate surface having bumps thereon.

In some embodiments, the release agent comprises a property that is capable of changing at the intervention site. In some embodiments, the property comprises a physical property. In some embodiments, the property comprises a chemical property. In some embodiments, the release agent is capable of changing a property when in contact with at least one of a biologic tissue and a biologic fluid. In some embodiments, the release agent is capable of changing a property when in contact with an aqueous liquid.

In some embodiments, the release agent is between the substrate and the coating.

In some embodiments, at least a portion of the pharmaceutical agent is encapsulated using a single emulsion/evaporation technique. In some embodiments, the technique comprises at least the steps of (1) combining a first polymer (e.g. PVA) and water to form a first polymer solution; combining a second polymer (e.g. PLGA) and an organic solvent (e.g. dichloromethane) to form a second polymer solution; combining the second polymer (e.g. PLGA) and the organic solvent (e.g. dichloromethane) to form a third polymer solution; and combining the pharmaceutical agent and a polar aprotic solvent (e.g. DMSO) to form a pharmaceutical agent solution, (2) mixing the second polymer solution and pharmaceutical agent solution, (3) adding the first polymer solution and homogenizing the resulting mixture; (4) adding the third polymer solution; (5) optionally, allowing the organic solvent to evaporate; and (6) filtering the remaining solution. In some embodiments, the filtration is accomplished using a centrifuge. In some embodiments, the filtration is accomplished by passing the mixture through filter paper. In some embodiments, the encapsulated pharmaceutical agent is further resuspended in water and lyophilized.

In some embodiments, the polymer concentration of the first polymer solutions is from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1.5% to about 2.5%, or about 2%. As used herein, the term "about" when used in reference to the polymer concentration expressed as a percentage means a variation of 0.05%, 0.1%, 0.2%, 0.25%, 0.3%, 0.4%, or 0.5%. For example a polymer concentration that is about 2% may be expressed as 2%+/−0.5% (i.e. 1.5%-2.5%), or may be from 1.95-2.05% (2%+/−0.05%), depending on the embodiment. In some embodiments, the polymer concentration of the first polymer solutions is from 1% to 10%, from 1% to 9%, from 1% to 8%, from 1% to 7%, from 1% to 6%, from 1% to 5%, from 1% to 4%, from 1% to 3%, from 1.5% to 2.5%, or 2%.

In some embodiments, the polymer concentration of the second polymer solution is from about 10 mg/mL to about 100 mg/mL, from about 15 mg/mL to about 95 mg/mL. from about 20 mg/mL to about 90 mg/mL, from about 25 mg/mL to about 85 mg/mL, from about 30 mg/mL to about 80 mg/mL, from about 35 mg/mL to about 75 mg/mL, from about 40 mg/mL to about 70 mg/mL, from about 40 mg/mL to about 60 mg/mL, from about 45 mg/mL to about 55 mg/mL, or about 50 mg/mL. As used herein, the term "about" when used in reference to the polymer concentration expressed in mg/mL means a variation of 1 mg/mL, 5 mg/mL, 10 mg/mL, or 15 mg/mL, depending on the embodiment. In some embodiments, the polymer concentration of the second polymer solution is from 10 mg/mL to 100 mg/mL, from 15 mg/mL to 95 mg/mL. from 20 mg/mL to 90 mg/mL, bet from ween 25 mg/mL to 85 mg/mL, from 30 mg/mL to 80 mg/mL, from 35 mg/mL to 75 mg/mL, from 40 mg/mL to 70 mg/mL, from 40 mg/mL to 60 mg/mL, from 45 mg/mL to 55 mg/mL, or 50 mg/mL In some embodiments, the polymer concentration of the third polymer solutions is from about 0.5% to about 5%, from about 0.5% to about 4.5%, from about 0.5% to about 4%, from about 0.5% to about 3.5%, from about 0.5% to about 3%, from about 0.5% to about 2.5%, from about 0.5% to about 2%, from about 0.5% to about 1.5%, or about 2%. As used herein, the term "about" when used in reference to the polymer concentration expressed as a percentage means a variation of 0.05%, 0.1%, 0.2%, 0.25%, 0.3%, 0.4%, or 0.5%. For example a polymer concentration that is about 2% may be expressed as 2%+/−0.5% (i.e. 1.5%-2.5%), or may be from 1.95-2.05% (2%+/−0.05%), depending on the embodiment. In some embodiments, the polymer concentration of the third polymer solutions is from 0.5% to 5%, from 0.5% to 4.5%, from 0.5% to 4%, from 0.5% to 3.5%, from 0.5% to 3%, from 0.5% to 2.5%, from 0.5% to 2%, from 0.5% to 1.5%, or 2%.

In some embodiments, the concentration of the pharmaceutical agent in the pharmaceutical agent solution is from about 1 mg/mL to about 50 mg/mL, from about 1 mg/mL to about 40 mg/mL. from about 1 mg/mL to about 30 mg/mL, from about 2 mg/mL to about 30 mg/mL, from about 5 mg/mL to about 30 mg/mL, from about 5 mg/mL to about 25 mg/mL, from about 5 mg/mL to about 20 mg/mL, from about 5 mg/mL to about 15 mg/mL, from about 7 mg/mL to about 12 mg/mL, or about 10 mg/mL. As used herein, the term "about" when used in reference to the polymer concentration expressed in mg/mL means a variation of 0.5 mg/mL, 1 mg/mL, 5 mg/mL, 10 mg/mL, or 15 mg/mL, depending on the embodiment. In some embodiments, the concentration of the pharmaceutical agent in the pharmaceutical agent solution is from 1 mg/mL to 50 mg/mL, between 1 mg/mL to 40 mg/mL. from 1 mg/mL to 30 mg/mL, from 2 mg/mL to 30 mg/mL, from 5 mg/mL to 30 mg/mL, from 5 mg/mL to 25 mg/mL, from 5 mg/mL to 20 mg/mL, from 5 mg/mL to 15 mg/mL, from 7 mg/mL to 12 mg/mL, or 10 mg/mL.

In some embodiments, the volume of the organic solvent removed by evaporation is at least 5%, at least 10%, at least 15%, at least 20%, at least 30%, at least 40%, at least 45%, at least 50%, at least, 55%, at least 60%, at least 65%, at least 70%, at least 75%, at least 80%, at least 85%, at least 90%, or at least 95%. In some embodiments, the volume of the organic solvent removed by evaporation is 5%-95%, at 5%-85%, 5%-50%, 5%-25%, 5%-10%, 10%-95%, 10%-50%, 10%-30%, 20%-95%, 30%-75%, 40%-95%, 50%-95%, 70%-90%, 75%-95%, or 80%-95%.

In some embodiment, a crystalline pharmaceutical agent can be encapsulated by emulsion-based encapsulation processes. In some embodiments, at least a portion of the pharmaceutical agent is encapsulated using a technique that comprises at least the steps of (1) combining a first polymer (e.g. PVA) and water to form a first polymer solution, combining a second polymer (e.g. PLGA) and an organic solvent (e.g. dichloromethane) to form a second polymer solution, and combining the second polymer and the organic solvent to form a third polymer solution; (2) mixing the first and second polymer solutions and allowing the organic solvent to evaporate to form an emulsion; (3) mixing the pharmaceutical agent to the third polymer solution to form a suspension; (4) combining the emulsion and suspension to form an emulsion-based mixture; and (5) filtering the emulsion-based mixture. In some embodiments, the filtration is accomplished using a centrifuge. In some embodiments the filtration is accomplished by pouring the solution through filter paper. In some embodiments, the encapsulated pharmaceutical agent is further resuspended in water and lyophilized.

In some embodiments, the polymer concentration of the first polymer solutions is from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1.5% to about 2.5%, or about 2%. As used herein, the term "about" when used in reference to the polymer concentration expressed as a percentage means a variation of 0.05%, 0.1%, 0.15%, 0.2%, 0.3%, 0.4%, or 0.5%. For example a polymer concentration that is about 2% may be expressed as 2%+/−0.5% (i.e. 1.5%-2.5%), or may be from 1.95-2.05% (2%+/−0.05%), depending on the embodiment. In some embodiments, the polymer concentration of the first polymer solutions is from 1% to 10%, from 1% to 9%, from 1% to 8%, from 1% to 7%, from 1% to 6%, from 1% to 5%, from 1% to 4%, from 1% to 3%, from 1.5% to 2.5%, or 2%.

In some embodiments, the polymer concentration of the second polymer solution is from about 10 mg/mL to about 100 mg/mL, from about 15 mg/mL to about 95 mg/mL. from about 20 mg/mL to about 90 mg/mL, from about 25 mg/mL to about 85 mg/mL, from about 30 mg/mL to about 80 mg/mL, from about 35 mg/mL to about 75 mg/mL, from about 40 mg/mL to about 70 mg/mL, from about 40 mg/mL to about 60 mg/mL, from about 45 mg/mL to about 55 mg/mL, or about 50 mg/mL. As used herein, the term "about" when used in reference to the polymer concentration expressed in mg/mL means a variation of 0.5 mg/mL, 1 mg/mL, 5 mg/mL, 10 mg/mL, or 15 mg/mL, depending on the embodiment. In some embodiments, the polymer concentration of the second polymer solution is from 10 mg/mL to 100 mg/mL, from 15 mg/mL to 95 mg/mL. from 20 mg/mL to 90 mg/mL, from 25 mg/mL to 85 mg/mL, from 30 mg/mL to 80 mg/mL, from 35 mg/mL to 75 mg/mL, from 40 mg/mL to 70 mg/mL, from 40 mg/mL to 60 mg/mL, from 45 mg/mL to 55 mg/mL, or 50 mg/mL.

In some embodiments, the polymer concentration of the third polymer solutions is from about 0.5% to about 5%, from about 0.5% to about 4.5%, from about 0.5% to about 4%, from about 0.5% to about 3.5%, from about 0.5% to about 3%, from about 0.5% to about 2.5%, from about 0.5% to about 2%, from about 0.5% to about 1.5%, or about 2%. As used herein, the term "about" when used in reference to the polymer concentration expressed as a percentage means a variation of 0.05%, 0.1%, 0.15%, 0.2%, 0.3%, 0.4%, or 0.5%. For example a polymer concentration that is about 2% may be expressed as 2%+/−0.5% (i.e. 1.5%-2.5%), or may be from 1.95-2.05% (2%+/−0.05%), depending on the embodiment. In some embodiments, the polymer concentration of the third polymer solutions is from 0.5% to 5%, from 0.5% to 4.5%, from 0.5% to 4%, from 0.5% to 3.5%, from 0.5% to 3%, from 0.5% to 2.5%, from 0.5% to 2%, from 0.5% to 1.5%, or 2%.

In some embodiments, the concentration of the pharmaceutical agent in the pharmaceutical agent-third polymer solution mixture is from about 0.01 mg/mL to about 0.1 mg/mL, from about 0.02 mg/mL to about 0.09 mg/mL. from about 0.03 mg/mL to about 0.08 mg/mL, from about 0.03 mg/mL to about 0.07 mg/mL, from about 0.04 mg/mL to about 0.07 mg/mL, from about 0.04 mg/mL to about 0.06 mg/mL, or about 0.05 mg/mL. As used herein, the term "about" when used in reference to the pharmaceutical agent concentration expressed in mg/mL means a variation of 0.001 mg/mL, 0.005 mg/mL, 5 mg/mL, 0.002 mg/mL, 0.0025 mg/mL, or 0.1 mg/mL, depending on the embodiment. In some embodiments, the concentration of the pharmaceutical agent in the pharmaceutical agent-third polymer solution mixture is from 0.01 mg/mL to 0.1 mg/mL, from 0.02 mg/mL to 0.09 mg/m, from 0.03 mg/mL to 0.08 mg/mL, from 0.03 mg/mL to 0.07 mg/mL, from 0.04 mg/mL to 0.07 mg/mL, from 0.04 mg/mL to about 0.06 mg/mL, or about 0.05 mg/mL.

In some embodiments, the volume of the organic solvent removed by evaporation during the encapsulation process is at least 5%, at least 10%, at least 15%, at least 20%, at least 30%, at least 40%, at least 45%, at least 50%, at least, 55%, at least 60%, at least 65%, at least 70%, at least 75%, at least 80%, at least 85%, at least 90%, and at least 95%. In some embodiments, the volume of the organic solvent removed by evaporation during the encapsulation process is 5%-95%, at 5%-85%, 5%-50%, 5%-25%, 5%-10%, 10%-95%, 10%-50%, 10%-30%, 20%-95%, 30%-75%, 40%-95%, 50%-95%, 70%-90%, 75%-95%, or 80%-95%.

In some embodiment, the polymer-encapsulated pharmaceutical agent is in the form of microspheres or microparticles. Examples of microspheres relevant to the present disclosure include: Luzzi, L. A., J. Pharm. Psy. 59:1367 (1970); U.S. Pat. No. 4,530,840; Lewis, D. H., "Controlled Release of Bioactive Agents from Lactides/Glycolide Polymers" in Biodegradable Polymers as Drug Delivery Systems, Chasin, M. and Langer, R., eds., Marcel Decker (1990); U.S. Pat. No. 4,675,189; Beck et al., "Poly(lactic acid) and Poly(lactic acid-co-glycolic acid) Contraceptive Delivery Systems," in Long Acting Steroid Contraception, Mishell, D. R., ed., Raven Press (1983); U.S. Pat. No. 4,758,435; U.S. Pat. No. 3,773,919; U.S. Pat. No. 4,474,572. Examples of protein therapeutics formulated as microspheres include: U.S. Pat. No. 6,458,387; U.S. Pat. No. 6,268,053; U.S. Pat. No. 6,090,925; U.S. Pat. No. 5,981,719; and U.S. Pat. No. 5,578,709, and are herein incorporated by reference for such disclosure.

Microspheres usually have a spherical shape, although irregularly-shaped microparticles are possible. Microspheres may vary in size, ranging from submicron to 1000 micron diameters. Microspheres suitable for use with the medical device coating disclosed herein are submicron to 250 micron diameter microspheres. The microspheres are prepared by any method which produces microspheres in a size range acceptable for use in the coating method disclosed herein.

Suitable examples of polymeric materials for use in the microsphere or microparticles herein include poly(glycolic acid), poly-d,l-lactic acid, poly-l-lactic acid, copolymers of the foregoing, poly(aliphatic carboxylic acids), copolyoxalates, polycaprolactone, polydioxonene, poly(orthocarbonates), poly(acetals), poly(lactic acid-caprolactone), polyorthoesters, poly(glycolic acid-caprolactone), polydioxonene, polyanhydrides, polyphosphazines, and natural polymers including albumin, casein, and some waxes, such as, glycerol mono- and distearate, and the like. Various commercially available poly(lactide-co-glycolide) materials (PLGA) are optionally used in the method disclosed herein. For example, poly(d,l-lactic-co-glycolic acid) is commercially available from Boehringer-Ingelheim as RESOMER RG 503 H. This product has a mole percent composition of 50% lactide and 50% glycolide. These copolymers are available in a wide range of molecular weights and ratios of lactic acid to glycolic acid. One embodiment includes the use of the polymer poly(d,l-lactide-co-glycolide). The molar ratio of lactide to glycolide in such a copolymer includes the range of from about 95:5 to about 50:50.

The molecular weight of the polymeric material is of some importance. In some embodiment, the molecular weight is high enough so that it forms satisfactory polymer coatings, i.e., the polymer should be a good film former. Usually, a satisfactory molecular weight is in the range of 5,000 to 500,000 daltons. The molecular weight of a polymer is also important from the point of view that molecular weight influences the biodegradation rate of the polymer. The pharmaceutical agent is released from the microparticles through diffusional through the polymer material, through biodegradation of the polymer material, or through a combination of both. By an appropriate selection of polymeric materials a microsphere formulation is made such that the resulting microspheres exhibit both diffusional release and biodegradation release properties. This is useful in affording multiphasic release patterns.

A variety of methods are known by which compounds are encapsulated in microspheres. In these methods, the pharmaceutical agent is generally dispersed or emulsified, using stirrers, agitators, or other dynamic mixing techniques, in a solvent containing a wall-forming material. Solvent is then removed from the microspheres, and thereafter the microsphere product is obtained.

In one embodiment, the polymer-encapsulated pharmaceutical agent used herein are made through the incorporation of the pharmaceutical agents and/or other pharmaceutical agents into poly(lactic-glycolic acid)-polyvinyl alcohol microspheres. In another embodiment, the auris sensory cell modulating agents are encapsulated into alginate microspheres. (See U.S. Pat. No. 6,036,978, incorporated herein for such disclosure). Biocompatible methacrylate-based polymers to encapsulate the pharmaceutical agent are optionally used in the formulations and methods disclosed herein. A wide range of methacrylate-based polymer systems are commercially available, such as the EUDRAGIT polymers marketed by Evonik. One useful aspect of methacrylate polymers is that the properties of the formulation are varied by incorporating various co-polymers. For example, poly(acrylic acid-co-methylmethacrylate) microparticles exhibit enhanced mucoadhesion properties as the carboxylic acid groups in the poly(acrylic acid) form hydrogen bonds with mucin (Park et al, Pharm. Res. (1987) 4(6):457-464). Variation of the ratio between acrylic acid and methylmethacrylate monomers serves to modulate the properties of the co-polymer. Methacrylate-based microparticles have also been used in protein therapeutic formulations (Naha et al, Journal of Microencapsulation 4 Feb. 2008 (online publication)).

An example of a conventional microencapsulation process for pharmaceutical preparations is shown in U.S. Pat. No. 3,737,337, incorporated herein by reference for such disclosure. The pharmaceutical agent to be encapsulated or embedded are dissolved or dispersed in the organic solution of the polymer (phase A), using conventional mixers, including (in the preparation of dispersion) vibrators and high-speed stirrers, etc. The dispersion of phase (A), containing the core material in solution or in suspension, is carried out in the aqueous phase (B), again using conventional mixers, such as high-speed mixers, vibration mixers, or even spray nozzles, in which case the particle size of the microspheres will be determined not only by the concentration of phase (A), but also by the emulsate or microsphere size. With conventional techniques for the microencapsulation of auris sensory cell modulating agents, the microspheres form when the solvent containing an active agent and a polymer is emulsified or dispersed in an immiscible solution by stirring, agitating, vibrating, or some other dynamic mixing technique.

Methods for the construction of microspheres are also described in U.S. Pat. No. 4,389,330, and U.S. Pat. No. 4,530,840, incorporated herein by reference for such disclosure. The pharmaceutical agent is dissolved or dispersed in an appropriate solvent. To the agent-containing medium is added the polymeric matrix material in an amount relative to the active ingredient which gives a product of the desired loading of active agent. Optionally, all of the ingredients of the auris sensory cell modulating agent microsphere product can be blended in the solvent medium together. Suitable solvents for the agent and the polymeric matrix material include organic solvents such as acetone, halogenated hydrocarbons such as chloroform, methylene chloride and the like, aromatic hydrocarbon compounds, halogenated aromatic hydrocarbon compounds, cyclic ethers, alcohols, ethyl acetate and the like.

The mixture of ingredients in the solvent is emulsified in a continuous-phase processing medium; the continuous-phase medium being such that a dispersion of microdroplets containing the indicated ingredients is formed in the continuous-phase medium. Naturally, the continuous-phase processing medium and the organic solvent must be immiscible, and includes water although nonaqueous media such as xylene and toluene and synthetic oils and natural oils are optionally used. Optionally, a surfactant is added to the continuous-phase processing medium to prevent the microparticles from agglomerating and to control the size of the solvent microdroplets in the emulsion. A preferred surfactant-dispersing medium combination is a 1 to 10 wt. % poly(vinyl alcohol) in water mixture. The dispersion is formed by mechanical agitation of the mixed materials. An emulsion is optionally formed by adding small drops of the active agent-wall forming material solution to the continuous phase processing medium. The temperature during the formation of the emulsion is not especially critical but influences the size and quality of the microspheres and the solubility of the drug in the continuous phase. It is desirable to have as little of the agent in the continuous phase as possible. Moreover, depending on the solvent and continuous-phase processing medium employed, the temperature must not be too low or the solvent and processing medium will solidify or the processing medium will become too viscous for practical purposes, or too high that the processing medium will evaporate, or that the liquid processing medium will not be maintained. Moreover, the temperature of the medium cannot be so high that the stability of the particular agent being incorporated in the microspheres is adversely affected. Accordingly, the dispersion process is conducted at any temperature which maintains stable operating conditions, which preferred temperature being about 15° C. to 60° C., depending upon the drug and excipient selected.

The dispersion which is formed is a stable emulsion and from this dispersion the organic solvent immiscible fluid is optionally partially removed in the first step of the solvent removal process. The solvent is removed by techniques such as through evaporation, heating, the application of a reduced pressure or a combination of both. The temperature employed to evaporate solvent from the microdroplets generally should not degrade the pharmaceutical agent employed in the preparation of a given microparticle, nor should it be so high as to evaporate solvent at such a rapid rate to cause defects in the wall forming material. Generally, from 5 to 95%, of the solvent is removed in the first solvent removal step.

After the first stage, the dispersed microparticles in the solvent immiscible fluid medium are isolated from the fluid medium by any convenient means of separation. Thus, for example, the fluid is decanted from the microsphere or the microsphere suspension is filtered. Still other, various combinations of separation techniques are used if desired.

Following the isolation of the microspheres from the continuous-phase processing medium, the remainder of the solvent in the microspheres is removed by optional extraction. In this step, the microspheres are suspended in the same continuous-phase processing medium used in step one, with or without surfactant, or in another liquid. The extraction medium removes the solvent from the microspheres and yet does not dissolve the microspheres. During the extraction, the extraction medium with dissolved solvent is optionally removed and replaced with fresh extraction medium. This is best done on a continual basis. The rate of extraction medium replenishment of a given process is a variable which is determined at the time the process is performed and, therefore, no precise limits for the rate must be predetermined After the majority of the solvent has been removed from the microspheres, the microspheres are dried by exposure to air or by other conventional drying techniques such as vacuum drying, drying over a desiccant, or the like. This process is very efficient in encapsulating the auris sensory cell modulating agent since core loadings of up to 80 wt. %, preferably up to 60 wt. % are obtained.

Methods of Manufacturing Generally

In some embodiments, a coating is formed on the substrate by a process comprising depositing a polymer and/or the active agent by an e-RESS, an e-SEDS, or an e-DPC process. In some embodiments, the process of forming the coating provides improved adherence of the coating to the substrate prior to deployment of the device at the intervention site and facilitates dissociation of the coating from the substrate at the intervention site. In some embodiments, the coating is formed on the substrate by a process comprising depositing the active agent by an e-RESS, an e-SEDS, or an e-DPC process without electrically charging the substrate. In some embodiments, the coating is formed on the substrate by a process comprising depositing the active agent on the substrate by an e-RESS, an e-SEDS, or an e-DPC process without creating an electrical potential between the substrate and a coating apparatus used to deposit the active agent.

Means for creating the bioabsorbable polymer(s)+drug (s) coating of the device with or without a substrate:

- Spray coat the coating-form with drug and polymer as is done in Micell process (e-RESS, e-DPC, compressed-gas sintering).
- Perform multiple and sequential coating-sintering steps where different materials may be deposited in each step, thus creating a laminated structure with a multitude of thin layers of drug(s), polymer(s) or drug+polymer that build the final device.
- Perform the deposition of polymer(s)+drug(s) laminates with the inclusion of a mask on the inner (luminal) surface of the device. Such a mask could be as simple as a non-conductive mandrel inserted through the internal diameter of the coating form. This masking could take place prior to any layers being added, or be purposefully inserted after several layers are deposited continuously around the entire coating-form.

In some embodiments, the coating comprises a microstructure. In some embodiments, particles of the active agent are sequestered or encapsulated within the microstructure. In some embodiments, the microstructure comprises microchannels, micropores and/or microcavities. In some embodiments, the microstructure is selected to allow sustained release of the active agent. In some embodiments, the microstructure is selected to allow controlled release of the active agent.

Other methods for preparing the coating include solvent based coating methods and plasma based coating methods. In some embodiments, the coating is prepared by a solvent based coating method. In some embodiments, the coating is prepared by a solvent plasma based coating method.

Another advantage of the present invention is the ability to create a delivery device with a controlled (dialed-in) drug-elution profile. Via the ability to have different materials in each layer of the laminate structure and the ability to control the location of drug(s) independently in these layers, the method enables a device that could release drugs at very specific elution profiles, programmed sequential and/or parallel elution profiles. Also, the present invention allows controlled elution of one drug without affecting the elution of a second drug (or different doses of the same drug).

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of an e-RESS, an e-SEDS, and an e-DPC process, wherein forming the coating results in at least a portion of the coating being adapted to transfer from the substrate to an intervention site upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of an e-RESS, an e-SEDS, and an e-DPC process without electrically charging the substrate, wherein forming the coating results in at least a portion of the coating being adapted to transfer from the substrate to an intervention site upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of an e-RESS, an e-SEDS, and an e-DPC process without creating an electrical potential between the substrate and a coating apparatus used in the at least one e-RESS, an e-SEDS, and an e-DPC process, wherein forming the coating results in at least a portion of the coating being adapted to transfer from the substrate to an intervention site upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of a dipping and/or a spraying process, wherein forming the coating results in at least a portion of the coating being adapted to transfer from the substrate to an intervention site upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of an e-RESS, an e-SEDS, and an e-DPC process, wherein forming the coating results in at least a portion of the coating being adapted to free from the substrate upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of a dipping and/or a spraying process, wherein forming the coating results in at least a portion of the coating being adapted to free from the substrate upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of an e-RESS, an e-SEDS, and an e-DPC process, wherein forming the coating results in at least a portion of the coating being adapted to dissociate from the substrate upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of a dipping and/or a spraying process, wherein forming the coating results in at least a portion of the coating being adapted to dissociate from the substrate upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of an e-RESS, an e-SEDS, and an e-DPC process, wherein forming the coating results in at least a portion of the coating being adapted to deliver to the intervention site upon stimulating the coating with a stimulation.

Provided herein is a method of forming a medical device comprising a substrate and a coating on at least a portion of the substrate, wherein the coating comprises an active agent, the method comprising: providing the substrate; and forming the coating on at least a portion of the substrate by depositing the active agent by on the substrate by at least one of a dipping and/or a spraying process, wherein forming the coating results in at least a portion of the coating being adapted to deliver to the intervention site upon stimulating the coating with a stimulation.

In some embodiments, the e-RESS, the e-SEDS, and/or the e-DPC process used in forming the coating is performed without electrically charging the substrate. In some embodiments, the e-RESS, the e-SEDS, and/or the e-DPC process used in forming the coating is performed without creating an electrical potential between the substrate and the coating apparatus used in the e-RESS, the e-SEDS, and/or the e-DPC process.

In some embodiments, forming the coating results in the coating adhering to the substrate prior to the substrate reaching the intervention site.

Some embodiments further comprise providing a release agent on the substrate. In some embodiments, providing the release agent step is performed prior to the forming the coating step. In some embodiments, the release agent comprises at least one of: a biocompatible release agent, a non-biocompatible release agent, a powder, a lubricant, a surface modification of the substrate, a viscous fluid, a gel, the active agent, a second active agent, a physical characteristic of the substrate. In some embodiments, the physical characteristic of the substrate comprises at least one of: a patterned coating surface of the substrate, and a ribbed surface of the substrate. In some embodiments, the release agent comprises a property that is capable of changing at the intervention site. In some embodiments, the property comprises a physical property. In some embodiments, the property comprises a chemical property. In some embodiments, the release agent is capable of changing a property when in contact with at least one of a biologic tissue and a biologic fluid. In some embodiments, the release agent is capable of changing a property when in contact with an aqueous liquid. In some embodiments, the coating results in a coating property that facilitates transfer of the coating to the intervention site. In some embodiments, the coating property comprises a physical characteristic of the coating. In some embodiments, the physical characteristic comprises a pattern.

In some embodiments, forming the coating facilitates transfer of the coating to the intervention site.

In some embodiments, transferring, freeing, dissociating, depositing, and/or tacking step comprises softening the polymer by hydration, degradation or by a combination of hydration and degradation. In some embodiments, the transferring, freeing, dissociating, depositing, and/or tacking step comprises softening the polymer by hydrolysis of the polymer.

In some embodiments, the providing step comprises forming the coating by a solvent based coating method. In some embodiments, the providing step comprises forming the coating by a solvent plasma based method.

In some embodiments, providing the device comprises depositing a plurality of layers on the substrate to form the coating, wherein at least one of the layers comprises the active agent. In some embodiments, at least one of the layers comprises a polymer. In some embodiments, the polymer is bioabsorbable. In some embodiments, the active agent and the polymer are in the same layer, in separate layers, or form overlapping layers. In some embodiments, the plurality of layers comprise five layers deposited as follows: a first polymer layer, a first active agent layer, a second polymer layer, a second active agent layer and a third polymer layer.

EXAMPLES

The following examples are provided to illustrate selected embodiments. They should not be considered as limiting the scope of the invention, but merely as being illustrative and representative thereof. For each example listed herein, multiple analytical techniques may be provided. Any single technique of the multiple techniques listed may be sufficient to indicate the parameter and/or characteristic being tested, or any combination of techniques may be used to indicate such parameter and/or characteristic. Those skilled in the art will be familiar with a wide range of analytical techniques for the characterization of drug/polymer coatings. Techniques presented here, but not limited to, may be used to additionally and/or alternatively characterize specific properties of the coatings with variations and adjustments employed which would be obvious to those skilled in the art.

Sample Preparation

Generally speaking, coatings on stents, on balloons, on coupons, on other substrates, or on samples prepared for in-vivo models are prepared as herein. Nevertheless, modifications for a given analytical method are presented within the examples described, and/or would be obvious to one having skill in the art. Thus, numerous variations, changes, and substitutions will now occur to those skilled in the art without departing from the invention. It should be understood that various alternatives to the embodiments of the invention described herein and examples provided may be employed in practicing the invention and indicating the parameters and/or characteristics described.

Coatings on Balloons

Coated balloons as described herein and/or made by a method disclosed herein are prepared. In some examples, the coated balloons have a targeted coating thickness of ~15 microns (~5 microns of active agent). In some examples, the coating process is PDPDP (Polymer, sinter, Drug, Polymer, sinter, Drug, Polymer, sinter) using deposition of drug in dry powder form and deposition of polymer particles by RESS methods and equipment described herein. In the illustrations herein, resulting coated balloons may have a 3-layer coating comprising polymer (for example, PLGA) in the first layer, drug (for example, rapamycin) in a second layer and polymer in the third layer, where a portion of the third layer is substantially drug free (e.g. a sub-layer within the third layer having a thickness equal to a fraction of the thickness of the third layer). As described layer, the middle layer (or drug layer) may be overlapping with one or both first (polymer) and third (polymer) layer. The overlap between the drug layer and the polymer layers is defined by extension of polymer material into physical space largely occupied by the drug. The overlap between the drug and polymer layers may relate to partial packing of the drug particles during the formation of the drug layer. When crystal drug particles are deposited on top of the first polymer layer, voids and or gaps may remain between dry crystal particles. The voids and gaps are available to be occupied by particles deposited during the formation of the third (polymer) layer. Some of the particles from the third (polymer) layer may rest in the vicinity of drug particles in the second (drug) layer. When the sintering step is completed for the third (polymer) layer, the third polymer layer particles fuse to form a continuous film that forms the third (polymer) layer. In some embodiments, the third (polymer) layer however will have a portion along the longitudinal axis of the stent whereby the portion is free of contacts between polymer material and drug particles. The portion of the third layer that is substantially of contact with drug particles can be as thin as 1 nanometer.

Polymer-coated balloons having coatings comprising polymer but no drug are made by a method disclosed herein and are prepared having a targeted coating thickness of, for example, about 0.5, 1, 2, 3, 4, 5, 10, 15, 20, 25, 30, 35, 40, 45, or 50 microns, depending in part on whether the coating expands upon hydration and if so whether it is hydrated. In embodiments, the coating thickness is 1-5 microns. In other embodiments, it is 1-10 microns.

An example coating process is PPP (PLGA, sinter, PLGA, sinter, PLGA, sinter) using RESS methods and equipment described herein. These polymer-coated balloons may be used as control samples in some of the examples, infra.

In some examples, the balloons are made of a compliant polymer. In some examples, the balloons are made of a non-compliant polymer. The balloons may be, in some examples, 5 to 50 mm in length, preferably 10-20 mm in length.

Balloons can be coated while inflated, and later compacted, or they can be coated while uninflated. If a balloon is coated while inflated and later folded or otherwise compacted, then a portion of the coating can be protected during insertion by virtue of being disposed within the portion of the balloon that is not exposed until inflation. The coating can also be protected by using a sheath or other covering, as described in the art for facilitating insertion of an angioplasty balloon.

The coating released from a balloon may be analyzed (for example, for analysis of a coating band and/or coating a portion of the balloon). Alternatively, in some examples, the coating is analyzed directly on the balloon. This coating, and/or coating and balloon, may be sliced into sections which may be turned 90 degrees and visualized using the surface composition techniques presented herein or other techniques known in the art for surface composition analysis (or other characteristics, such as crystallinity, for example). In this way, what could be an analysis of coating composition through a depth when the coating is on the balloon or as removed from the balloon (i.e. a depth from the abluminal surface of the coating to the surface of the removed coating that once contacted the balloon or a portion thereof), becomes a surface analysis of the coating which can, for example, indicate the layers in the slice of coating, at much higher resolution. Residual coating on an extracted balloon also can be analyzed and compared to the amount of coating on an unused balloon, using, e.g., HPLC, as noted herein. Coating removed from the balloon, or analyzed without removal and/or release from the balloon, may be treated the same way, and assayed, visualized, and/or characterized as presented herein using the techniques described and/or other techniques known to a person of skill in the art.

Sample Preparation for In-Vivo Models

Devices comprising balloons having coatings disclosed herein are deployed in the porcine coronary arteries of pigs (domestic swine, juvenile farm pigs, or Yucatan miniature swine). Porcine coronary angioplasty is exploited herein since such model yields results that are comparable to other investigations assaying neointimal hyperplasia in human subjects. The balloons are expanded to a 1:1.1 balloon:artery ratio. At multiple time points, animals are euthanized (e.g. t=1 day, 7 days, 14 days, 21 days, and 28 days), the tissue surrounding the intervention site is extracted, and assayed.

Devices comprising balloons having coatings disclosed herein alternatively are implanted in the common iliac arteries of New Zealand white rabbits. The balloons are expanded to a 1:1.1 balloon:artery ratio. At multiple time points, animals are euthanized (e.g., t=1 day, 7 days, 14 days, 21 days, and 28 days), the tissue surrounding the intervention site is extracted, and assayed.

Example 1: Cutting Balloons

Cutting Balloon (1)—Mechanical Stimulation to Free the Coating

A cutting balloon is coated comprising a polymer and an active agent. The coated cutting balloon is positioned at the intervention site. The balloon is inflated to at least 25% below its nominal inflation pressure. Upon deflation and removal of the cutting balloon from the intervention site, at least about 5% to at least about 30% of the coating is freed from the surface of the cutting balloon and is deposited at the intervention site.

In some examples, the balloon unfolds during inflation, causing mechanical shearing forces to at least augment transfer and/or freeing and/or deposition of the coating from the balloon to the intervention site.

In some examples, the balloon twists during inflation, causing mechanical shearing forces to at least augment transfer and/or freeing and/or deposition of the coating from the balloon.

In one example, the polymer of the coating is about 50:50 PLGA-Ester End Group, MW~19 kD, degradation rate~1-2 months or about 50:50 PLGA-Carboxylate End Group, MW~10 kD, degradation rate~28 days. The active agent is a pharmaceutical agent such as a macrolide immunosuppressive drug. Equipment and coating process similar to Example 1 is employed. The intervention site is a vascular lumen wall. Upon inflation of the cutting balloon, at least about 50% of the coating is freed from the device at the intervention site.

In another example, a cutting balloon is coated with a formulation of PLGA+sirolimus with total loading of sirolimus~20 μg with the coating preferentially on the wire of the cutting balloon. Equipment and process similar to Example 1 is employed. The intervention site is a coronary artery. Upon inflation of the cutting balloon, about 5% to about 15% of the coating is freed from the device resulting in delivery of ~2.0 μg of drug delivered to the artery.

In another example, the polymer of the coating is about 50:50 PLGA-Ester End Group, MW~19 kD, degradation rate~1-2 months or about 50:50 PLGA-Carboxylate End Group, MW~10 kD, degradation rate~28 days. The active agent is a chemotherapeutic agent. Equipment and coating process similar to Example 1 is employed. The intervention site is a cavity resulting from removal of a tumor. Upon inflation of the cutting balloon, at least about 75% of the coating is transferred from the device to the intervention site.

In-vivo testing: A group of 27 New Zealand white rabbits is prepared for a Seldinger procedure using a cutting balloon coated with a formulation of about 50:50 PLGA-Ester End Group (MW~19 kD, degradation rate~1-2 months) and sirolimus with total loading of sirolimus~20 μg with the coating preferentially on the wire of the cutting balloon. The device is placed at a coronary artery intervention site with the assistance of fluoroscopy to aid in positioning the device at the same location in each subject. Six animals are subjected to the procedure using a coated balloon that does not have sirolimus in the coating. After deployment and removal of the device, 3 control animals are sacrificed at 1 hour post deployment and serum and tissue samples are collected. The 3 remaining control animals are sacrificed at 56 days post deployment. During the course of the study, serum samples are collected from control and drug-treated animals every five days. The drug treated animals, 3 each, are sacrificed at 1 hour, 24 hours, 7 days, 14 days, 28 days, 42 days and 56 days post deployment. A serum sample as well as a tissue sample from the deployment site is collected.

The tissue and serum samples may be subjected to analysis for sirolimus concentration. In order to determine the amount of coating freed from the device and/or delivered to the intervention site as a percent of the total amount of coating on the substrate, the tissue concentration of sirolimus at the one hour time point (or any time point within the first day following of the procedure) may be used along with the total content expected for the coating (based on the total content for the manufacturing lot) or along with the content of coating remaining on the device once removed and the percentage calculated. This percentage is correlative of the percent of coating freed, dissociated, and/or transferred from the device and delivered to the intervention site. Alternatively, the tissue may be analyzed by various means (noted herein, including but not limited to SEM, TEM, and, where image enhanced polymers are used, various imaging means capable of detecting these enhanced polymers) to detect the percent of the coating freed, dissociated and/or transferred from the substrate and delivered to the intervention site. Again, the amount of coating known to be on the substrate based on manufacturing lot characteristics, and/or an assessment of the coating remaining on the device following removal of the device from the subject (for example, wherein the device is an angioplasty catheter and the substrate is the balloon of the catheter) may be used to determine the percent of coating freed, dissociated, and/or transferred from the device. In some instances, an assessment of the device following the procedure alone is sufficient to assess the amount freed or dissociated from the substrate, without determination of the amount delivered to the intervention site. Additionally, where a determination of improvement and/or disease treatment is desired, levels of proinflammatory markers could be tested to indicate improvement and/or treatment of a disease and/or ailment, for example, by testing high sensitive C-reactive protein (hsCRP), interleukin-6 (IL-6), interleukin-1β (IL-1β) and/or monocyte chemoattractant protein-1 (MCP-1). The release kinetics of the drug may be indicated by plotting the sirolimus concentrations at the timepoints noted above.

For embodiments using different drugs other than sirolimus, the biomarkers are selected based on the disease to be treated and the drugs administered during the course of therapy as determined by one of skill in the art. These biomarkers may be used to indicate the treatment results for each subject.

Other in-vivo tests described herein may be used instead of this test and/or in addition to this test, adjusted for the particularities of this device, as would be known to one of ordinary skill in the art.

In-vitro testing: One sample of the coated cutting balloon prepared in Example 1 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. Optical microscopy is performed on the tubing and/or the balloon (which is inflated to at least 25% below the balloon's nominal pressure, at least) to determine the presence and amount of coating transferred to the tubing and/or the amount of coating freed, dissociated, and/or transferred from the balloon. Other in-vitro tests described herein may be used instead of this test and/or in addition to this test, adjusted for the particularities of this device, as would be known to one of ordinary skill in the art.

Cutting Balloon (2)—Mechanical Stimulation to Free the Coating

A cutting balloon is coated using a solution-based system (spray or dip coating) comprising a polymer and an active agent. The coated cutting balloon is positioned at the intervention site. The balloon is inflated to at least 25% below its nominal inflation pressure. At least about 5% to at least about 30% of the coating is freed from the surface of the cutting balloon and is deposited at the intervention site.

In some examples, the balloon unfolds during inflation, causing mechanical shearing forces to at least augment transfer and/or freeing and/or deposition of the coating from the balloon to the intervention site.

In some examples, the balloon twists during inflation, causing mechanical shearing forces to at least augment transfer and/or freeing and/or deposition of the coating from the balloon.

In one example, the polymer of the coating is about 50:50 PLGA-Ester End Group, MW~19 kD, degradation rate~1-2 months or about 50:50 PLGA-Carboxylate End Group, MW~10 kD, degradation rate~28 days. The active agent is a pharmaceutical agent such as a macrolide immunosuppressive drug. Equipment and coating process using a spray and/or dip coating process is employed. The intervention site is a vascular lumen wall. Upon inflation of the cutting balloon, at least about 50% of the coating is freed from the device at the intervention site.

In another example, a cutting balloon is coated with a formulation of PLGA+sirolimus with total loading of sirolimus~20 μg with the coating preferentially on the wire of the cutting balloon. Equipment and coating process using a spray and/or dip coating process is employed. The intervention site is a coronary artery. Upon inflation of the cutting balloon, about 5% to about 15% of the coating is freed from the device resulting in delivery of ~2.0 μg of drug delivered to the artery.

In another example, the polymer of the coating is about 50:50 PLGA-Ester End Group, MW~19 kD, degradation rate~1-2 months or about 50:50 PLGA-Carboxylate End Group, MW~10 kD, degradation rate~28 days. The active agent is a chemotherapeutic agent. Equipment and coating process using a spray and/or dip coating process is employed. The intervention site is a cavity resulting from removal of a tumor. Upon inflation of the cutting balloon, at least about 75% of the coating is transferred from the device to the intervention site.

In-vivo testing: A group of 27 New Zealand white rabbits is prepared for a Seldinger procedure using a cutting balloon coated with a formulation of about 50:50 PLGA-Ester End Group (MW~19 kD, degradation rate~1-2 months) and sirolimus with total loading of sirolimus~20 μg with the coating preferentially on the wire of the cutting balloon. The device is placed at a coronary artery intervention site with the assistance of fluoroscopy to aid in positioning the device at the same location in each subject. Six animals are subjected to the procedure using a coated balloon that does not have sirolimus in the coating. After deployment and removal of the device, 3 control animals are sacrificed at 1 hour post deployment and serum and tissue samples are collected. The 3 remaining control animals are sacrificed at 56 days post deployment. During the course of the study, serum samples are collected from control and drug-treated animals every five days. The drug treated animals, 3 each, are sacrificed at 1 hour, 24 hours, 7 days, 14 days, 28 days, 42 days and 56 days post deployment.

The tissue and serum samples may be subjected to analysis for sirolimus concentration. In order to determine the amount of coating freed from the device and/or delivered to the intervention site as a percent of the total amount of coating on the substrate, the tissue concentration of sirolimus at the one hour time point (or any time point within the first day following of the procedure) may be used along with the total content expected for the coating (based on the total content for the manufacturing lot) or along with the content of coating remaining on the device once removed and the percentage calculated. This percentage is correlative of the percent of coating freed, dissociated, and/or transferred from the device and delivered to the intervention site. Alternatively, the tissue may be analyzed by various means (noted herein, including but not limited to SEM, TEM, and, where image enhanced polymers are used, various imaging means capable of detecting these enhanced polymers) to detect the percent of the coating freed, dissociated and/or transferred from the substrate and delivered to the intervention site. Again, the amount of coating known to be on the substrate based on manufacturing lot characteristics, and/or an assessment of the coating remaining on the device following removal of the device from the subject (for example, wherein the device is an angioplasty catheter and the substrate is the balloon of the catheter) may be used to determine the percent of coating freed, dissociated, and/or transferred from the device. In some instances, an assessment of the device following the procedure alone is sufficient to assess the amount freed or dissociated from the substrate, without determination of the amount delivered to the intervention site. Additionally, where a determination of improvement and/or disease treatment is desired, levels of proinflammatory markers could be tested to indicate improvement and/or treatment of a disease and/or ailment, for example, by testing high sensitive C-reactive protein (hsCRP), interleukin-6 (IL-6), interleukin-1β (IL-1β) and/or monocyte chemoattractant protein-1 (MCP-1). The release kinetics of the drug may be indicated by plotting the sirolimus concentrations at the timepoints noted above.

For embodiments using different drugs other than sirolimus, the biomarkers are selected based on the disease to be treated and the drugs administered during the course of therapy as determined by one of skill in the art. These biomarkers may be used to indicate the treatment results for each subject.

Other in-vivo tests described herein may be used instead of this test and/or in addition to this test, adjusted for the particularities of this device, as would be known to one of ordinary skill in the art.

In-vitro testing: One sample of the coated cutting balloon prepared in using spray and/or dip coating process is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. Optical microscopy is performed on the tubing and/or the balloon (which is inflated to at least 25% below the balloon's nominal pressure, at least) to determine the presence and amount of coating transferred to the tubing and/or the amount of coating freed, dissociated, and/or transferred from the balloon. Other in-vitro tests described herein may be used instead of this test and/or in addition to this test, adjusted for the particularities of this device, as would be known to one of ordinary skill in the art.

Cutting Balloon (3)—Mechanical Stimulation to Free the Coating

A cutting balloon is coated comprising a release agent, a polymer and an active agent. The coated cutting balloon is positioned at the intervention site. The balloon is inflated to at least 25% below its nominal inflation pressure. At least about 5% to at least about 50% of the coating is freed from the surface of the cutting balloon and is deposited at the intervention site.

In some examples, the balloon unfolds during inflation, causing mechanical shearing forces to at least augment transfer and/or freeing and/or deposition of the coating from the balloon to the intervention site.

In some examples, the balloon twists during inflation, causing mechanical shearing forces to at least augment transfer and/or freeing and/or deposition of the coating from the balloon.

In one example, the polymer of the coating is about 50:50 PLGA-Ester End Group, MW~19 kD, degradation rate~1-2 months or about 50:50 PLGA-Carboxylate End Group, MW~10 kD, degradation rate~28 days. The active agent is a pharmaceutical agent such as a macrolide immunosuppressive drug. Equipment and coating process similar to Example 2 is employed. The intervention site is a vascular lumen wall. Upon inflation of the cutting balloon, at least about 50% of the coating is freed from the device at the intervention site.

In another example, a cutting balloon is coated with a formulation of PLGA+sirolimus with total loading of sirolimus~20 µg with the coating preferentially on the wire of the cutting balloon. Equipment and process similar to Example 2 is employed. The intervention site is a coronary artery. The release agent is ePTFE powder. Upon inflation of the cutting balloon, about 5% to about 15% of the coating is freed from the device resulting in delivery of ~2.0 µg of drug delivered to the artery.

In another example, the polymer of the coating is about 50:50 PLGA-Ester End Group, MW~19 kD, degradation rate~1-2 months or about 50:50 PLGA-Carboxylate End Group, MW~10 kD, degradation rate~28 days. The active agent is a chemotherapeutic agent. Equipment and coating process similar to Example 2 is employed. The release agent a micronized active agent or another active agent in a micronized form. The intervention site is a cavity resulting from removal of a tumor. Upon inflation of the cutting balloon, at least about 75% of the coating is transferred from the device to the intervention site.

In-vivo testing: A group of 27 New Zealand white rabbits is prepared for a Seldinger procedure using a cutting balloon coated with a formulation of about 50:50 PLGA-Ester End Group (MW~19 kD, degradation rate~1-2 months) and sirolimus with total loading of sirolimus~20 µg with the coating preferentially on the wire of the cutting balloon. The device is placed at a coronary artery intervention site with the assistance of fluoroscopy to aid in positioning the device at the same location in each subject. Six animals are subjected to the procedure using a coated balloon that does not have sirolimus in the coating. After deployment and removal of the device, 3 control animals are sacrificed at 1 hour post deployment and serum and tissue samples are collected. The 3 remaining control animals are sacrificed at 56 days post deployment. During the course of the study, serum samples are collected from control and drug-treated animals every five days. The drug treated animals, 3 each, are sacrificed at 1 hour, 24 hours, 7 days, 14 days, 28 days, 42 days and 56 days post deployment. The tissue and serum samples may be subjected to analysis for sirolimus concentration.

In order to determine the amount of coating freed from the device and/or delivered to the intervention site as a percent of the total amount of coating on the substrate, the tissue concentration of sirolimus at the one hour time point (or any time point within the first day following of the procedure) may be used along with the total content expected for the coating (based on the total content for the manufacturing lot) or along with the content of coating remaining on the device once removed and the percentage calculated. This percentage is correlative of the percent of coating freed, dissociated, and/or transferred from the device and delivered to the intervention site. Alternatively, the tissue may be analyzed by various means (noted herein, including but not limited to SEM, TEM, and, where image enhanced polymers are used, various imaging means capable of detecting these enhanced polymers) to detect the percent of the coating freed, dissociated and/or transferred from the substrate and delivered to the intervention site. Again, the amount of coating known to be on the substrate based on manufacturing lot characteristics, and/or an assessment of the coating remaining on the device following removal of the device from the subject (for example, wherein the device is an angioplasty catheter and the substrate is the balloon of the catheter) may be used to determine the percent of coating freed, dissociated, and/or transferred from the device. In some instances, an assessment of the device following the procedure alone is sufficient to assess the amount freed or dissociated from the substrate, without determination of the amount delivered to the intervention site. Additionally, where a determination of improvement and/or disease treatment is desired, levels of proinflammatory markers could be tested to indicate improvement and/or treatment of a disease and/or ailment, for example, by testing high sensitive C-reactive protein (hsCRP), interleukin-6 (IL-6), interleukin-1β (IL-1β) and/or monocyte chemoattractant protein-1 (MCP-1). The release kinetics of the drug may be indicated by plotting the sirolimus concentrations at the timepoints noted above.

For embodiments using different drugs other than sirolimus, the biomarkers are selected based on the disease to be treated and the drugs administered during the course of therapy as determined by one of skill in the art. These biomarkers may be used to indicate the treatment results for each subject.

Other in-vivo tests described herein may be used instead of this test and/or in addition to this test, adjusted for the particularities of this device, as would be known to one of ordinary skill in the art.

In-vitro testing: One sample of the coated cutting balloon prepared in Example 2 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. Optical microscopy is performed on the tubing and/or the balloon (which is inflated to at least 25% below the balloon's nominal pressure, at least) to determine the presence and amount of coating transferred to the tubing and/or the amount of coating transferred from the balloon. Other in-vitro tests described herein may be used instead of this test and/or in addition to this test, adjusted for the particularities of this device, as would be known to one of ordinary skill in the art.

Cutting Balloon (4)—Mechanical Stimulation to Free the Coating

A cutting balloon is coated comprising a polymer and an active agent. The coated cutting balloon is positioned at the intervention site. The balloon is inflated to at least 25% below its nominal inflation pressure. At least about 10% to at least about 50% of the coating is freed from the surface of the cutting balloon and is deposited at the intervention site.

In some examples, the balloon unfolds during inflation, causing mechanical shearing forces to at least augment transfer and/or freeing and/or deposition of the coating from the balloon to the intervention site.

In some examples, the balloon twists during inflation, causing mechanical shearing forces to at least augment transfer and/or freeing and/or deposition of the coating from the balloon.

In one example, the polymer of the coating is about 50:50 PLGA-Ester End Group, MW~19 kD, degradation rate~1-2 months or about 50:50 PLGA-Carboxylate End Group, MW~10 kD, degradation rate~28 days. The active agent is a pharmaceutical agent such as a macrolide immunosuppressive drug. Equipment and coating process similar to Example 3 is employed. The intervention site is a vascular lumen wall. Upon inflation of the cutting balloon, at least about 50% of the coating is freed from the device at the intervention site.

In another example, a cutting balloon is coated with a formulation of PLGA+sirolimus with total loading of sirolimus~20 µg with the coating preferentially on the wire of the cutting balloon. Equipment and process similar to Example 3 is employed. The intervention site is a coronary artery. Upon inflation of the cutting balloon, about 5% to about 15% of the coating is freed from the device resulting in delivery of ~2.0 µg of drug delivered to the artery.

In another example, the polymer of the coating is about 50:50 PLGA-Ester End Group, MW~19 kD, degradation rate~1-2 months or about 50:50 PLGA-Carboxylate End Group, MW~10 kD, degradation rate~28 days. The active agent is a chemotherapeutic agent. Equipment and coating process similar to Example 3 is employed. The intervention site is a cavity resulting from removal of a tumor. Upon inflation of the cutting balloon, at least about 75% of the coating is transferred from the device to the intervention site.

In-vivo testing: A group of 27 New Zealand white rabbits is prepared for a Seldinger procedure using a cutting balloon coated with a formulation of about 50:50 PLGA-Ester End Group (MW~19 kD, degradation rate~1-2 months) and sirolimus with total loading of sirolimus~20 µg with the coating preferentially on the wire of the cutting balloon. The device is placed at a coronary artery intervention site with the assistance of fluoroscopy to aid in positioning the device at the same location in each subject. Six animals are subjected to the procedure using a coated balloon that does not have sirolimus in the coating. After deployment and removal of the device, 3 control animals are sacrificed at 1 hour post deployment and serum and tissue samples are collected. The 3 remaining control animals are sacrificed at 56 days post deployment. During the course of the study, serum samples are collected from control and drug-treated animals every five days. The drug treated animals, 3 each, are sacrificed at 1 hour, 24 hours, 7 days, 14 days, 28 days, 42 days and 56 days post deployment.

The tissue and serum samples may be subjected to analysis for sirolimus concentration. In order to determine the amount of coating freed from the device and/or delivered to the intervention site as a percent of the total amount of coating on the substrate, the tissue concentration of sirolimus at the one hour time point (or any time point within the first day following of the procedure) may be used along with the total content expected for the coating (based on the total content for the manufacturing lot) or along with the content of coating remaining on the device once removed and the percentage calculated. This percentage is correlative of the percent of coating freed, dissociated, and/or transferred from the device and delivered to the intervention site. Alternatively, the tissue may be analyzed by various means (noted herein, including but not limited to SEM, TEM, and, where image enhanced polymers are used, various imaging means capable of detecting these enhanced polymers) to detect the percent of the coating freed, dissociated and/or transferred from the substrate and delivered to the intervention site. Again, the amount of coating known to be on the substrate based on manufacturing lot characteristics, and/or an assessment of the coating remaining on the device following removal of the device from the subject (for example, wherein the device is a cutting angioplasty catheter and the substrate is the cutting balloon of the catheter) may be used to determine the percent of coating freed, dissociated, and/or transferred from the device. In some instances, an assessment of the device following the procedure alone is sufficient to assess the amount freed or dissociated from the substrate, without determination of the amount delivered to the intervention site. Additionally, where a determination of improvement and/or disease treatment is desired, levels of proinflammatory markers could be tested to indicate improvement and/or treatment of a disease and/or ailment, for example, by testing high sensitive C-reactive protein (hsCRP), interleukin-6 (IL-6), interleukin-1β (IL-1β) and/or monocyte chemoattractant protein-1 (MCP-1). The release kinetics of the drug may be indicated by plotting the sirolimus concentrations at the timepoints noted above.

For embodiments using different drugs other than sirolimus, the biomarkers are selected based on the disease to be treated and the drugs administered during the course of therapy as determined by one of skill in the art. These biomarkers may be used to indicate the treatment results for each subject.

Other in-vivo tests described herein may be used instead of this test and/or in addition to this test, adjusted for the particularities of this device, as would be known to one of ordinary skill in the art.

In-vitro testing: One sample of the coated cutting balloon prepared in Example 3 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. Optical microscopy is performed on the tubing and/or the balloon (which is inflated to at least 25% below the balloon's nominal pressure, at least) to determine the presence and amount of coating transferred to the tubing and/or the amount of coating freed, dissociated, and/or transferred from the balloon. Other in-vitro tests described herein may be used instead of this test and/or in addition to this test, adjusted for the particularities of this device, as would be known to one of ordinary skill in the art.

Cutting Balloon (5)—Mechanical and Chemical Stimulation to Free the Coating

A cutting balloon is coated with a formulation comprising a base layer of methyl acrylate-methacrylic acid copolymer and additional layers of PLGA+paclitaxel with total dose of paclitaxel approx. 0.5 μg/mm2 of the wire. The coating and sintering process is similar to that as described in Example 1. The balloon is constructed of a semipermable polymer. The pressurization medium is pH 8 phosphate buffer. The coated cutting balloon is positioned at the intervention site. The balloon is pressurized to at least to at least 25% below its nominal inflation pressure. Upon pressurization of the cutting balloon in the diseased artery, at least about 10% to at least about 30% of the coating is released into the intervention site and upon depressurization and removal of the device, this material is deposited at the intervention site.

In some examples, the balloon unfolds during inflation, causing mechanical shearing forces to at least augment the pH mediated release of the coating from the balloon to the intervention site.

In some examples, the balloon twists during inflation, causing mechanical shearing forces to at least augment the pH mediated release of the coating from the balloon.

In one example, a base layer of methyl acrylate-methacrylic acid copolymer is formed and additional layers of the coating is about 50:50 PLGA-Ester End Group, MW~19 kD, degradation rate~1-2 months or about 50:50 PLGA-Carboxylate End Group, MW~10 kD, degradation rate~28 days. The active agent is a pharmaceutical agent such as a macrolide immunosuppressive drug. Equipment and coating process similar to Example 1 is employed. The balloon is constructed of a semipermable polymer. The pressurization medium is pH 8 phosphate buffer. The intervention site is a vascular lumen wall. Upon inflation of the cutting balloon, at least about 50% of the coating is freed from the device at the intervention site.

In another example, a cutting balloon is coated with a base layer of methyl acrylate-methacrylic acid copolymer and additional layers of PLGA+sirolimus with total loading of sirolimus~20μ. Equipment and process similar to Example 1 is employed. The intervention site is a coronary artery. The balloon is constructed of a semipermable polymer. The pressurization medium is pH 8 phosphate buffer. Upon inflation of the cutting balloon, about 5% to about 15% of the coating is freed from the device resulting in delivery of ~2.0 μg of drug delivered to the artery.

In another example, the polymer of the coating is about 50:50 PLGA-Ester End Group, MW~19 kD, degradation rate~1-2 months or about 50:50 PLGA-Carboxylate End Group, MW~10 kD, degradation rate~28 days. The active agent is a chemotherapeutic agent. Equipment and coating process similar to Example 1 is employed. The intervention site is a cavity resulting from removal of a tumor. Upon inflation of the cutting balloon, at least about 75% of the coating is transferred from the device to the intervention site.

In-vivo testing: A group of 27 New Zealand white rabbits is prepared for a Seldinger procedure using a cutting balloon coated with a formulation of about 50:50 PLGA-Ester End Group (MW~19 kD, degradation rate~1-2 months) and sirolimus with total loading of sirolimus~20 μg with the coating preferentially on the wire of the cutting balloon. The device is placed at a coronary artery intervention site with the assistance of fluoroscopy to aid in positioning the device at the same location in each subject. Six animals are subjected to the procedure using a coated balloon that does not have sirolimus in the coating. After deployment and removal of the device, 3 control animals are sacrificed at 1 hour post deployment and serum and tissue samples are collected. The 3 remaining control animals are sacrificed at 56 days post deployment. During the course of the study, serum samples are collected from control and drug-treated animals every five days. The drug treated animals, 3 each, are sacrificed at 1 hour, 24 hours, 7 days, 14 days, 28 days, 42 days and 56 days post deployment.

The tissue and serum samples may be subjected to analysis for sirolimus concentration. In order to determine the amount of coating freed from the device and/or delivered to the intervention site as a percent of the total amount of coating on the substrate, the tissue concentration of sirolimus at the one hour time point (or any time point within the first day following of the procedure) may be used along with the total content expected for the coating (based on the total content for the manufacturing lot) or along with the content of coating remaining on the device once removed and the percentage calculated. This percentage is correlative of the percent of coating freed, dissociated, and/or transferred from the device and delivered to the intervention site. Alternatively, the tissue may be analyzed by various means (noted herein, including but not limited to SEM, TEM, and, where image enhanced polymers are used, various imaging means capable of detecting these enhanced polymers) to detect the percent of the coating freed, dissociated and/or transferred from the substrate and delivered to the intervention site. Again, the amount of coating known to be on the substrate based on manufacturing lot characteristics, and/or an assessment of the coating remaining on the device following removal of the device from the subject (for example, wherein the device is an cutting angioplasty catheter and the substrate is the cutting balloon of the catheter) may be used to determine the percent of coating freed, dissociated, and/or transferred from the device. In some instances, an assessment of the device following the procedure alone is sufficient to assess the amount freed or dissociated from the substrate, without determination of the amount delivered to the intervention site. Additionally, where a determination of improvement and/or disease treatment is desired, levels of proinflammatory markers could be tested to indicate improvement and/or treatment of a disease and/or ailment, for example, by testing high sensitive C-reactive protein (hsCRP), interleukin-6 (IL-6), interleukin-1β (IL-1β) and/or monocyte chemoattractant protein-1 (MCP-1). The release kinetics of the drug may be indicated by plotting the sirolimus concentrations at the timepoints noted above.

For embodiments using different drugs other than sirolimus, the biomarkers are selected based on the disease to be treated and the drugs administered during the course of therapy as determined by one of skill in the art. These biomarkers may be used to indicate the treatment results for each subject.

Other in-vivo tests described herein may be used instead of this test and/or in addition to this test, adjusted for the particularities of this device, as would be known to one of ordinary skill in the art.

In-vitro testing: One sample of the coated cutting balloon prepared in Example 1 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. Optical microscopy is performed on the tubing and/or the balloon (which is inflated to at least 25% below the balloon's nominal pressure, at least) to determine the presence and amount of coating transferred to the tubing and/or the amount of coating freed, dissociated, and/or transferred from the balloon. Other in-vitro tests described herein may be used instead of this test and/or in addition to this test, adjusted for the particularities of this device, as would be known to one of ordinary skill in the art.

Example 2: Drug-Delivery Balloon Catheters

Drug-Delivery Balloon (1)—Compliant Balloon

A compliant balloon is coated with a material comprising a polymer and an active agent. The coated compliant balloon is positioned at the intervention site. The balloon is inflated to at least 25% below its nominal inflation pressure. Upon deflation and removal of the compliant balloon from the intervention site, at least about 5% to at least about 30% of the coating is freed from the surface of the compliant balloon and is deposited at the intervention site.

In some examples, the balloon unfolds during inflation, causing mechanical shearing forces to at least augment transfer and/or freeing and/or deposition of the coating from the balloon to the intervention site.

In some examples, the balloon twists during inflation, causing mechanical shearing forces to at least augment transfer and/or freeing and/or deposition of the coating from the balloon.

In one example, the polymer of the coating is about 50:50 PLGA-Ester End Group, MW~19 kD, degradation rate~1-2 months or about 50:50 PLGA-Carboxylate End Group, MW~10 kD, degradation rate~28 days. The active agent is a pharmaceutical agent such as a macrolide immunosuppressive drug. Equipment and coating process similar to Example 1 is employed. The intervention site is a vascular lumen wall. Upon inflation of the compliant balloon, at least about 50% of the coating is freed from the device at the intervention site.

In another example, a compliant balloon is coated with a formulation of PLGA+sirolimus with total loading of sirolimus~20 µg. Equipment and process similar to Example 1 is employed. The intervention site is a coronary artery. Upon inflation of the compliant balloon, about 5% to about 15% of the coating is freed from the device resulting in delivery of ~2.0 µg of drug delivered to the artery.

In another example, the polymer of the coating is 50:50 PLGA-Ester End Group, MW~19 kD, degradation rate~1-2 months or 50:50 PLGA-Carboxylate End Group, MW~10 kD, degradation rate~28 days. The active agent is a chemotherapeutic agent. Equipment and coating process similar to Example 1 is employed. The intervention site is a cavity resulting from removal of a tumor. Upon inflation of the compliant balloon, at least about 75% of the coating is transferred from the device to the intervention site.

In-vivo testing: A group of 27 New Zealand white rabbits is prepared for a Seldinger procedure using a compliant balloon coated with a formulation of about 50:50 PLGA-Ester End Group (MW~19 kD, degradation rate~1-2 months) and sirolimus with total loading of sirolimus~20 µg. The device is placed at a coronary artery intervention site with the assistance of fluoroscopy to aid in positioning the device at the same location in each subject. Six animals are subjected to the procedure using a coated balloon that does not have sirolimus in the coating. After deployment and removal of the device, 3 control animals are sacrificed at 1 hour post deployment and serum and tissue samples are collected. The 3 remaining control animals are sacrificed at 56 days post deployment. During the course of the study, serum samples are collected from control and drug-treated animals every five days. The drug treated animals, 3 each, are sacrificed at 1 hour, 24 hours, 7 days, 14 days, 28 days, 42 days and 56 days post deployment. The tissue and serum samples may be subjected to analysis for sirolimus concentration.

In order to determine the amount of coating freed from the device and/or delivered to the intervention site as a percent of the total amount of coating on the substrate, the tissue concentration of sirolimus at the one hour time point (or any time point within the first day following of the procedure) may be used along with the total content expected for the coating (based on the total content for the manufacturing lot) or along with the content of coating remaining on the device once removed and the percentage calculated. This percentage is correlative of the percent of coating freed, dissociated, and/or transferred from the device and delivered to the intervention site. Alternatively, the tissue may be analyzed by various means (noted herein, including but not limited to SEM, TEM, and, where image enhanced polymers are used, various imaging means capable of detecting these enhanced polymers) to detect the percent of the coating freed, dissociated and/or transferred from the substrate and delivered to the intervention site. Again, the amount of coating known to be on the substrate based on manufacturing lot characteristics, and/or an assessment of the coating remaining on the device following removal of the device from the subject (for example, wherein the device is a cutting angioplasty catheter and the substrate is the balloon of the catheter) may be used to determine the percent of coating freed, dissociated, and/or transferred from the device. In some instances, an assessment of the device following the procedure alone is sufficient to assess the amount freed or dissociated from the substrate, without determination of the amount delivered to the intervention site. Additionally, where a determination of improvement and/or disease treatment is desired, levels of proinflammatory markers could be tested to indicate improvement and/or treatment of a disease and/or ailment, for example, by testing high sensitive C-reactive protein (hsCRP), interleukin-6 (IL-6), interleukin-1β (IL-1β) and/or monocyte chemoattractant protein-1 (MCP-1). The release kinetics of the drug may be indicated by plotting the sirolimus concentrations at the timepoints noted above.

For embodiments using different drugs other than sirolimus, the biomarkers are selected based on the disease to be treated and the drugs administered during the course of therapy as determined by one of skill in the art. These biomarkers may be used to indicate the treatment results for each subject.

In-vitro testing: One sample of the coated compliant balloon prepared in Example 1 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. Optical microscopy is performed on the tubing and/or the balloon (which is inflated to at least 25% below the balloon's nominal pressure, at least) to determine the presence and amount of coating transferred to the tubing and/or the amount of coating freed, dissociated, and/or transferred from the balloon.

Method for the determination of sirolimus levels: Media may be assayed for sirolimus content using HPLC. Calibration standards containing known amounts of drug are to determine the amount of drug eluted. The multiple peaks present for the sirolimus (also present in the calibration standards) are added to give the amount of drug eluted at that time period (in absolute amount and as a cumulative amount eluted). HPLC analysis is performed using Waters HPLC system, set up and run on each sample as provided in the Table 1 below using an injection volume of 100 □L.

TABLE 1

| Time point (minutes) | % Acetonitrile | % Ammonium Acetate (0.5%), pH 7.4 | Flow Rate (mL/min) |
|---|---|---|---|
| 0.00 | 10 | 90 | 1.2 |
| 1.00 | 10 | 90 | 1.2 |
| 12.5 | 95 | 5 | 1.2 |
| 13.5 | 100 | 0 | 1.2 |
| 14.0 | 100 | 0 | 3 |
| 16.0 | 100 | 0 | 3 |
| 17.0 | 10 | 90 | 2 |
| 20.0 | 10 | 90 | 0 |

In-vitro Mass Loss test: One sample of the coated compliant balloon prepared in Example 1 is weighed on a microbalance and then secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. After drying, the balloon is removed from the guidewire, further dried and weighed on a microbalance. Comparison of the pre- and post-deployment weights indicates how much coating is freed, dissociated, and/or transferred from the balloon. This analysis may instead and/or alternatively include testing of the tubing to determine the amount of coating freed, dissociated, and/or transferred from the device during this in-vitro test.

In-vitro Coating test: One sample of the coated compliant balloon prepared in Example 1 is secured to a balloon catheter. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing and the balloon is inflated to at least 25% below the balloon's nominal pressure to mechanically transfer the coating from the balloon to the tubing wall. The balloon is deflated and removed from the tubing. The section of tubing exposed to the deployed balloon is cut away from the remainder of the tubing and the interior of the excised tubing rinsed with a small amount of ethanol and an amount of methylene chloride to make up 25 mL total volume of rinsings which are collected in a flask for analysis. Analysis by HPLC as described above is performed to determine the amount of material freed, dissociated, and/or transferred from the balloon. This analysis may instead and/or alternatively include testing of the substrate itself to determine the amount of coating freed, dissociated, and/or transferred from the device during this in-vitro test.

In-vitro testing: One sample of the coated compliant balloon prepared in Example 1 is secured to a balloon catheter. A segment of resected coronary artery from Yucatan miniature swine is positionally fixed and filled with phosphate-buffered saline solution and immersed in a water bath at 37° C. to mimic physiological conditions of deployment into a subject. The coated balloon is inserted into the artery and the balloon is inflated to at least 25% below the balloon's nominal pressure to mechanically transfer the coating from the balloon to the arterial wall. The balloon is deflated and removed from the artery. The section of artery exposed to the deployed balloon is cut away from the remainder of the artery section, placed into a tissue homogonizer and the homogonized material is extracted with methylene chloride to make up 25 mL total volume of rinsings which are collected in a flask for analysis. Analysis by HPLC as described above is performed to determine the amount of material freed, dissociated, and/or transferred from the balloon. This analysis may instead and/or alternatively include testing of the substrate itself to determine the amount of coating freed, dissociated, and/or transferred from the device during this in-vitro test.

For embodiments related to non-vascular or non-lumenal applications, e.g. a tumor site or other cavity or a cannulized site, the same technique is employed with the modification that the tissue to be assayed is resected from the tissue adjoining cavity receiving drug treatment.

In-vitro testing: One sample of the coated compliant balloon prepared in Example 1 is secured to a balloon catheter. A segment of resected coronary artery from Yucatan miniature swine is positionally fixed and filled with phosphate-buffered saline solution and immersed in a water bath at 37° C. to mimic physiological conditions of deployment into a subject. The coated balloon is inserted into the artery and the balloon is inflated to at least 25% below the balloon's nominal pressure to mechanically transfer the coating from the balloon to the arterial wall. The balloon is deflated and removed from the artery. The section of artery exposed to the deployed balloon is cut away from the remainder of the artery section and incised lengthwise to lay open the artery. Optical microscopy is performed on the interior of artery to determine the presence and amount of coating transferred to the artery and/or the amount of coating transferred from the balloon. The tissue sample is also subjected to TEM-SEM analysis.

In-vitro testing of release kinetics: One sample of the coated compliant balloon with total loading of sirolimus~20 μg prepared in Example 1 is secured to a balloon catheter. A flask containing exactly 25 mL of pH 7.4 aqueous phosphate buffer equilibrated to 37° C. equipped for magnetic stirring is prepared. Into this flask is placed the coated balloon and the catheter portion of the apparatus is secured such that the balloon does not touch the sides of the flask. The balloon is inflated to 120 psi with sterile water. Aliquots of 100 μL are removed prior to addition of the balloon, after placement of the balloon but prior to inflation of the balloon, and at regular time intervals of 2, 4, 6, 8, 10, 12, and 14 minutes. Upon removal of each aliquot an equivalent volume of aqueous buffer is added to maintain the volume at 25 mL. The aliquots are analyzed by HPLC as described above for the concentration of sirolimus.

In-vitro testing for distal flow particulates: One sample of the coated compliant balloon prepared in Example 1 is secured to a guidewire incorporating a porous filter of 100 micron pore size, such as the Cordis AngioGuard emboli capture guidewire. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject. The coated balloon is inserted into the tubing, the proximal end of the tubing surrounding the guidewire sealed with epoxy, and a hypodermic needle which is attached to an infusion pump and reservoir of 37° C. phosphate-buffered saline solution is inserted into the tubing proximal to the balloon assembly. The flow of saline is commenced, the distal filter is deployed and the balloon is inflated to at least 25% below the balloon's nominal pressure to mechanically transfer the coating from the balloon to the tubing wall. The balloon is deflated and removed from the tubing. The filter is deployed for 5 minutes after removal of the balloon, the flow of saline is halted, the tubing cut adjacent to the epoxy seal, the filter retracted and removed from the tubing. The content of the filter is analyzed.

In-vitro testing for distal flow particulates: One sample of the coated compliant balloon prepared in Example 1 is secured to a guidewire. A segment of optically clear TYGON® B-44-3 tubing with O.D.=0.125", I.D.=0.0625" (Available from McMaster-Carr Part Number: 5114K11 (www.mcmaster.com)) is filled with phosphate-buffered saline solution and immersed in a water bath at 37° C. to mimic physiological conditions of deployment into a subject and the distal end of the tubing is connected to a turbidity light scattering detector as described in Analytical Ultracentrifugation of Polymers and Nanoparticles, W. Machtle and L. Borger, (Springer) 2006, p. 41. The coated balloon is inserted into the proximal end of the tubing, the proximal end of the tubing surrounding the guidewire sealed with epoxy, and a hypodermic needle which is attached to an infusion pump and reservoir of 37° C. phosphate-buffered saline solution is inserted into the tubing proximal to the balloon assembly. The flow of saline is commenced, a baseline for light transmission through the detector is established and the balloon is inflated to at least 25% below the balloon's nominal pressure to mechanically transfer the coating from the balloon to the tubing wall. The balloon is deflated and removed from the tubing. The flow is maintained for 10 minutes after removal of the balloon, and the flow is analyzed for the presence of particles based on detector response.

Drug-Delivery Balloon (2)—Non-Compliant Balloon

A non-compliant balloon is coated with a material comprising a polymer and an active agent. The coated non-compliant balloon is positioned at the intervention site. The balloon is inflated to at least 25% below its nominal inflation pressure. Upon deflation and removal of the non-compliant balloon from the intervention site, at least about 5% to at least about 30% of the coating is freed from the surface of the non-compliant balloon and is deposited at the intervention site.

In some examples, the balloon unfolds during inflation, causing mechanical shearing forces to at least augment transfer and/or freeing and/or deposition of the coating from the balloon to the intervention site.

In some examples, the balloon twists during inflation, causing mechanical shearing forces to at least augment transfer and/or freeing and/or deposition of the coating from the balloon.

In one example, the polymer of the coating is about 50:50 PLGA-Ester End Group, MW~19 kD, degradation rate~1-2 months or about 50:50 PLGA-Carboxylate End Group, MW~10 kD, degradation rate~28 days. The active agent is a pharmaceutical agent such as a macrolide immunosuppressive drug. Equipment and coating process similar to Example 1 is employed. The intervention site is a vascular lumen wall. Upon inflation of the non-compliant balloon, at least about 50% of the coating is freed from the device at the intervention site.

In another example, a non-compliant balloon is coated with a formulation of PLGA+sirolimus with total loading of sirolimus~20 μg. Equipment and process similar to Example 1 is employed. The intervention site is a coronary artery. Upon inflation of the non-compliant balloon, about 5% to about 15% of the coating is freed from the device resulting in delivery of ~2.0 μg of drug delivered to the artery.

In another example, the polymer of the coating is about 50:50 PLGA-Ester End Group, MW~19 kD, degradation rate~1-2 months or about 50:50 PLGA-Carboxylate End Group, MW~10 kD, degradation rate~28 days. The active agent is a chemotherapeutic agent. Equipment and coating process similar to Example 1 is employed. The intervention site is a cavity resulting from removal of a tumor. Upon inflation of the non-compliant balloon, at least about 75% of the coating is transferred from the device to the intervention site.

In-vivo and/or in-vitro testing may be performed according to the methods described herein.

Example 3: In Vivo Delivery of Rapamycin from Coated Balloons

Sirolimus Coated Balloon Formulation Tested in Rabbits

GHOST Rapid Exchange (Rx) Catheter was used in this example. Ghost 3.0×18 mm Rx catheter balloons were coated and used in animal study. The study was conducted according to the following design. Several tests were run to determine in-vivo drug delivery characteristics of the rapamycin from the coated balloons.

The first test included expansion of the coated balloons in rabbit iliac arteries. 8 coated balloons were manufactured and tested in 4 rabbits. Four of the coated balloons were inflated in pre-dilated arteries (right iliac) for 60 seconds, and four of the coated balloons were inflated in non-dilated arteries (left iliac) for 60 seconds. The amount of drug (sirolimus) found in the arterial tissue at the site of expansion was determined. The following table indicates the results of the testing of these arteries for sirolimus concentration in arterial tissue and total amount of sirolimus in each artery. Drug coated balloons in right iliac arteries were inflated/deflated about 10-20 min before sacrifice. Drug coated balloons in left iliac arteries were inflated/deflated about 5-15 min before sacrifice.

| Iliac Artery | Average Sirolimus (ng/mg) | SD | Total Sirolimus per Artery Average (μg) | SD |
|---|---|---|---|---|
| Right Iliac (denuded) (n = 4) | 178.3 | 32.1 | 5.4 | 1.1 |
| Left Iliac (uninjured) (n = 4) | 216.1 | 122.4 | 3.9 | 1.7 |

-continued

| Iliac Artery | Average Sirolimus (ng/mg) | SD | Total Sirolimus per Artery Average (μg) | SD |
|---|---|---|---|---|
| Combined Right + Left Iliac Arteries (n = 8) | 197.2 | 85.3 | 4.7 | 1.6 |

The following table indicates the raw data of the testing of these same arteries for the total amount of sirolimus in each artery. It also indicates a calculated transfer efficiency of sirolimus to the rabbit iliac arteries and the estimated time that the artery was exposed to blood flow. The percent (%) sirolimus transferred to the artery was calculated using an estimated total amount of sirolimus on the balloon. The estimated total amount of sirolimus on the balloon which was based on the batch average total amount of sirolimus coated on the same batch of balloons as the test sample balloon as determined by UV-Viscometric testing of the balloon. The estimated time that the artery was exposed to blood flow was the amount of time between balloon inflation and the balloon testing, and/or the time between balloon inflation and until the animal was sacrificed and the artery extracted for testing by HPLC for content of drug.

| Rabbit # | Balloon # | Total Sirolimus per Artery (μg) | % Sirolimus Transferred to Artery | Estimated Time Artery Exposed to Blood Flow (min) |
|---|---|---|---|---|
| #1 Right Iliac Artery | N185 | 5.0 | 7.76% | 20 |
| #1 Left Iliac Artery | N157 | 3.2 | 5.58% | 15 |
| #2 Right Iliac Artery | N164 | 7.0 | 12.62% | 10 |
| #2 Left Iliac Artery | N167 | 5.0 | 8.98% | 5 |
| #3 Right Iliac Artery | N175 | 5.1 | 9.17% | 10 |
| #3 Left Iliac Artery | N178 | 1.8 | 2.88% | 5 |
| #4 Right Iliac Artery | N191 | 4.5 | 7.59% | 15 |
| #4 Left Iliac Artery | N117 | 5.7 | 7.95% | 10 |
| Tracking Average | — | 4.7 | 7.8% | — |
| SD | — | 1.6 | 2.8% | — |

The following table indicates the blood concentrations of sirolimus (whole blood) taken from the animals used in this test. A baseline concentration of sirolimus was taken prior to exposure to the coated balloon for each animal, that is, taken before balloon inflation. The whole blood samples were taken 5 to 15 minutes after the second balloon was inflated in each animal, since two coated balloons were delivered to each animal in this test. The results indicated in the table below, therefore, indicate the cumulative whole blood Sirolimus concentration from the inflation of 2 drug coated balloons per animal. The total sirolimus in blood is based on 56 mL of blood per kg (i.e. per kg weight of the rabbit tested).

| Rabbit # | Extraction Conc. (ng/mL) | Est. Total Sirolimus in Blood (μg) |
|---|---|---|
| #1 Baseline | Below Quality Level | — |
| #2 Baseline | Below Quality Level | — |
| #3 Baseline | Below Quality Level | — |
| #4 Baseline | Below Quality Level | — |
| #1 (15 min) | 11.4 | 2.7 |
| #2 (5 min) | 30.8 | 8.2 |
| #3 (5 min) | 22.2 | 5.9 |
| #4 (10 min) | 19.3 | 4.8 |
| Average (5-15 min) | 20.9 | 5.4 |
| SD | 8.0 | 2.3 |

The following table indicates the concentrations of sirolimus on each balloon used in this test following the test itself, to indicate the percent (%) of sirolimus lost following the test procedure. As noted above, each of the balloons was tracked to the respective artery, and inflated for 60 seconds (1 minute), then deflated and removed from the animal and tested for the percent of sirolimus remaining on the balloon. The percent (%) sirolimus lost is based on the amount of sirolimus remaining on the balloon following the test and the total amount of sirolimus coated on the balloon which is estimated from the balloon batch average as tested using UV-Viscometric methods. The variables which contribute to the amount (or percent) of sirolimus lost include the following: Balloon insertion into iliac (via jugular+aorta); Blood flow; Pleat/Fold/Sheath methods and procedures; ~10% lost during shipping; and/or Balloon inflation/contact with artery wall.

| Balloon ID | Total Sirolimus per Balloon (μg) | % Sirolimus Lost |
|---|---|---|
| Rabbit #1 RIA Balloon N185 | 13.2 | 79.3% |
| Robbie #1 LIA Balloon N157 | 17.3 | 69.9% |
| Rabbit #2 RIA Balloon N164 | 4.8 | 91.5% |
| Rabbit #2 LIA Balloon N167 | 11.7 | 79.1% |
| Rabbit #3 RIA Balloon N175 | 16.0 | 71.4% |
| Rabbit #3 LIA Balloon N178 | 14.7 | 77.0% |
| Rabbit #4 RIA Balloon N191 | 9.6 | 83.6% |
| Rabbit #4 LIA Balloon N117 | 14.9 | 79.1% |
| Tracking Average | 12.8 | 78.9% |
| SD | 4.0 | 6.8% |

In another test, tracking studies were conducted. The test comprises tracking 4 coated balloons to the aorta of a rabbit. Each of 4 coated balloons was inserted, tracked to the aorta of the rabbit, and left in the aorta for 2 minutes without inflating the balloon. Following insertion, tracking, and resting the balloon in the aorta for 2 minutes, the catheter including the coated balloon was removed from the animal.

The following table indicates the concentrations of sirolimus on each balloon used in this test following the test itself, to indicate the percent (%) of sirolimus lost following the test procedure. The percent (%) sirolimus lost is based on the amount of sirolimus remaining on the balloon following the test and the total amount of sirolimus coated on the balloon which is estimated from the balloon batch average as tested using UV-Viscometric methods. The variables which contribute to the amount (or percent) of sirolimus lost include the following: Balloon insertion into iliac (via jugular+aorta); Blood flow; Pleat/Fold/Sheath methods and procedures; and/or ~10% lost during shipping.

| Balloon ID | Total Sirolimus per Balloon (μg) | % Sirolimus Lost |
|---|---|---|
| Tracking #1 Balloon (N120) | 23.6 | 66.9% |
| Tracking #2 Balloon (N160) | 20.8 | 63.9% |
| Tracking #3 Balloon (N166) | 19.0 | 66.0% |

| Balloon ID | Total Sirolimus per Balloon (μg) | % Sirolimus Lost |
|---|---|---|
| Tracking #4 Balloon (N176) | 22.0 | 65.5% |
| Tracking Average | 21.3 | 65.6% |
| SD | 2.0 | 1.3% |

Sirolimus quantification was performed on the balloons and blood samples from the previous two tests (as indicated in the "Total Sirolimus per Balloon (ug)" columns of the previous two tables, and as indicated in the blood concentration table generally). That is, sirolimus content was determined from the 8 balloons inflated in rabbit iliac arteries, the 4 balloons tracked to but not inflated in rabbit aorta, and the 8 whole blood samples (2 samples/rabbit). The liver, kidney, spleens, hearts and lungs were stored (80° C.) for later drug analysis.

In summary, the tests performed in this Example indicate the following: 197.2±85.3 ng/mg of Sirolimus embedded in artery walls. The Efficiency of Sirolimus transferred from balloons to artery walls was 7.8±2.8%. The amount of sirolimus washed away into circulation was 5.4±2.3 μg. Following inflation in arteries, 78.9±6.8% of the sirolimus coated on the balloon was removed from the balloon. Prior to inflation in the arteries, 65.6±1.3% of the sirolimus coated on the balloon was removed from the balloon. For reference, 50-100 μg of sirolimus was coated on each balloon. From 1% to 5% of the drug (sirolimus) was transferred to the artery. 1 ng of sirolimus per mg tissue was found during the testing as described in this example.

Example 4: In Vivo Delivery of Rapamycin from Coated Balloons

Binding agents may be incorporated into the coating to improve active agent retention in the artery. Example binding agents include cationic agents and/or positively charged molecules. An example binding agent may be a surfactant. Other agents may also and/or alternatively be used. Binding agents may include, for non-limiting example, at least one of: Polyarginine, Polyarginine 9-L-pArg, DEAE-Dextran (Diethylaminoethyl cellulose-Dextran), DMAB (Didodecyldimethylammonium bromide), PEI (Polyethyleneimine), TAB (Tetradodecylammonium bromide), and DMTAB (Dimethylditetradecylammonium bromide). In some embodiments of the devices, coatings and/or methods provided herein the coating comprises a positive surface charge on a surface of the coating configured to contact the treatment site.

In some embodiments the surfactant comprises at least one of a primary amine having pH<10, and a secondary amine having pH<4. In some embodiments surfactant comprises octenidine dihydrochloride. In some embodiments the surfactant comprises a permanently charged quaternary ammonium cation. In some embodiments the permanently charged quaternary ammonium cation comprises at least one of: an Alkyltrimethylammonium salt such as cetyl trimethylammonium bromide (CTAB), hexadecyl trimethyl ammonium bromide, cetyl trimethylammonium chloride (CTAC); Cetylpyridinium chloride (CPC); Polyethoxylated tallow amine (POEA); Benzalkonium chloride (BAC); Benzethonium chloride (BZT); 5-Bromo-5-nitro-1,3-dioxane; Dimethyldioctadecylammonium chloride; and Dioctadecyldimethylammonium bromide (DODAB). In some embodiments the surfactant comprises at least one of: didodecyldimethylammonium bromide (DMAB), linear isoform Polyethylenimine (linear PEI), Branched Low MW Polyethylenimine (PEI) (of about <25 KDa), Branched Low MW Polyethylenimine (PEI) (of about <15 KDa), Branched Low MW Polyethylenimine (PEI) (of about <10 KDa), Branched High MW Polyethylenimine (of about >/=25 KDa), Poly-L-Arginine (average or nominal MW of about 70,000 Da), Poly-L-Arginine (average or nominal MW>about 50,000 Da), Poly-L-Arginine (average or nominal MW of about 5,000 to about 15,000 Da), Poly-L-Lysine (average or nominal MW of about 28,200 Da), Poly-L-Lysine (average or nominal MW of about 67,000 Da), Poly Histidine, Ethylhexadecyldimethylammonium Bromide, Dodecyltrimethyl Ammonium Bromide, Tetradodecylammonium bromide, Dimethylditetradecyl Ammonium bromide, Tetrabutylammonium iodide, DEAE-Dextran hydrochloride, and Hexadimethrine Bromide. In some embodiments, the molecular weight of the binding agent is controlled. In some embodiments, the average size of the binding agent is controlled.

In some embodiments of the devices, coatings and/or methods provided herein the binding agent and the active agent are mixed and deposited together on the device. In some embodiments, the active agent and binding agent are lyophilized prior to deposition on the device. In some embodiments dry particles of the active agent and binding agent are generated in another manner familiar to one of skill in the art and then coated on the balloon or other medical device as described herein, such as by an eSTAT coating process. In some embodiments of the devices, coatings and/or methods provided herein the surfactant is deposited on a balloon after the active agent is deposited thereon.

The positive surface charge of the coating may be about 20 mV to about 40 mV. The positive surface charge may be at least one of: at least about 1 mV, over about 1 mV, at least about 5 mV, at least about 10 mV, about 10 mV to about 50 mV, about 20 mV to about 50 mV, about 10 mV to about 40 mV, about 30 mV to about 40 mV, about 20 mV to about 30 mV, and about 25 mV to about 35 mV.

In some embodiments the average molecular weight of the binding agent is controlled. For example, Polyarginine may have an average molecular weight of 70 kDa, 5-15 kDa, another controlled molecular weight, or a combination thereof. In some embodiments the molecular weight of the binding agent is controlled. For example, in some embodiments, Polyarginine is the binding agent and at least 75% of the Polyarginine as is 70 kDa, 5-15 kDa, or another controlled molecular weight. In some embodiments, Polyarginine is the binding agent and at least 50% of the Polyarginine as is 70 kDa, 5-15 kDa, or another controlled molecular weight. In some embodiments, Polyarginine is the binding agent and at least 90% of the Polyarginine as is 70 kDa, 5-15 kDa, or another controlled molecular weight. In some embodiments, Polyarginine is the binding agent and at least 95% of the Polyarginine as is 70 kDa, 5-15 kDa, or another controlled molecular weight. In some embodiments, Polyarginine is the binding agent and at least 98% of the Polyarginine as is 70 kDa, 5-15 kDa, or another controlled molecular weight. In some embodiments, Polyarginine is the binding agent and at least 99% of the Polyarginine as is 70 kDa, 5-15 kDa, or another controlled molecular weight.

In some embodiments, the size of the active agent in the coating is controlled in order to improve drug retention in the artery. For non-limiting example, in the case of sirolimus as an active agent, the sirolimus may have an average size (mean diameter) of at least one of: 1.5 μm, 2.5 μm, 645 nm, 100-200 nm, another controlled size, or a combination thereof. In some embodiments, the active agent is sirolimus and wherein the sirolimus has a median size of at least one of: 1.5 µm, 2.5 µm, 645 nm, 100-200 nm, another controlled size, or a combination thereof. In some embodiments, the active agent is sirolimus and wherein the sirolimus has an average size (mean diameter) of at least one of: about 1.5 µm, about 2.5 µm, about 645 nm, about 100-200 nm, another controlled size, or a combination thereof. In some embodiments, the active agent is sirolimus and wherein the sirolimus has a median size of at least one of: about 1.5 µm, about 2.5 µm, about 645 nm, about 100-200 nm, another controlled size, or a combination thereof. In some embodiments the size of the active agent is controlled. For example, in some embodiments, sirolimus is the active agent and at least 75% of the sirolimus as is 1.5 µm, 2.5 µm, 645 nm, 100-200 nm, or another controlled size. In some embodiments, sirolimus is the active agent and at least 50% of the sirolimus as is 1.5 µm, 2.5 µm, 645 nm, 100-200 nm, or another controlled size. In some embodiments, sirolimus is the active agent and at least 90% of the sirolimus as is 1.5 µm, 2.5 µm, 645 nm, 100-200 nm, or another controlled size. In some embodiments, sirolimus is the active agent and at least 95% of the sirolimus as is 1.5 µm, 2.5 µm, 645 nm, 100-200 nm, or another controlled size. In some embodiments, sirolimus is the active agent and at least 98% of the sirolimus as is 1.5 µm, 2.5 µm, 645 nm, 100-200 nm, or another controlled size. In some embodiments, sirolimus is the active agent and at least 99% of the sirolimus as is 1.5 µm, 2.5 µm, 645 nm, 100-200 nm, or another controlled size. The active agent may be, on average, at least one of: at most 5 microns, over 1 micrometer, between 1 micrometer and 5 micrometers, about 1.5 micrometers on average, and about 2.5 micrometers on average.

In some embodiments, the ratio of the active agent to the binding agent is controlled. In some embodiments, the ratio of active agent to binding agent is 1:1, 1:2, 1:3, 1:4, 1:5, 1:10, 1:20, 2:1, 3:1, 4:1, 5:1, 10:1, 15:1, 20:1, 3:2, 2:3, 5:2, 5:3, 2:5, 3:5, or another controlled ratio.

In some embodiments, the coating may comprise nanoparticles, and the nanoparticles may comprise an active agent and a polymer.

Multiple coating formulations were coated on balloons 3.0×18 or 3.0×17 balloons of GHOST Rapid Exchange (Rx) Catheters and delivered in rabbits to their iliac arteries. The arterial tissue of the rabbits was extracted at certain time points up to 72 hours and the amount of drug found in the arterial tissue was determined by methods known to one of skill in the art, such as by HPLC methods testing the arterial tissue or by UV-Viscometric methods looking at loss of coating or agent during the procedure, expressed in ng drug (Sirolimus) per mg of tissue, indicated in the following table (sample size indicated therein). In most cases, the necropsy time points were 5 minutes+/−5%, 24 h+/−5%, and 72 hrs+/−5%. For example, the necropsy was conducted about 5 minutes, 24 h, or 72 hr after deflation of the second drug coated balloon per animal (+/−5% of the time point) where two vessels were used in the study.

| Formulation Composition | 5 minutes Sirolimus Concentration (ng/mg) | 24 hours Sirolimus Concentration (ng/mg) | 72 hours Sirolimus Concentration (ng/mg) |
|---|---|---|---|
| F1 | 127.9 ± 80.2 (n = 20) | 0.8 ± 0.9 (n = 12) | N/A |
| F2 | N/A | 10.4 ± 14.7 (n = 2) | N/A |
| F3 | 39.0 ± 11.6 (n = 8) | 25.2 ± 20.2 (n = 10) | 4.7 ± 3.7 (n = 7) |
| F4 | 90.6 ± 59.1 (n = 4) | 1.3 ± 1.9 (n = 2) | N/A |
| F5 | 6.6 ± 2.1 (n = 4) | 15.2 ± 27.6 (n = 6) | BQL (n = 4) |
| F6 | 226.0 ± 22.6 (n = 2) | 5.4 ± 7.6 (n = 2) | N/A |
| F7 | 97.2 ± 54.7 (n = 2) | 40.5 ± 25.0 (n = 6) | 2.7 ± 1.7 (n = 4) |
| F8 | N/A | BQL (n = 2) | N/A |
| F9 | N/A | BQL (n = 2) | N/A |
| F10 | 100.5 ± 17.6 (n = 4) | 28.4 ± 10.9 (n = 6) | 10.2 ± 5.6 (n = 4) |
| F11 | 92.4 ± 18.9 (n = 4) | 6.4 ± 11.7 (n = 6) | 3.9 ± 5.7 (n = 4) |
| F12 | N/A | BQL (n = 2) | N/A |
| F13A | N/A | BQL (n = 2) | N/A |
| F13B | 74.2 ± 13.1 (n = 4) | 14.0 ± 11.7 (n = 6)* | 0.9 ± 1.7 (n = 4) |
| F13C | N/A | BQL (n = 2) | N/A |
| F13D | N/A | 53.0 ± 5.5 (n = 2) | N/A |
| F14A | N/A | BQL (n = 2) | N/A |
| F14B | N/A | BQL (n = 2) | N/A |
| F14C | Unable to make formulation | | |
| F14D | N/A | BQL (n = 2) | N/A |
| F15 | 114.7 ± 66.2 (n = 4) | 108.2 ± 119.8 (n = 4) | 46.5 ± 46.1 (n = 4) |
| F16 | 73.7 ± 38.5 (n = 4) | N/A | BQL (n = 4) |
| F17 | 404.5 ± 96.0 (n = 4) | N/A | 0.9 ± 1.1 (n = 4) |
| F18 | 191.3 ± 40.0 (n = 4) | N/A | 1.4 ± 2.8 (n = 4) |

*Two studies, were conducted and data was combined here, Study 1: n = 2 8.1 +/− 5.2, Study 2: n = 4 17.0 +/− 13.5.

The results were calculated as total amount of sirolimus extracted in the artery, as indicated in the following table:

| Formulation Composition | 5 minutes Sirolimus amount (µg) | 24 hours Sirolimus amount (µg) | 72 hours Sirolimus amount (µg) |
|---|---|---|---|
| F1 | 4.7 ± 1.6 (n = 8) | — | — |
| F1 (2$^{nd}$ lot) | 5.9 ± 1.6 (n = 12) | 0.1 ± 0.1 (n = 12) | — |
| F2 | — | 0.4 ± 0.6 (n = 2) | — |
| F3 study 1** | 2.6 +/− 0.9 (n = 4 | 0.8 +/− 0.4 (n = 4) | 0.3 +/− 0.2 (n = 4) |
| F3 study 2** | 2.4 +/− 2.3 (n = 4) | 0.8 +/− 1.0 (n = 4) | 0.4 +/− 0.5 (n = 3*) |
| F3 (1$^{st}$ lot**) | 3.0 ± 1.5 (n = 6) | 0.8 ± 0.5 (n = 8) | 0.2 ± 0.1 (n = 6) |

-continued

| Formulation Composition | 5 minutes Sirolimus amount (μg) | 24 hours Sirolimus amount (μg) | 72 hours Sirolimus amount (μg) |
|---|---|---|---|
| F3 (2$^{nd}$ lot**) | 1.0 ± 0.4 (n = 2) | 1.2 ± 1.6 (n = 2) | 1.0 (n = 1) |
| F4 | 4.5 ± 3.2 (n = 4) | 0.07 ± 0.1 (n = 2) | — |
| F5 | 0.4 ± 0.2 (n = 4) | 0.6 ± 1.0 (n = 6) | BQL (n = 4) |
| F6 | 8.8 ± 1.2 (n = 2) | 0.2 ± 0.2 (n = 2) | — |
| F7 | 6.2 ± 3.7 (n = 4) | 2.1 ± 1.3 (n = 6) | 0.2 ± 0.1 (n = 4) |
| F8 | — | BQL (n = 2) | — |
| F9 | — | BQL (n = 2) | — |
| F10 | 2.0 ± 0.4 (n = 4) | 1.0 ± 0.8 (n = 6) | 0.2 ± 0.1 (n = 4) |
| F11 | 2.3 ± 0.5 (n = 4) | 0.3 ± 0.5 (n = 6) | 0.1 ± 0.1 (n = 4) |
| F12 | — | BQL (n = 2) | — |
| F13A | — | BQL (n = 2) | — |
| F13B | 2.2 ± 0.4 (n = 4) | 0.4 ± 0.3 (n = 6) | 0.02 ± 0.03 (n = 4) |
| F13C | — | BQL (n = 2) | — |
| F13D | — | 0.8 ± 0.2 (n = 2) | — |
| F14A | — | BQL (n = 2) | — |
| F14B | — | BQL (n = 2) | — |
| F14D | — | BQL (n = 2) | — |
| F15 | 4.8 ± 0.6 (n = 4) | 2.0 ± 1.9 (n = 4) | 1.2 ± 1.0 (n = 4) |
| F16 | 2.2 ± 0.8 (n = 4) | — | BQL (n = 4) |
| F17 | 9.4 ± 2.7 (n = 4) | — | 0.02 ± 0.03 (n = 4) |
| F18 | 4.4 ± 0.9 (n = 4) | — | 0.03 ± 0.07 (n = 4) |

*one outlier removed
**note that data from F3 was divided two ways for analysis, by study and also by manufacturing lot, thus the same results are represented in both groups (study 1, 2 and lot 1, 2).

Certain formulations were selected for additional analysis, and their test results were normalized for the balloon length and the artery segment size extracted. The following results were found for these selected formulations:

| Formulation Composition | 5 minutes - Sirolimus Concentration (ng/mg) | 24 hours - Sirolimus Concentration (ng/mg) | 72 hours - Sirolimus Concentration (ng/mg) |
|---|---|---|---|
| F1 | 278.5 ± 112.2 (n = 20) | 2.3 ± 2.6 (n = 12) | N/A |
| F3 | 97.1 ± 49.3 (n = 8) | 60.1 ± 39.4 (n = 10) | 11.9 ± 10.7 (n = 7) |
| F5 | 19.7 ± 6.4 (n = 4) | 45.5 ± 82.9 (n = 6) | BQL (n = 4) |
| F7 | 291.5 ± 164.0 (n = 4) | 121.5 ± 75.0 (n = 6) | 8.0 ± 5.1 (n = 4) |
| F10 | 167.5 ± 29.4 (n = 4) | 58.8 ± 33.3 (n = 6) | 17.1 ± 9.3 (n = 4) |
| F11 | 153.9 ± 31.4 (n = 4) | 17.1 ± 34.8 (n = 6) | 6.5 ± 9.5 (n = 4) |
| F13B | 130.9 ± 23.2 (n = 4) | 24.7 ± 20.6 (n = 6) | 1.5 ± 3.0 (n = 4) |
| F15 | 202.5 ± 116.8 (n = 4) | 190.9 ± 211.5 (n = 4) | 82.0 ± 81.3 (n = 4) |
| F16 | 130.0 ± 67.9 (n = 4) | N/A | BQL (n = 4) |
| F17 | 713.8 ± 169.5 (n = 4) | N/A | 1.6 ± 1.9 (n = 4) |
| F18 | 337.5 ± 70.6 (n = 4) | N/A | 2.5 ± 5.0 (n = 4) |

Certain formulations were selected for another analysis, and concentration results were normalized for the artery weight (normalized to 0.025 g). The following results were found for these selected formulations.

| Formulation Composition | 5 minutes - Sirolimus Conc. (ng/mg) | 24 hours - Sirolimus Conc. (ng/mg) | 72 hours - Sirolimus Conc. (ng/mg) |
|---|---|---|---|
| F1 (LOT 1) (PLGA, Sirolimus 2.5 μm) | 186.5 ± 62.7 (n = 8) | N/A | N/A |
| F1 (LOT 2) (PLGA, Sirolimus 2.5 μm) | 234.8 ± 66.0 (n = 12) | 2.4 ± 2.3 (n = 12) | N/A |
| F3 (PLGA, Sirolimus 2.5 μm, Polyarginine 70 kDa) | 99.0 ± 61.6 (n = 8) | 36.0 ± 27.3 (n = 10) | 12.8 ± 13.5 (n = 7) |
| F5 (PLGA, Sirolimus 2.5 μm, DMAB) | 16.3 ± 6.3 (n = 4) | 23.5 ± 39.9 (n = 6) | BQL (n = 4) |
| F7 (PLGA, Sirolimus 2.5 μm, PEI) | 248.6 ± 147.7 (n = 4) | 83.2 ± 53.6 (n = 6) | 7.6 ± 4.4 (n = 4) |
| F10 (PLGA, Sirolimus 2.5 μm, Polyarginine 70 kDa, PEI) | 80.3 ± 14.9 (n = 4) | 38.9 ± 31.8 (n = 6) | 9.2 ± 3.8 (n = 4) |
| F11 (PLGA, Sirolimus 2.5 μm, DEAE-Dextran, TAB) | 91.5 ± 19.5 (n = 4) | 10.2 ± 21.3 (n = 6) | 3.3 ± 4.9 (n = 4) |
| F13B (PLGA, Sirolimus 645 nm, Polyarginine 70 kDa) | 87.6 ± 15.4 (n = 4) | 17.4 ± 13.6 (n = 6) | 0.6 ± 1.2 (n = 4) |
| F15 (LOT 1) (PLGA, Sirolimus 1.5 μm, Polyarginine 5-15 kDa) | 192.6 ± 23.6 (n = 4) | 78.2 ± 76.8 (n = 4) | 49.8 ± 41.8 (n = 4) |

In the rabbit arterial and blood tests noted in this example, the following coating details and formulations were used.

F1 (Formulation 1) comprised PLGA i.e. about 50:50 Lactic acid:Glycolic acid, and Sirolimus having an average size of 2.5 µm.

F2 (Formulation 2) comprised PLGA i.e. about 50:50 Lactic acid:Glycolic acid, and a 1:1 ratio of Sirolimus having an average size of 2.5 µm to Polyarginine 70 kDa.

F3 (Formulation 3) comprised PLGA i.e. about 50:50 Lactic acid:Glycolic acid, and a 10:1 ratio of Sirolimus having an average size of 1.5 µm or 2.5 µm to Polyarginine 70 kDa.

F4 (Formulation 4) comprised PLGA i.e. about 50:50 Lactic acid:Glycolic acid, and a 10:1 ratio of Sirolimus having an average size of 2.5 µm to DEAE-Dextran (Diethylaminoethyl cellulose-Dextran).

F5 (Formulation 5) comprised PLGA i.e. about 50:50 Lactic acid:Glycolic acid, and a 1:1 ratio of Sirolimus having an average size of 2.5 µm and DMAB (Didodecyldimethylammonium bromide).

F6 (Formulation 6) comprised PLGA i.e. about 50:50 Lactic acid:Glycolic acid, and a 10:1 ratio of Sirolimus having an average size of 2.5 µm and DMAB (Didodecyldimethylammonium bromide).

F7 (Formulation 7) comprised PLGA i.e. about 50:50 Lactic acid:Glycolic acid, and a 10:1 ratio of Sirolimus having an average size of 2.5 µm and PEI (Polyethyleneimine)

F8 (Formulation 8) comprised PLGA i.e. about 50:50 Lactic acid:Glycolic acid, and a 10:1 ratio of Sirolimus having an average size of 2.5 µm and TAB (Tetradodecylammonium bromide).

F9 (Formulation 9) comprised PLGA i.e. about 50:50 Lactic acid:Glycolic acid, and a 10:1 ratio of Sirolimus having an average size of 2.5 µm and DMTAB (Dimethylditetradecylammonium bromide).

F10 (Formulation 10) comprised PLGA i.e. about 50:50 Lactic acid:Glycolic acid, and a 1:1:1 ratio of Sirolimus having an average size of 2.5 µm to Polyarginine 70 kDa to PEI (Polyethyleneimine)

F11 (Formulation 11) comprised PLGA i.e. about 50:50 Lactic acid:Glycolic acid, and a 10:1:1 ratio of Sirolimus having an average size of 2.5 µm to TAB (Tetradodecykammonium bromide to DEAE-Dextran (Diethylaminoethyl cellulose-Dextran).

F12 (Formulation 12) comprised PLGA Nanospheres (130 nm) where the PLGA is 50:50 Lactic acid:Glycolic acid, and 6.3% Sirolimus.

F13A (Formulation 13A) comprised PLGA i.e. about 50:50 Lactic acid:Glycolic acid, and Sirolimus having an average size of 645 nm F13B (Formulation 13B) comprised PLGA i.e. about 50:50 Lactic acid:Glycolic acid, and a 10:1 ratio of Sirolimus having an average size of 645 nm to Polyarginine 70 kDa.

F13C (Formulation 13C) comprised PLGA i.e. about 50:50 Lactic acid:Glycolic acid, and a 1:1 ratio of Sirolimus having an average size of 645 nm to DMAB (Didodecyldimethylammonium bromide).

F13D (Formulation 13D) comprised PLGA i.e. about 50:50 Lactic acid:Glycolic acid, and a 10:1 ratio of Sirolimus having an average size of 645 nm to PEI (Polyethyleneimine)

F14A (Formulation 14A) comprised PLGA i.e. about 50:50 Lactic acid:Glycolic acid, and Sirolimus having an average size of 100-200 nm.

F14B (Formulation 14B) comprised PLGA i.e. about 50:50 Lactic acid:Glycolic acid, and a 10:1 ratio of Sirolimus having an average size of 100-200 nm to Polyarginine 70 kDa.

F14C (Formulation 14C) comprised PLGA i.e. about 50:50 Lactic acid:Glycolic acid, and a 1:1 ratio of Sirolimus having an average size of 100-200 nm to DMAB (Didodecyldimethylammonium bromide). Note that this formulation was not able to be made, therefore, no animal study results were obtained.

F14D (Formulation 14D) comprised PLGA i.e. about 50:50 Lactic acid:Glycolic acid, and a 10:1 ratio of Sirolimus having an average size of 100-200 nm to PEI (Polyethyleneimine)

F15 (Formulation 15) comprised PLGA i.e. about 50:50 Lactic acid:Glycolic acid, and a 10:1 ratio of Sirolimus having an average size of 1.5 µm to Polyarginine 5-15 kDa.

F16 (Formulation 16) comprised PLGA i.e. about 50:50 Lactic acid:Glycolic acid, and a 10:1 ratio of Sirolimus having an average size of 1.5 µm to Polyarginine 9-L-pArg.

F17 (Formulation 17) comprised PLGA i.e. about 50:50 Lactic acid:Glycolic acid, and a 10:1 ratio of Sirolimus having an average size of 645 nm to Polyarginine 5-15 kDa.

F18 (Formulation 18) comprised PLGA i.e. about 50:50 Lactic acid:Glycolic acid, and a 10:1 ratio of Sirolimus having an average size of 645 nm to Polyarginine 9-L-pArg.

With the exception of F12, all methods comprised using an RESS process for coating the PLGA on the balloon, and using an eSTAT process for coating the Sirolimus and the positive charged molecule to the balloon. The general process for coating was 1) Polymer coat by RESS processes, 2) Sirolimus and binding agent coat (or sirolimus alone, if there was no binding agent used in the formulation e.g. 14A) by eSTAT processes, 3) sinter the coated balloon. The binding agent (i.e. charged particle, surfactant, and/or cationic particle) was part of the Sirolimus coating step wherein the balloon was coated with both the Sirolimus and the binding agent using an eSTAT process. Formulation 12 was coated on the balloon using only an eSTAT or an RESS process and a sinter step.

The sirolimus was mixed with the binding agent (e.g. the surfactant, the cationic particle, the charged molecule, for non-limiting example) if present in the particular formulation in the following manner. The process may be adapted to different binding agents and different active agents, however, it is described herein as used with respect to sirolimus and the binding agents which were surfactants in the formulations noted in this example. Lyophilisation or "freeze drying" processed produced a dry powder of associated drug and binding agent (e.g. surfactant) suitable for depositing onto balloons via the eSTAT method. Other processes familiar to one of skill in the art may be used as an alternative to lyophilisation in order to associate the drug and binding agent in a form suitable for deposition on the balloons via a method described herein. In this example, rapamycin (sirolimus) was suspended in water with a binding agent to coat the sirolimus with binding agent. The well-suspended sirolimus and binding agent solution was frozen, retaining the sirolimus and binding agent assembly, and the water was removed by sublimation to produce the dry sirolimus and binding agent material.

A pre-lyophilisation set of steps may be used in the process of creating the dried sirolimus and binding agent solution for use in the eSTAT coating process. The solution created thereby may be used in a freeze dryer. The desired quantity of drug (e.g. sirolimus) and binding agent were weighed out into a 100 mL Schott bottle. Then 50 mL of water is added, in increments of 10 mL, to the Schott bottle. During each increment the solution is mixed with a stir rod to insure the sirolimus is being wetted. After the 50 mL is added the solution is sonicated in a bath sonicator (Branson 1510) for 1 hr. In the final pre-lyophilisation step, the well-suspended solution is carefully transferred to a 50 mL conical centrifuge tube using a plastic pipette; unsuspended sirolimus and/or binding agent particles (typically found floating on the surface of the suspension, are not transferred. Note: the efficiency of the sirolimus suspension by the binding agent affects the actual sirolimus to surfactant ratio of the transferred solution and the final recovered powder, often changing it from the initial sirolimus and binding agent ratio weighed out.

The Lyophilisation steps may be as follows: The recovered suspension in the 50 mL centrifuge tube is immersed in liquid nitrogen until the solution is completely frozen. Parafilm is used to cover the opening of the tube containing the frozen suspension, while perforations are made in the film to allow escape of the vapor phase water. The tube containing the frozen sample is loaded into a freeze dryer containment vessel and the vessel is attached to one of the freeze dryer stations. The switch above the nozzle for the loaded station is activated to begin the process. The lyophilisation step is complete when all of the frozen moisture is visibly absent from the tube. The sample, which may exist as a xerogel following lyophilisation, is easily converted to a free-flowing dry powder by shaking or stirring when the process is complete. It usually takes 1-2 days for a sample prepared as described above to complete the lyophilisation step. Note: the freeze-drier may need to be periodically be defrosted to remove the accumulated moisture from the samples in order to work effectively.

The following steps were taken to make the sirolimus and binding agent dry solution in the eSTAT coating process of the balloons (which had been pre-coated using an RESS process with PLGA as noted elsewhere herein). Measure out required quantities of sirolimus and binding agent into a 100 mL Schott bottle. Add 50 mL of water, in increments of 10 mL, to the Schott bottle. During each increment use a stir rod to mix the sirolimus and binding agent solution. After 50 mL of water is added, sonicate the solution for 1 hr. After sonication use a plastic pipette to transfer the suspended solution to a 50 mL centrifuge tube. Avoid transfer of any unsuspended sirolimus and binding agent particles. Place 50 mL conical tube (without lid) in liquid nitrogen until solution is completely frozen. Cover the top of the conical tube with parafilm and make holes in film for water to travel through. Seal the 50 mL conical bottle in the lyophilisation vessel and connect the vessel to a freeze dryer nozzle station. Turn switch above the nozzle to evacuate the air from the vessel. Keep sample on the freeze-drier until all water has been removed (typically 1-2 days)

Rabbit Blood Concentration results follow. The amount of drug as a concentration per mL of blood was determined for several formulations, as indicated in the following table. BQL herein means below quantitation limit (1-2 ng/ml with respect to whole blood quantitation of sirolimus)

| Formulation | Sirolimus in whole blood (ng/mL) | | |
|---|---|---|---|
| | 5 min | 24 hours | 72 hours |
| F1 | 20.9 ± 8.0 (n = 4) | N/A | N/A |
| F1 (2nd lot) | 5.7 ± 1.6 (n = 6) | BQL (n = 6) | N/A |
| F2 | N/A | BQL (n = 1) | N/A |
| F3 (Study 1)* | 8.9 ± 4.4 (n = 2) | BQL (n = 2) | BQL (n = 2) |
| F3 (Study 2)* | 7.1 ± 2.2 (n = 2) | BQL (n = 2) | BQL (n = 2) |
| F3 (1st lot)* | 7.7 ± 3.7 (n = 3) | 0.8 ± 0.7 (n = 3) | BQL (n = 3) |
| F3 (2nd lot)* | 5.5 (n = 1) | BQL (n = 1) | BQL (n = 1) |
| F4 | N/A | BQL (n = 1) | N/A |
| F5 | 0.99 ± 0.1 (n = 2) | BQL (n = 3) | BQL (n = 2) |
| F6 | N/A | 2.72 (n = 1) | N/A |
| F7 | 11.2 ± 3.4 (n = 2) | 1.7 ± 0.3 (n = 3) | 1.3 ± 0.9 (n = 2) |
| F8 | N/A | BQL (n = 1) | N/A |
| F9 | N/A | 2.06 (n = 1) | N/A |
| F10 | BQL (n = 2) | 0.36 ± 0.6 (n = 3) | BQL (n = 2) |
| F11 | 10.1 ± 0.2 (n = 2) | BQL (n = 3) | BQL (n = 2) |
| F12 | N/A | BQL (n = 1) | N/A |
| F13A | N/A | 1.13 (n = 1) | N/A |
| F13B | 6.4 ± 3.1 (n = 2) | 1.0 ± 0.9 (n = 3)** | BQL (n = 2) |
| F13C | N/A | BQL (n = 1) | N/A |
| F13D | N/A | 2.99 (n = 1) | N/A |
| F14A | N/A | BQL (n = 1) | N/A |
| F14B | N/A | BQL (n = 1) | N/A |
| F14D | N/A | BQL (n = 1) | N/A |
| F15 | 5.7 ± 3.2 (n = 2) | 1.8 ± 0.01 (n = 2) | BQL (n = 2) |
| F16 | 76.8 ± 89.4 (n = 2) | N/A | BQL (n = 2) |
| F17 | 25.6 ± 1.3 (n = 2) | N/A | BQL (n = 2) |
| F18 | 23.5 ± 3.3 (n = 2) | N/A | 0.5 ± 0.8 (n = 2) |

*note that data from F3 was divided two ways for analysis, by study and also by manufacturing lot, thus the same results are represented in both groups (study 1, 2 versus lot 1, 2).
**This data represents two lots of coated balloons, for one of the lots the sirolimus in whole blood (ng/mL) results were: (n = 2), 0.7 +/− 1.0

The amount of drug as a total amount found in the arterial tissue was determined for several formulations, as indicated in the following table.

| Formulation | Sirolimus in whole blood (µg) based on 56 mL blood per kg | | |
|---|---|---|---|
| | 5 min | 24 hours | 72 hours |
| F1 | 5.4 ± 2.3 (n = 4) | N/A | N/A |
| F1 (2nd lot) | 1.0 ± 0.3 (n = 6) | BQL (n = 6) | N/A |
| F2 | N/A | BQL (n = 1) | N/A |
| F3 (Study 1)* | 1.5 ± 0.7 (n = 3) | BQL (n = 2) | BQL (n = 2) |
| F3 (Study 2)* | 1.6 ± 0.5 (n = 1) | BQL (n = 2) | BQL (n = 2) |
| F3 (1st lot)* | 1.7 ± 0.6 (n = 3) | 0.1 ± 0.1 (n = 3) | BQL (n = 3) |
| F3 (2nd lot)* | 1.2 (n = 1) | BQL (n = 1) | BQL (n = 1) |
| F4 | N/A | BQL (n = 1) | N/A |
| F5 | 0.18 ± 0.2 (n = 2) | BQL (n = 3) | BQL (n = 2) |
| F6 | — | 0.4 (n = 1) | N/A |
| F7 | 1.9 ± 0.6 (n = 2) | 0.3 ± 0.1 (n = 3) | 0.25 ± 0.01 (n = 2) |
| F8 | N/A | BQL (n = 1) | N/A |
| F9 | N/A | 0.3 (n = 1) | N/A |
| F10 | BQL (n = 2) | 0.1 ± 0.1 (n = 3) | BQL (n = 2) |
| F11 | 2.0 ± 0.05 (n = 2) | BQL (n = 3) | BQL (n = 2) |
| F12 | N/A | BQL (n = 1) | N/A |
| F13A | N/A | 0.2 (n = 1) | N/A |
| F13B | 1.3 ± 0.7 (n = 2) | 0.2 ± 0.2 (n = 3) | BQL (n = 2) |
| F13C | N/A | BQL (n = 1) | N/A |
| F13D | N/A | 0.6 (n = 1) | N/A |
| F14A | N/A | BQL (n = 1) | N/A |
| F14B | N/A | BQL (n = 1) | N/A |
| F14D | N/A | BQL (n = 1) | N/A |

| Formula-tion | Sirolimus in whole blood (µg) based on 56 mL blood per kg | | |
|---|---|---|---|
| | 5 min | 24 hours | 72 hours |
| F15 | 1.2 ± 0.7 (n = 2) | 0.4 ± 0.0 (n = 2) | BQL (n = 2) |
| F16 | 18.7 ± 21.9 (n = 2) | N/A | BQL (n = 2) |
| F17 | 6.2 ± 0.3 (n = 2) | N/A | BQL (n = 2) |
| F18 | 5.5 ± 0.6 (n = 2) | N/A | 0.12 ± 0.17 (n = 2) |

*note that data from F3 was divided two ways for analysis, by study and also by manufacturing lot, thus the same results are represented in both groups (study 1, 2 versus lot 1, 2).

The various formulations had the following average amount of sirolimus coated on each of the balloons tested in the rabbit arteries. These were average amounts of drug found on sample balloons coated according to the same procedures noted herein and from the same lots and batches as those tested in the rabbits as noted above. The amount of sirolimus coated on the balloon is the average sirolimus concentration based on UV-Vis analysis before pleating, folding, and sterilization of the balloons.

| Formulation | Sirolimus Coated on Balloons (µg) |
|---|---|
| F1 | 64.52 ± 8.73 |
| F1 (2$^{nd}$ lot) | 63.40 ± 2.89 |
| F2 | 41.05 ± 7.17 |
| F3 | 89.54 ± 19.61 |
| F3 (2$^{nd}$ lot) | 128.71 ± 26.86 |
| F4 | 115.12 ± 16.92 |
| F5 | 68.49 ± 4.73 |
| F6 | 316.95 ± 82.66 |
| F7 | 165.25 ± 17.47 |
| F8 | 97.19 ± 16.46 |
| F9 | 218.86 ± 26.73 |
| F10 | 65.38 ± 24.45 |
| F11 | 170.66 ± 14.30 |
| F12 | 74.20 ± 15.77 |
| F13A | 134.23 ± 17.03 |
| F13B | 144.63 ± 51.84 |
| F13C | 55.46 ± 13.14 |
| F13D | 105.31 ± 16.02 |
| F14A | 83.10 ± 15.19 |
| F14B | 175.96 ± 78.30 |
| F14D | 77.50 ± 31.02 |
| F15 | 106.53 ± 22.55 |
| F16 | 75.84 ± 5.98 |
| F17 | 197.64 ± 15.89 |
| F18 | 196.43 ± 45.89 |

Following expansion of the balloons in the rabbit arteries, each of the balloons was removed from the animal and the residual sirolimus on each balloon was determined. Using the 5 minute data as an indication of the amount (and therefore percent) of sirolimus transferred to the artery, and using the amount of drug remaining on the balloon following the procedure, and using the average amount of drug on balloons of the same batch as an estimate of the total amount of drug on the original device (see the previous table), the percent of sirolimus transferred to the rabbit artery and the total percent of sirolimus released during the entire procedure was determined. The following table summarizes the results from the formulations tested in this manner.

| Formulation | Sirolimus on Balloon Post-Deployment (µg) | % Sirolimus Transferred to Artery (5 min) From Sirolimus Released off Respective Balloon | % Sirolimus Released |
|---|---|---|---|
| F1 | 12.8 ± 4.0 (n = 8) | 9.8 ± 3.1% (n = 8) | 78.9 ± 6.8% (n = 8) |
| F1 (2$^{nd}$ lot) | 45.7 ± 7.3 (n = 36) | 23.0 ± 8.5% (n = 12) | 35.9 ± 10.2% (n = 36) |
| F2 | 6.1 ± 2.7 (n = 2) | N/A | 85.1 ± 3.6% (n = 2) |
| F3 Study 1* | 25.8 ± 9.6 (n = 12) | N/A | 68.8 ± 16.2% (n = 12) |
| F3 Study 2* (2.5 µm) | 28.1 ± 4.9 (n = 6) | N/A | 73.1 ± 7.6% (n = 6) |
| F3 (1$^{st}$ lot)* | 27.6 ± 9.1 (n = 20) | 4.8 ± 1.4% (n = 6) | 68.4 ± 15.4% (n = 20) |
| F3 (2$^{nd}$ lot-1.5 µm)* | 56.8 ± 15.6 (n = 6) | 1.2 ± 0.6% (n = 2) | 59.0 ± 8.6% (n = 6) |
| F4 | 16.0 ± 2.9 (n = 6) | 5.1 ± 3.5% (n = 4) | 84.9 ± 2.5% (n = 6) |
| F5 | 5.0 ± 2.7 (n = 14) | 0.6 ± 0.2% (n = 4) | 92.8 ± 3.7% (n = 14) |
| F6 | 49.4 ± 6.9 (n = 4) | 3.5 ± 0.2% (n = 2) | 84.4 ± 3.7% (n = 4) |
| F7 | 7.1 ± 3.0 (n = 14) | 3.9 ± 2.4% (n = 4) | 95.7 ± 1.7% (n = 14) |
| F8 | 20.5 ± 0.1 (n = 2) | N/A | 78.1 ± 3.8% (n = 2) |
| F9 | 37.0 ± 4.1 (n = 2) | N/A | 82.6 ± 0.3% (n = 2) |
| F10 | 1.4 ± 0.8 (n = 14) | 4.0 ± 0.3% (n = 4) | 98.1 ± 0.8% (n = 14) |
| F11 | 43.6 ± 11.2 (n = 14) | 1.7 ± 0.4% (n = 4) | 74.4 ± 6.9% (n = 14) |
| F12 | 2.3 ± 0.8 (n = 2) | N/A | 97.1 ± 1.0% (n = 2) |
| F13A | 21.6 ± 1.0 (n = 2) | N/A | 85.0 ± 0.8% (n = 2) |
| F13B | 30.4 ± 7.4 (n = 14) | 3.8 ± 0.6% (n = 4) | 76.5 ± 7.2% (n = 14) |
| F13C | 2.1 ± 0.1 (n = 2) | N/A | 96.6 ± 0.0% (n = 2) |
| F13D | 9.2 ± 2.6 (n = 2) | N/A | 92.1 ± 2.3% (n = 2) |
| F14A | 11.6 ± 0.8 (n = 2) | N/A | 87.5 ± 0.3% (n = 2) |
| F14B | 16.4 ± 0.6 (n = 2) | N/A | 91.9 ± 0.8% (n = 2) |
| F14D | 1.7 ± 0.1 (n = 2) | N/A | 98.5 ± 0.1% (n = 2) |
| F15 | 24.9 ± 5.6 (n = 12) | 5.3 ± 0.7% (n = 4) | 76.4 ± 6.3% (n = 12) |
| F16 | 21.4 ± 3.9 (n = 12) | 4.2 ± 1.6% (n = 4) | 72.0 ± 4.6% (n = 12) |
| F17 | 49.3 ± 6.9 (n = 12) | 6.6 ± 1.9% (n = 4) | 74.6 ± 3.6% (n = 12) |
| F18 | 44.5 ± 8.7 (n = 12) | 2.5 ± 0.8% (n = 4) | 76.4 ± 3.3% (n = 12) |

*note that several lots of coated balloons were manufactured and tested in several studies, and the data presented represents data from at two studies and from at two lots. Some data is represented, thus, both in a study and also in a lot listing in the above chart (i.e. coated balloons from manufacturing lot 1 were tested in both Study 1 and Study 2, and thus the results are presented in groups F3 Study 1, F3 Study 2, and F3 1$^{st}$ lot above).

The following summary observations may be made with regard to the Rabbit arterial and blood testing noted in this Example. Formulation 15 has the most drug retention at 72 hours of any other formulation. Formulation 3 had a sirolimus retention of 3.9+/−3.4 ng/mg at 72 hours (both lots combined), and 3.2% of the drug released from the balloons (both lots combined) was retained in the artery five minutes after expansion of the balloon in the artery. Formulation 13B had a sirolimus retention of 0.9+/−1.7 ng/mg at 72 hours, and 3.8% of the drug released from the balloons was retained in the artery five minutes after expansion of the balloon in the artery. Formulation 15 had a sirolimus retention of 46.5+/−46.1 ng/mg at 72 hours, and 5.3% of the drug released from the balloons was retained in the artery five minutes after expansion of the balloon in the artery.

Additional findings were as follows, which demonstrate for certain formulations the Tissue concentrations versus the total amount of sirolimus per artery. Sirolimus tissue levels as an absolute amount instead of a concentration removes experimental variability in the specific amount of tissue harvested in the necropsy procedures.

|  | Sirolimus Concentration in Artery (ng/mg) | Total Sirolimus per Artery (µg) |
|---|---|---|
| F3 Lot 1 (5 minutes) | 45.8 ± 11.2 (n = 4) | 2.6 ± 0.9 (n = 4) |
| F3 Lot 2 (5 minutes) | 32.3 ± 8.0 (n = 4) | 2.4 ± 2.3 (n = 4) |
| F 13B (5 minutes) | 74.2 ± 13.1 (n = 4) | 2.2 ± 0.4 (n = 4) |
| F 15 (5 minutes) | 114.7 ± 66.2 (n = 4) | 4.8 ± 0.6 (n = 4) |
| F3 Lot 1 (24 h) | 16.6 ± 8.5 (n = 4) | 0.8 ± 0.4 (n = 4) |
| F3 Lot 2 (24 h) | 31.5 ± 30.9 (n = 4) | 0.8 ± 1.0 (n = 4) |
| F 13B (24 h) | 17.0 ± 13.5 (n = 4) | 0.6 ± 0.3 (n = 4) |
| F 15 (24 h) | 108.2 ± 119.8 (n = 4) | 2.0 ± 1.9 (n = 4) |
| F3 Lot 1 (72 h) | 5.2 ± 4.2 (n = 4) | 0.3 ± 0.2 (n = 4) |
| F3 Lot 2 (72 h) | 3.9 ± 3.4 (n = 3)* | 0.4 ± 0.5 (n = 3)* |
| F 13B (72 h) | 0.9 ± 1.7 (n = 4) | 0.02 ± 0.03 (n = 4) |
| F 15 (5 minutes) | 46.5 ± 46.1 (n = 4) | 1.2 ± 1.1 (n = 4) |

*Excludes outlier of 137 ng/mg or 4.99 total µg at 72 hours

In some embodiments of the methods, coatings, or devices provided herein, the coating comprises and a 10:1 ratio of the active agent to the binding agent, wherein the active agent comprises sirolimus wherein the binding agent comprises Polyarginine. In some embodiments, the sirolimus has an average size of 1.5 µm or 2.5 µm. In some embodiments, the Polyarginine average molecular weight is 70 kDa. In some embodiments, the Polyarginine average molecular weight is 5-15 kDa. In some embodiments, the active agent and the binding agent are deposited on the balloon together using an eSTAT coating process. In some embodiments, the active agent and the binding agent are lyophilized prior to deposition on the balloon. In some embodiments, at least about 2 ng/mg of active agent are found in arterial tissue 72 hours after inflation of the balloon in the artery. In some embodiments, at least about 3 ng/mg of active agent are found in arterial tissue 72 hours after inflation of the balloon in the artery. In some embodiments, at least about 5 ng/mg of active agent are found in arterial tissue 72 hours after inflation of the balloon in the artery. In some embodiments, at least about 10 ng/mg of active agent are found in arterial tissue 72 hours after inflation of the balloon in the artery. In some embodiments, at least about 20 ng/mg of active agent are found in arterial tissue 72 hours after inflation of the balloon in the artery. In some embodiments, at least about 30 ng/mg of active agent are found in arterial tissue 72 hours after inflation of the balloon in the artery. In some embodiments, at least about 40 ng/mg of active agent are found in arterial tissue 72 hours after inflation of the balloon in the artery.

In some embodiments of the methods, coatings, or devices provided herein, in vivo measurement comprises inflating the balloon inside the artery of a porcine for about 1 minute and wherein the amount of active agent transferred to the artery is measured by UV-Vis evaluation of the coating remaining on the balloon as determined about five minutes after inflation of the balloon in the artery. In some embodiments of the methods, coatings, or devices provided herein, in vivo measurement comprises inflating the balloon inside the artery of a porcine for about 1 minute and wherein the amount of active agent transferred to the artery is measured by extracting the artery about five minutes after inflation of the balloon in the artery and determining the amount of drug in the extracted artery using standard methods described herein and/or known to one of skill in the art. In some embodiments of the methods, coatings, or devices provided herein, in vivo measurement comprises inflating the balloon inside the artery of a rabbit for about 1 minute and wherein the amount of active agent transferred to the artery is measured by UV-Vis evaluation of the coating remaining on the balloon as determined about five minutes after inflation of the balloon in the artery. In some embodiments of the methods, coatings, or devices provided herein, in vivo measurement comprises inflating the balloon inside the artery of a rabbit for about 1 minute and wherein the amount of active agent transferred to the artery is measured by extracting the artery about five minutes after inflation of the balloon in the artery and determining the amount of drug in the extracted artery using standard methods described herein and/or known to one of skill in the art.

Provided herein is a method of forming a coating on a medical device comprising depositing a polymer on the medical device using an RESS process, mixing a binding agent and active agent to create an active agent-binding agent mixture, lyophilizing the active agent-binding agent mixture and depositing the active agent-binding agent mixture on the medical device using an eSTAT process. In some embodiments, the binding agent comprises a surfactant.

Pharmacokinetic Studies in Porcine Models:

Formulation 3 (F3) was coated on balloons of 3.0×17 Ghost Rapid Exchange (Rx) Catheters according to the procedures noted above and delivered in porcine to their coronary and mammary arteries. The animals were sacrificed and arterial tissue was extracted at several time points. The amount of drug found in the coronary arterial tissue was determined and is expressed in ng drug (Sirolimus) per mg of tissue, and is expressed in normalized form, i.e. normalized per mg of tissue and expressed in micrograms (µg) in the following table.

| Time Point | Arterial Sirolimus Concentration (ng/mg) | SD | Total Sirolimus per Artery (µg) | SD |
|---|---|---|---|---|
| Day 1: Coronary (n = 5) | 5.528 | 4.806 | 0.3647 | 0.3056 |
| Day 3: Coronary (n = 6) | 2.559 | 2.927 | 0.1436 | 0.1402 |
| Day 7: Coronary (n = 5) | 1.141 | 1.324 | 0.0948 | 0.1375 |
| Day 14: Coronary (n = 5) | 0.764 | 0.858 | 0.0645 | 0.0940 |
| Day 30: Coronary (n = 5) | 0.038 | 0.085 | 0.0013 | 0.0029 |

The amount of drug found in the mammary arterial tissue was determined and is expressed in ng drug (Sirolimus) per mg of tissue, and is expressed in normalized form, i.e. normalized per mg of tissue and expressed in micrograms (μg) in the following table.

| Time Point | Arterial Sirolimus Concentration (ng/mg) | SD | Total Sirolimus per Artery (μg) | SD |
|---|---|---|---|---|
| Day 1: Mammary (n = 5) | 2.722 | 2.931 | 0.1303 | 0.1285 |
| Day 3: Mammary (n = 4) | 0.243 | 0.386 | 0.0129 | 0.0200 |
| Day 7: Mammary (n = 9) | 0.277 | 0.648 | 0.0100 | 0.0225 |
| Day 14: Mammary (n = 4) | 0.105 | 0.066 | 0.0058 | 0.0037 |
| Day 30: Mammary (n = 9) | 0.030 | 0.090 | 0.0014 | 0.0043 |

A comparison was performed between arterial drug retention in a rabbit versus the porcine model, using the F3 formulation as described above. The comparison indicated that at Day 1, the Rabbit Iliac artery concentration of sirolimus was 25.20+/−20.20 in ng sirolimus per mg tissue, or 0.901 mg+/−0.684 mg when normalized by the amount of tissue in the sample (n=7-10). At the same time point at Day 1, the Porcine Coronary artery concentration of sirolimus was 5.528+/−4.806 in ng sirolimus per mg tissue, or 0.365 mg+/−0.306 mg when normalized by the amount of tissue in the sample (n=5-6). At Day 3, the rabbit iliac artery concentration of sirolimus was 4.66+/−3.65 in ng sirolimus per mg tissue, or 0.319 mg+/−0.338 mg when normalized by the amount of tissue in the sample. At the same time point at Day 3, the porcine coronary artery concentration of sirolimus was 2.559+/−2.927 in ng sirolimus per mg tissue, or 0.144 mg+/−0.144 mg when normalized by the amount of tissue in the sample.

Several formulations that were selected for 72-hour testing in the rabbit iliac model were submitted for elution testing using a standard elution method. FIG. 1 indicates the Average percent Sirolimus Eluted from the balloons at various time points for Formulations F3, F5, and F7. At time 0 days, the F5 is the highest percent elution at about 60%, and the F3 elution is the next highest data point at about 45% elution at 0 days, whereas F7 is the lowest line throughout all time points, at about 30% eluted at 0 days. The line for F5 is the top line of the graph, eluting the fastest of the three formulations indicated in the graph, whereas F3 is the middle line of the graph, and F7 eluting the slowest only reaching 100% elution at about day 13.

The coating may release the active agent into a treatment site over at least one of: about 3 days, about 5 days, about 1 week, about 1.5 weeks, about 2 weeks, about 14 days, about 3 weeks, about 21 days, about 4 weeks, about 28 days, about 1 month, about 1.5 months, about 2 months, at least about 3 days, at least about 5 days, at least about 1 week, at least about 1.5 weeks, at least about 2 weeks, at least about 14 days, at least about 3 weeks, at least about 21 days, at least about 4 weeks, at least about 28 days, at least about 1 month, at least about 1.5 months, at least about 2 months, about 7 to about 14 days, about 14 to about 21 days, about 14 to about 28 days, about 21 to about 28 days, and about 7 to about 28 days.

Provided herein is a coated medical device comprising: a medical device for delivering encapsulated active agent to a treatment site; and a coating on the medical device comprising the encapsulated active agent wherein the encapsulated active agent comprise active agent encapsulated in a polymer, and wherein the encapsulated active agent has a positive surface charge.

Provided herein is a coated medical device comprising: a medical device for delivering encapsulated active agent to a treatment site; and a coating on the medical device comprising the encapsulated active agent wherein the encapsulated active agent comprise a polymer that encapsules at least a portion of an active agent, and wherein the encapsulated active agent has a positive surface charge.

In some embodiments, the active agent is not completely encapsulated. An active agent (or a portion thereof) need not be completely surrounded in order to be encapsulated by the polymer. In some embodiments, at least 10% of the surface area of the active agent is encapsulated in the polymer. In some embodiments, at least 20% of the surface area of the active agent is encapsulated in the polymer. In some embodiments, at least 25% of the surface area of the active agent is encapsulated in the polymer. In some embodiments, at least 30% of the surface area of the active agent is encapsulated in the polymer. In some embodiments, at least 40% of the surface area of the active agent is encapsulated in the polymer. In some embodiments, at least 50% of the surface area of the active agent is encapsulated in the polymer. In some embodiments, at least 60% of the surface area of the active agent is encapsulated in the polymer. In some embodiments, at least 70% of the surface area of the active agent is encapsulated in the polymer. In some embodiments, at least 75% of the surface area of the active agent is encapsulated in the polymer. In some embodiments, at least 80% of the surface area of the active agent is encapsulated in the polymer. In some embodiments, at least 90% of the surface area of the active agent is encapsulated in the polymer. In some embodiments, at least 95% of the surface area of the active agent is encapsulated in the polymer. In some embodiments, at least one of: at least 5% of the surface area of the active agent is at least partially surrounded by the polymer, at least 10% of the surface area of the active agent is at least partially surrounded by the polymer, at least 15% of the surface area of the active agent is at least partially surrounded by the polymer, at least 20% of the surface area of the active agent is at least partially surrounded by the polymer, at least 25% of the surface area of the active agent is at least partially surrounded by the polymer, at least 30% of the surface area of the active agent is at least partially surrounded by the polymer, at least 40% of the surface area of the active agent is at least partially surrounded by the polymer, at least 50% of the surface area of the active agent is at least partially surrounded by the polymer, at least 60% of the surface area of the active agent is at least partially surrounded by the polymer, at least 70% of the surface area of the active agent is at least partially surrounded by the polymer, at least 75% of the surface area of the active agent is at least partially surrounded by the polymer, at least 80% of the surface area of the active agent is at least partially surrounded by the polymer, at least 90% of the surface area of the active agent is at least partially surrounded by the polymer, and at least 95% of the surface area of the active agent is at least partially surrounded by the polymer.

Provided herein is a coating for a medical device comprising encapsulated active agent comprising active agent encapsulated in a polymer, wherein the encapsulated active agent has a positive surface charge, and wherein the coating delivers active agent to a treatment site over at least about 1 day.

Provided herein is a method of forming a coating on a medical device comprising providing encapsulated active agent comprising a polymer and active agent, wherein the encapsulated active agent have a positive surface charge, depositing the encapsulated active agent on the medical device. In some embodiments, the coating delivers the active agent to the treatment site over at least about 1 day.

Provided herein is a method of forming a coating on a medical device comprising providing encapsulated active agent comprising a polymer at least partially encapsulating at least a portion of an active agent wherein the encapsulated active agent has a positive surface charge, and depositing the encapsulated active agent on the medical device. In some embodiments, the coating delivers the active agent to the treatment site over at least about 1 day.

Provided herein is a coated medical device comprising: a medical device for delivering an active agent to a treatment site; and a coating on the device comprising the active agent, wherein the coated medical device delivers at least a portion of the coating to the treatment site which portion releases active agent into the treatment site over at least about 1 day.

Provided herein is a coating for a medical device comprising an active agent, wherein the coating delivers the into a treatment site over at least about 1 day.

Provided herein is a method of forming coating on a medical device with of an active agent comprising depositing the active agent on the medical device using an eSTAT process.

In some embodiments of the devices, coatings and/or methods provided herein the polymer comprises PLGA. The PLGA may have at least one of: a MW of about 30 KDa and a Mn of about 15 KDa, a Mn of about 10 KDa to about 25 KDa, and a MW of about 15 KDa to about 40 KDa.

In some embodiments of the methods and/or devices provided herein, the coating comprises a bioabsorbable polymer. In some embodiments, the active agent comprises a bioabsorbable polymer. In some embodiments, the bioabsorbable polymer comprises at least one of: Polylactides (PLA); PLGA (poly(lactide-co-glycolide)); Polyanhydrides; Polyorthoesters; Poly(N-(2-hydroxypropyl) methacrylamide); DLPLA—poly(dl-lactide); LPLA—poly(l-lactide); PGA—polyglycolide; PDO—poly(dioxanone); PGA-TMC—poly(glycolide-co-trimethylene carbonate); PGA-LPLA—poly(l-lactide-co-glycolide); PGA-DLPLA—poly(dl-lactide-co-glycolide); LPLA-DLPLA—poly(l-lactide-co-dl-lactide); and PDO-PGA-TMC—poly(glycolide-co-trimethylene carbonate-co-dioxanone), and combinations, copolymers, and derivatives thereof. In some embodiments, the bioabsorbable polymer comprises between 1% and 95% glycolic acid content PLGA-based polymer.

In some embodiments of the methods and/or devices provided herein, the polymer comprises at least one of polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, aliphatic polyesters, polyurethanes, polystyrenes, copolymers, silicones, silicone containing polymers, polyalkyl siloxanes, polyorthoesters, polyanhydrides, copolymers of vinyl monomers, polycarbonates, polyethylenes, polypropytenes, polylactic acids, polylactides, polyglycolic acids, polyglycolides, polylactide-co-glycolides, polycaprolactones, poly(e-caprolactone)s, polyhydroxybutyrate valerates, polyacrylamides, polyethers, polyurethane dispersions, polyacrylates, acrylic latex dispersions, polyacrylic acid, polyalkyl methacrylates, polyalkylene-co-vinyl acetates, polyalkylenes, aliphatic polycarbonates polyhydroxyalkanoates, polytetrahalooalkylenes, poly(phosphasones), polytetrahalooalkylenes, poly(phosphasones), and mixtures, combinations, and copolymers thereof. The polymers of the present invention may be natural or synthetic in origin, including gelatin, chitosan, dextrin, cyclodextrin, Poly(urethanes), Poly(siloxanes) or silicones, Poly(acrylates) such as [rho]oly(methyl methacrylate), poly(butyl methacrylate), and Poly(2-hydroxy ethyl methacrylate), Poly(vinyl alcohol)Poly(olefins) such as poly(ethylene), [rho]oly(isoprene), halogenated polymers such as Poly(tetrafluoroethylene)- and derivatives and copolymers such as those commonly sold as Teflon® products, Poly(vinylidine fluoride), Poly(vinyl acetate), Poly(vinyl pyrrolidone), Poly(acrylic acid), Polyacrylamide, Poly(ethylene-co-vinyl acetate), Poly(ethylene glycol), Poly(propylene glycol), Poly(methacrylic acid); etc. Suitable polymers also include absorbable and/or resorbable polymers including the following, combinations, copolymers and derivatives of the following: Polylactides (PLA), Polyglycolides (PGA), PolyLactide-co-glycolides (PLGA), Polyanhydrides, Polyorthoesters, Poly(N-(2-hydroxypropyl) methacrylamide), Poly(l-aspartamide), including the derivatives DLPLA—poly(dl-lactide); LPLA—poly(l-lactide); PDO—poly(dioxanone); PGA-TMC—poly(glycolide-co-trimethylene carbonate); PGA-LPLA—poly(l-lactide-co-glycolide); PGA-DLPLA—poly(dl-lactide-co-glycolide); LPLA-DLPLA—poly(l-lactide-co-dl-lactide); and PDO-PGA-TMC—poly(glycolide-co-trimethylene carbonate-co-dioxanone), and combinations thereof.

In some embodiments of the methods and/or devices provided herein, the polymer has a dry modulus between 3,000 and 12,000 KPa. In some embodiments, the polymer is capable of becoming soft after implantation. In some embodiments, the polymer is capable of becoming soft after implantation by hydration, degradation or by a combination of hydration and degradation. In some embodiments, the polymer is adapted to transfer, free, and/or dissociate from the substrate when at the intervention site due to hydrolysis of the polymer.

In some embodiments of the methods and/or devices provided herein, the bioabsorbable polymer is capable of resorbtion in at least one of: about 1 day, about 3 days, about 5 days, about 7 days, about 14 days, about 3 weeks, about 4 weeks, about 45 days, about 60 days, about 90 days, about 180 days, about 6 months, about 9 months, about 1 year, about 1 to about 2 days, about 1 to about 5 days, about 1 to about 2 weeks, about 2 to about 4 weeks, about 45 to about 60 days, about 45 to about 90 days, about 30 to about 90 days, about 60 to about 90 days, about 90 to about 180 days, about 60 to about 180 days, about 180 to about 365 days, about 6 months to about 9 months, about 9 months to about 12 months, about 9 months to about 15 months, and about 1 year to about 2 years.

In some embodiments of the methods and/or devices provided herein, the coating comprises a microstructure. In some embodiments, particles of the active agent are sequestered or encapsulated within the microstructure. In some embodiments, the microstructure comprises microchannels, micropores and/or microcavities. In some embodiments, the microstructure is selected to allow sustained release of the active agent. In some embodiments, the microstructure is selected to allow controlled release of the active agent.

In some embodiments of the devices, coatings and/or methods provided herein the coating comprises a positive surface charge. The positive surface charge may be about 20 mV to about 40 mV. The positive surface charge may be at least one of: at least about 1 mV, over about 1 mV, at least about 5 mV, at least about 10 mV, about 10 mV to about 50 mV, about 20 mV to about 50 mV, about 10 mV to about 40 mV, about 30 mV to about 40 mV, about 20 mV to about 30 mV, and about 25 mV to about 35 mV.

In some embodiments of the devices, coatings and/or methods provided herein, the w/w percent of active agent in the encapsulated active agent is about 5%. In some embodiments of the devices, coatings and/or methods provided herein, the w/w percent of active agent in the encapsulated active agent is about 10-25%.

In some embodiments, the encapsulated active agent comprises a polymer at least partially encapsulating at least a portion of an active agent wherein the encapsulated active agent has a positive surface charge. In some embodiments, the active agent is not completely encapsulated. An active agent (or a portion thereof) need not be completely surrounded in order to be encapsulated by the polymer. In some embodiments, at least 10% of the surface area of the active agent is encapsulated in the polymer. In some embodiments, at least 20% of the surface area of the active agent is encapsulated in the polymer. In some embodiments, at least 25% of the surface area of the active agent is encapsulated in the polymer. In some embodiments, at least 30% of the surface area of the active agent is encapsulated in the polymer. In some embodiments, at least 40% of the surface area of the active agent is encapsulated in the polymer. In some embodiments, at least 50% of the surface area of the active agent is encapsulated in the polymer. In some embodiments, at least 60% of the surface area of the active agent is encapsulated in the polymer. In some embodiments, at least 70% of the surface area of the active agent is encapsulated in the polymer. In some embodiments, at least 75% of the surface area of the active agent is encapsulated in the polymer. In some embodiments, at least 80% of the surface area of the active agent is encapsulated in the polymer. In some embodiments, at least 90% of the surface area of the active agent is encapsulated in the polymer. In some embodiments, at least 95% of the surface area of the active agent is encapsulated in the polymer. In some embodiments, at least one of: at least 5% of the surface area of the active agent is at least partially surrounded by the polymer, at least 10% of the surface area of the active agent is at least partially surrounded by the polymer, at least 15% of the surface area of the active agent is at least partially surrounded by the polymer, at least 20% of the surface area of the active agent is at least partially surrounded by the polymer, at least 25% of the surface area of the active agent is at least partially surrounded by the polymer, at least 30% of the surface area of the active agent is at least partially surrounded by the polymer, at least 40% of the surface area of the active agent is at least partially surrounded by the polymer, at least 50% of the surface area of the active agent is at least partially surrounded by the polymer, at least 60% of the surface area of the active agent is at least partially surrounded by the polymer, at least 70% of the surface area of the active agent is at least partially surrounded by the polymer, at least 75% of the surface area of the active agent is at least partially surrounded by the polymer, at least 80% of the surface area of the active agent is at least partially surrounded by the polymer, at least 90% of the surface area of the active agent is at least partially surrounded by the polymer, and at least 95% of the surface area of the active agent is at least partially surrounded by the polymer.

In some embodiments of the devices, coatings and/or methods provided herein, at least a portion of the encapsulated active agent are nanoparticles. At least a portion of the encapsulated active agent may be at least one of: a spherical shape, a discoidal shape, a hemispherical shape, a cylindrical shape, a conical shape, a nanoreef shape, a nanobox shape, a cluster shape, a nanotube shape, a whisker shape, a rod shape, a fiber shape, a cup shape, a jack shape, a hexagonal shape, an ellipsoid shape, an oblate ellipsoid shape, a prolate ellipsoid shape, a torus shape, a spheroid shape, a taco-like shape, a bullet shape, a barrel shape, a lens shape, a capsule shape, a pulley wheel shape, a circular disc shape, a rectangular disc shape, a hexagonal disc shape, a flying saucer-like shape, a worm shape, a ribbon-like shape, and a ravioli-like shape.

The active agent in some embodiments of the devices, coatings and/or methods provided herein comprises a macrolide immunosuppressive drug. The active agent may be selected from sirolimus, a prodrug, a hydrate, an ester, a salt, a polymorph, a derivative, and an analog thereof. A portion of the active agent may be in crystalline form.

The active agent may be, on average, at least one of: at most 5 microns, over 1 micrometer, between 1 micrometer and 5 micrometers, about 1.5 micrometers on average, and about 2.5 micrometers on average. In some embodiments, the size of the active agent in the coating is controlled in order to improve drug retention in the artery. For non-limiting example, in the case of sirolimus as an active agent, the sirolimus may have an average size (mean diameter) of at least one of: 1.5 µm, 2.5 µm, 645 nm, 100-200 nm, another controlled size, or a combination thereof. In some embodiments, the active agent is sirolimus and wherein the sirolimus has a median size of at least one of: 1.5 µm, 2.5 µm, 645 nm, 100-200 nm, another controlled size, or a combination thereof. In some embodiments, the active agent is sirolimus and wherein the sirolimus has an average size (mean diameter) of at least one of: about 1.5 µm, about 2.5 µm, about 645 nm, about 100-200 nm, another controlled size, or a combination thereof. In some embodiments, the active agent is sirolimus and wherein the sirolimus has a median size of at least one of: about 1.5 µm, about 2.5 µm, about 645 nm, about 100-200 nm, another controlled size, or a combination thereof. In some embodiments the size of the active agent is controlled. For example, in some embodiments, sirolimus is the active agent and at least 75% of the sirolimus as is 1.5 µm, 2.5 µm, 645 nm, 100-200 nm, or another controlled size. In some embodiments, sirolimus is the active agent and at least 50% of the sirolimus as is 1.5 µm, 2.5 µm, 645 nm, 100-200 nm, or another controlled size. In some embodiments, sirolimus is the active agent and at least 90% of the sirolimus as is 1.5 µm, 2.5 µm, 645 nm, 100-200 nm, or another controlled size. In some embodiments, sirolimus is the active agent and at least 95% of the sirolimus as is 1.5 µm, 2.5 µm, 645 nm, 100-200 nm, or another controlled size. In some embodiments, sirolimus is the active agent and at least 98% of the sirolimus as is 1.5 µm, 2.5 µm, 645 nm, 100-200 nm, or another controlled size. In some embodiments, sirolimus is the active agent and at least 99% of the sirolimus as is 1.5 µm, 2.5 µm, 645 nm, 100-200 nm, or another controlled size.

In some embodiments of the devices, coatings and/or methods provided herein the coating delivers the active agent to the treatment site over at least about 1 day. In some embodiments of the devices, coatings and/or methods provided herein the coating delivers the active agent to the treatment site over at least one of: about 3 days, about 5 days, about 1 week, about 1.5 weeks, about 2 weeks, about 14 days, about 3 weeks, about 21 days, about 4 weeks, about 28 days, about 1 month, about 1.5 months, about 2 months, at least about 3 days, at least about 5 days, at least about 1 week, at least about 1.5 weeks, at least about 2 weeks, at least about 14 days, at least about 3 weeks, at least about 21 days, at least about 4 weeks, at least about 28 days, at least about 1 month, at least about 1.5 months, at least about 2 months, about 7 to about 14 days, about 14 to about 21 days, about 14 to about 28 days, about 21 to about 28 days, and about 7 to about 28 days.

In some embodiments of the devices, coatings and/or methods provided herein the treatment site is a vessel wall. In some embodiments of the devices, coatings and/or methods provided herein the treatment site is a coronary artery. In some embodiments of the devices, coatings and/or methods provided herein the treatment site is bypass graft. In some embodiments of the devices, coatings and/or methods provided herein the treatment site is a bifurcated lesion. In some embodiments of the devices, coatings and/or methods provided herein the treatment site is a small coronary lesions (for example, with reference diameter<2.5 mm) In some embodiments of the devices, coatings and/or methods provided herein the treatment site is a peripheral artery. In some embodiments of the devices, coatings and/or methods provided herein the treatment site is vein. In some embodiments of the devices, coatings and/or methods provided herein the treatment site is an AV graft. In some embodiments of the devices, coatings and/or methods provided herein the treatment site is an AV fistula. In some embodiments of the devices, coatings and/or methods provided herein the treatment site is a biliary tract. In some embodiments of the devices, coatings and/or methods provided herein the treatment site is a biliary duct. In some embodiments of the devices, coatings and/or methods provided herein the treatment site is a sinus. In some embodiments of the devices, coatings and/or methods provided herein the treatment site is a vein graft.

In some embodiments of the devices, coatings and/or methods provided herein the coating comprises a positive surface charge on a surface of the coating configured to contact the treatment site.

In some embodiments of the devices, coatings and/or methods provided herein the encapsulated active agent are micelles.

In some embodiments of the devices, coatings and/or methods provided herein the medical device comprises a balloon. In some embodiments the medical device is a balloon of a balloon catheter.

In some embodiments of the devices, coatings and/or methods provided herein depositing the encapsulated active agent comprises using an eSTAT process. In some embodiments of the devices, coatings and/or methods provided herein depositing a second polymer on the medical device following depositing the encapsulated active agent on the medical device.

In some embodiments of the methods, coatings or and/or devices provided herein, the coating is formed on the substrate by a process comprising depositing a polymer and/or the active agent by an RESS, e-RESS, an e-SEDS, or an e-DPC process. In some embodiments of the methods and/or devices provided herein, wherein the coating is formed on the substrate by a process comprising at least one of: depositing a polymer by an RESS, e-RESS, an e-SEDS, or an e-DPC process, and depositing the pharmaceutical agent by an e-RESS, an e-SEDS, eSTAT, or an e-DPC process. In some embodiments of the methods and/or devices provided herein, the coating is formed on the substrate by a process comprising at least one of: depositing a polymer by an RESS, e-RESS, an e-SEDS, or an e-DPC process, and depositing the active agent by an eSTAT, e-RESS, an e-SEDS, or an e-DPC process. In some embodiments, the process of forming the coating provides improved adherence of the coating to the substrate prior to deployment of the device at the intervention site and facilitates dissociation of the coating from the substrate at the intervention site. In some embodiments, the coating is formed on the substrate by a process comprising depositing the active agent by an eSTAT, e-RESS, an e-SEDS, or an e-DPC process without electrically charging the substrate. In some embodiments, the coating is formed on the substrate by a process comprising depositing the active agent on the substrate by an e-RESS, an e-SEDS, or an e-DPC process without creating an electrical potential between the substrate and a coating apparatus used to deposit the coating.

In some embodiments of the devices, coatings and/or methods provided herein the second polymer comprises PLGA. The PLGA may have at least one of: a MW of about 30 KDa and a Mn of about 15 KDa, a Mn of about 10 KDa to about 25 KDa, and a MW of about 15 KDa to about 40 KDa. Depositing the second polymer on the medical device may use at least one of a RESS coating process, an eSTAT coating process, a dip coating process, and a spray coating process.

In some embodiments of the methods, coatings, and/or devices provided herein, the intervention site is in or on the body of a subject. In some embodiments, the intervention site is a vascular wall. In some embodiments, the intervention site is a non-vascular lumen wall. In some embodiments, the intervention site is a vascular cavity wall. In some embodiments of the methods and/or devices provided herein, the intervention site is a wall of a body cavity. In some embodiments, the body cavity is the result of a lumpectomy. In some embodiments, the intervention site is a cannulized site within a subject. In some embodiments of the methods and/or devices provided herein, the intervention site is a sinus wall. In some embodiments, the intervention site is a sinus cavity wall. In some embodiments, the active agent comprises a corticosteroid.

In some embodiments of the methods, coatings, and/or devices provided herein, the coating is capable of at least one of: retarding healing, delaying healing, and preventing healing. In some embodiments, the coating is capable of at least one of: retarding, delaying, and preventing the inflammatory phase of healing. In some embodiments, the coating is capable of at least one of: retarding, delaying, and preventing the proliferative phase of healing. In some embodiments, the coating is capable of at least one of: retarding, delaying, and preventing the maturation phase of healing. In some embodiments, the coating is capable of at least one of: retarding, delaying, and preventing the remodeling phase of healing. In some embodiments, the active agent comprises an anti-angiogenic agent.

Provided herein is a method comprising providing a medical device, wherein the medical device comprises a substrate and a coating on at least a portion of the substrate, and wherein the coating comprises a plurality of layers, wherein at least one layer comprises a pharmaceutical agent in a therapeutically desirable morphology, and transferring at least a portion of the coating from the substrate to the intervention site upon stimulating the coating with a stimulation.

Other compounds that may be used in lieu of Sirolimus (or in addition thereto) include, for non-limiting example: Sirolimus which has a FKBP12 binding (nM) of 0.4-2.3 nM and an Antiproliferative potency (nM) of 0.1-3.5 nM; Everolimus which has a FKBP12 binding (nM) of 1.8-2.6 nM and an Antiproliferative potency (nM) of 0.9-3.6 nM; Zotarolimus which has a FKBP12 binding (nM) of 2.0-3.2 nM and an Antiproliferative potency (nM) of 0.2-2.7 nM; Biolimus which has an Antiproliferative potency (nM) of about 10 nM; Temsirolimus which has a FKBP12 binding (nM) and an Antiproliferative potency (nM) that is about the same as Sirolimus; Tacrolimus which has a FKBP12 binding (nM) of 0.2-0.4 nM and an Antiproliferative potency (nM)

of about 350 nM; Pimecrolimus which has a FKBP12 binding (nM) of about 1.2 nM and an Antiproliferative potency (nM) of about 1 μM.

Alternative compounds that may be used in lieu of sirolimus (or in addition thereto) include drugs that were not sufficiently potent to effectively deliver from a drug stent platform may be more effective when delivered from a coated balloon (if the drug is highly lipophilic), for non-limiting example: Dipyradamole, Cerivastatin, Troglitazone, and/or Cilostazol. Dipyradamole may be an appropriate drug for use on a coating of a balloon, for example, since it inhibits VSMC (vascular smooth muscle cell) proliferation, is anti-inflammatory, improves endothelial function, and provides local release of t-PA (tissue plasminogen activator). Cerivastatin may be an appropriate drug for use on a coating of a balloon, for example, since it inhibits VSMC proliferation, is anti-inflammatory, improves endothelial function, and can stabilize vulnerable plaque. Troglitazone may be an appropriate drug for use on a coating of a balloon, for example, since it inhibits VSMC proliferation, is anti-inflammatory, improves endothelial function, and may provide vascular lipid reduction. Cilostazol may be an appropriate drug for use on a coating of a balloon, for example, since it inhibits VSMC proliferation, may be anti-inflammatory, improves endothelial function, and is a vasodilator and/or increases NO (nitric oxide) release and/or production of NO.

Other drugs that may be appropriate for use on a drug balloon as a coating that is released thereby include the following: Drugs to prevent elastic recoil such as smooth muscle cell relaxants and/or agents that bind elastin; Drugs to prevent reperfusion injury such as ANP, atorvastatin, erythropoietin, and/or glucagon-like peptide 1; Drugs to stimulate collateral blood flow such as Vasodilators and/or Growth factors (GF) and GF activators. Drug coated balloons may be useful in lower extremities and in peripheral indications, such as in PTA (Percutaneous transluminal angioplasty) and in combination with a bare stent, in situations of in stent restenosis, following atherectomy. Drug coated balloons may be particularly useful in certain coronary indications, such as following in stent restenosis, in small vessel angioplasty situations, in bifurcations, and in combination with a bare metal stent. Other uses include in AV Fistulae and Grafts (dialysis), in the nasal sinus, in neurovascular vessels, in renal vessels or applications, in anti-cancer applications, and in urological applications. a) Fistulae and Grafts (dialysis) Fistulae and Grafts (dialysis) Fistulae and Grafts (dialysis).

In some embodiments, the device releases at least 3% of the active agent to artery in vivo. In some embodiments, the device releases at least 5% of the active agent to artery in vivo. In some embodiments, the device releases at least 10% of the active agent in vivo. In some embodiments, the device releases at least 5% of the active agent to artery upon inflation of the balloon in vivo. In some embodiments, the device releases at least 7% of the active agent to artery upon inflation of the balloon in vivo. In some embodiments, the device releases at least 10% of the active agent to artery upon inflation of the balloon in vivo. In some embodiments, the device releases at least 15% of the active agent to artery upon inflation of the balloon in vivo. In some embodiments, the device releases at least 20% of the active agent to artery upon inflation of the balloon in vivo. In some embodiments, the device releases at least 25% of the active agent to artery upon inflation of the balloon in vivo. In some embodiments, the device releases at least 30% of the active agent to artery upon inflation of the balloon in vivo. In some embodiments, the device releases at least 40% of the active agent to artery upon inflation of the balloon in vivo. In some embodiments, the device releases at least 50% of the active agent to artery upon inflation of the balloon in vivo. In some embodiments, the device releases between 2% and 50% of the active agent to artery upon inflation of the balloon in vivo. In some embodiments, the device releases between 3% and 50% of the active agent to artery upon inflation of the balloon in vivo. In some embodiments, the device releases between 5% and 50% of the active agent to artery upon inflation of the balloon in vivo. In some embodiments, the device releases between 3% and 30% of the active agent to artery upon inflation of the balloon in vivo. In some embodiments, the device releases between 3% and 25% of the active agent to artery upon inflation of the balloon in vivo. In some embodiments, the device releases between 3% and 20% of the active agent to artery upon inflation of the balloon in vivo. In some embodiments, the device releases between 3% and 15% of the active agent to artery upon inflation of the balloon in vivo. In some embodiments, the device releases between 1% and 15% of the active agent to artery upon inflation of the balloon in vivo. In some embodiments, the device releases between 1% and 10% of the active agent to artery upon inflation of the balloon in vivo. In some embodiments, the device releases between 3% and 10% of the active agent to artery upon inflation of the balloon in vivo. In some embodiments, the device releases between 1% and 5% of the active agent to artery upon inflation of the balloon in vivo.

As used herein, depending on the embodiment, "upon inflation" means as soon as reasonably possible following removal of the device from the treatment site. This may include timings such as about 1 minute, about 5 minutes from removal of the device from the treatment site, within 1 to 15 minutes from the removal of the device from the treatment site, within 1 to 15 minutes from the removal of the device from the treatment site, within 1 to 20 minutes from the removal of the device from the treatment site, within 1 minute to 1 hour from the removal of the device from the treatment site, within 1 minute to 2 hour from the removal of the device from the treatment site, and/or within 1 minute to 3 hours from the removal of the device from the treatment site.

Example 5: Delivery of Rapamycin from Coated Invertable Balloons

Provided herein is a device comprising an invertable balloon, a coating on the abluminal side of the invertable balloon, wherein the coating comprises an active agent and a binding agent. In some embodiments, the device releases at least 3% of the active agent to artery upon inflation of the balloon in vivo.

In some embodiments, the device releases at least 5% of the active agent to artery upon inflation of the balloon in vivo. In some embodiments, the device releases at least 7% of the active agent to artery upon inflation of the balloon in vivo. In some embodiments, the device releases at least 10% of the active agent to artery upon inflation of the balloon in vivo. In some embodiments, the device releases at least 15% of the active agent to artery upon inflation of the balloon in vivo. In some embodiments, the device releases at least 20% of the active agent to artery upon inflation of the balloon in vivo. In some embodiments, the device releases at least 25% of the active agent to artery upon inflation of the balloon in vivo. In some embodiments, the device releases at least 30% of the active agent to artery upon inflation of the balloon in vivo. In some embodiments, the device releases at least 40% of the active agent to artery upon inflation of the balloon in vivo. In some embodiments, the device releases at least 50% of the active agent to artery upon inflation of the balloon in vivo. In some embodiments, the device releases between 2% and 50% of the active agent to artery upon inflation of the balloon in vivo. In some embodiments, the device releases between 3% and 50% of the active agent to artery upon inflation of the balloon in vivo. In some embodiments, the device releases between 5% and 50% of the active agent to artery upon inflation of the balloon in vivo. In some embodiments, the device releases between 3% and 30% of the active agent to artery upon inflation of the balloon in vivo. In some embodiments, the device releases between 3% and 25% of the active agent to artery upon inflation of the balloon in vivo. In some embodiments, the device releases between 3% and 20% of the active agent to artery upon inflation of the balloon in vivo. In some embodiments, the device releases between 3% and 15% of the active agent to artery upon inflation of the balloon in vivo. In some embodiments, the device releases between 1% and 15% of the active agent to artery upon inflation of the balloon in vivo. In some embodiments, the device releases between 1% and 10% of the active agent to artery upon inflation of the balloon in vivo. In some embodiments, the device releases between 3% and 10% of the active agent to artery upon inflation of the balloon in vivo. In some embodiments, the device releases between 1% and 5% of the active agent to artery upon inflation of the balloon in vivo.

Example invertable balloons (which may also and/or alternatively be called evertable balloons) include, but are not limited to, those described in U.S. Pat. No. 6,039,721 filed Dec. 3, 1997; and U.S. Pat. No. 4,606,347 filed Aug. 8, 1985 which patents are incorporated herein by reference in their entirety. In some embodiments the abluminal surface of the balloon is coated prior to inversion, and once coated, the balloon is inverted such that the abluminal surface of the balloon is protected from either blood flow during tracking or tracking contact with the vessel wall, or both, until the balloon catheter is positioned near the treatment site, usually just proximally to the site. As used herein, "abluminal side" or "abluminal surface" refers to a portion of the balloon having coating thereon, and intended to deliver the coating (agent) to the treatment site or location—i.e. the lumen of the vessel in the case of a treatment site that is a vessel. The balloon is then un-inverted such that the abluminal surface is positioned within the treatment site.

In an embodiment wherein the balloon is inverted within a catheter, it may be pushed out of the catheter using either pressure from the indeflator or another form of un-inversion of the balloon, such as for nonlimiting example, by moving the distal end of the balloon distally through the balloon itself, essentially unrolling the balloon into the treatment site such that the coated portion of the balloon is adjacent the treatment site. In certain embodiments where the balloon in inverted on the outside of the catheter, a similar movement and/or pressure from the indeflator can move the distal end of the balloon distally thereby unrolling the coated side of the balloon into proximity of the treatment site. In some embodiments, the balloon may be partially un-inverted, such that the treatment length may be controlled. The balloon thereafter is inflated such that the abluminal surface that is coated contacts and/or dilates the treatment site, thereby delivering the coating or a portion thereof to the treatment site.

Any of the devices, coatings, and/or methods described herein may be combined with an inverteable type of balloon to deliver the coating in a manner that reduces and/or substantially eliminates loss of coating due to tracking and/or blood flow and/or other in-transit coating loss prior to locating the device at the treatment site (i.e. delivering the device to the treatment site). In some embodiments, at most 1% of coating is removed from the balloon due to tracking of the coated balloon to the treatment site. In some embodiments, at most 3% of coating is removed from the balloon due to tracking of the coated balloon to the treatment site. In some embodiments, at most 5% of coating is removed from the balloon due to tracking of the coated balloon to the treatment site. In some embodiments, at most 10% of coating is removed from the balloon due to tracking of the coated balloon to the treatment site. In some embodiments, at most 15% of coating is removed from the balloon due to tracking of the coated balloon to the treatment site. In some embodiments, at most 20% of coating is removed from the balloon due to tracking of the coated balloon to the treatment site. In some embodiments, at most 25% of coating is removed from the balloon due to tracking of the coated balloon to the treatment site. In some embodiments, at most 30% of coating is removed from the balloon due to tracking of the coated balloon to the treatment site.

As used herein, depending on the embodiment, "upon inflation" means as soon as reasonably possible following removal of the device from the treatment site. This may include timings such as about 1 minute, about 5 minutes from removal of the device from the treatment site, within 1 to 15 minutes from the removal of the device from the treatment site, within 1 to 15 minutes from the removal of the device from the treatment site, within 1 to 20 minutes from the removal of the device from the treatment site, within 1 minute to 1 hour from the removal of the device from the treatment site, within 1 minute to 2 hour from the removal of the device from the treatment site, and/or within 1 minute to 3 hours from the removal of the device from the treatment site.

Example 6: Delivery of Rapamycin from Sheathed Coated Balloons

Provided herein is a device comprising an balloon, a coating on the abluminal side of the balloon, and a sheath over the balloon, wherein the coating comprises an active agent and a binding agent. In some embodiments, the device releases at least 3% of the active agent to artery upon inflation of the balloon in vivo. In some embodiments, the sheath may be retracted. In some embodiments, the sheath may be retracted to expose the coating to the treatment site. In some embodiments, the sheath covers the coated balloon until the balloon reaches the treatment site. In some embodiments the sheath may be retracted once the coated balloon is positioned near and/or at the treatment site. In some embodiments, the sheath covers the coated balloon until the balloon is proximal to the treatment site. In some embodiments, the sheath covers the coated balloon until the balloon is distal to the treatment site. In some embodiments, the sheath covers the coated balloon until the balloon is within to the treatment site. In some embodiments, the sheath may be moved over the balloon following deflation of the balloon after the coating (or a portion thereof) has been released to the artery, and the catheter may be removed such that the coated balloon is covered during removal from the subject. In some embodiments, the sheath may remain in a retracted state following deflation of the balloon after the coating (or a portion thereof) has been released to the artery, and the catheter may be removed such that the coated balloon is exposed to the delivery track during removal from the subject.

Any of the devices, coatings, and/or methods described herein may be combined with a sheath to deliver the coating in a manner that reduces and/or substantially eliminates loss of coating due to tracking and/or blood flow and/or other in-transit coating loss prior to locating the device at the treatment site (i.e. delivering the device to the treatment site). In some embodiments, at most 1% of coating is removed from the balloon due to tracking of the coated balloon to the treatment site. In some embodiments, at most 3% of coating is removed from the balloon due to tracking of the coated balloon to the treatment site. In some embodiments, at most 5% of coating is removed from the balloon due to tracking of the coated balloon to the treatment site. In some embodiments, at most 10% of coating is removed from the balloon due to tracking of the coated balloon to the treatment site. In some embodiments, at most 15% of coating is removed from the balloon due to tracking of the coated balloon to the treatment site. In some embodiments, at most 20% of coating is removed from the balloon due to tracking of the coated balloon to the treatment site. In some embodiments, at most 25% of coating is removed from the balloon due to tracking of the coated balloon to the treatment site. In some embodiments, at most 30% of coating is removed from the balloon due to tracking of the coated balloon to the treatment site.

In some embodiments, the device releases at least 5% of the active agent to artery upon inflation of the balloon in vivo. In some embodiments, the device releases at least 7% of the active agent to artery upon inflation of the balloon in vivo. In some embodiments, the device releases at least 10% of the active agent to artery upon inflation of the balloon in vivo. In some embodiments, the device releases at least 15% of the active agent to artery upon inflation of the balloon in vivo. In some embodiments, the device releases at least 20% of the active agent to artery upon inflation of the balloon in vivo. In some embodiments, the device releases at least 25% of the active agent to artery upon inflation of the balloon in vivo. In some embodiments, the device releases at least 30% of the active agent to artery upon inflation of the balloon in vivo. In some embodiments, the device releases at least 40% of the active agent to artery upon inflation of the balloon in vivo. In some embodiments, the device releases at least 50% of the active agent to artery upon inflation of the balloon in vivo. In some embodiments, the device releases between 2% and 50% of the active agent to artery upon inflation of the balloon in vivo. In some embodiments, the device releases between 3% and 50% of the active agent to artery upon inflation of the balloon in vivo. In some embodiments, the device releases between 5% and 50% of the active agent to artery upon inflation of the balloon in vivo. In some embodiments, the device releases between 3% and 30% of the active agent to artery upon inflation of the balloon in vivo. In some embodiments, the device releases between 3% and 25% of the active agent to artery upon inflation of the balloon in vivo. In some embodiments, the device releases between 3% and 20% of the active agent to artery upon inflation of the balloon in vivo. In some embodiments, the device releases between 3% and 15% of the active agent to artery upon inflation of the balloon in vivo. In some embodiments, the device releases between 1% and 15% of the active agent to artery upon inflation of the balloon in vivo. In some embodiments, the device releases between 1% and 10% of the active agent to artery upon inflation of the balloon in vivo. In some embodiments, the device releases between 3% and 10% of the active agent to artery upon inflation of the balloon in vivo. In some embodiments, the device releases between 1% and 5% of the active agent to artery upon inflation of the balloon in vivo.

As used herein, depending on the embodiment, "upon inflation" means as soon as reasonably possible following removal of the device from the treatment site. This may include timings such as about 1 minute, about 5 minutes from removal of the device from the treatment site, within 1 to 15 minutes from the removal of the device from the treatment site, within 1 to 15 minutes from the removal of the device from the treatment site, within 1 to 20 minutes from the removal of the device from the treatment site, within 1 minute to 1 hour from the removal of the device from the treatment site, within 1 minute to 2 hour from the removal of the device from the treatment site, and/or within 1 minute to 3 hours from the removal of the device from the treatment site.

Example 7: Delivery of Rapamycin from Coated Balloons with Occluder

Provided herein is a device comprising a balloon, a coating on the balloon, and an occluder, wherein the coating comprises an active agent and a binding agent. In some embodiments, the occluder is a flow occluder configured to block the flow of bodily fluids (e.g. blood) at the treatment site during exposure of the coating to the treatment site. In some embodiments, the device releases at least 3% of the active agent to artery upon inflation of the balloon in vivo. In some embodiments, the occluder comprises a second balloon that occludes the flow of the blood at the treatment site. In some embodiments, the balloon comprises the occluder, such that the balloon has two sections the flow occluder and the coated portion, wherein the flow occluder occludes the flow of the blood at the treatment site. In some embodiments, the balloon is dual-noded, wherein the distal node is coated and wherein the proximal node is the occluder. In some embodiments, the occluder is located proximally from the balloon, and/or portion thereof, having coating thereon. In some embodiments, the balloon is dual-noded, wherein the proximal node is coated and wherein the distal node is the occluder. In some embodiments the occluder is located distally from the balloon, and/or portion thereof, having coating thereon. In some embodiments, the balloon is a shape appropriate for the treatment site, such that the occluder portion of the balloon is the appropriate shape to occlude flow of blood at the treatment site. In some embodiments, the occluder substantially conforms to the shape of a treatment area near the treatment site such blood flow at the treatment site is occluded thereby. In some embodiments, the balloon is only partially coated, such that either or both the distal and proximal end of the balloon is not coated, and the distal and/or proximal end of the balloon is the occluder.

Provided herein is a device comprising a first balloon, a coating on the first balloon, and a second balloon capable of occluding flow of blood at the treatment site during expansion of the first balloon at the treatment site. In some embodiments, the occluder is a second balloon which is not the balloon having coating thereon. In some embodiments, the occluder is located proximally from the balloon, and/or portion thereof, having coating thereon. In some embodiments the occluder is located distally from the balloon, and/or portion thereof, having coating thereon.

Provided herein is a device comprising a first balloon, a coating on the first balloon, and a second balloon configured such that the second balloon expands prior to expansion of the first balloon. In some embodiments the occluder occludes the flow of the blood at the treatment prior to expansion of the portion of the balloon. In some embodiments, the occluder is located proximally from the balloon, and/or portion thereof, having coating thereon. In some embodiments the occluder is located distally from the balloon, and/or portion thereof, having coating thereon.

In some embodiments, the occluder is not a balloon, but is another form of occluder that is configured to occlude flow of blood at the treatment site. In some embodiments, the occluder is deployable and retractable, such that it can be deployed prior to inflation of the balloon having coating thereon, and following balloon inflation and delivery of the agent to the treatment site, the occluder can be retracted and removed either with the removal of the balloon, or following removal of the balloon from the treatment site.

In some embodiments, the occluder has a second coating thereon, having a second agent and/or polymer coated thereon as described elsewhere herein, according to any of the methods and processes as noted herein. The second coating in some embodiments comprises a binding agent. The second coating in some embodiments does not comprise a binding agent.

In some embodiments, the device releases at least 5% of the active agent to artery upon inflation of the balloon in vivo. In some embodiments, the device releases at least 7% of the active agent to artery upon inflation of the balloon in vivo. In some embodiments, the device releases at least 10% of the active agent to artery upon inflation of the balloon in vivo. In some embodiments, the device releases at least 15% of the active agent to artery upon inflation of the balloon in vivo. In some embodiments, the device releases at least 20% of the active agent to artery upon inflation of the balloon in vivo. In some embodiments, the device releases at least 25% of the active agent to artery upon inflation of the balloon in vivo. In some embodiments, the device releases at least 30% of the active agent to artery upon inflation of the balloon in vivo. In some embodiments, the device releases at least 40% of the active agent to artery upon inflation of the balloon in vivo. In some embodiments, the device releases at least 50% of the active agent to artery upon inflation of the balloon in vivo. In some embodiments, the device releases between 2% and 50% of the active agent to artery upon inflation of the balloon in vivo. In some embodiments, the device releases between 3% and 50% of the active agent to artery upon inflation of the balloon in vivo. In some embodiments, the device releases between 5% and 50% of the active agent to artery upon inflation of the balloon in vivo. In some embodiments, the device releases between 3% and 30% of the active agent to artery upon inflation of the balloon in vivo. In some embodiments, the device releases between 3% and 25% of the active agent to artery upon inflation of the balloon in vivo. In some embodiments, the device releases between 3% and 20% of the active agent to artery upon inflation of the balloon in vivo. In some embodiments, the device releases between 3% and 15% of the active agent to artery upon inflation of the balloon in vivo. In some embodiments, the device releases between 1% and 15% of the active agent to artery upon inflation of the balloon in vivo. In some embodiments, the device releases between 1% and 10% of the active agent to artery upon inflation of the balloon in vivo. In some embodiments, the device releases between 3% and 10% of the active agent to artery upon inflation of the balloon in vivo. In some embodiments, the device releases between 1% and 5% of the active agent to artery upon inflation of the balloon in vivo.

Example 8: Coatings Prepared with and without Shear Mixing

F15 (Formulation 15) as described in Example 4 was produced in multiple lots and having various rapamycin:polyarginine ratios. Regardless of the rapamycin:polyarginine ratio, however, indicative of F15 is that it comprises PLGA i.e. about 50:50 Lactic acid:Glycolic acid, Sirolimus having an average size of 1.5 µm, and Polyarginine 5-15 kDa. The sirolimus was in crystalline form. The following Rapamycin:Polyarginine Ratios were produced for this Example: 1:1, 5:1, 10:1, and 50:1.

Figure 4:
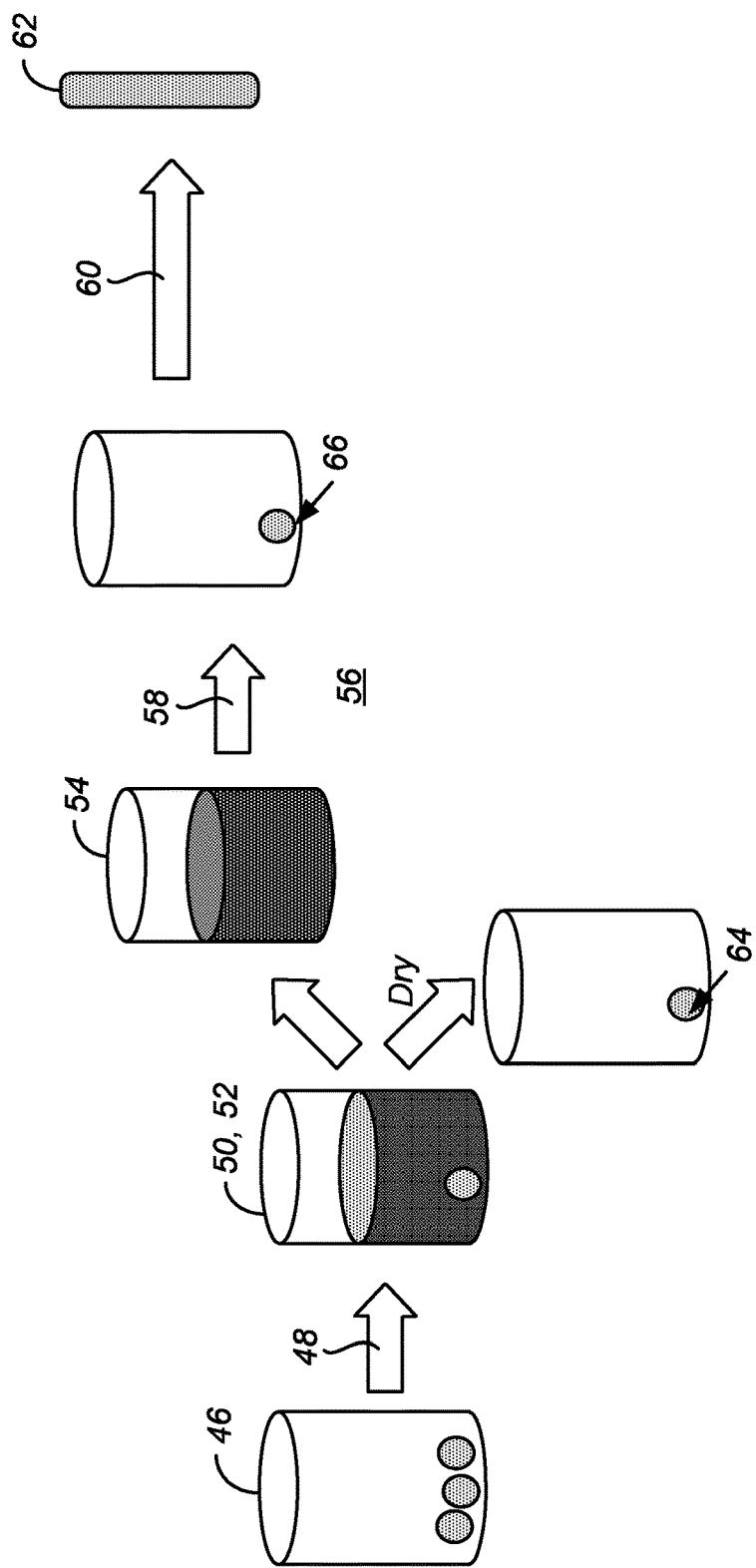
FIG. 4 depicts a method of preparing a coating formulation according to an embodiment herein.

In some lots (generally called F15 Lot 3 1:1, 5:1, 10:1, or 50:1), the production method for the formulation was as depicted in FIG. 4. The method for these lots was as follows: Dissolve 25 mg Poly-L-arginine hydrochloride (Aldrich P4663) (also called polyarginine herein) (cas 26982-20-7, 5-15 kDa) in 50 ml deionized water in 100 ml bottle and add 250 mg encapsulated rapamycin (1.5 micron particle size, crystalline form) (step 46). Sonicate (Branson 1510 bench top ultrasonic cleaner) for 2 h (step 48). Manually separate well-suspended liquid portion from unsuspended solids using pipette (step 50). Centrifuge~50 ml suspension for 30 min at 10,000 rpm (ThermoElectronCorp. IEC Multi RF Centrifuge) (step 52). Decant supernatant without allowing sediment to come to dryness (step 54). There will be an amount of unsuspended fraction 64 following centrifuge step 52. Add aqueous solution of poly-L-arginine hydrochloride concentration to produce desired encapsulated Sirolimus/poly-L-arginine hydrochloride ratio (step 56). Re-suspend sediment by shaking and 10 minute sonication. Lyophilize suspension to produce un-agglomerated encapsulated rapamycin/polyarginine powder solid lyophilisate 66 (Flexi-Dry MP) (step 58). This step took two to three days to achieve completion. This lyophilized solid 66 was eSTAT coated onto a balloon or a PLGA-coated balloons as a powder (dry coating as described herein) (step 60) to produce a coated balloon 62 comprising PLGA, rapamycin, and polyarginine, wherein the rapamycin is crystalline in form.

For the ratio-forming step, the ratios were produced as follows: 95 ml Masterbatch (combination of "well-suspended" portions of 4 sonicated solutions), estimated to be ~5 mg/ml solids, was divided into 5 portions. For the 50:1 ratio of sirolimus to polyarginine, 20 ml water was added to the first 18 ml portion, it was sonicated to re-suspend and lyophilized to produce 50.3 mg solid lyophilisate. For the 10:1 ratio of sirolimus to polyarginine, 9 mg polyarginine was dissolved in 20 ml water and was added to the second 18 ml portion whis was sonicated to re-suspend and lyophilized to produce 116.6 mg solid lyophilisate. For the 5:1 ratio of sirolimus to polyarginine, 18 mg polyarginine was dissolved in 20 ml water and was added to the third 18 ml portion, it was sonicated to re-suspend and lyophilized to produce 127.4 mg solid lyophilisate. For the 1:1 ratio of sirolimus to polyarginine, 90 mg polyarginine was dissolved in 20 ml water and was added to the fourth 18 ml portion, it was sonicated to re-suspend and lyophilized to produce 142.4 mg solid lyophilisate.

In some lots (generally called F15 Lot 4 5:1 or 10:1), the production methods for a F15 formulation having a 5:1 ratio of rapamycin to polyarginine lot and a F15 formulation having a 10:1 ratio of rapamycin to polyarginine lot were as follows. Dissolve 25 mg (10:1) or 50 mg (5:1) Poly-L-arginine hydrochloride (Aldrich P4663) (cas 26982-20-7) (5-15 kDa) (also called polyarginine) in 25 ml deionized water in 20 ml vial. Add 250 mg Sirolimus (1.5 micron particle size, crystalline in form). Mix for 10 min at 10,000 rpm in Laboratory Mixer (Silverson L4RT) using micro mixer head attachment to form a suspension (this mixing leaves little or no sediment). The Lab Mixer is a High Shear Mixer having an impeller for mechanical mixing. Run mixer with 25 ml pure water to recover residual material (rinse water). Combine suspension with rinse water. Lyophilize suspension to produce un-agglomerated Sirolimus/polyarginine powder (Flexi-Dry MP), which took two to three days to achieve completion. This lyophilized solid 66 was eSTAT coated onto PLGA coated balloons as a powder (dry coating as described herein) to produce a coated balloon comprising PLGA, rapamycin, and polyarginine, wherein the rapamycin is crystalline in form.

The amount of rapamycin that was found in the actual coated balloon was also determined and could be used to determine an actual rapamycin:polyarginine ratio (as opposed to the target ratio provided as noted elsewhere herein). To measure the amount of sirolimus on individual balloons ultraviolet-visible spectroscopy (UV-Vis) was employed. After sintering, coated balloons are cut (the stylus is removed before cutting) from the catheter wires leaving only ~¼" of the wires remaining connected to the balloons. Balloons were placed in individual 5 ml scintillation vials containing 4 ml of ethanol or methanol (sirolimus is soluble in ethanol up to 50 mg/ml). Sonication for 3 h removes sirolimus from the balloons. Following sonication UV-Vis is performed. Due to sirolimus being a triene (containing three double bonds) it produces UV absorbance at 3 wavelengths: 1 major peak at 277 nm and two smaller peaks at 267 nm and 288 nm. Uncoated GHOST rapid exchange nylon balloons and PLGA have also been individually sonicated for 3 h in ethanol and showed no interfering extractives for sirolimus measurements. The absorbance of sirolimus subtracted from the absorbance of an uncoated balloon at 277 nm is used in conjunction with a standard curve to calculate the amount of sirolimus per coated balloon. A standard of 3 from a batch of 12 coated balloons underwent UV-Vis analysis to obtain a batch average of sirolimus per balloon (measured in µg). The UV-Vis analysis could also be used to determine the presence and/or quantitate the amount of polymer (in this Example, PLGA) in the coating. UV-Vis testing of both lots 3 and 4 revealed presence of both polyarginine and rapamycin on the coated balloons. For Lot 3, the following actual ratios were determined: for Lot 3 1:1 (ideal) actual was about 1.3:1, for Lot 3 5:1 (ideal) actual was about 7.1:1, Lot 3 10:1 (ideal) actual was about 14.3:1, for Lot 3 50:1 (ideal) actual was about 43.1:1. Likewise, for Lot 4 5:1 (ideal) actual was about 6.1:1.

F15 Lot 3 coated balloons were delivered to arteries of animals of a rabbit study to assess if and how much of the rapamycin was retained in rabbit iliac arteries for 72 hours. The following coated balloon formulations were as follows in Table 18.

TABLE 18

| Sirolimus:Polyarginine Ratio | Sirolimus/Balloon (µg) (n = 6)* | Coating Appearance |
|---|---|---|
| 1:1 | 65.37 ± 3.84 | Transparent, Speckled |
| 5:1 | 79.02 ± 9.83 | Translucent, Very Thick |

TABLE 18-continued

| Sirolimus:Polyarginine Ratio | Sirolimus/Balloon (µg) (n = 6)* | Coating Appearance |
|---|---|---|
| 10:1 | 89.71 ± 5.27 | Translucent, Very Thick |
| 50:1 | 81.28 ± 4.61 | Translucent, Very Thick |

*Average Sirolimus concentrations based on UV-Vis analysis before pleating/folding and sterilization of balloons.

Study design for this study was as depicted in Table 19.

TABLE 19

| Test Article | Animals | Number of Vessels Per Animal | Blood PK Per Animal | Necropsy Time Points |
|---|---|---|---|---|
| F15 Sirolimus: Polyarginine Ratios: 1:1, 5:1, 10:1, 50:1 | n = 3 per ratio | n = 2 denuded rabbit iliac arteries | n = 2 time points (baseline/before necropsy) | 3 days (±5%) |
| Totals | 12 | 24 | 24 | 3 days (±5%) |

Deployed balloons, blood samples and denuded iliac arteries analyzed for Sirolimus levels.

The following results were determined as shown in Tables 20, 21, 22. Most retention from 10:1 ratio of F15 Lot 3 (1.8±1.2 ng/mg). Sirolimus blood levels below 1 ng/ml by 3 days.

TABLE 20

| F15 Ratio | Arterial Sirolimus Concentration (ng/mg) | SD | Total Sirolimus per Artery (µg) | SD |
|---|---|---|---|---|
| F15 1:1 Lot 3, n = 6 | 1.52 | 2.63 | 0.022 | 0.035 |
| F15 5:1 Lot 3, n = 6 | 0.67 | 0.53 | 0.013 | 0.011 |
| F15 10:1 Lot 3, n = 6 | 1.77 | 1.18 | 0.041 | 0.030 |
| F15 50:1 Lot 3, n = 6 | 0.63 | 0.18 | 0.010 | 0.003 |

TABLE 21

| 4F15 Ratio | Sirolimus Concentration on Balloon After Deployment (ug) | % Sirolimus Released/Lost* |
|---|---|---|
| 1:1 Lot 3 | 20.6 ± 9.8 (n = 6) | 68.9 ± 14.0% (n = 6) |
| 5:1 Lot 3 | 37.9 ± 6.3 (n = 6) | 52.0 ± 7.8% (n = 6) |
| 10:1 Lot 3 | 41.3 ± 7.2 (n = 6) | 53.7 ± 9.1% (n = 6) |
| 50:1 Lot 3 | 45.4 ± 6.9 (n = 6) | 44.2 ± 8.6% (n = 6) |

*Based on Balloon Batch Averages of Sirolimus

The amount of Sirolimus coated on balloons was as follows: F15 (1:1, Lot 3) Sirolimus coated on balloons=65.37±3.84; F15 (5:1, Lot 3) Sirolimus coated on balloons=79.02±9.83; F15 (10:1, Lot 3) Sirolimus coated on balloons=89.71±5.27; F15 (50:1, Lot 3) Sirolimus coated on balloons=81.28±4.61.

TABLE 22

| F15 Ratio | Sirolimus Concentration in Whole Blood (ng/mL) | Est. Total Sirolimus in Blood (µg)* |
|---|---|---|
| 1:1 Lot 3 | 0.29 ± 0.03 (n = 3) | 0.054 ± 0.01 (n = 3) |
| 5:1 Lot 3 | 0.50 ± 0.15 (n = 3) | 0.096 ± 0.03 (n = 3) |
| 10:1 Lot 3 | 0.43 ± 0.12 (n = 3) | 0.081 ± 0.02 (n = 3) |
| 50:1 Lot 3 | 0.38 ± 0.08 (n = 3) | 0.064 ± 0.01 (n = 3) |

*Based on 56 mL Blood per kg; BQL = below quantitation limit (0.1 ng/ml)

F15 Lot 4 coated balloons were delivered to arteries of animals of a rabbit study to assess if and how much of the rapamycin was retained in rabbit iliac arteries for 72 hours.

Provided herein is a method of coating at least a portion of a medical device comprising a balloon, thereby forming on the medical device a coating on the balloon comprising an active agent and a binding agent, wherein the method comprises: dissolving the binding agent to form a binding agent solution, combining the binding agent solution and the active agent, mixing the combined binding agent and active agent using a high shear mixer, forming a suspension comprising the combined mixed active agent and binding agent, lyophilising the suspension to form a lyophilisate of the active agent and the binding agent, and coating the balloon with the lyophilisate in powder form using an eSTAT process, wherein the active agent coated on the balloon comprises active agent in crystalline form.

In some embodiments, the high shear mixer is a mechanical mixer. In some embodiments, the mechanical mixer comprises an impeller, propeller, and/or a high speed saw tooth disperser. In some embodiments, the mechanical mixer comprise a high pressure pump. In some embodiments, the high shear mixer comprises a sonic mixer. In some embodiments, the sonic mixer comprises a sonicator. In some embodiments, the sonic mixer comprises a benchtop bath based sonicator. In some embodiments, the sonic mixer comprises an ultrasonic mixer. In some embodiments, the sonic mixer comprises an megasonic mixer.

In some embodiments, the mechanical mixer comprise a high pressure pump (up to 40,000 psi (2578 bar)) that forces particles into an interaction chamber at speeds up to 400 m/s. The interaction chamber may comprise engineered microchannels. Inside the chamber, the product may be exposed to consistent impact and shear forces and then cooled.

A high shear mixer disperses, or transports, one phase or ingredient (liquid, solid, gas) into a main continuous phase (liquid), with which it would normally be immiscible. In some embodiments of a mechanical mixer that is a high shear mixer, a rotor or impellor, together with a stationary component known as a stator, or an array of rotors and stators, is used either in a tank containing the solution to be mixed, or in a pipe through which the solution passes, to create shear. A high shear mixer can be used to create emulsions, suspensions, lyosols (gas dispersed in liquid), and granular products.

Fluid undergoes shear when one area of fluid travels with a different velocity relative to an adjacent area. In some embodiments of a mechanical mixer that is a high shear mixer, the high shear mixer uses a rotating impeller or high-speed rotor, or a series of such impellers or inline rotors, usually powered by an electric motor, to "work" the fluid, creating flow and shear. The tip velocity, or speed of the fluid at the outside diameter of the rotor, will be higher than the velocity at the centre of the rotor, and it is this velocity difference that creates shear.

A stationary component may be used in combination with the rotor, and is referred to as the stator. The stator creates a close-clearance gap between the rotor and itself and forms an extremely high shear zone for the material as it exits the rotor. The rotor and stator combined together are often referred to as the mixing head, or generator. A large high shear rotor-stator mixer may contain a number of generators.

In some embodiments the mechanical mixer comprises a batch high shear mixer. In a batch high shear mixer, the components to be mixed (whether immiscible liquids or powder in liquid) are fed from the top into a mixing tank containing the mixer on a rotating shaft at the bottom of the tank. A batch high shear mixer can process a given volume of material approximately twice as fast as an inline rotor-stator mixer of the same power rating; such mixers continue to be used where faster processing by volume is the major requirement, and space is not limited. When mixing sticky solutions, some of the product may be left in the tank, necessitating cleaning. However, there are designs of batch high shear mixers that clean the tank as part of the operating run. Some high shear mixers are designed to run dry, limiting the amount of cleaning needed in the tank.

In some embodiments the mechanical mixer comprises an inline high shear rotor-stator mixer. Generally speaking this version takes the same rotor and stator from the batch high shear mixer and installs it in a housing with inlet and outlet connections. Then the rotor is driven through a shaft seal thus resulting in a rotor-stator mixer that behaves like a centrifugal pumping device. That is, in an inline high shear rotor-stator mixer, the rotor-stator array is contained in a housing with an inlet at one end and an outlet at the other, and the rotor driven through a seal. The components to be mixed are drawn through the generator array in a continuous stream, with the whole acting as a centrifugal pumping device. Inline high shear mixers offer a more controlled mixing environment, take up less space, and can be used as part of a continuous process. Equilibrium mixing can be achieved by passing the product through the inline high shear mixer more than once. Since the inline mixer may be positioned in a flowing stream, the mixing may be more controlled than in a batch configuration, so the number of passes through the high shear zone can be monitored.

An inline rotor-stator mixer equipped for powder induction offers flexibility, capability, and portability to serve multiple mix vessels of virtually any size. Its straightforward operation and convenience further maximize equipment utility while simplifying material handling.

When used with a vacuum pump and hopper, an inline shear mixer can be a very effective way to incorporate powders into liquid streams. Otherwise known as high shear powder inductors, these systems have the advantage of keeping the process on the floor level instead of working with heavy bags on mezzanines. High shear powder induction systems also offer easy interchangeability with multiple tanks.

A high shear granulator is a process array consisting of an inline or batch high shear mixer and a fluid-bed dryer. In a granulation process, only the solid component of the mixture is required. Fluid is used only as an aid to processing. The high shear mixer processes the solid material down to the desired particle size, and the mixture is then pumped to the drying bed where the fluid is removed, leaving behind the granular product.

In an ultra-high shear inline mixer, the high shear mixing takes place in a single or multiple passes through a rotor-stator array. The mixer is designed to subject the product to higher shear and a larger number of shearing events than a standard inline rotor-stator mixer, producing an exceptionally narrow particle-size distribution. Sub-micrometer particle sizes are possible using the ultra-high shear technology. To achieve this, the machine is equipped with stators with precision-machined holes or slots through which the product is forced by the rotors. The rotor-stator array can also include a mechanism whereby the momentum of the flow is changed (for example by forcing it sideways through the stator), allowing for more processing in a single pass.

High shear mixers may be used to produce standard mixtures of ingredients that do not naturally mix. When the total fluid is composed of two or more liquids, the final result is an emulsion; when composed of a solid and a liquid, it is termed a suspension and when a gas is dispersed throughout a liquid, the result is a lyosol. Each class may or may not be homogenized, depending on the amount of input energy.

To achieve a standard mix, the technique of equilibrium mixing may be used. A target characteristic is identified, such that once the mixed product has acquired that characteristic, it will not change significantly thereafter, no matter how long the product is processed. For dispersions, this is the equilibrium particle size. For emulsions, it is the equilibrium droplet size. The amount of mixing required to achieve equilibrium mixing is measured in tank turnover—the number of times the volume of material must pass through the high shear zone.

In some embodiments, the sonic mixer comprises a sonicator. In some embodiments, the sonic mixer comprises a benchtop bath based sonicator. In some embodiments, the sonic mixer comprises an ultrasonic mixer. The ultrasonic mixer may employ ultrasonic frequencies of any one or more of: about 18 kHz at least, about 20 kHz at least, less than 400 kHz, less than 500 kHz, about 18 kHz to about 400 kHz, about 20 kHz to about 500 kHz, at most about 400 kHz, and at most about 500 kHz. In some embodiments, the sonic mixer comprises an megasonic mixer. The megasonic mixer may employ megasonic frequencies of any one or more of: about 500 kHz at least, about 700 kHz at least, about 800 kHz at least, less than about 5 MHz, less than about 4 MHz, about 500 kHz to about 5 MHz, about 700 kHz to about 4 MHz, at most about 5 MHz, at most about 4 MHz, at least about 1 MHz, and any frequency in the MHz range.

In some embodiments, a ratio of the active agent to the binding agent is 1:1, 1:2, 1:3, 1:4, 1:5, 1:10, 1:20, 2:1, 3:1, 4:1, 5:1, 10:1, 15:1, 20:1, 3:2, 2:3, 5:2, 5:3, 2:5, or 3:5 as a target ratio. In some embodiments, the actual ratio of the active agent to the binding agent is +/−10% of the ideal ratio, +/−20% of the ideal ratio, +/−25% of the ideal ratio, or +/−30% of the target ratio. In some embodiments, the actual ratio is calculated based on UV-Vis testing of the medical device.

In some embodiments when the balloon of the device is delivered to an artery in vivo, at least 3% of the active agent is transferred to tissue of the artery. In some embodiments, at least 5% of the active agent is transferred to tissue of the artery. In some embodiments, at least 10% of the active agent is transferred to tissue of the artery.

In some embodiments, the binding agents comprises at least one of: Polyarginine, Polyarginine 9-L-pArg, DEAE-Dextran (Diethylaminoethyl cellulose-Dextran), DMAB (Didodecyldimethylammonium bromide), PEI (Polyethyleneimine), TAB (Tetradodecylammonium bromide), and DMTAB (Dimethylditetradecylammonium bromide).

In some embodiments, an average molecular weight of the binding agent is controlled. In some embodiments, a size of the active agent in the coating is controlled.

In some embodiments, the active agent is sirolimus and wherein the sirolimus has have an average size of at least one of: about 1.5 µm, about 2.5 µm, about 645 nm, about 100-200 nm, another controlled size, or a combination thereof. In some embodiments, the active agent is sirolimus and wherein sirolimus at least 75% of the sirolimus as is 1.5 µm, 2.5 µm, 645 nm, 100-200 nm, or another controlled size. In some embodiments, the active agent is sirolimus and wherein sirolimus at least 50% of the sirolimus as is 1.5 µm, 2.5 µm, 645 nm, 100-200 nm, or another controlled size. In some embodiments, the active agent is sirolimus and wherein sirolimus at least 90% of the sirolimus as is 1.5 µm, 2.5 µm, 645 nm, 100-200 nm, or another controlled size. In some embodiments, the coating may comprise nanoparticles, and the nanoparticles may comprise an active agent and a polymer.

In some embodiments, the coating comprises PLGA comprising about 50:50 Lactic acid:Glycolic acid. In some embodiments, the coating comprised and about a 10:1 ratio of the active agent to the binding agent, wherein the active agent comprises sirolimus wherein the binding agent comprises Polyarginine. In some embodiments, the sirolimus has an average size of 1.5 µm or 2.5 µm. In some embodiments, the Polyarginine average molecular weight is 70 kDa. In some embodiments, the Polyarginine average molecular weight is 5-15 kDa. In some embodiments, the active agent and the binding agent are lyophilized prior to deposition on the balloon. In some embodiments, at least about 2 ng/mg of active agent, at least about 3 ng/mg of active agent, at least about 5 ng/mg of active agent, at least about 10 ng/mg of active agent, at least about 20 ng/mg of active agent, at least about 30 ng/mg of active agent, and/or at least about 40 ng/mg of active agent are found in arterial tissue 72 hours after inflation of the balloon in the artery.

In some embodiments, in vivo measurement comprises inflating the balloon inside the artery of a porcine for about 1 minute and the amount of active agent transferred to the artery is measured by UV-Vis evaluation of the coating remaining on the balloon as determined five minutes after inflation of the balloon in the artery. In some embodiments, in vivo measurement comprises inflating the balloon inside the artery of a rabbit for about 1 minute and the amount of active agent transferred to the artery is measured by UV-Vis evaluation of the coating remaining on the balloon as determined five In some embodiments, the device releases at least one of: at least 5% of the active agent to artery upon inflation of the balloon in vivo, at least 7% of the active agent to artery upon inflation of the balloon in vivo, at least 10% of the active agent to artery upon inflation of the balloon in vivo, at least 15% of the active agent to artery upon inflation of the balloon in vivo, at least 20% of the active agent to artery upon inflation of the balloon in vivo, at least 25% of the active agent to artery upon inflation of the balloon in vivo, at least 25% of the active agent to artery upon inflation of the balloon in vivo, at least 30% of the active agent to artery upon inflation of the balloon in vivo, at least 40% of the active agent to artery upon inflation of the balloon in vivo, at least 50% of the active agent to artery upon inflation of the balloon in vivo, between 2% and 50% of the active agent to artery upon inflation of the balloon in vivo, between 3% and 50% of the active agent to artery upon inflation of the balloon in vivo, between 5% and 50% of the active agent to artery upon inflation of the balloon in vivo, between 3% and 30% of the active agent to artery upon inflation of the balloon in vivo, between 3% and 25% of the active agent to artery upon inflation of the balloon in vivo, between 3% and 20% of the active agent to artery upon inflation of the balloon in vivo, between 3% and 15% of the active agent to artery upon inflation of the balloon in vivo, between 1% and 15% of the active agent to artery upon inflation of the balloon in vivo, between 1% and 10% of the active agent to artery upon inflation of the balloon in vivo, between 3% and 10% of the active agent to artery upon inflation of the balloon in vivo, and between 1% and 5% of the active agent to artery upon inflation of the balloon in vivo.

In some embodiments, at least one of: at most 1% of coating is removed from the balloon due to tracking of the coated balloon to a treatment site, at most 5% of coating is removed from the balloon due to tracking of the coated balloon to the treatment site, at most 10% of coating is removed from the balloon due to tracking of the coated balloon to the treatment site, at most 15% of coating is removed from the balloon due to tracking of the coated balloon to the treatment site, at most 20% of coating is removed from the balloon due to tracking of the coated balloon to the treatment site, at most 25% of coating is removed from the balloon due to tracking of the coated balloon to the treatment site, and at most 30% of coating is removed from the balloon due to tracking of the coated balloon to the treatment site.

Provided herein is a device made according to any of the methods provided herein, and having features as described therein.

Example 9: Sirolimus Coated Balloon Animal (Rabbit) Study

Formulations 3, 19, 20, 21, 22, 23 were coated on balloons and the balloons were inflated in rabbit iliac arteries, and the arteries were studied at 5 minutes, 72 hours and 14 days after inflation. The objective was to assess if Sirolimus from a drug coated balloon having Formulations 3, 19, 20, 21, 22, or 23 coated thereon is retained in rabbit iliac arteries up to 72 hours and 14 days. The Formulation, coating composition, amount of sirolimus coated per balloon (in micrograms), the sample size (n), and the coating appearance on the balloon is noted in Table 23. The study outline is noted in Table 24.

As a result of the studies, it was found that Formulations 3 and 20 most retained in arteries at 3 days. Remaining formulations did not provide high levels of arterial retention. The 5 Minute Retention results showed that F19 (no PLGA) retained ~2 times more compared to F3 (w/PLGA). The 3 Day Retention results showed that F3 and F20 were within the same level of retention (~4 ng/mg). There was retention variability in all formulations. In Whole Blood results showed that Sirolimus blood levels were below 1 ng/ml by 3 days. Drug released from balloons results showed that 70% to 97% Sirolimus was released depending on formulation.

Arterial sirolimus retention as a concentration in ng/mg, or as a total sirolimus per artery in micrograms is shown in Table 25. Whole blood sirolimus concentration in ng/mL, and estimated total sirolimus in the blood in micrograms is shown in Table 26. The quantitation limit for whole blood sirolimus detection was 0.1 ng/mL. The balloon sirolimus levels (tested on the balloon after deployment) and a calculated percent of sirolimus released or lost is provided in Table 27. The calculation of percent of sirolimus released or lost was based on batch average of sirolimus on the balloon for each formulation, respectively.

TABLE 25

| Formulation | Arterial Sirolimus Conc. (ng/mg) | Total Sirolimus per Artery (µg) |
|---|---|---|
| F3: 5 Minutes Sirolimus (1.5 µm), PLGA, Polyarginine 70 kDa | 47.6 ± 30.1 (n = 6) | 1.2 ± 0.8 (n = 6) |

TABLE 23

| Formulation | Coating Composition* | Sirolimus/Balloon (µg)** | Coating Appearance |
|---|---|---|---|
| F3 (Lot 3) | Sirolimus (1.5 µm), PLGA, Polyarginine 70 kDa | 114.49 ± 25.18 (n = 18) | Translucent, Very Thick |
| F19 (Lot 1) | Sirolimus (1.5 µm), Polyarginine 5-15 kDa | 138.99 ± 19.33 (n = 8) | Transparent, Speckled |
| F20 (Lot 1) | Sirolimus (1.5 µm), 25% PLGA, Polyarginine 5-15 kDa | 223.36 ± 80.21 (n = 15) | Opaque, Extremely Thick |
| F21 (Lot 1) | Sirolimus (1.5 µm), Pullulan 200 kDa, Polyarginine 5-15 kDa | 118.29 ± 27.23 (n = 15) | Transparent, Thick, Speckled |
| F22 (Lot 1) | Sirolimus (1.5 µm), Ultravist, Polyarginine 5-15 kDa | 85.19 ± 13.20 (n = 6) | Tranparent, Light, Speckled |
| F23 (Lot 1) | Sirolimus (1.5 µm), 25% PLGA, Pullulan 200 kDa, Polyarginine 5-15 kDa | 143.97 ± 33.58 (n = 6) | Translucent, Thick |

*Sirolimus:Polyarginine ratio is 10:1 for all formulations.
**Sirolimus/Balloon based on UV-Vis before pleating/folding and sterilization of balloons

TABLE 24

| Micell DCB Formulation | Animals | Treated Vessels Per Animal | Blood PK | Necropsy Time Points |
|---|---|---|---|---|
| Formulation 3 Formulation 19 Formulation 20 Formulation 21 Formulation 22 Formulation 23 | 3 per time point | 2 balloon denuded iliac arteries treated with Micell DCB via one 60 second inflation | 2 (baseline/before necropsy) | 5 Minutes, 3 Days, 14 Days (±5%) 3 days (±5%) |
| Totals | 30 Animals | 60 Vessels | 60 Bloods | 5 min., 3 and 14 Days (±5%) |

Deployed balloons, blood samples and denuded iliac arteries analyzed for Sirolimus levels.
* Day 14 blood samples will be sent for analysis only if drug detected in Day 3 blood samples.
** Day 14 animals may be sacrificed at a later time point based on arterial drug levels at Day 3.

TABLE 25-continued

| Formulation | Arterial Sirolimus Conc. (ng/mg) | Total Sirolimus per Artery (µg) |
|---|---|---|
| F19: 5 Minutes Sirolimus (1.5 µm), Polyarginine 5-15 kDa | 88.1 ± 97.6 (n = 6) | 2.5 ± 3.1 (n = 6) |
| F3: 3 Days Sirolimus (1.5 µm), PLGA, Polyarginine 70 kDa | 4.6 ± 5.1 (n = 6) | 0.103 ± 0.117 (n = 6) |
| F19: 3 Days Sirolimus (1.5 µm), Polyarginine 5-15 kDa | 0.30 ± 0.26 (n = 6) | 0.008 ± 0.007 (n = 6) |
| F20: 3 Days Sirolimus (1.5 µm), 25% PLGA, Polyarginine 5-15 kDa | 3.8 ± 5.1 (n = 6) | 0.089 ± 0.119 (n = 6) |
| F21: 3 Days Sirolimus (1.5 µm), Pullulan 200 kDa, Polyarginine 5-15 kDa | 0.11 ± 0.05 (n = 6) | 0.003 ± 0.002 (n = 6) |
| F22: 3 Days Sirolimus (1.5 µm), Ultravist, Polyarginine 5-15 kDa | 0.34 ± 0.17 (n = 6) | 0.008 ± 0.004 (n = 6) |
| F23: 3 Days Sirolimus (1.5 µm), 25% PLGA, Pullulan 200 kDa, Polyarginine 5-15 kDa | 1.2 ± 1.9 (n = 6) | 0.028 ± 0.040 (n = 6) |

TABLE 26

| Formulation: Time Point | Sirolimus Conc. in Whole Blood (ng/mL) | Est. Total Sirolimus in Blood (µg)* |
|---|---|---|
| F3: 5 Minutes- Sirolimus (1.5 µm), PLGA, Polyarginine 70 kDa | 6.02 ± 1.43 (n = 4) | 1.49 ± 0.39 (n = 4) |
| F19: 5 Minutes- Sirolimus (1.5 µm), Polyarginine 5-15 kDa | 25.47 ± 10.08 (n = 3) | 6.12 ± 2.43 (n = 3) |
| F3: 3 Days- Sirolimus (1.5 µm), PLGA, Polyarginine 70 kDa | 0.38 ± 0.26 (n = 3) | 0.09 ± 0.06 (n = 3) |
| F19: 3 Days- Sirolimus (1.5 µm), Polyarginine 5-15 kDa | 0.34 ± 0.08 (n = 3) | 0.08 ± 0.02 (n = 3) |
| F20: 3 Days- Sirolimus (1.5 µm), 25% PLGA, Polyarginine 5-15 kDa | 0.66 ± 0.26 (n = 3) | 0.15 ± 0.06 (n = 3) |
| F21: 3 Days- Sirolimus (1.5 µm), Pullulan 200 kDa Polyarginine 5-15 kDa | 0.39 ± 0.02 (n = 3) | 0.09 ± 0.01 (n = 3) |
| F22: 3 Days- Sirolimus (1.5 µm), Ultravist, Polyarginine 5-15 kDa | 0.23 ± 0.05 (n = 3) | 0.05 ± 0.02 (n = 3) |
| F23: 3 Days- Sirolimus (1.5 µm), 25% PLGA, Pullulan 200 kDa, Polyarginine 5-15 kDa | 0.68 ± 0.13 (n = 3) | 0.15 ± 0.02 (n = 3) |

*Based on 56 mL Blood per kg

TABLE 27

| Formulation | Sirolimus Conc. on Balloon post Deployment (ug) | % Sirolimus Released/Lost* |
|---|---|---|
| F3 - Sirolimus (1.5 µm), PLGA, Polyarginine 70 kDa | 36.5 ± 7.9 (n = 20) | 69.7 ± 7.7% (n = 20) |
| F19 - Sirolimus (1.5 µm), Polyarginine 5-15 kDa | 6.9 ± 2.1 (n = 18) | 95.0 ± 1.5% (n = 18) |
| F20 - Sirolimus (1.5 µm), 25% PLGA, Polyarginine 5-15 kDa | 27.9 ± 8.6 (n = 6) | 87.4 ± 3.4% (n = 6) |
| F21 - Sirolimus (1.5 µm), Pullulan 200 kDa, Polyarginine 5-15 kDa | 3.9 ± 1.5 (n = 6) | 96.8 ± 1.2% (n = 6) |
| F22 - Sirolimus (1.5 µm), Ultravist, Polyarginine 5-15 kDa | 5.1 ± 0.8 (n = 6) | 93.9 ± 0.9% (n = 6) |
| F23 - Sirolimus (1.5 µm), 25% PLGA, Pullulan 200 kDa, Polyarginine 5-15 kDa | 21.0 ± 6.0 (n = 6) | 85.3 ± 3.6% (n = 6) |

*Based on Balloon Batch Averages of Sirolimus

Multiple lots of Formulation 3 were produced to evaluation variability and effects generally of the sirolimus size (e.g. sirolimus having an average size of 2.5 microns versus sirolimus having an average size of 1.5 microns). The results are presented in Table 28, Table 29, and Table 30. Concentrations in Table 28 were normalized using a normalized artery weight of 0.025 grams. The calculation of percent of sirolimus released or lost for Table 29 was based on batch average of sirolimus on the balloon for each formulation, respectively. The quantitation limit for whole blood sirolimus detection was 0.1 ng/mL (for Table 30).

TABLE 28

| Formulation Composition | 5 minutes Sirolimus Concentration (ng/mg) | 24 hours Sirolimus Concentration (ng/mg) | 72 hours Sirolimus Concentration (ng/mg) |
|---|---|---|---|
| F3 (LOT 1) - (PLGA, Sirolimus 2.5 µm, Polyarginine 70 kDa) | 119.2 ± 57.6 (n = 6) | 32.9 ± 18.0 (n = 8) | 8.1 ± 5.7 (n = 6) |
| F3 (LOT 2) - (PLGA, Sirolimus 1.5 µm, Polyarginine 70 kDa) | 38.6 ± 16.3 (n = 2) | 48.5 ± 63.7 (n = 2) | 41.1 (n = 1) |
| F3 (LOT 3) - (PLGA, Sirolimus 1.5 µm, Polyarginine 70 kDa) | 47.6 ± 31.4 (n = 6) | N/A | 4.1 ± 4.7 (n = 6) |

TABLE 29

| Formulation Composition | Sirolimus on Balloon Before Deployment (ug) | Sirolimus on Balloon After Deployment (ug) | % Sirolimus Released/Lost* |
|---|---|---|---|
| F3 (LOT 1) - (PLGA, Sirolimus 2.5 μm, Polyarginine 70 kDa) | 89.5 ± 19.6 (n = 9) | 27.6 ± 9.1 (n = 20) | 68.4 ± 15.4% (n = 20) |
| F3 (LOT 2) - (PLGA, Sirolimus 1.5 μm, Polyarginine 70 kDa) | 128.7 ± 26.9 (n = 42) | 56.8 ± 15.6 (n = 6) | 59.0 ± 8.6% (n = 6) |
| F3 (LOT 3) - (PLGA, Sirolimus 1.5 μm, Polyarginine 70 kDa) | 114.5 ± 25.2 (n = 18) | 36.5 ± 7.9 (n = 20) | 69.7 ± 7.7% (n = 20) |

*Based on Balloon Batch Averages of Sirolimus

TABLE 30

| Formulation Composition | Sirolimus Concentration in Whole Blood (ng/mL) | | |
|---|---|---|---|
| | 5 minutes | 24 hours | 72 hours |
| F3 (LOT 1) - (PLGA, Sirolimus 2.5 μm, Polyarginine 70 kDa) | 7.7 ± 3.7 (n = 3) | 0.8 ± 0.7 (n = 4) | BQL (n = 3) |
| F3 (LOT 2) - (PLGA, Sirolimus 1.5 μm, Polyarginine 70 kDa) | 5.5 (n = 1) | BQL (n = 1) | BQL (n = 1) |
| F3 (LOT 3) - (PLGA, Sirolimus 1.5 μm, Polyarginine 70 kDa) | 6.0 ± 1.4 (n = 4) | N/A | 0.4 ± 0.3 (n = 3) |

Example 10: Coating of Rapamycin with PLGA Through Spray-Drying

In this example, rapamycin is coated with PLGA through a spray-drying process. A mixture of 75 (w/w) % PLGA and 25 (w/w) % rapamycin is dissolved in THF to form a solution. Other polar aprotic solvent, such as acetonitrile, or mixtures of polar aprotic solvents, can also be used to form the solution. The solution is discharged from a spray nozzle and the solvent is evaporated in a drying chamber to form the PLGA-encapsulate rapamycin particles, which are collected via continuous discharge from the drying chamber to minimize thermal degradation. In another example, a slurry of rapamycin, PLGA, and water are spray dried to form the PLGA-encapsulated rapamycin particles.

The particle size of rapamycin can be controlled by adjusting spraying parameters (e.g. pressure, temperature) and nozzle configurations (e.g. size, swirl chamber, rotory disk). In this example, the spraying parameters and nozzle configuration are adjusted to produce rapamycin particles having an average particle size of from 5 to 150 nm, and more preferably from 10 to 100 nm. In other examples, the spraying parameters and nozzle configuration are adjusted to produce rapamycin particles having an average particle size of from 1 to 10 microns, and more preferably from 1 to 5 microns.

Example 11: Coating of Rapamycin with PLGA Through Fluid Bed Coating

In this example, rapamycin particles (preferably crystallined, e.g. crystallinity of 25% to 95%) are micronized and suspended on a bed of air, wherein a PLGA solution (e.g. 10-50 wt % in THF) is sprayed on the suspended rapamycin particles. Other polar aprotic solvent may also be used. The particles are then transported to a drying chamber, where the solvent are evaporated to form the PLGA-encapsulated rapamycin particles. If needed, the encapsulated particles are re-suspended, sprayed with the PLGA solution, and dried until the coating thickness of the PLGA-encapsulated rapamycin particles reaches the desired level, e.g. 2 to 20 micron or about 10 microns.

Example 12: Coating of Rapamycin with PLGA Through Pan Coating

In this example, particles of PLGA, such as PLGA pellets, are added to rapamycin particles in a tumbling vessel to form the PLGA-encapsulated rapamycin particles. For example, PLGA may be ground, such as through ball mill, jet mill, or cryogenic grinding, to appropriate particle size (e.g. about 30 microns). The particle size and PLGA layer thickness of the encapsulated rapamycin can be controlled by the feeding rate of the PLGA pellets. In this example, the PLGA pellets are fed into the tumbling vessel at a rate of from 100 to 1000 μg per minute, preferably from 300 to 500 μg per minute.

While Examples 10, 11, and 12 provide mechanical or physical method for encapsulation of the rapamycin in the PLGA, they should not be interpreted as limiting the scope of the present disclosure. Chemical methods of encapsulation, such as core-shell emulsion preparation complex coacervation or in situ polymerization, can also be used to form the encapsulated rapamycin.

Much of the description herein is provided with reference to a balloon and a treatment site that is an artery or blood vessel for ease of description and brevity. Nevertheless, the methods, descriptions, devices, and coatings described herein apply to alternative devices and treatment locations.

Unless otherwise stated, use of the term "about" in this description can mean variations of 0.1%, 0.5%, 1%, 2%, 3%, 5%, 10%, 15%, 20%, 25%, 30%, 40%, and/or 50%, depending on the particular embodiment. Where the element being described is itself expressed as a percent, the variations are not meant to be percents of percents, rather they are variations as an absolute percent—i.e. an element that is expressed as "about 5%" may be actually 5%+/−1%, or from 4% to 6%, depending on the embodiment. Only the variations that would be rational to one of ordinary skill in the art are contemplated herein. For example, where the element itself is expressed as a small percent, and a person of ordinary skill would know that the element is not rational to go below 0, the variations contemplated would not go below zero (i.e. about 5% could mean 5%+/−5% or 0-10%, but not 5%+/−10% or −5% to 15%, where this is not reasonable to one of skill in the art for the element being described).

The foregoing is illustrative of the present invention, and is not to be construed as limiting thereof. While embodiments of the present invention have been indicated and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 13: Coating of Rapamycin with PLGA Through Single Emulsion/Evaporation with Centrifuge In this example, rapamycin is coated with PLGA through a single emulsion/evaporation technique using a centrifuge to filter the emulsion. 200 mg poly(lactic-co-glycolic)acid (RG504H 0 viscosity 0.45-0.6) was dissolved in 4 ml dichloromethane (oil phase). One hundred µl of a stock solution of rapamycin in Dimethyl Sulfoxide (10 mg/ml) was dissolved in the oil phase, which was then homogenized at 10100 rpm for 1 min in a 2% PVA (MW~25,000, 98% hydrolyzed) solution, using a homogenizer. This emulsion was immediately poured into 90 ml of a 1% PVA solution, and dichloromethane was allowed to evaporate. After 3 hours, the particles were centrifuged (1500 g, 10 min, 4° C.) and washed four times in deionized water. Microparticles were then re-suspended in 5 ml of deionized water, frozen on dry ice and lyophilized. Fluorescently labeled rapamycin-microparticles were prepared by adding 100 µl of 2 mg/ml Alexa Fluor 647 carboxylic acid, succinimidyl ester to the oil phase along with the rapamycin and following the same protocol as above.

Example 14: Coating of Rapamycin with PLGA Through Single Emulsion/Evaporation with Filter Paper In this example, rapamycin is coated with PLGA through a single emulsion/evaporation technique using filter paper to filter the emulsion. Five to 10 grams of PVA (Polyscience Inc, MW~25,000, 98% hydrolyzed) was dissolved in warmed HPLC grade water to create 1% and 2% PVA solutions. Approximately 400 mg of 50:50 Poly DL-lactide-co-glycolide (Ester terminated, IV 0.55-0.75, Durect Corporation, Pelham, Ala.) was added to a 50 ml centrifuge tube and dissolved in 8 ml of Dichloromethane (oil phase). Approximately 10 mg of rapamycin was added to 1 mL Dimethylsulfoxide and swirled until white particles were no longer visible. 200 µl of the stock rapamycin solution was added to the oil phase. This solution was then poured into ~100 ml of 2% PVA and homogenized for 1 min at ~17,500 rpm. The emulsion was then poured into 180 ml of 1% PVA and left uncovered overnight to allow the dichloromethane to evaporate. A frit funnel was lined with two size 3 Whatman filter paper pieces (pre-wetted with HPLC grade water) prior to filtering the solution. The solution was poured through the filter paper, leaving the particles on the filter paper. The particles were re-suspended by submerging the filter paper in 10 ml of water. The liquid was transferred to a 100 ml round bottom flask which was frozen on dry ice and then lyophilized.

Figure 5:
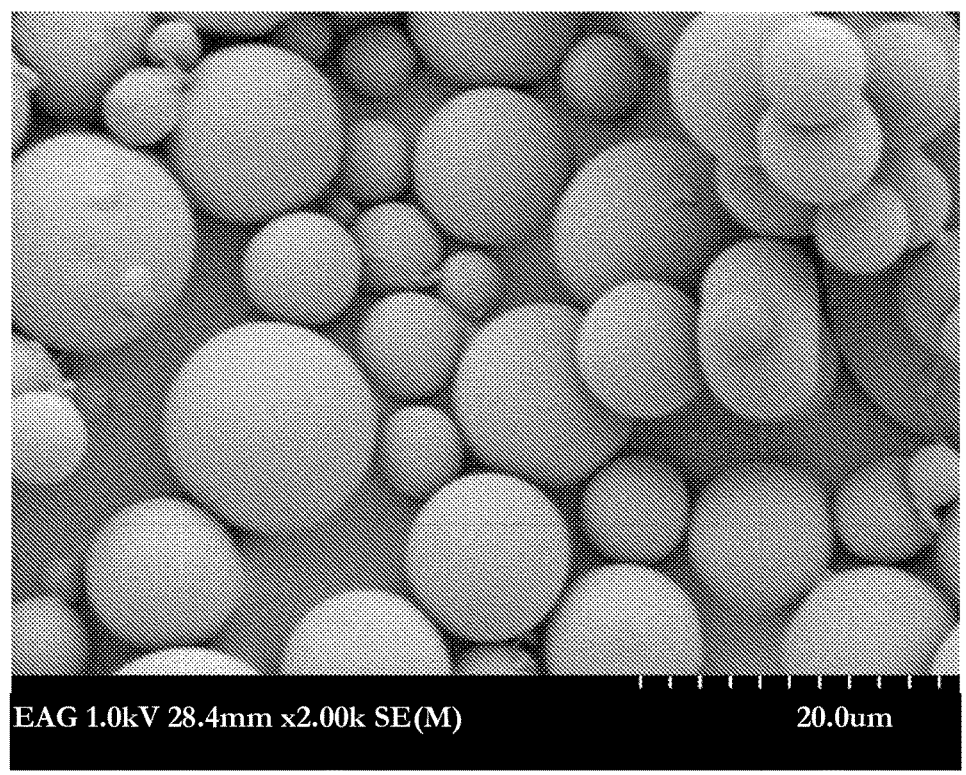
FIG. 5 is an SEM image of microparticles of encapsulated rapamycin according to one embodiment herein.

Referring now to FIG. 5, the encapsulated microparticles prepared in this Example were examined for size and shape using a Hitachi Model S-4700 scanning electron microscope (SEM). The SEM image shows that the encapsulated rapamycin particles prepared in this Example are generally smooth and spherical. For example, at least 50%, 60%, 70%, 80%, or 90% of the particles have a generally spherical shape. FIG. 5 also shows a general particle size range of from about 0.5 µm to about 10 µm. For example, at least 50%, 60%, 70%, 80%, or 90% of the particles have a size range of about 0.5 µm to about 10 µm. The particles prepare in this Example have an average particle size of from about 0.5 µm to about 10 µm, from about 1 µm to about 10 µm, from about 1 µm to about 8 µm, from about 1 µm to about 7 µm, from about 1 µm to about 6 µm, from about 1 µm to about 5 µm, or from about 2 µm to about 4 µm. The presence of rapamycin inside the microparticles was confirmed by UV-VIS spectroscopy (Perkin-Elmer Lambda 25 UV-Vis Spectrophotometer).

Example 15: Crystalline Rapamycin Encapsulation

Five to 10 g of PVA (MW 25,000, 98% hydrolyzed) was dissolved in warmed HPLC grade water to create 1% and 2% PVA solutions. Approximately 200 mg of 50:50 Poly DL-lactide-co-glycolide (Ester terminated, IV 0.55-0.75) was added to a 50 ml centrifuge tube and dissolved in 4 ml of dichloromethane (oil phase). Approximately 50 ml of 1% PVA was added to the oil phase and homogenized for 2 mins at ~17,500 rpm. The emulsion was left uncovered over night to allow the dichloromethane to evaporate. Approximately 1 mg of rapamycin was homogenized in 20 ml of 2% PVA for two minutes at ~17,500 rpm. The rapamycin mixture was then added to the polymer emulsion and homogenized for two minutes at ~17,500 rpm. A frit funnel was lined with two size 3 Whatman filter paper pieces (pre-wetted with HPLC grade water) prior to filtering the solution. The solution was poured through the filter paper, leaving the particles on the filter paper. The particles were re-suspended by submerging the filter paper in 10 ml of water. The liquid was transferred to a 100 ml round bottom flask which was frozen on dry ice then lyophilized.

Figure 6:
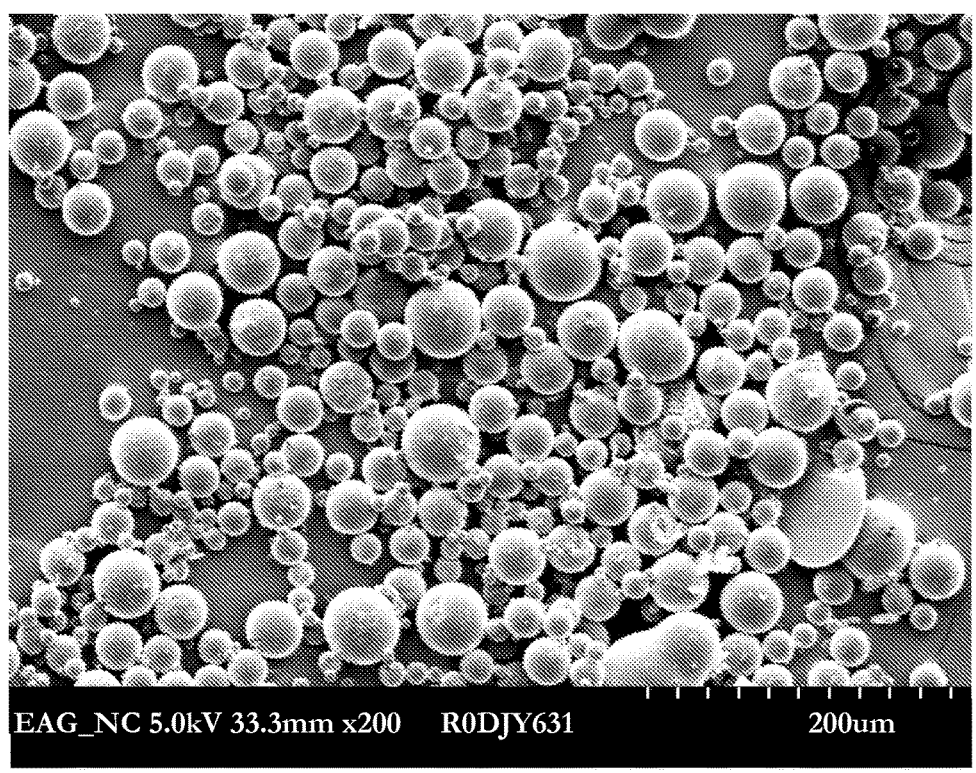
FIG. 6 is an SEM image of microparticles of encapsulated rapamycin according to another embodiment herein.

Referring now to FIG. 6, the particles prepared in this Example were examined for size and shape using a Hitachi Model S-4700 scanning electron microscope (SEM). The SEM image shows that the encapsulated rapamycin particles prepared in this Example are generally smooth and spherical. For example, at least 50%, 60%, 70%, 80%, or 90% of the particles have a generally spherical shape. FIG. 6 also shows a general particle size range of from about 1 µm to about 50 µm. For example, at least 50%, 60%, 70%, 80%, or 90% of the particles have a size range of about 1 µm to about 50 µm. The particles prepare in this Example have an average particle size of from about 1 µm to about 50 µm, from about 1 µm to about 40 µm, from about 5 µm to about 40 µm, from about 5 µm to about 35 µm, from about 5 µm to about 30 µm, from about 10 µm to about 30 µm, or from about 10 µm to about 20 µm. The presence of Rapamycin inside the microparticles was confirmed by UV-VIS spectroscopy (Perkin-Elmer Lambda 25 UV-Vis Spectrophotometer).

Example 16: Encapsulated Microparticle Characterization

Encapsulated microparticles are sized and counted using volume impedance measurements on a Beckman Coulter Counter. Average size was determined by counting at least 10,000 particles. Microparticle surface morphology and shape were examined using a scanning electronic microscope. The surface charge of the microparticles was determined by zeta potential measurements.

SEM images of the particles show smooth surface morphology and confirm the size obtained from the volume impedance measurements. The size distribution observed in SEM images is characteristic of the microparticle encapsulation process described herein.

Example 17: Encapsulation Efficiency Characterization

Five mg of encapsulated rapamycin microparticles was dissolved in 1 ml of acetonitrile (HPLC grade), sonicated for 5 minutes and left under a constant vortex for 30 min. The amount of rapamycin was then determined by measuring absorbance of the solution at 278 nm using a UV-equipped plate reader. Encapsulation efficiency was calculated as the ratio of rapamycin present inside particles to the amount of rapamycin that was initially added.

What is claimed is:

1. A medical device comprising:
a balloon; and
a coating on at least a portion of the balloon,
wherein the coating comprises smooth and spherical particles having rapamycin particles encapsulated in a first polymer material prior to inclusion in the coating, the particles being from about 0.5 μm to about 10 μm in size and the first polymer being PLGA, and
wherein each particle is at least partially encapsulated in a second polymer material in the coating.

2. The medical device of claim 1, wherein at least 50% of the surface area of certain of the particles is encapsulated in the second polymer material.

3. The medical device of claim 1, wherein at least 75% of the surface area of certain of the particles is encapsulated in the second polymer material.

4. The medical device of claim 1, wherein at least 90% of the surface area of certain of the particles is encapsulated in the second polymer material.

5. The medical device of claim 1, wherein at least 95% of the surface area of certain of the particles is encapsulated in the second polymer material.

6. The medical device of claim 1, wherein the coating has an average thickness of from 2 microns to 20 microns.

7. The medical device of claim 1, wherein the pharmaceutical agent has a crystallinity of from 25% to 95%.

8. The medical device of claim 1, wherein a weight ratio of the pharmaceutical agent and the second polymer material is from 40:60 to 60:40.

9. The medical device of claim 1, wherein the particles are at least partially encapsulated in the second polymer material by spray-drying a mixture of the pharmaceutical agent, the polymer material, and a solvent.

10. The medical device of claim 9, wherein the mixture is a solution and the solvent is a polar aprotic solvent.

11. The medical device of claim 9, wherein the mixture is a slurry and the solvent is water.

12. The medical device of claim 1, wherein the particles are at least partially encapsulated in the first polymer material by adding particles of the first polymer material to the pharmaceutical agent in a tumbling vessel.

13. The medical device of claim 12, wherein the particles of the first polymer material have an average particle size of from 10 microns to 100 microns.

14. The medical device of claim 12, wherein the particles of the first polymer material are added at a rate of from 100 μg to 1000 μg per minute.

15. The medical device of claim 1 wherein the particles are at least partially encapsulated in the first polymer material by forming an emulsion-based mixture comprising the pharmaceutical agent and the polymer material, and separating the polymer-encapsulated pharmaceutical agent from the emulsion-based mixture.

16. The medical device of claim 1, wherein the second polymer material comprises a bioabsorbable polymer.

17. The medical device of claim 16, wherein the bioabsorbable polymer is selected from the group consisting of polylactides (PLA); poly(lactide-co-glycolide) (PLGA); polyanhydrides; polyorthoesters; poly(N-(2-hydroxypropyl) methacrylamide); poly(dl-lactide) (DLPLA); poly(l-lactide) (LPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); poly(glycolide-co-trimethylene carbonate-co-dioxanone) (PDO-PGA-TMC), polyvinyl alcohol (PVA), polyarginine, and mixtures or co-polymers thereof.

18. The medical device of claim 17, wherein the bioabsorbable polymer is selected from the group consisting of PLGA, PVA, polyarginine, and mixtures thereof.

19. The medical device of claim 1, further comprising a binding agent deposited on an exterior surface of the encapsulated particles.

20. The medical device of claim 19, wherein a weight ratio between the binding agent and the second polymer material is from 1:99 to 25:75.

21. The medical device of claim 19, wherein the binding agent is deposited by spraying and drying a solution of the binging agent on the encapsulated particles of the pharmaceutical agent.

22. The medical device of claim 21, wherein the solution comprises the binding agent and water.

23. The medical device of claim 19, wherein the binding agent comprises at least one of: polyarginine, polyarginine 9-L-pArg, DEAE-Dextran (Diethylaminoethyl cellulose-Dextran), DMAB (Didodecyldimethylammonium bromide), PEI (Polyethyleneimine), TAB (Tetradodecylammonium bromide), and DMTAB (Dimethylditetradecylammonium bromide).

24. The medical device of claim 19, wherein the binding agent is polyarginine.

25. The medical device of claim 24, wherein the polyarginine has an average molecular weight of about 70 kDa.

26. The medical device of claim 24, wherein the polyarginine has an average molecular weight of 5-15 kDa.

27. The medical device of claim 1 wherein the encapsulated particles of the pharmaceutical agent are deposited on the balloon using an eSTAT coating process.

28. The medical device of claim 1, wherein the device releases at least 3% of the pharmaceutical agent upon inflation of the balloon.

29. A method of releasing a pharmaceutical agent at a target site, comprising
providing a device comprising a balloon, and a coating on at least a portion of the balloon, wherein the coating comprises smooth and spherical particles having rapamycin particles encapsulated in a first polymer prior to inclusion in the coating, the particles being from about 0.5 μm to about 10 μm in size and the first polymer being PLGA, and wherein each particle is at least partially encapsulated in a second polymer material in the coating;

positioning the device to allow the balloon to reach the target site; and inflating the balloon of the device, wherein at least some of the pharmaceutical agent is released to the target site upon inflating the balloon.

30. The method of claim 29, wherein at least 3% of the pharmaceutical agent is released to the blood vessel upon inflation of the balloon.

31. The method of claim 29, wherein the second polymer material comprises a biodegradable polymer.

32. The method of claim 31 wherein the bioabsorbable polymer is selected from the group consisting of polylactides (PLA); poly(lactide-co-glycolide) (PLGA); polyanhydrides; polyorthoesters; poly(N-(2-hydroxypropyl) methacrylamide); poly(dl-lactide) (DLPLA); poly(l-lactide) (LPLA); polyglycolide (PGA); poly(dioxanone) (PDO); poly(glycolide-co-trimethylene carbonate) (PGA-TMC); poly(l-lactide-co-glycolide) (PGA-LPLA); poly(dl-lactide-co-glycolide) (PGA-DLPLA); poly(l-lactide-co-dl-lactide) (LPLA-DLPLA); poly(glycolide-co-trimethylene carbonate-co-dioxanone) (PDO-PGA-TMC), polyvinyl alcohol (PVA), and mixtures or co-polymers thereof.

33. The method of claim 29, wherein the device further comprises a binding agent deposited on an exterior surface of the encapsulated particles of the pharmaceutical agent.

34. The method of claim 33, wherein the binding agents comprises at least one of: polyarginine, polyarginine 9-L-pArg, DEAE-Dextran (Diethylaminoethyl cellulose-Dextran), DMAB (Didodecyldimethylammonium bromide), PEI (Polyethyleneimine), TAB (Tetradodecylammonium bromide), and DMTAB (Dimethylditetradecylammonium bromide).

35. The method of claim 29, wherein the encapsulated particles of the pharmaceutical agent are deposited on the balloon using an eSTAT coating process.

36. A method of forming polymer-encapsulated crystalline rapamycin, the method comprising: forming the emulsion-based mixture comprising the pharmaceutical agent and the polymer material; evaporating a portion of the emulsion-based mixture, and filtering the remaining emulsion-based mixture.

37. The method claim 36, further comprising resuspending and lyophilizing the encapsulated pharmaceutical agent.

38. The medical device of claim 1, wherein the first and second polymer materials are different.

39. The medical device of claim 1, wherein the first and second polymer materials are the same.

* * * * *